(12) United States Patent
Messersmith et al.

(10) Patent No.: US 8,269,009 B2
(45) Date of Patent: Sep. 18, 2012

(54) METHODS AND COMPOSITIONS FOR TREATING LIQUID TUMORS

(75) Inventors: Elizabeth Messersmith, El Cerrito, CA (US); Ivan Lieberburg, Berkeley, CA (US)

(73) Assignee: Elan Pharmaceuticals, Inc., South San Francisco, CA (US)

( * ) Notice: Subject to any disclaimer, the term of this patent is extended or adjusted under 35 U.S.C. 154(b) by 476 days.

(21) Appl. No.: 12/314,261

(22) Filed: Dec. 5, 2008

(65) Prior Publication Data

US 2009/0312353 A1 Dec. 17, 2009

Related U.S. Application Data

(60) Provisional application No. 60/996,846, filed on Dec. 7, 2007.

(51) Int. Cl.
*C07D 513/02* (2006.01)
(52) U.S. Cl. .............. 546/118; 514/210.18; 514/210.2; 514/275; 544/323; 544/324
(58) Field of Classification Search .............. 546/118
See application file for complete search history.

(56) References Cited

U.S. PATENT DOCUMENTS

| | | |
|---|---|---|
| 2003/0171359 A1 | 9/2003 | Dahmann et al. |
| 2005/0255118 A1 | 11/2005 | Wehner |
| 2005/0276803 A1 | 12/2005 | Chan et al. |
| 2007/0021555 A1 | 1/2007 | Konradi et al. |
| 2007/0027131 A1 | 2/2007 | Konradi et al. |

FOREIGN PATENT DOCUMENTS

| | | |
|---|---|---|
| WO | WO 03/099231 A2 | 12/2003 |
| WO | WO 03/099809 A1 | 12/2003 |
| WO | WO 2005/122379 A2 | 12/2005 |
| WO | WO 2007/041270 A1 | 4/2007 |
| WO | WO 2007/101165 A1 | 9/2007 |

OTHER PUBLICATIONS

European Search Report dated May 25, 2012 (Thirteen (13) pages).

*Primary Examiner* — James D Anderson
*Assistant Examiner* — Ibrahim D Bori
(74) *Attorney, Agent, or Firm* — Crowell & Moring LLP

(57) ABSTRACT

The application relates to a method of using compositions having anti-alpha-4 integrin and/or anti-alpha-9 integrin activity to inhibit liquid tumor growth, malignancies thereof and/or development of metastases thereof that involve expression of an alpha-4 integrin and/or alpha-9 integrin. Pharmaceutical compositions and combination therapies (for example, with chemotherapies) for the inhibition of liquid tumor growth, malignancies thereof and/or development of metastases thereof are also provided.

7 Claims, 13 Drawing Sheets

Anti-VLA-4 Therapeutic Treatment in Combination with Melphalan Reduced Circulating IgG2b Levels and 5GTM1/luc Tumor Burden in the Bone Binding of ELND002 on Guinea Pig Lymphocytes ELND002 Induces Down-Regulation of Receptor Expression α4 and β1 Expression on MOLT-4 Cells VCAM-1/Fc Binding to MOLT-4 Cells ELND002 inhibition of VCAM-1/Fc binding to MOLT-4 cells

METHODS AND COMPOSITIONS FOR TREATING LIQUID TUMORS

This application claims priority to U.S. Provisional Application Ser. No. 60/996,846, filed Dec. 7, 2007, the contents of which are herein incorporated by reference in their entirety.

FIELD OF THE INVENTION

The application relates to a method of using compounds having anti-alpha-4 integrin and/or anti-alpha-9 integrin activity to inhibit liquid tumor growth, malignancies thereof and/or development of metastases thereof that involve expression of an alpha-4 integrin and/or alpha-9 integrin. Pharmaceutical compositions and combination therapies for the inhibition of liquid tumor growth, malignancies thereof and/or development of metastases thereof are also provided.

BACKGROUND OF THE INVENTION

While solid tumors occur in organs, liquid tumors consist of blood cells that have become cancerous. Tumors express proteins in patterns not found in normal cells. The pattern of proteins exhibited by tumor or malignant cells can reflect the stage of disease (i.e., early stage or metastatic disease). As a malignancy progresses, the cells tend to differ more and more from the tissue from which they originated. As a cancer progresses becoming more undifferentiated, regardless of the staging schema used to determine the cancer's progression, the cells become more likely to metastasize and/or are more refractory to treatment by traditional therapies. Leukemias and myelomas are among the most common blood cancers.

Integrins are a family of cell-surface glycoproteins involved in cell-adhesion, immune cell migration and activation. Alpha-4 integrin is expressed by all circulating leukocytes except neutrophils, and forms heterodimeric receptors in conjunction with either the beta-1 ($\beta$1) or beta-7 ($\beta$7) integrin subunits. Both alpha-4beta-1 ($\alpha$4$\beta$1) integrin and alpha-4beta-7 ($\alpha$4$\beta$7) integrin play a role in migration of leukocytes across the vascular endothelium (Springer et al., *Cell*, 1994, 76: 301-14; Butcher et al., *Science*, 1996, 272: 60-6) and contribute to cell activation and survival within the parenchyma (Damle et al., *J. Immunol.*, 1993; 151: 2368-79; Koopman et al., *J. Immunol.*, 1994, 152: 3760-7; Leussink et al., *Acta Neuropathol.*, 2002, 103: 131-136). Alpha-4beta-1 integrin is constitutively expressed on lymphocytes, monocytes, macrophages, mast cells, basophils, and eosinophils.

Alpha-4beta-7 (also known as very late antigen-4, VLA-4), binds to vascular cell adhesion molecule-1 (VCAM-1) (Lobb et al., *J. Clin. Invest.* 1994, 94: 1722-8), which is expressed by the vascular endothelium at many sites of chronic inflammation (Bevilacqua et al., 1993, *Annu. Rev. Immunol.*, 11: 767-804; Postigo et al., 1993, *Res. Immunol.*, 144: 723-35). Alpha-4beta-1 integrin has other ligands, including fibronectin and other extracellular matrix (ECM) components.

Alpha-4beta-7 integrin interacts with mucosal addressin cell adhesion molecule (MAdCAM-1), and mediates homing of lymphocytes to the gut (Farstad et al., 1997, *Am. J. Pathol.*, 150: 187-99; Issekutz, 1991, *J. Immunol.* 147: 4178-84). The alpha unit is the most important in binding actions within the alpha4 set. Accordingly, anti-alpha-4 intregrin agents may have activity despite being mixed inhibitors of alpha4beta1 and alpha4beta7. Further, it has been found that the disruption of alpha-4 integrin-mediated call adhesion restores drug sensitivities. Anti-alpha-4 treatment with chemotherapeutic agents, such as melphalan, is more effective against myeloma than a single agent treatment. Alpha-4 interaction with VCAM-1 or fibronectin promotes resistance to fludarabine. Alpha-4beta-1-fibronectin interaction promotes chemoresistance of acute myelogenous leukemia (AML) cells lines.

Many hematological tumors, such as leukemia, myeloma, and melanoma, may be positive for alpha-4 integrins. Accordingly, the growth and survival of these tumors depends on interaction with alpha-4 integrin. Metastatic tumors express VCAM-1. It has been seen that anti-alpha-4 treatment decreased bone destruction and increased apoptosis of myeloma cells in the bone marrow compartment. Alpha-4 interaction with VCAM-1 or fibronectin promotes survival of patient derived chronic lymphoblastic leukemia (CLL) cells. Alpha-4beta-1-fibronectin interaction has been seen to promote survival of AML cells lines in vitro.

Alpha-9 integrins play a role in development of lymphatics, granulocytes, osteoclasts and angiogenesis. Alpha-9 plays a role in lymphangiogenic growth, probably through VEGFC and/or VEGFA binding (which mediates vascular growth and angiogenesis). Alpha-9 integrin also affects granulocytes, the development of osteoclasts, and neutrophils. Alpha-9 has been shown to accelerate cell migration in vitro.

In alpha-9 knock out mice, there is a dramatic defect specific for neutophils. Knock downs of Kir4.2 inhibits alpha-9 mediated cell migration of microvascular endothelial cells. Further, there is reduced G-CSF induced colony formation in alpha-9 deficient bone marrow cells. Accordingly, there are strong implications for the use of anti-alpha-9 agents in the treatment of cancers.

Of the alpha-9 integrins, alpha-9beta-1 is most closely homologous to alpha-4 beta-1. Alpha-9beta-1 recognizes growth factor receptors, e.g., VEGFC (lymphangiogenesis) as well as VEGFA (vascular growth mediator). Alpha-9beta-1 integrin is expressed on microvascular endothelial cells and interacts with thrombospondin-1. This interaction is involved in modulation of angiogenesis. Alpha-9beta-1 directly binds to VEGF-C and D and contributes to lymphangiogenesis. Thus, the integrin alpha-9beta-1 as a potential pharmacotherapeutic target for inhibition of pathogenic angiogenesis and lymphangiogenesis.

Alpha-9 integrins have been shown to have activity in relation to solid tumors. For example, Basora et al. report the expression of alpha-9beta-1 integrin in human colonic epithelial cells in subsets of colon cancer (*Int J Cancer.* 1998 Mar. 2; 75(5): 738). Häkkinen et al. report the expression of alpha-9 integrin in oral leukoplakia, lichen planus and squamous cell carcinoma. (*Oral Dis.* 1999 July; 5(3): 210-7) Tomczuk et al. report the activity of multiple beta-1 integrins in cell adhesion to the disintegrin domain of ADAMs 2 and 3. (*Exp Cell Res.* 2003 Oct. 15; 290(1): 68-81). Chen et al. showed that mice lacking alpha-9beta-1 have a dramatic reduction in neutrophil development and numbers. (*Immunity,* 2006, 17137800).

However, new agents, compositions and methods for using these agents and compositions that inhibit growth and metastasis of liquid tumors are needed, which can be used alone or in concert with other agents.

SUMMARY OF THE INVENTION

The invention provides for new methods, compositions, and combination therapies for treating liquid tumors and/or inhibiting the growth and metastases of liquid tumors. The methods, compositions and combination therapies are preferably directed towards the treatment of alpha-4 and/or alpha-9 expressing cancers of the blood, such as leukemias and myelomas.

DETAILED DESCRIPTION OF THE INVENTION

Definitions and Acronyms

Figure 1B:
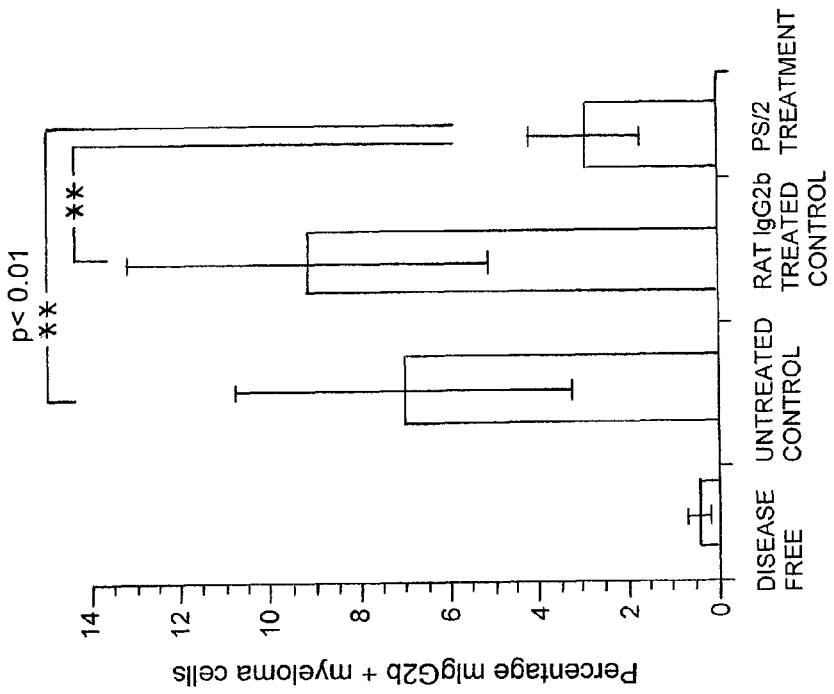
FIG. 1 shows anti-VLA-4 treatment reduced circulating IgG2b levels and IgG2b positive myeloma cells in the blood. Animals injected with tumor cells on Day 0 were dosed with anti-VLA-4 antibody PS/2 (rat IgG2b) at 10 mg/kg on Days 4, 5, 6, 9, 12, 15, and 18. Evaluations were subsequently performed on Day 21. A) Circulating levels of mIgG2b were expressed as mg/mL in control and PS/2 treated animals (N=8 in disease free group, 14 in untreated control group, 10 in isotype control group and 13 in PS/2 treated group). Plasma IgG2b levels were determined by ELISA. B) IgG2b-positive myeloma cells in the whole blood from the treatment groups described in A were identified by FACS analysis gating for total lymphocyte population using standard lineage markers, then staining for intracellular IgG2b. Lineage-negative IgG2b myeloma positive cells are expressed as percentage of the total lymphocyte count.
Figure 1A:
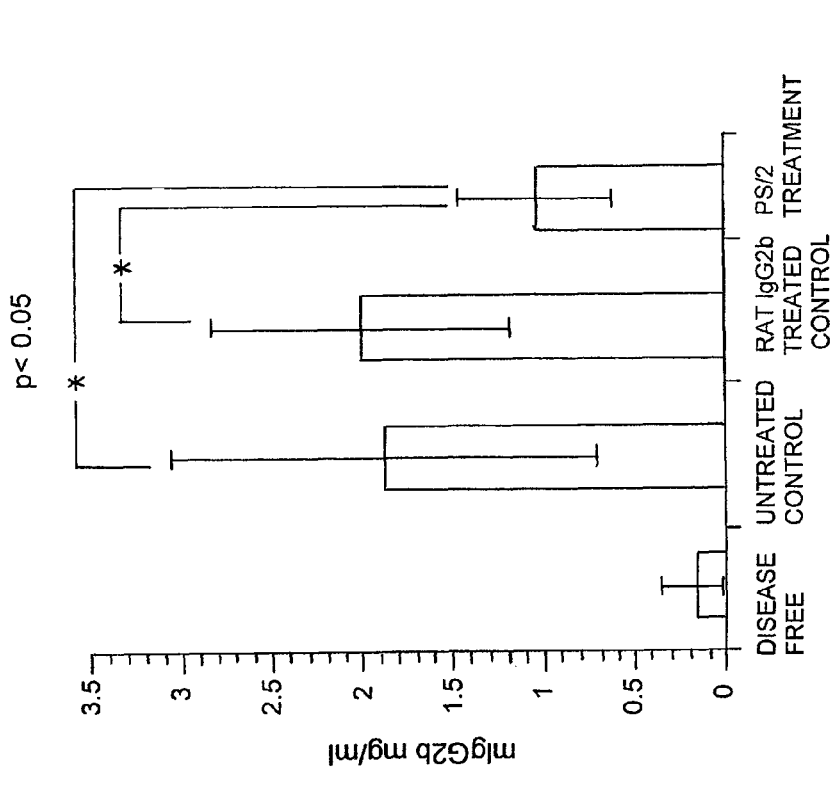
Figures 2A, 2B:
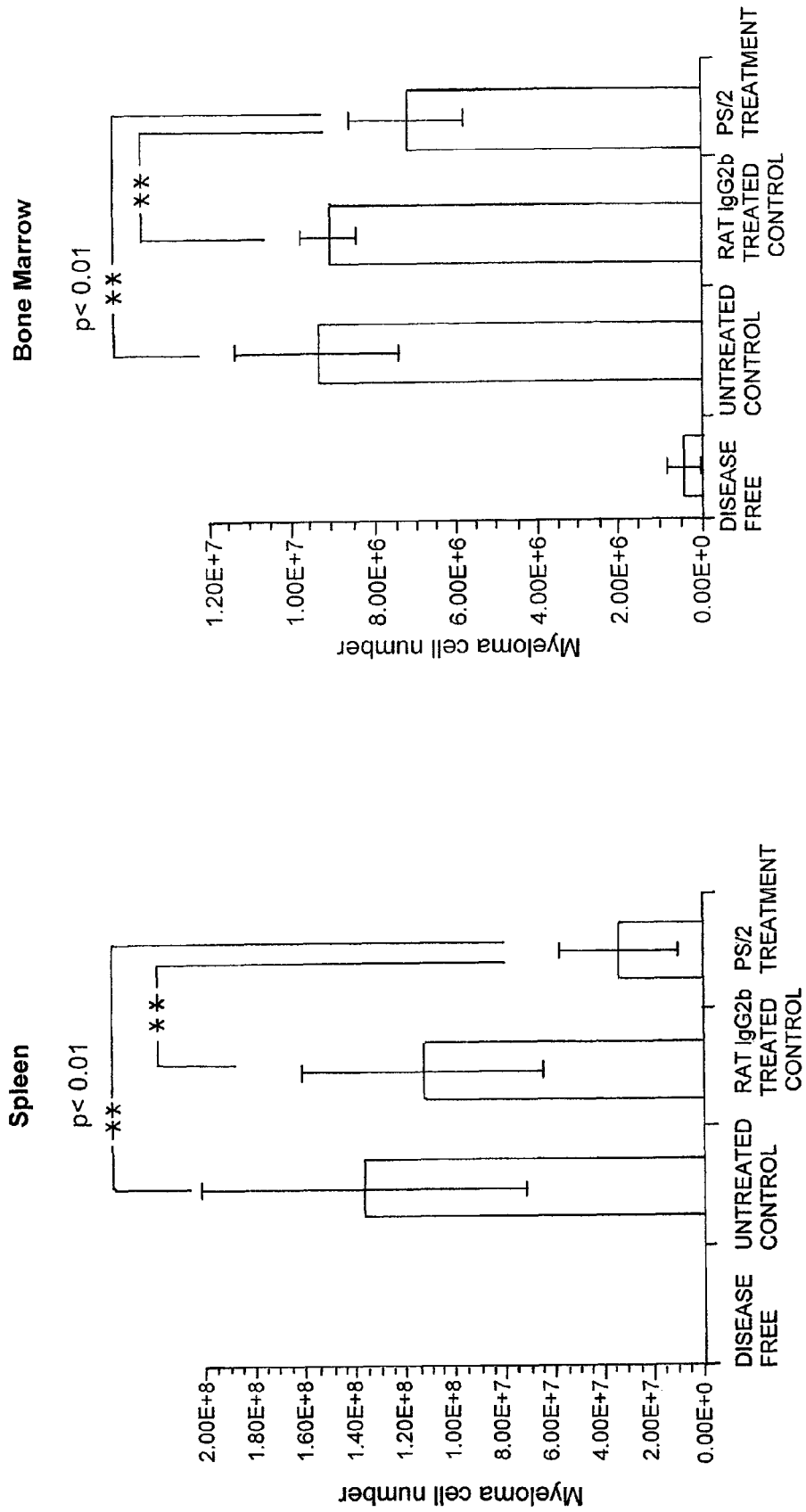
FIG. 2 shows anti-VLA-4 treatment reduced the number of IgG2b positive myeloma cells in the spleen and bone marrow. A) To determine tumor burden in spleen, splenocytes were isolated from half the organ and counted. Cells were then stained by lineage markers and IgG2b as described in FIG. 1. Tumor burden was determined by multiplying the percentage of lineage-negative IgG2b positive cells by the total cell number calculated to be in the spleen. B) Bone marrow cells were isolated from single tibia/fibula pairs, counted and stained for lineage markers as described. Tumor burden was calculated in the same manner as described for the spleen.
Figure 3A:
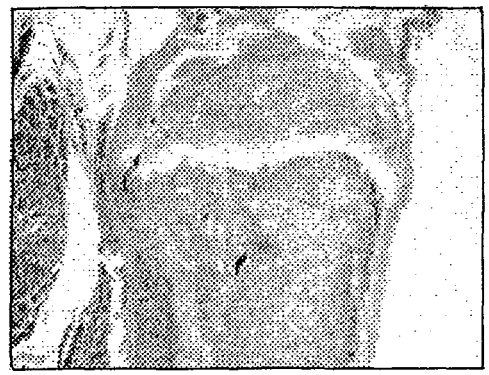
FIG. 3 shows anti-VLA-4 treatment reduced osteoclastic lesions in the trabecular bone. Mice were killed at day 27 and right hindlimbs harvested and subjected to histological examination. Sections were stained with hematoxylin and eosin (H-E) and examined using Olympus BX-40F4 microscope equipped with a camera. Panels A and B: lower magnification (H-E x 40); panels C and D: higher magnification (H-E x 200). Histomorphometric analysis of remaining trabecular bone/total area (E) and osteoclast number at the interface between myeloma and bone (F). Histological view of the tibia of untreated and anti-alpha-4 antibody treated 5TGM1/luc bearing mice. (A,C) Bone marrow cavity is occupied by 5TGM1/luc myeloma cells and no trabecular bones were seen in the untreated group. (B, D) Normal marrow elements and trabecular bones were still observed in the anti-alpha 4 Ab-treated group. Data are mean±SEM (n=5). * Significantly different from non-tumor bearing (NTB) mice. ** Significantly different from untreated 5TGM1/luc bearing mice.
Figure 3B:
Figure 3C:
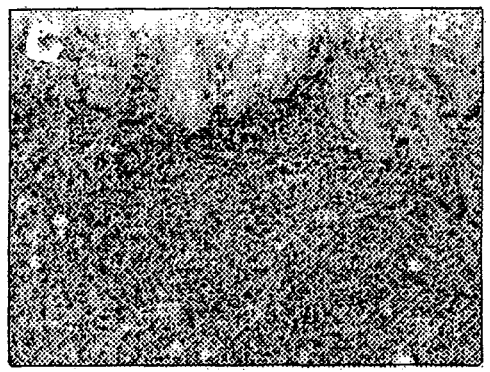
Figure 3D:
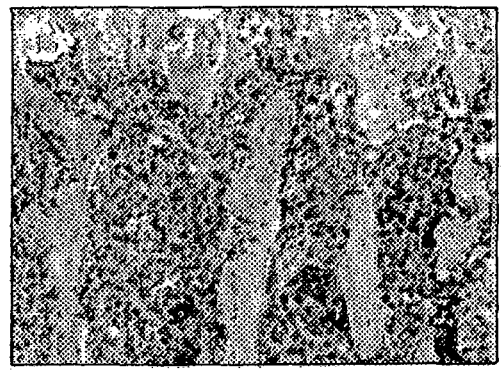
Figure 3F:
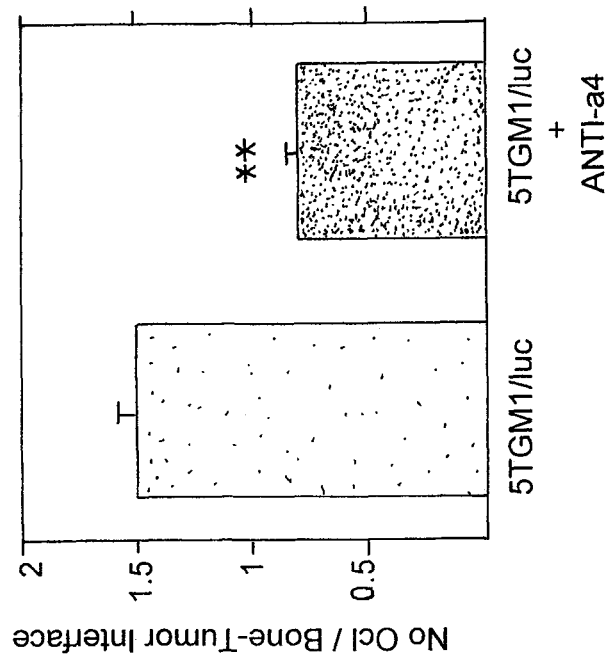
Figure 3E:
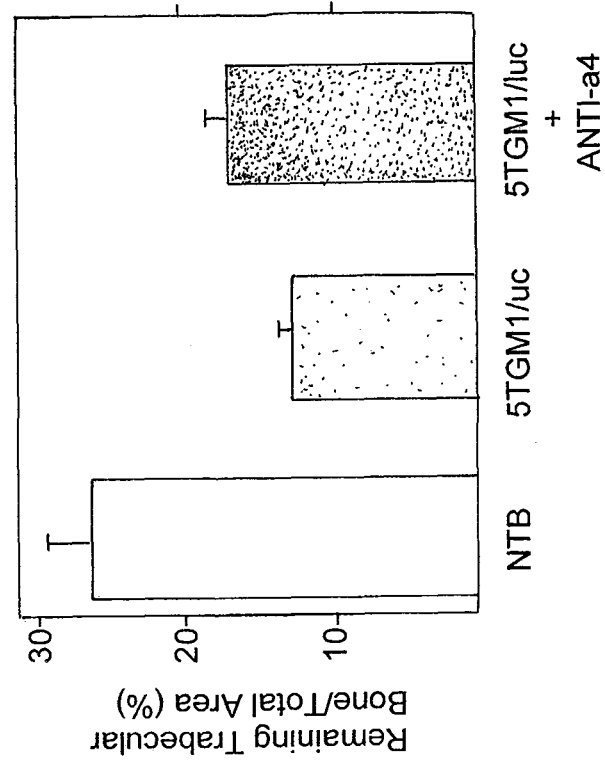
Figure 4:
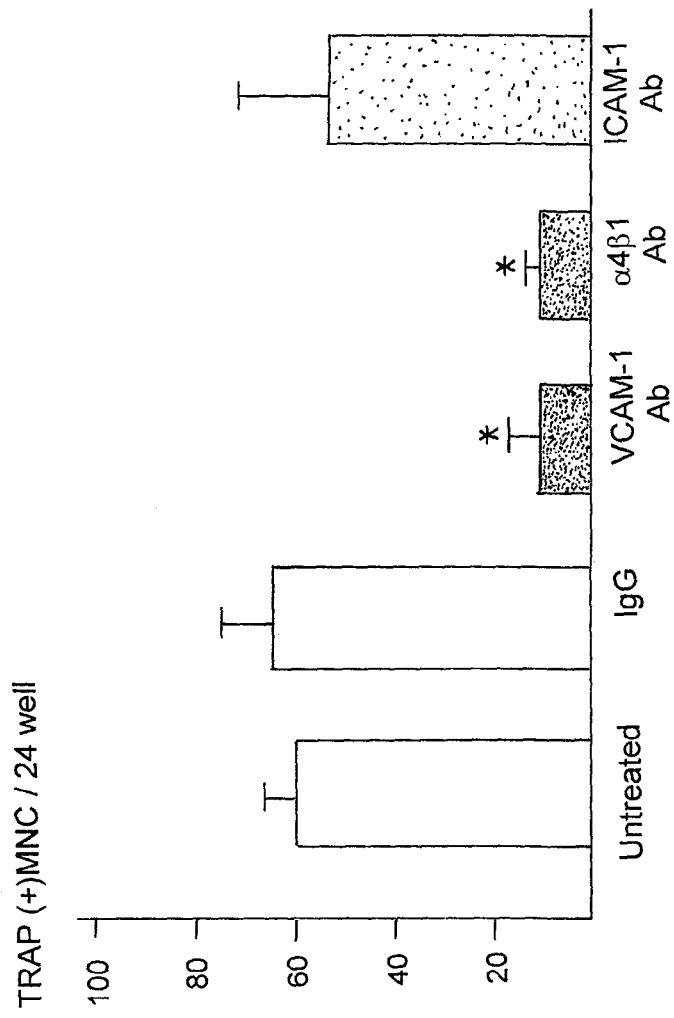
FIG. 4 shows anti-VLA-4 and anti-VCAM-1 inhibited TRAP-positive multinucleated osteoclast formation. Inhibitory effects of neutralizing antibody to VCAM-1 and VLA-4 on tartarate-resistant acid phosphatase-positive (TRAP$^+$) multinucleated osteoclast formation in the co-cultures of 5TGM1 myeloma cells and primary mouse bone marrow cells. A mixture of 5TGM1 cells ($1\times10^3$) and primary mouse marrow cells ($1\times10^6$) in suspension was inoculated in 48-well plates and cultures with or without 10 µg/mL of anti-VCAM-1 Ab, anti-VLA-4 Ab, anti-ICAM-1 Ab or control IgG. After 6 days of culture, cultures were fixed and the number of TRAP$^+$ multinucleated osteoclasts was determined. Data are expressed as mean±SE (n=4). * Significantly different from IgG control (p<0.01).
Figure 5A:
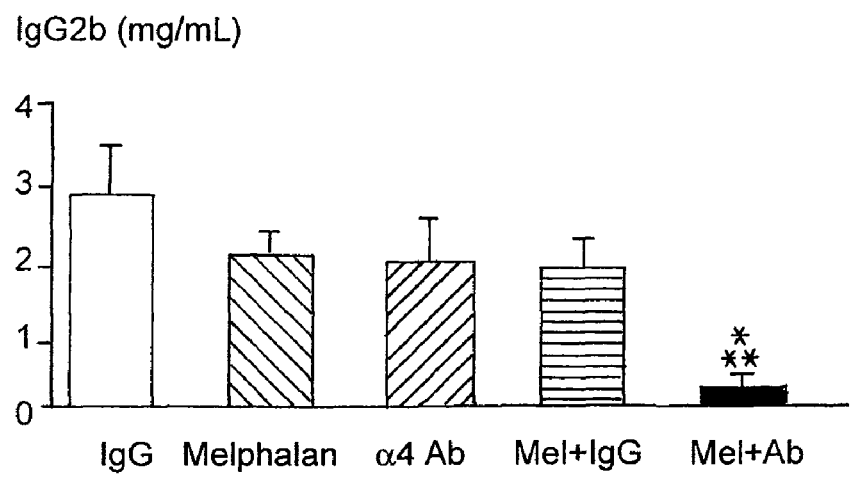
FIG. 5 shows anti-VLA-4 therapeutic treatment in combination with melphalan reduced circulating IgG2b levels and 5GTM1/luc tumor burden in the bone. One million 5TGM1/luc cells in 200 µl PBS suspension was inoculated into 6 to 8 week old bg/nd/xid female mice via tail vein. Each group had 8 to 10 mice, and experiments conducted twice (n=8-10× 2=16-20 per group). Data are mean±SEM of 2 separate experiments. The anti-alpha-4 antibody (PS/2, rat anti-mouse anti-alpha 4 integrin antibody) was given at 200 µg/mouse, intraperitoneally, daily, from day 14 to 16 and thereafter 80 µg/mouse, intraperitoneally, twice per week until the end of the experiments combined with or without melphalan (100 µg, intraperitoneally, once a week, SIGMA). Rat IgG served as control. A) Circulating levels of mIgG2b were expressed as mg/mL across groups and were determined by ELISA. B) Luciferase activity was measured to assess 5TGM1/luc tumor burden in the bone. *Significantly different from control IgG. ** Significantly different from anti-alpha-4 Ab or Melphalan alone.
Figure 5B:
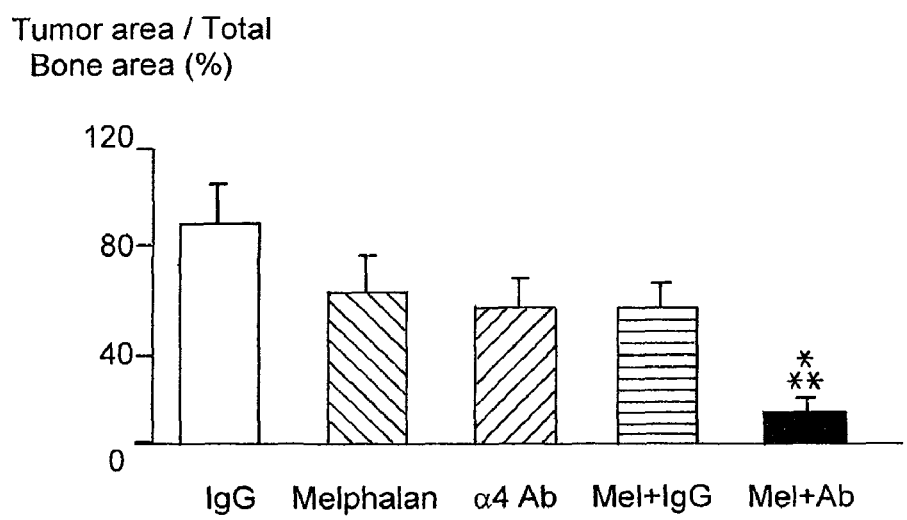
Figure 6A:
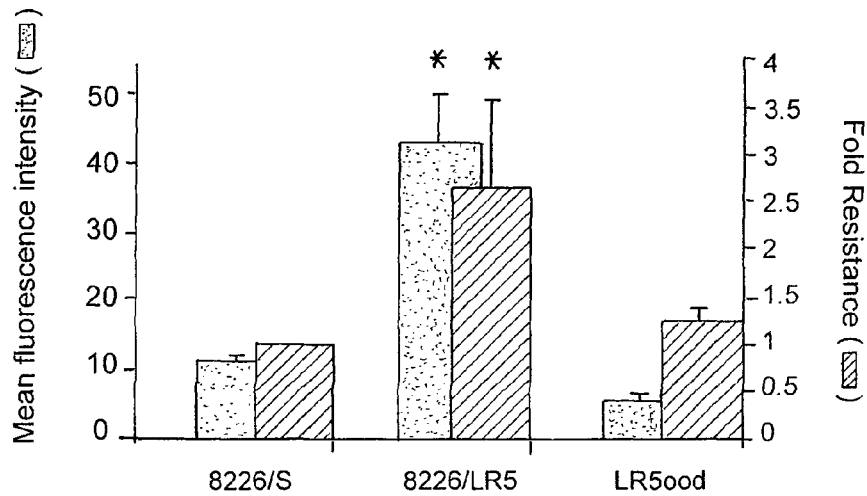
FIG. 6 shows that drug resistance is associated with an increase in expression of the α4 subunit. This experiment demonstrated a correlation between levels of α4 expression and drug resistance in the 8226 myeloma cell line. A4 expression was measured by flow cytometry and drug resistance was measured by MTT cytotoxicity analysis. Resistance values are reported as the $IC_{50}$ dose LPAM or doxorubicin, respectively, relative to 8226/S. Bars are the SD of three different experiments. (A) 8226/LR5 were maintained in $5\times10^{-5}$ mmol/L melphalan (LPAM: L-phenylalanine nitrogen mustard) and LR5ood were maintained out of drug for 20 weeks. α4 expression levels and melphalan resistance levels of 8226/LR5 were found to be higher than 8226/S (*p<0.05). α4 expression levels and melphalan resistance of LR5ood were found to be equal to those of 8226/S parent line. (B) 8226/DOX6 were maintained in 6×10-8 mol/L doxorubicin an dDOX6ood were maintained out of drug for 20 weeks. α4 expression levels and doxorubicin resistance levels of 8226/DOX6 were found to be higher than 8226/S (p<0.05). α4 expression and doxorubicin resistance of DOX6ood were found to be equal to those of 8226/S parent line.
Figure 6B:
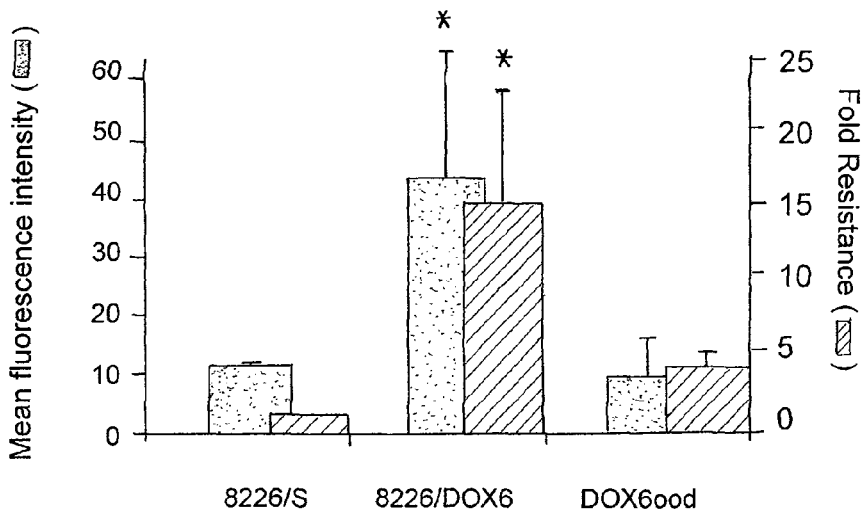

In accordance with this detailed description, the following abbreviations and definitions apply. It must be noted that as used herein, the singular forms "a", "and", and "the" include plural referents unless the context clearly dictates otherwise. Thus, for example, reference to "the dosage" includes reference to one or more dosages and equivalents thereof known to those skilled in the art.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

By the term "subject" or "patient" as used herein is meant to include a mammal. The mammal can be a canine, feline, primate, bovine, ovine, porcine, camelid, caprine, rodent, or equine. Preferably the mammal is human.

The term "efficacy" as used herein refers to the effectiveness of a particular treatment regime. Efficacy can be measured based on such characteristics (but not limited to these) as inhibition of liquid tumor growth, reduction of tumor mass, reduction of metastatic lesions as assessed, for example, by radiologic imaging, slowed tumor growth, and lack of detectable tumor associated antigens. Additional methods of assessing tumor progression are discussed herein and would be known to the treating and diagnosing medical professionals.

The term "composition" and phrase "compositions of the present invention" are intended to include any compound(s) and/or conjugate(s) as disclosed herein.

By the phrases "pharmaceutically acceptable carrier" and "pharmaceutically acceptable excipient" are intended to mean any compound(s) used in forming a part of the formulation that is intended to act merely as a carrier. The pharmaceutically acceptable carrier or excipient is generally safe, non-toxic, and neither biologically nor otherwise undesirable. A pharmaceutically acceptable carrier or excipient as used herein includes both one and more than one such carrier or excipient.

"Pharmaceutically acceptable salt" refers to salts which retain the biological effectiveness and properties of the compounds of this invention and which are not biologically or otherwise undesirable. In many cases, the compounds of this invention are capable of forming acid and/or base salts by virtue of the presence of amino and/or carboxyl groups or groups similar thereto.

Pharmaceutically-acceptable base addition salts can be prepared from inorganic and organic bases. Salts derived from inorganic bases, include by way of example only, sodium, potassium, lithium, ammonium, calcium, and magnesium salts. Salts derived from organic bases include, but are not limited to, salts of primary, secondary, and tertiary amines, such as alkyl amines, dialkyl amines, trialkyl amines, substituted alkyl amines, di(substituted alkyl) amines, tri(substituted alkyl)amines, alkenyl amines, dialkenyl amines, trialkenyl amines, substituted alkenyl amines, di(substituted alkenyl)amines, tri(substituted alkenyl)amines, cycloalkyl amines, di(cycloalkyl)amines, tri(cycloalkyl)amines, substituted cycloalkyl amines, disubstituted cycloalkyl amine, trisubstituted cycloalkyl amines, cycloalkenyl amines, di(cycloalkenyl)amines, tri(cycloalkenyl)amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Examples of suitable amines include, by way of example only, isopropylamine, trimethyl amine, diethyl amine, tri(isopropyl)amine, tri(n-propyl)amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like. It should also be understood that other carboxylic acid derivatives would be useful in the practice of this invention, for example, carboxylic acid amides, including carboxamides, lower alkyl carboxamides, dialkyl carboxamides, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

The term "pharmaceutically-acceptable cation" refers to the cation of a pharmaceutically-acceptable salt.

It is understood that in all substituted groups defined herein, polymers arrived at by defining substituents with further substituents to themselves (e.g., substituted aryl having a substituted aryl group as a substituent which is itself substituted with a substituted aryl group, etc.) are not intended for inclusion herein. In such cases, the maximum number of such substituents is three. That is to say that each of the above definitions is constrained by a limitation that, for example, substituted aryl groups are limited to -substituted aryl-(substituted aryl)-(substituted aryl).

Integrins are a large family of homologous transmembrane linker proteins that are the principal receptors on animal cells for binding most extracellular matrix proteins, such as collagen, fibronectin, and laminin. The integrins are heterodimers comprised of an α chain and a β chain. To date, twenty different integrin heterodimers, made from 9 different α subunits and 14 different β subunits, have been identified. The term "α 4 integrins" refers to the class of heterodimer, enzyme-linked cell-surface receptors that contain the α 4 subunit paired with any of the β subunits. VLA-4 is an example of an α 4 integrin, and is a heterodimer of the α 4 and β1 subunits, and is also referred to as α 4 β1 integrin.

"Prodrug" refers to any pharmaceutically acceptable derivative of a compound of this invention that is capable of directly or indirectly providing a compound of this invention or an active metabolite or residue thereof when administered to a subject. Particularly favored derivatives and prodrugs are those that increase the bioavailability of the compounds of this invention when such compounds are administered to a subject (e.g., by allowing an orally administered compound to be more readily absorbed into the blood) or which enhance delivery of the parent compound to a biological compartment (e.g., the brain or lymphatic system) relative to the parent species. Prodrugs include ester forms of the compounds of the invention. Examples of ester prodrugs include formate, acetate, propionate, butyrate, acrylate, and ethylsuccinate derivatives. An general overview of prodrugs is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

The terms "treating", and "treatment", and the like are used herein to generally mean obtaining a desired pharmacological and physiological effect. More specifically, the compositions described herein which are used to treat a subject with a liquid tumor and/or metastatic disease generally are provided in a therapeutically effective amount to achieve any one or more of the following: inhibited tumor growth, reduction in tumor mass, loss of metastatic lesions, inhibited development of new metastatic lesions after treatment has started, or reduction in tumor such that there is no detectable disease (as assessed by e.g., radiologic imaging, biological fluid analysis, cytogenetics, fluorescence in situ hybridization, immunocytochemistry, colony assays, multiparameter flow cytometry, or polymerase chain reaction). The term "treatment", as used herein, covers any treatment of a disease in a mammal, particularly a human.

By "therapeutically effective amount" is meant an amount of an agent, reagent, compound, composition, or combination of reagents disclosed herein that when administered to a mammal is sufficient to be effective against the tumor.

By the term "tumor" is meant to include both benign and malignant growths or cancer. Thus, the term "cancer", unless otherwise stated, can include both benign and malignant growths. By "liquid tumor" is meant a liquid and/or soft tissue tumor, such as a leukemia or a bone cancer.

By the terms "metastatic disease", "metastases", and "metastatic lesion" are meant a group of cells which have migrated to a site distant relative to the primary tumor.

The following acronyms are commonly used for the associated terms and would be known in the art.

| | |
|---|---|
| α4β1 | alpha-4beta-1 |
| α4β1 | alpha-4beta-7 |
| ABDIC | doxorubicin, bleomycin, dacarbazine, lomustine, and prednisone |
| ALL | acute lymphocytic leukemia |
| AML | acute myelogenous leukemia |
| CLL | chronic lymphocytic leukemia |
| CML | chronic myelogenous leukemia |
| MGUS | monoclomal gammopathy of underminded significance |
| MM | multiple myeloma |
| PBMC | peripheral blood monocytic cells |
| SMM | smoldering multiple myeloma |
| VCAM-1 | vascular cell adhesion molecule 1 (also known as CD106 and INCAM-110) |
| VLA-4 | very late antigen 4 (also known as alpha-4beta-1, α4β1 integrin, VLA-4a, and CD49d) |

Diseases

In one aspect of the invention, the methods and compositions disclosed herein can be used to inhibit or slow the progression of malignancies. These malignancies are preferably liquid tumors. Liquid tumors may include, but are not limited to, myelomas and leukemias. Another aspect of the invention is to use the methods and compositions to inhibit or prevent metastases or metastatic progression.

Thus, an aspect of the invention is to treat liquid tumors or metastatic disease with the compositions of the present invention. The compositions contemplated herein can target alpha-4 and/or alpha-9 integrins. These compositions may be used alone, in combination with each other, or in combination with other cancer treatments, such as chemotherapy, surgery, radiotherapy, hyperthermia, immunotherapy, hormone therapy, biologic therapy (e.g., immune effector mechanisms resulting in cell destruction, cytokines, immunotherapy, interferons, interleukin-2, cancer vaccine therapy, and adoptive therapy). The compositions may also be used in combination with other known therapies for adverse side effects associated with cancer treatments, including, but not limited to, nausea and pain.

Treatment

The term cancer embraces a collection of malignancies with each cancer of each organ consisting of numerous subsets. Typically, at the time of cancer diagnosis, "the cancer" consists in fact of multiple subpopulations of cells with diverse genetic, biochemical, immunologic, and biologic characteristics.

The types of cancers to be treated by the compositions and methods of the present invention are those that exhibit alpha-4 integrins and/or alpha-9 integrins or their ligands (for example, ligands of alpha-4 integrins include VCAM-1 and/or MadCAM-1). Preferred cancers include, but are not limited to, hematological malignancies, including acute lymphoblastic leukemia (ALL), acute myelogenous leukemia (AML), chronic myelogenous leukemia (CML), chronic lymphocytic leukemia (CLL), and multiple myeloma (MM). Leukemias may be lymphoblastic or myelogenous. Lymphoblastic (or lymphocytic) leukemia affects lymphocytes. Myelogenous leukemia affects myelocytes.

Lymphocytic neoplastic diseases may be characterized by a massive expansion of a single B-cell clone, detectable by measuring the excessively-produced antibodies, measured in a serum protein electrophoresis test or peripheral blood flow cytometry. Such an expansion is said to be "monoclonal," and monoclonal antibodies produced by such a group of B-cells can cause illnesses such as amyloidosis and lupus, or can be indicative of an underlying malignancy. The concept of clonality is closely associated with malignancy, for example in diagnosing lymphomatoid skin lesions. The expansion of a particular clone of immune B-cells is usually interpreted by clinicians as evidence of unrestricted cell growth, the hallmark of cancer. Lymphoid leukemia (or lymphocytic leukemia) is a type of leukemia affecting lymphoid tissue. These leukemias are commonly divided by the stage of maturation at which the clonal (neoplastic) lymphoid population stopped maturing (i.e., acute lymphoblastic leukemia or chronic lymphoblastic leukemia).

Acute lymphoblastic leukemia (ALL), also known as acute lymphocytic leukemia, is a form of leukemia of the white blood cells. Malignant, immature white blood cells continuously multiply and are overproduced in the bone marrow. As a result, normal cells are crowded out of the bone marrow, and metastasize to other organs. "Acute" refers to the undifferentiated, immature state of the circulating lymphocytes, and to the rapid progression of disease, which can be fatal in weeks to months if left untreated.

Chronic lymphoblastic leukemia (CLL; also known as chronic lymphoid leukemia), affects B cells. B cells normally originate in the bone marrow and develop in the lymph nodes. In CLL, the DNA of B cells are damaged, so the cells no longer fight infection. However, the B cells continue to grow and crowd out the healthy blood cells. Thus, CLL is characterized by an abnormal neoplastic proliferation of B cells.

Most people are diagnosed without symptoms as the result of a routine blood test that returns a high white blood cell count. However, as it advances, CLL causes swollen lymph nodes, spleen, and liver, and eventually anemia and infections. Early CLL is not treated, and late CLL is treated with chemotherapy and monoclonal antibodies. Survival varies from 5 years to more than 25 years.

Acute myelogenous leukemia (AML), also known as acute myeloid leukemia, is a cancer of the myeloid line of white blood cells, characterized by the rapid proliferation of abnormal cells which accumulate in the bone marrow and interfere with the production of normal blood cells. The symptoms of AML are caused by replacement of normal bone marrow with leukemic cells, resulting in a drop in red blood cells, platelets, and normal white blood cells. These symptoms include fatigue, shortness of breath, easy bruising and bleeding, and increased risk of infection. As an acute leukemia, AML progresses rapidly and is typically fatal within weeks or months if left untreated.

Acute myelogenous leukemia is a potentially curable disease; but only a minority of patients are cured with current therapy. AML is treated initially with chemotherapy aimed at inducing a remission. Some patients may further receive a hematopoietic stem cell transplant.

Chronic myelogenous leukemia (CML) is a form of leukemia characterized by the increased and unregulated growth of predominantly myeloid cells in the bone marrow and the accumulation of these cells in the blood. CML is a clonal bone marrow stem cell disorder causing the proliferation of mature granulocytes (neutrophils, eosinophils, and basophils) and their precursors. Historically, it has been treated with chemotherapy, interferon and bone marrow transplantation.

Multiple myeloma (MM) is a malignant proliferation of plasma cells that typically originates in bone marrow and involves the skeleton. MM presents clinical features attributable to the particular sites of involvement and abnormalities in formation of plasma proteins. The condition is usually characterized by numerous diffuse foci or nodular accumulations of abnormal or malignant plasma cells in the marrow of various bones (especially the skull), causing palpable swellings of the bones, and occasionally in extraskeletal sites. Upon radiological exam, the bone lesions may have a characteristic "punched out" appearance.

The cells involved in the myeloma typically produce abnormal proteins and/or abnormal protein levels in the serum and urine. MM typically develops from monoclonal gammopathy of undetermined significance (MGUS) to smoldering multiple myeloma (SMM) to multiple myeloma (MM). Symptoms of these conditions may include hypercalcemia, renal insufficiency, fatigue, anemia, bone pain, spontaneous fractures, increased frequency or duration of infection, or abnormal urine color or odor. An "M-spike" refers to a monoclonal peak that is typically visualized as a narrow band on electrophoretic gel, or an abnormal arc in immunoelectrophoresis. It represents a proliferation of homogenous immunoglobulin produced by clone cells originating from a single common cell, e.g., a monoclonal immunoglobulin characterized by a heavy chain of a single class and subclass, and light chain of a single type (also referred to as M-protein, a monoclonal protein, and more broadly as a paraprotein).

Metastatic Disease

Once a liquid tumor is diagnosed in a patient, one large concern is whether the tumor has progressed and spread to the regional lymph nodes and to distant organs. Most cancer deaths result from metastases that are resistant to conventional cancer therapies. Metastases can be located in different areas of the body than the original tumor, making complete eradication by surgery, radiation, drugs, and/or biotherapy nearly impossible. Thus, contemplated for treatment with the methods, combination therapies, and compounds disclosed herein is the treatment of metastatic cancer.

Cancers typically begin their growth in only one location. As the cancer progresses, the cancer may migrate to a distal location in the patient. Several integrin subunits (i.e., alpha-2, alpha-4 and beta-3) have been found to have increased expression in metastasis as compared to normal prostate tissue and normal melanocytes. Hartstein et al., 1997, *Ophthal. Plast Reconstr. Surg.*, 13(4): 227-38.

There are essential steps in the formation of metastasis in all tumors. The steps include the following:

(1) After neoplastic transformation, progressive proliferation of neoplastic cells supported by the organ/tissue environment in which the neoplasm is located.

(2) Neovascularization or angiogenesis of the tumor for further growth beyond 1 to 2 mm in diameter.

(3) Down-regulation of expression of cohesive molecules wherein the cells have increased motility or ability to detach from the primary lesion.

(4) Detachment and embolization of single tumor cells or cell aggregates, with the vast majority of these cells being rapidly destroyed.

(5) Once tumor cells survive the detachment and embolization step, they must go on to proliferate within the lumen of the blood vessel. The cells will then go on to extravasate into the organ parenchyma by mechanism similar to those operative during invasion.

(6) Tumor cells with the appropriate cell surface receptors can respond to paracrine growth factors and hence proliferate in the organ parenchyma.

(7) Tumor cell evasion of host defenses (both specific and nonspecific immune responses).

(8) For a metastasis to proliferate beyond 1 to 2 mm in diameter, the metastases must develop a vascular network.

Thus, if a primary tumor is given enough time to progress through these steps, it will metastasize at a site or sites distant to the primary tumor. The methods and therapies disclosed inhibit or prevent one or more of these steps in the metastatic process. For additional details on the mechanism and pathology of tumor metastasis, see Isaiah J. Fidler, "Molecular Biology of Cancer: Invasion and Metastasis," in CANCER: PRINCIPLES & PRACTICE OF ONCOLOGY 135-152 (Vincent T. DeVita et al., editors, 5th ed., 1997).

Accordingly, one aspect of the invention provides for methods using and compositions comprising compounds and conjugates having anti-alpha-4 integrin and/or anti-alpha-9 integrin activity or that target ligands of alpha-4 integrin and/or alpha-9 integrin. These compositions can be used alone or in combination with other agents or cancer treatments that prevent metastases or inhibit progression of metastatic lesions. Thus, the compositions and methods can be used to treat any metastases of any primary tumor that exhibits an alpha-4 integrin and/or an alpha-9 integrin or ligands thereof.

Compounds and Conjugates that Selectively Bind to Alpha-4 Integrin and/or Alpha-9 Integrin Various compositions with the ability to bind to and inhibit alpha-4 integrin and/or alpha-9 integrin can be used in the practice of the invention. Many such compositions have been identified and characterized, and specific compositions are described below. Preferably, these compositions include the compounds, homologs and derivatives and conjugates of the formulae illustrated below. It is also contemplated that combinations of these compositions may also be useful.

In one aspect, the compounds that can be utilized are compounds of formula I:

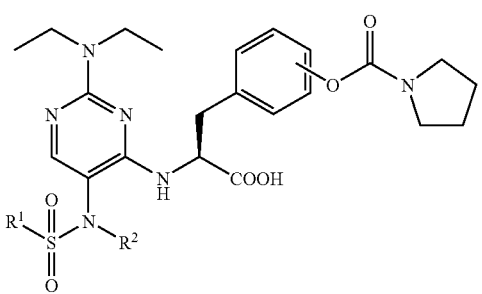

I wherein:
R[1] is selected from the group consisting of $C_1$ to $C_4$ alkyl and $C_1$ to $C_4$ haloalkyl; and
R[2] is selected from the group consisting of $C_1$ to $C_4$ alkyl, $C_2$ to $C_4$ alkenyl, $C_2$ to $C_4$ alkynyl, and $C_3$-$C_6$ cycloalkyl;
or pharmaceutically acceptable salts, or esters thereof.

In some embodiments, R[1] is $C_1$ to $C_2$ alkyl. In other embodiments, R[1] is methyl or trifluoromethyl. In still other embodiments, R[1] is methyl.

In some embodiments, R[2] is $C_1$ to $C_4$ alkyl. In other embodiments, R[2] is $C_1$ to $C_3$ alkyl. In still other embodiments, R[2] is methyl, ethyl, isopropyl or n-propyl. In another embodiment R[2] is methyl or ethyl, and in yet another embodiment, R[2] is isopropyl.

In some embodiments, R[2] is $C_3$ to $C_6$ cycloalkyl. In other embodiments, R[2] is cyclopentyl.

In some embodiments, R[2] is $C_2$ to $C_4$ alkenyl. In other embodiments, R[2] is allyl.

In some embodiments, R[2] is $C_2$ to $C_4$ alkynyl. In other embodiments, R[2] is propargyl.

Examples of compounds of the above formula I include those having the R[1] and R[2] groups recited in Table 1 (including pharmaceutically acceptable salts, or esters thereof).

TABLE 1

| R[1] | R[2] |
|---|---|
| trifluoromethyl | ethyl |
| methyl | isopropyl |
| methyl | cyclopentyl |
| methyl | methyl |
| methyl | propargyl |
| methyl | ethyl |
| methyl | allyl |
| butyl | ethyl |
| 3-chloropropyl | ethyl |
| 3-chloropropyl | methyl |
| 3,3,3-trifluoropropyl | ethyl |
| propyl | ethyl |
| isopropyl | ethyl |

In another aspect, the compounds that can be utilized are compounds of formula II:

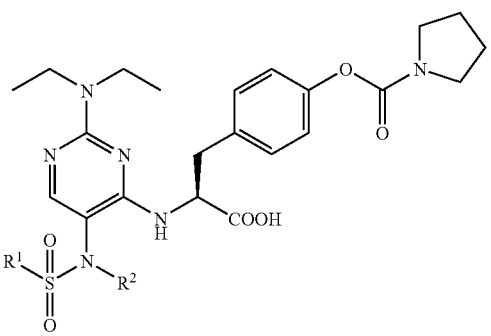

II wherein:
R[1] is selected from the group consisting of $C_1$ to $C_4$ alkyl and $C_1$ to $C_4$ haloalkyl; and
R[2] is selected from the group consisting of $C_1$ to $C_4$ alkyl, $C_2$ to $C_4$ alkenyl, $C_2$ to $C_4$ alkynyl, and $C_3$-$C_6$ cycloalkyl;
or pharmaceutically acceptable salts, or esters, thereof.

In some embodiments, R[1] is $C_1$ to $C_2$ alkyl. In other embodiments, R[1] is methyl or trifluoromethyl. In still other embodiments, R[1] is methyl.

In some embodiments, R[2] is $C_1$ to $C_4$ alkyl. In other embodiments, R[2] is $C_1$ to $C_3$ alkyl. In still other embodiments, R[2] is methyl, ethyl, isopropyl or n-propyl. In another embodiment R[2] is methyl or ethyl, and in yet another embodiment, R[2] is isopropyl.

In some embodiments, R[2] is $C_3$ to $C_6$ cycloalkyl. In other embodiments, R[2] is cyclopentyl.

In some embodiments, R[2] is $C_2$ to $C_4$ alkenyl. In other embodiments, R[2] is allyl.

In some embodiments, R[2] is $C_2$ to $C_4$ alkynyl. In other embodiments, R[2] is propargyl.

Examples of compounds of the above formula II include those having the R[1] and R[2] groups recited in Table 2 (including pharmaceutically acceptable salts, or esters thereof).

TABLE 2

| R[1] | R[2] |
|---|---|
| trifluoromethyl | ethyl |
| methyl | isopropyl |
| methyl | cyclopentyl |
| methyl | methyl |
| methyl | propargyl |
| methyl | ethyl |
| methyl | allyl |
| butyl | ethyl |
| 3-chloropropyl | ethyl |
| 3-chloropropyl | methyl |
| 3,3,3-trifluoropropyl | ethyl |
| propyl | ethyl |

TABLE 2-continued

| R¹ | R² |
|---|---|
| isopropyl | ethyl |

Ortho and meta substitution of the pyrrolidinylcarbonyloxy group on the phenyl ring are also within the scope of the above formula II.

In yet another aspect, the compounds that can be utilized include specifically the following:

(S)-2-(2-(diethylamino)-5-(N-ethyl-1,1,1-trifluoromethylsulfonamido)pyrimidin-4-ylamino)-3-(4-(pyrrolidine-1-carbonyloxy)phenyl)propanoic acid;

(S)-2-(2-(diethylamino)-5-(N-isopropylmethylsulfonamido)pyrimidin-4-ylamino)-3-(4-(pyrrolidine-1-carbonyloxy)phenyl)propanoic acid;

(S)-2-(5-(N-cyclopentylmethylsulfonamido)-2-(diethylamino)pyrimidin-4-ylamino)-3-(4-(pyrrolidine-1-carbonyloxy)phenyl)propanoic acid;

(S)-2-(2-(diethylamino)-5-(N-methylmethylsulfonamido)pyrimidin-4-ylamino)-3-(4-(pyrrolidine-1-carbonyloxy)phenyl)propanoic acid;

(S)-2-(2-(diethylamino)-5-(N-(prop-2-ynyl)methylsulfonamido)pyrimidin-4-ylamino)-3-(4-(pyrrolidine-1-carbonyloxy)phenyl)propanoic acid;

(S)-2-(2-(diethylamino)-5-(N-ethylmethylsulfonamido)pyrimidin-4-ylamino)-3-(4-(pyrrolidine-1-carbonyloxy)phenyl)propanoic acid;

(S)-2-(5-(N-allylmethylsulfonamido)-2-(diethylamino)pyrimidin-4-ylamino)-3-(4-(pyrrolidine-1-carbonyloxy)phenyl)propanoic acid; (S)-2-(2-(diethylamino)-5-(N-ethylbutylsulfonamido)pyrimidin-4-ylamino)-3-(4-(pyrrolidine-1-carbonyloxy)phenyl)-propanoic acid; (S)-2-(5-(3-chloro-N-ethylpropylsulfonamido)-2-(diethylamino)-pyrimidin-4-ylamino)-3-(4-(pyrrolidine-1-carbonyloxy)phenyl)propanoic acid;

(S)-2-(5-(3-chloro-N-methylpropyl-sulfonamido)-2-(diethylamino)pyrimidin-4-ylamino)-3-(4-(pyrrolidine-1-carbonyloxy)phenyl)propanoic acid;

(S)-2-(2-(diethylamino)-5-(N-ethyl-3,3,3-trifluoropropylsulfonamido)-pyrimidin-4-ylamino)-3-(4-(pyrrolidine-1-carbonyloxy)phenyl)propanoic acid;

(S)-2-(2-(diethylamino)-5-(N-ethylpropylsulfonamido)pyrimidin-4-ylamino)-3-(4-(pyrrolidine-1-carbonyloxy)phenyl)-propanoic acid; and (S)-2-(2-(diethylamino)-5-(N-ethyl-2-methylpropylsulfonamido)pyrimidin-4-ylamino)-3-(4-(pyrrolidine-1-carbonyloxy)-phenyl)propanoic acid;

as well as pharmaceutically acceptable salts or esters, thereof.

The following terms used in the specification and claims with reference to the above formulae I and II have the meanings given below:

"Alkyl" refers to monovalent straight and branched hydrocarbyl groups having from 1 to 4 carbon atoms and preferably 1 to 3 carbon atoms. This term is exemplified by groups such as methyl, ethyl, n-propyl, iso-propyl, n-butyl, iso-butyl, sec-butyl, and t-butyl.

"Alkenyl" refers to straight or branched monovalent hydrocarbyl groups from 2 to 4 carbon atoms and preferably 2 to 3 carbon atoms and having at least 1 and preferably 1 site of vinyl (>C=C<) unsaturation. Examples of such alkenyl groups include vinyl (—CH=CH$_2$), allyl (—CH$_2$CH=CH$_2$), n-propen-1-yl (—CH=CHCH$_3$), n-buten-2-yl (—CH$_2$CH=CHCH$_3$), and the like. Included within this term are the cis and trans isomers or mixtures of these isomers.

"Alkynyl" refers to straight or branched monovalent hydrocarbyl groups having from 2 to 4 carbon atoms and preferably 2 to 3 carbon atoms and having at least 1 and preferably 1 site of acetylenic —C≡C— unsaturation. Examples of such alkynyl groups include acetylenyl (—C≡CH), propargyl (—CH$_2$C≡CH), n-propyn-1-yl (—CH=CHCH$_3$), and the like.

"Halo" or "halogen" refers to fluoro, chloro, bromo and iodo and preferably is either fluoro or chloro.

"Haloalkyl" refers to alkyl groups having from 1 to 5 halo groups. Preferably, such groups have from 1 to 3 halo groups and 1 to 2 carbon atoms. Exemplary haloalkyl groups include halomethyl (e.g., fluoromethyl), dihalomethyl (e.g., difluoromethyl), trihalomethyl (e.g., trifluoromethyl), haloethyl (e.g. 2-chloroeth-1-yl), trihaloethyl (e.g., 2,2,2-trifluoroeth-1-yl), halopropyl (e.g., 3-chloroprop-1-yl and trihalopropyl (e.g., 3,3,3-trifluoroprop-1-yl).

Compound Preparation

The compounds of the above formulae I and II can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, *Protecting Groups in Organic Synthesis*, Second Edition, Wiley, New York, 1991, and references cited therein.

Furthermore, the compounds of the above formulae I and II will typically contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of the above formulae I and II, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

Most compounds of the above formulae I and II were named using ChemDraw v. 10.0, (available from Cambridgesoft at 100 Cambridge Park Drive, Cambridge, Mass. 02140).

In one embodiment, the compounds of the above formulae I and II can be prepared as described below in Scheme 1 where for illustrative purposes only, $R^1$ is methyl and $R^2$ is isopropyl.

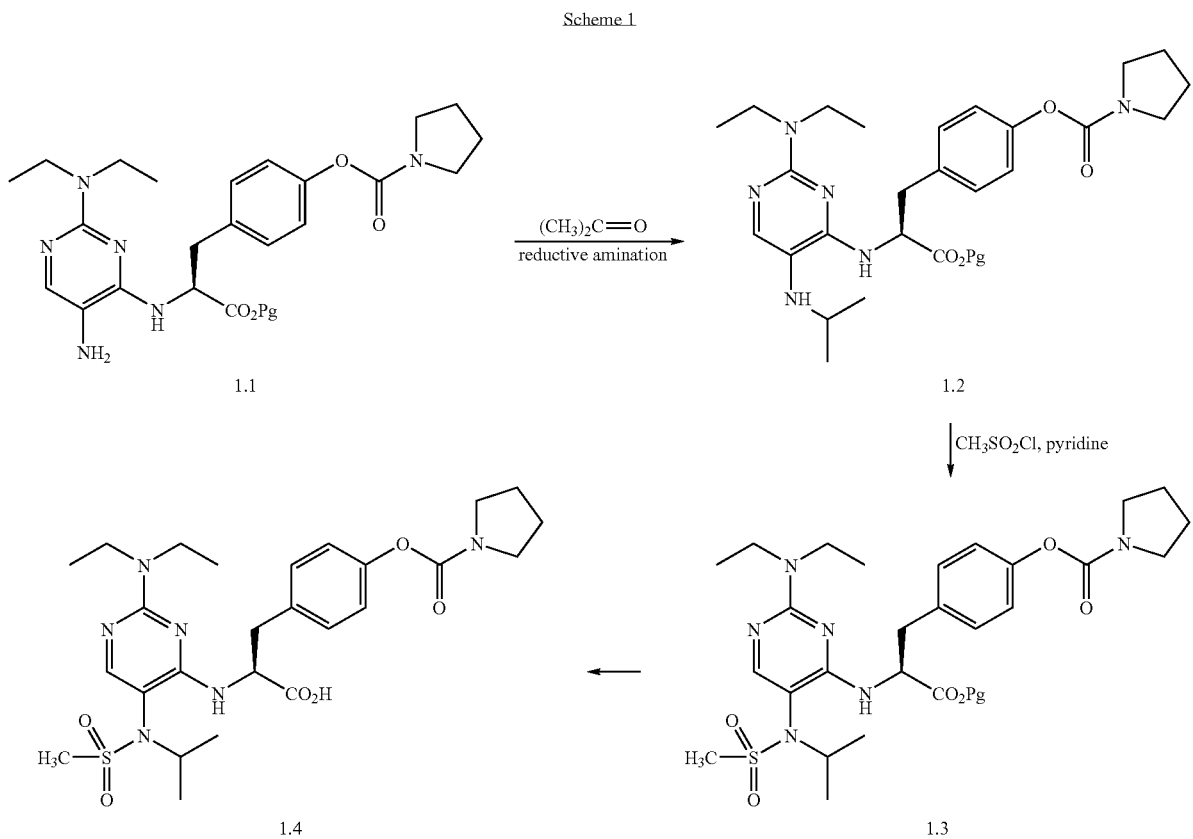

where Pg is a carboxyl protecting group such as benzyl, t-butyl, and the like.

Scheme 1 is particularly useful in the preparation of compounds where $R^2$ is alkyl or cycloalkyl.

In Scheme 1, the starting 5-aminopyrimidine intermediates, compound 1.1, are described in detail in U.S. Pat. No. 7,026,328 B1 and, for the sake of illustration only, are shown in this scheme as the preferred 4-substituted phenylalanine derivatives. It is understood, of course, that 2- and 3-substituted phenylalanine derivatives would follow a similar reaction pathway.

Specifically, in Scheme 1,5-amino-2-diethylamino-4-substituted pyrimidine, compound 1.1 (prepared from by corresponding 5-nitro-pyrimidine by reduction with 5% Pd/C or 5% $PtO_2$ by weight) is reacted under conventional reductive amination conditions with a slight excess of a $C_1$-$C_4$ aldehyde or ketone which is Scheme 1 is illustrated by acetone. In Scheme 1, the 5-amino group of compound 1.1 forms an intermediate imine (not shown) which is in situ reduced to the corresponding amine, compound 1.2, by conventional reducing agents such as sodium cyanoborohydride, sodium borohydride, hydrogen over a suitable catalyst such as $PtO_2$, and the like. The reaction is conducted in a suitable inert diluent such as tetrahydrofuran, methylene chloride, and the like. The reaction is maintained at from about 0° C. to about 30° C. until the reaction is substantially complete which typically occurs within about 0.5 to 16 hours. Upon completion of the reaction, the compound 1.2 is recovered by conventional methods including neutralization, evaporation, extraction, precipitation, chromatography, filtration, and the like or, alternatively, is employed in the next step without purification and/or isolation.

Conversion of the amine group in compound 1.2 to the corresponding alkylsulfonylamido group, compound 1.3, proceeds via conventional methods. For example, in one method, compound 1.2 is contacted with a slight excess of an alkanesulfonyl halide, such as methanesulfonyl chloride, in the presence of a suitable base such as triethylamine, diisopropylethylamine and the like in order to scavenge the acid generated. The reaction is preferably conducted in a suitable inert solvent such as tetrahydrofuran, dioxane, chloroform and the like. The reaction is preferably conducted at from about −5° to −30° C. and is continued until the reaction is substantially complete which typically occurs in 0.5 to 16 hours. Upon completion of the reaction, compound 1.3 can be recovered by conventional methods including neutralization, evaporation, extraction, precipitation, chromatography, filtration, and the like or, alternatively, is employed in the next step without purification and/or isolation.

Alkylsulfonyl halides are either known compounds or compounds that can be prepared by convention synthetic procedures. Such compounds are typically prepared from the corresponding sulfonic acid, i.e., from the compounds of the formula R¹—SO₃H where R¹ is as defined above, using phosphorus trichloride and phosphorus pentachloride. The reaction is generally conducted by contacting the sulfonic acid with about 2 to 5 molar equivalents of phosphorus trichloride or phosphorus pentachloride, either neat or in an inert solvent, such as dichloromethane, at a temperature in the range of 0° C. to about 80° C. for about 1 to about 48 hours to afford the sulfonyl chloride. Alternatively, the sulfonyl chloride can be prepared from the corresponding thiol compound, i.e., from compounds of the formula R¹—SH where R¹ is as defined above, by treating the thiol with chlorine (Cl₂) and water under conventional reaction conditions.

Examples of sulfonyl chlorides for use in the above formulae I and II include, but are not limited to, methanesulfonyl chloride, ethanesulfonyl chloride, 2-propanesulfonyl chloride, 1-butanesulfonyl chloride, trifluoromethanesulfonyl chloride, 2,2,2-trifluoroethanesulfonyl chloride, and the like.

The carboxyl protecting group of compound 1.3 is then removed by conventional conditions to provide for compound 1.4, a compound of formula I. In one embodiment, a t-butyl protecting group can be removed by contact with formic acid. In another embodiment, a benzyl protecting group can be removed by contact with hydrogen in the presence of a palladium/carbon catalyst typically in a protic solvent such as methanol under elevated hydrogen pressures. Upon completion of the reaction, compound 1.4 can be recovered by conventional methods including neutralization, evaporation, extraction, precipitation, chromatography, filtration, and the like.

In another embodiment, the compounds of the above formulae I and II can be prepared as described below in Scheme 2:

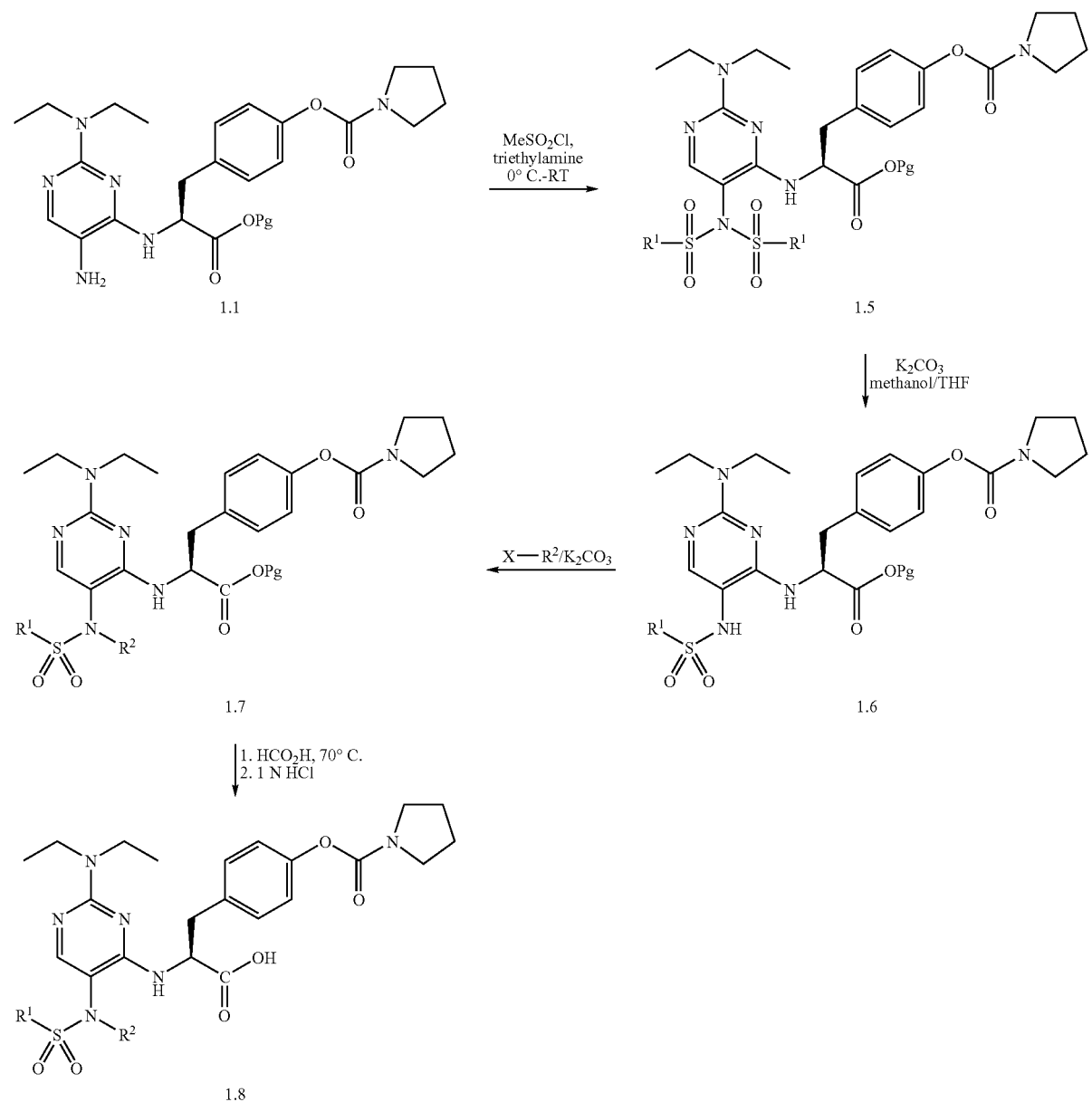

where $R^1$ and $R^2$ is as defined herein; Pg is a carboxyl protecting group and X is halo.

In Scheme 2, the starting 5-aminopyrimidine intermediates, compound 1.1, are described in detail in U.S. Pat. No. 7,026,328 B1 and, for the sake of illustration only, are shown in this scheme as the preferred 4-substituted phenylalanine derivatives. It is understood, of course, that 2- and 3-substituted phenylalanine derivatives would follow a similar reaction pathway.

Specifically, in Scheme 2,5-amino-2-diethylamino-4-substituted pyrimidine, compound 1.1 (prepared from by corresponding 5-nitro-pyrimidine by reduction with 5% Pd/C or 5% $PtO_2$ by weight) is reacted with a slight excess of an $R^1$-sulfonyl halide, such as methanesulfonyl chloride, in the presence of a suitable base such as triethylamine, diisopropylethylamine and the like in order to scavenge the acid generated. The reaction is preferably conducted in a suitable inert solvent such as tetrahydrofuran, dioxane, dichloromethane, chloroform and the like. The reaction is preferably conducted at from about −5° to 30° C. and is continued until the reaction is substantially complete which typically occurs in 0.5 to 16 hours. Upon completion of the reaction, compound 1.5 can be recovered by conventional methods including neutralization, evaporation, extraction, precipitation, chromatography, filtration, and the like or, alternatively, is employed in the next step without purification and/or isolation.

Selective removal of a single $R^1SO_2$— group from compound 1.5 proceeds under conventional conditions. For example, reaction of compound 1.5 with base in a protic solvent such as methanol, ethanol, or water, optionally in the presence of THF and the like, e.g. a 1:1 mixture of methanol/tetrahydrofuran or 1:1 mixture of water/tetrahydrofuran provides for compound 1.6. The reaction mixture comprises an excess of a suitable base such as potassium carbonate, sodium carbonate and the like and the reaction is preferably maintained at elevated temperatures such 20° to 60° C. The reaction is continued until substantially complete which typically occurs in 24-144 hours. Upon completion of the reaction, compound 1.6 can be recovered by conventional methods including neutralization, evaporation, extraction, precipitation, chromatography, filtration, and the like or, alternatively, is employed in the next step without purification and/or isolation.

Reaction of compound 1.6 with an excess of an alkyl halide, a dialkyl sulfate, an alkenyl halide, an alkynyl halide, or a cycloalkyl halide (i.e., X—$R^2$— the "halide compound") proceeds under conventional conditions to provide for compound 1.7. The reaction is typically conducted by contacting compound 1.6 with from about 1.1 to 20 equivalent so of the halide compound in an inert diluent such as acetone, chloroform, methylene chloride and the like in the presence of a base such as potassium carbonate, triethylamine and the like to scavenge the acid generated during reaction. The reaction is preferably conducted at from about 20° to 60° C. and is continued until the reaction is substantially complete which typically occurs in 0.1 to 16 hours. Upon completion of the reaction, compound 1.6 can be recovered by conventional methods including neutralization, evaporation, extraction, precipitation, chromatography, filtration, and the like or, alternatively, is employed in the next step without purification and/or isolation.

The carboxyl protecting group of compound 1.7 is then removed by conventional conditions to provide for compound 1.8, a compound of formula I. In one embodiment, a t-butyl protecting group can be removed by contact with formic acid. In another embodiment, a benzyl protecting group can be removed by contact with hydrogen in the presence of a palladium/carbon catalyst typically in a protic solvent such as methanol under elevated hydrogen pressures. Upon completion of the reaction, compound 1.8 can be recovered by conventional methods including neutralization, evaporation, extraction, precipitation, chromatography, filtration, and the like.

In still another embodiment, the compounds of the above formulae I and II can be prepared as described below in Scheme 3:

Scheme 3

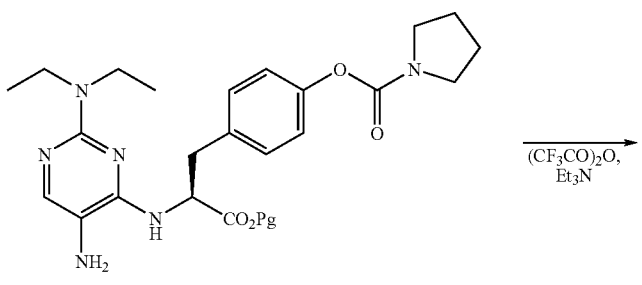

1.1

$(CF_3CO)_2O,$
$Et_3N$

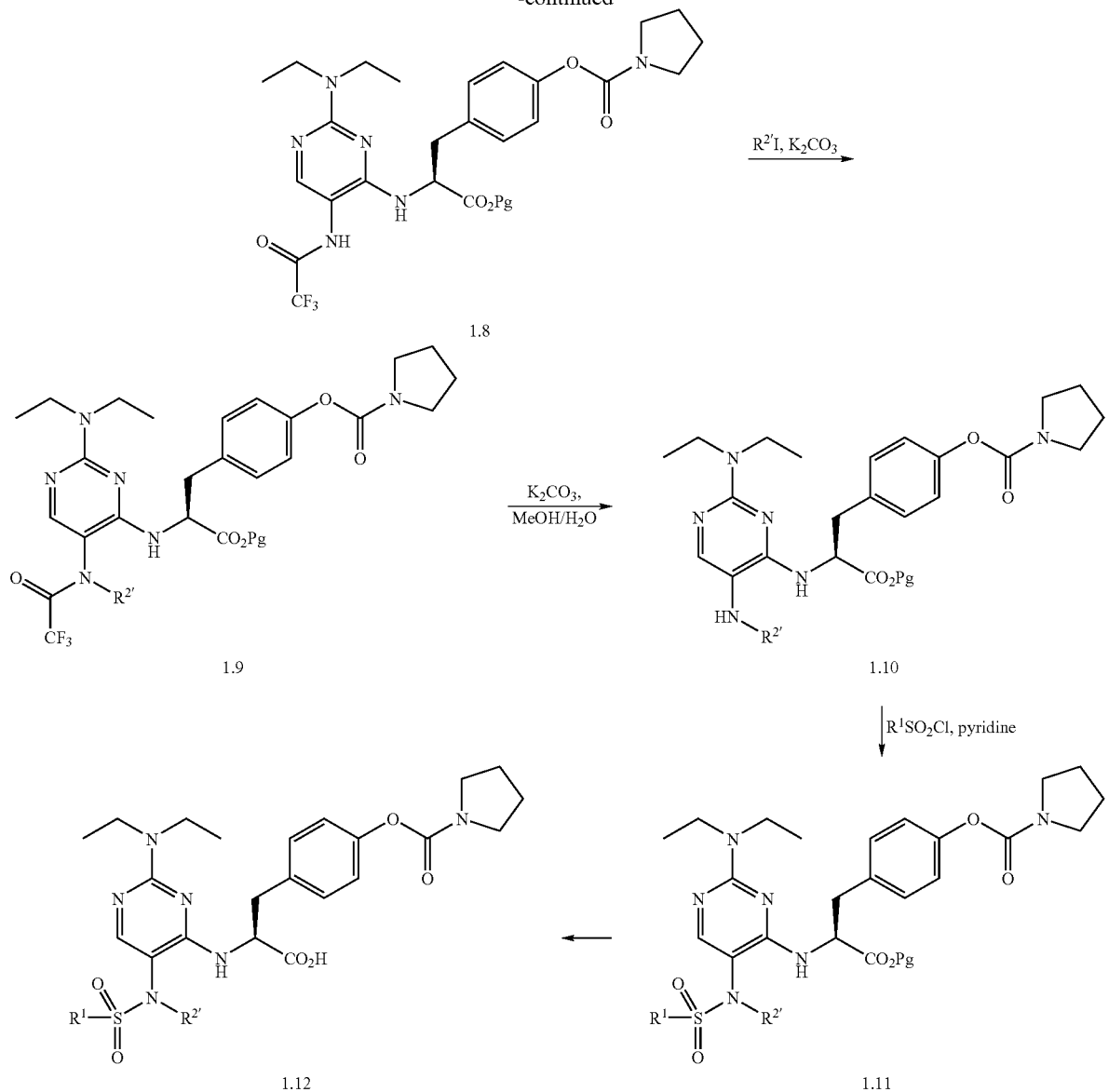

where $R^1$ is as defined above, Pg is a carboxyl protecting group such as benzyl, t-butyl, and the like and $R^1$ is an alkyl, alkenyl, alkynyl, or phenylalkylene group having a $CH_2$ moiety attached to the iodo group.

In Scheme 3, the starting 5-aminopyrimidine intermediates, compound 1.1, are described in detail in U.S. Pat. No. 7,026,328 B1 and, for the sake of illustration only, are shown in this scheme as the preferred 4-substituted phenylalanine derivatives. It is understood, of course, that 2- and 3-substituted phenylalanine derivatives would follow a similar reaction pathway.

Specifically, in Scheme 3,5-amino-2-diethylamino-4-substituted pyrimidine, compound 1.1 (prepared from by corresponding 5-nitro-pyrimidine by reduction with 5% Pd/C or 5% $PtO_2$ by weight) is converted to the corresponding trifluoroacetamide, compound 1.8, by conventional methods. For example, a slight excess of trifluoroacetic anhydride is combined with compound 1.1 in a suitable inert diluent such as tetrahydrofuran, methylene chloride, pyridine, and the like. The reaction is maintained at from about 0° C. to about 30° C. until the reaction is substantially complete which typically occurs within about 0.5 to 24 hours. Upon completion of the reaction, the compound 1.8 is recovered by conventional methods including neutralization, evaporation, extraction, precipitation, chromatography, filtration, and the like or, alternatively, is employed in the next step without purification and/or isolation.

Conversion of compound 1.8 to the corresponding N($R^{2'}$), N-trifluoroacetamido-pyrimidine, compound 1.9, again proceeds via conventional techniques. For example, an excess of the halide, $R^{2'}$—I, is combined with compound 1.8 in a suitable inert diluent such as DMF in the presence of an excess of a suitable base such as potassium carbonate. In one embodiment, approximately two equivalents of $R^{2'}$—I and potassium carbonate are employed. The reaction is maintained under ambient conditions in a sealed container and is continued until the reaction is substantially complete which typically occurs in 20-72 hours. Upon completion of the reaction, the compound 1.9 is recovered by conventional methods including neutralization, evaporation, extraction, precipitation, chromatography, filtration, and the like or, alternatively, is employed in the next step without purification and/or isolation.

The trifluoroacetyl group is then removed to provide for the corresponding amine, compound 1.10. In this embodiment, the trifluoroacetyl group acts as an amine protecting group. As above, this reaction conventionally proceeds, for example, by contacting compound 1.9 with a large excess of a suitable base such as potassium carbonate in a mixture of water and a protic solvent such as methanol. The reaction is conducted at elevated temperatures such as 40° to 60° C. and is continued until the reaction is substantially complete. Upon completion of the reaction, the compound 1.10 is recovered by conventional methods including neutralization, evaporation, extraction, precipitation, chromatography, filtration, and the like or, alternatively, is employed in the next step without purification and/or isolation.

Next, conversion of the amine group in compound 1.10 to the corresponding alkylsulfonylamido group, compound 1.11, proceeds via conventional methods. For example, in one method, compound 1.10 is contacted with a slight excess of an alkylsulfonyl halide in the presence of a suitable base such as triethylamine, diisopropylethylamine and the like in order to scavenge the acid generated. The reaction is preferably conducted in a suitable inert solvent such as tetrahydrofuran, dioxane, chloroform and the like. The reaction is preferably conducted at from about 0° to 30° C. and is continued until the reaction is substantially complete which typically occurs in 2-48 hours. Upon completion of the reaction, compound 1.11 can be recovered by conventional methods including neutralization, evaporation, extraction, precipitation, chromatography, filtration, and the like or, alternatively, is employed in the next step without purification and/or isolation.

The carboxyl protecting group of compound 1.11 can be removed by conventional conditions to provide for compound 1.12, a compound of formula I. In one embodiment, a t-butyl protecting group can be removed by contact with formic acid. In another embodiment, a benzyl protecting group can be removed by contact with hydrogen in the presence of a palladium/carbon catalyst typically in a protic solvent such as methanol under elevated hydrogen pressures. Upon completion of the reaction, compound 1.12 can be recovered by conventional methods including neutralization, evaporation, extraction, precipitation, chromatography, filtration, and the like.

The present invention also include esters of the compounds of the above formulae I and II. The preparation of esters is illustrated in the various schemes described above, such as in scheme 1, (compound 1.3), in scheme 2 (compound 1.7), and in scheme 3 (compound 1.11). Furthermore, Example 1 describes the preparation of (S)-4-(3-tert-butoxy-2-(2-(diethylamino)-5-(N-isopropylmethylsulfonamido)-pyrimidin-4-ylamino)-3-oxopropyl)phenyl pyrrolidine-1-carboxylate, and Example 4 describes the preparation of (S)-4-(3-tert-butoxy-2-(2-(diethylamino)-5-(N-(prop-2-ynyl)methyl-sulfonamido)pyrimidin-4-ylamino)-3-oxopropyl)phenyl pyrrolidine-1-carboxylate. Esters of the acids of the above formulae I and II can also be prepared from the acids by ways well known in the art. For example, amino acid methyl esters can be prepared using the method of Brenner and Huber, Helv. Chim. Acta 1953, 36, 1109.

Further description of the above listed compounds and the compounds of the above formulae I and II and procedures and reaction conditions for preparing these compounds are also described in WO 2007/101165, entitled Pyrimidinyl Sulfonamide Compounds which Inhibit Leukocyte Adhesion Mediated by VLA-4, filed Feb. 26, 2007, incorporated in its entirety by reference.

In another aspect, the compounds that can be utilized are compounds of formula III:

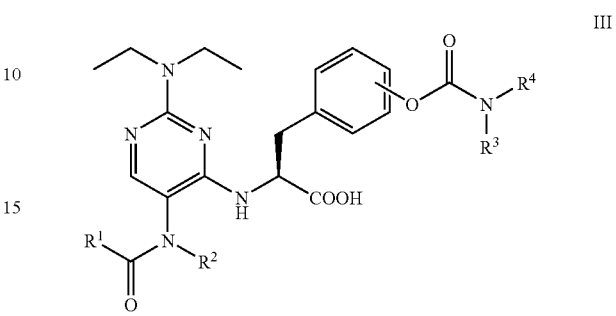

III wherein:

$R^1$ is selected from the group consisting of $C_1$ to $C_4$ alkyl, $C_1$ to $C_4$ haloalkyl, heteroaryl, and —$NR^5R^6$ wherein $R^5$ and $R^6$ are independently selected from the group consisting of hydrogen and $C_1$ to $C_4$ alkyl, or $R^5$ and $R^6$ together with the nitrogen atom pendent thereto form a heterocyclic ring;

$R^1$ is selected from the group consisting of $C_1$ to $C_4$ alkyl, $C_2$ to $C_4$ alkenyl, and $C_2$ to $C_4$ alkynyl; and $R^3$ and $R^4$ are independently $C_1$ to $C_3$ alkyl or $R^3$ and $R^4$ together with the nitrogen atom pendent thereto join to form a heterocyclic ring;

or a pharmaceutically acceptable salt, ester, or prodrug thereof.

In some embodiments, the —$OC(O)NR^3R^4$ group is in the para position of the phenyl ring.

In some embodiments, $R^3$ and $R^4$ are joined to form a heterocyclic ring. In other embodiments, $R^3$ and $R^4$ are joined to form a pyrrolidinyl ring.

In some embodiments, $R^2$ is $C_1$ to $C_4$ alkyl. In other embodiments, $R^2$ is ethyl.

In still other embodiments, $R^3$ and $R^4$ are joined to form a heterocyclic ring and $R^2$ is $C_1$ to $C_4$ alkyl. In yet other embodiments, $R^3$ and $R^4$ are joined to form a pyrrolidinyl ring and $R^2$ is ethyl.

Examples of compounds of the above formula III include those having the $R^1$, $R^2$, $R^3$, and $R^4$ groups recited in Table 3.

TABLE 3

| $R^1$ | $R^2$ | $R^3$ | $R^4$ |
|---|---|---|---|
| trifluoromethyl | ethyl | $R^3$ and $R^4$ together with the pendent nitrogen form a pyrrolidine ring | |
| iso-propyl | ethyl | $R^3$ and $R^4$ together with the pendent nitrogen form a pyrrolidine ring | |
| t-butyl | ethyl | $R^3$ and $R^4$ together with the pendent nitrogen form a pyrrolidine ring | |
| furan-2-yl | ethyl | $R^3$ and $R^4$ together with the pendent nitrogen form a pyrrolidine ring | |
| piperidin-1-yl | ethyl | $R^3$ and $R^4$ together with the pendent nitrogen form a pyrrolidine ring | |
| N-ethyl-N-iso-propylamino | ethyl | $R^3$ and $R^4$ together with the pendent nitrogen form a pyrrolidine ring | |
| thien-3-yl | ethyl | $R^3$ and $R^4$ together with the | |

TABLE 3-continued

| $R^1$ | $R^2$ | $R^3$ | $R^4$ |
|---|---|---|---|
| thien-2-yl | ethyl | $R^3$ and $R^4$ together with the pendent nitrogen form a pyrrolidine ring | |
| furan-3-yl | ethyl | $R^3$ and $R^4$ together with the pendent nitrogen form a pyrrolidine ring | |
| 3-thiapyrrolidin-1-yl | ethyl | $R^3$ and $R^4$ together with the pendent nitrogen form a pyrrolidine ring | |

In another aspect, the compounds that can be utilized are compounds of formula IV:

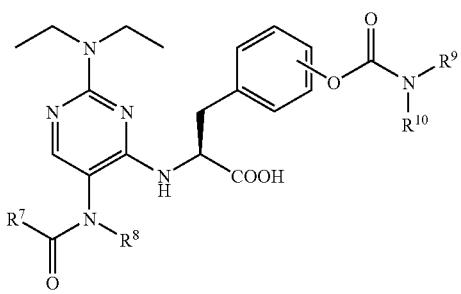

IV wherein:
$R^7$ is $C_1$ to $C_4$ alkyl, $C_1$ to $C_4$ haloalkyl, or heteroaryl;
$R^8$ is $C_1$ to $C_4$ alkyl;
$R^9$ and $R^{10}$ are independently $C_1$ to $C_3$ alkyl, or $R^9$ and $R^{10}$ together with the nitrogen atom pendent thereto form a heterocyclic ring;
or a pharmaceutically acceptable salt, ester, or prodrug thereof.

In some embodiments, the —OC(O)NR$^9$R$^{10}$ group is in the para position of the phenyl ring.

In some embodiments, $R^9$ and $R^{10}$ are joined to form a heterocyclic ring. In other embodiments, $R^9$ and $R^{10}$ are joined to form a pyrrolidinyl ring.

In some embodiments, $R^8$ is $C_1$ to $C_4$ alkyl. In other embodiments, $R^8$ is ethyl.

In some embodiments, $R^7$ is $C_1$ to $C_4$ alkyl. In other embodiments, $R^7$ is selected from the group consisting of isopropyl and t-butyl.

In some embodiments, $R^7$ is $C_1$ to $C_4$ haloalkyl. In other embodiments $R^7$ is trifluoromethyl.

In some embodiments, $R^7$ is heteroaryl. In other embodiments, $R^7$ is selected from the group consisting of furan-2-yl, furan-3-yl, thien-2-yl, and thien-3-yl.

In some embodiments, $R^9$ and $R^{10}$ are joined to form a heterocyclic ring, $R^8$ is $C_1$ to $C_4$ alkyl, and $R^7$ is heteroaryl. In other embodiments, $R^9$ and $R^{10}$ (together with the pendent nitrogen form a pyrrolidine ring, $R^8$ is ethyl, and $R^7$ is heteroaryl.

In some embodiments, $R^9$ and $R^{10}$ are joined to form a heterocyclic ring, $R^8$ is $C_1$ to $C_4$ alkyl, and $R^7$ is alkyl. In other embodiments, $R^9$ and $R^{10}$ together with the pendent nitrogen form a pyrrolidine ring, $R^8$ is ethyl, and $R^7$ is alkyl.

The present invention further provides the compounds of the above formula IV having the $R^7$, $R^8$, $R^9$, and $R^{10}$ groups recited in Table 4.

TABLE 4

| $R^7$ | $R^8$ | $R^9$ | $R^{10}$ |
|---|---|---|---|
| trifluoromethyl | ethyl | $R^9$ and $R^{10}$ together with the pendent nitrogen form a pyrrolidine ring | |
| iso-propyl | ethyl | $R^9$ and $R^{10}$ together with the pendent nitrogen form a pyrrolidine ring | |
| t-butyl | ethyl | $R^9$ and $R^{10}$ together with the pendent nitrogen form a pyrrolidine ring | |
| furan-2-yl | ethyl | $R^9$ and $R^{10}$ together with the pendent nitrogen form a pyrrolidine ring | |
| thien-3-yl | ethyl | $R^9$ and $R^{10}$ together with the pendent nitrogen form a pyrrolidine ring | |
| thien-2-yl | ethyl | $R^9$ and $R^{10}$ together with the pendent nitrogen form a pyrrolidine ring | |
| furan-3-yl | ethyl | $R^9$ and $R^{10}$ together with the pendent nitrogen form a pyrrolidine ring | |

In yet another aspect, the compounds that can be utilized are compounds of formula V:

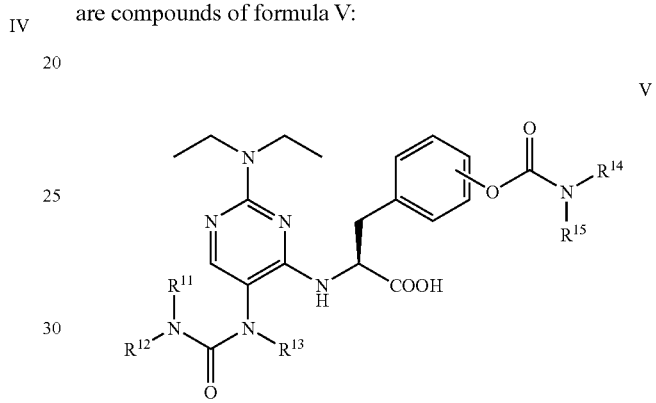

V wherein:
$R^{11}$ and $R^{12}$ are independently $C_1$ to $C_4$ alkyl, or $R^{11}$ and $R^{12}$ together with the nitrogen atom pendent thereto form a heterocyclic ring;
$R^{13}$ is $C_1$ to $C_4$ alkyl; and
$R^{14}$ and $R^{15}$ are independently $C_1$ to $C_3$ alkyl or $R^{14}$ and $R^{15}$ together with the nitrogen atom pendent thereto form a heterocyclic ring;
or a pharmaceutically acceptable salt, ester, or prodrug thereof.

In some embodiments, the —OC(O)NR$^{14}$R$^{15}$ group is in the para position of the phenyl ring.

In some embodiments, $R^{14}$ and $R^{15}$ are joined to form a heterocyclic ring. In other embodiments, $R^{14}$ and $R^{15}$ are joined to form a pyrrolidinyl ring.

In some embodiments, $R^{13}$ is $C_1$ to $C_4$ alkyl. In other embodiments, $R^3$ is ethyl.

In some embodiments, $R^{11}$ and $R^{12}$ are independently $C_1$ to $C_4$ alkyl. In other embodiments $R^{11}$ is ethyl and $R^{12}$ is isopropyl.

In some embodiments, $R^{11}$ and $R^{12}$, together with the nitrogen atom pendent thereto, are joined to form a heterocyclic ring. In other embodiments, the heterocyclic ring is selected from the group consisting of piperidin-1-yl and 3-thiapyrrolidin-1-yl.

In yet other embodiments, $R^{14}$ and $R^{15}$ are joined to form a heterocyclic ring, $R^{13}$ is $C_1$ to $C_4$ alkyl, and $R^{11}$ and $R^{12}$, together with the nitrogen atom pendent thereto, are joined to form a heterocyclic ring.

The present invention further provides compounds of the above formula V having the $R^{11}$, $R^{12}$, $R^{13}$, $R^{14}$, and $R^{15}$ and groups recited in Table 5.

TABLE 5

| R[11] | R[12] | R[13] | R[14] | R[15] |
|---|---|---|---|---|
| R[11] and R[12] together with the pendent nitrogen form a piperidine ring | | ethyl | R[14] and R[15] together with the pendent nitrogen form a pyrrolidine ring | |
| iso-propyl | ethyl | ethyl | R[14] and R[15] together with the pendent nitrogen form a pyrrolidine ring | |
| R[11] and R[12] together with the pendent nitrogen form a 3-thiapyrrolidine ring | | ethyl | R[14] and R[15] together with the pendent nitrogen form a pyrrolidine ring | |

In some embodiments, the present invention provides compounds of the above formulae III, IV, and V having the carbamyl substituents:

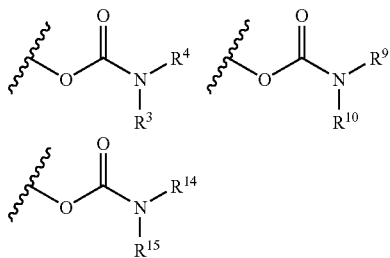

in their respective formulae attached to the phenyl ring at the para position. In still other embodiments, the compounds in Tables 3, 4, and 5 have the carbamyl substituents attached at the para position.

In some embodiments, the present invention also provides compounds of the above formulae III, IV, and V, including those in Tables 3, 4, and 5, having the carbamyl substituents attached at the ortho or meta positions.

In yet another aspect, the compounds that can be utilized include the following:

N-[2-diethylamino-5-{N-ethyl-N-(trifluoroacetyl)amino}pyrimidin-4-yl]-L-4'-{(pyrrolidin-1-yl)carbonyloxy}phenylalanine;

N-[2-diethylamino-5-{N-ethyl-N-(iso-propylcarbonyl)amino}pyrimidin-4-yl]-L-4'-{(pyrrolidin-1-yl)carbonyloxy}phenylalanine;

N-[2-diethylamino-5-{N-ethyl-N-(t-butylcarbonyl)amino}pyrimidin-4-yl]-L-4'-{(pyrrolidin-1-yl)carbonyloxy}phenylalanine;

N-[2-diethylamino-5-{N-ethyl-N-(furan-2-ylcarbonyl)amino}pyrimidin-4-yl]-L-4'-{(pyrrolidin-1-yl)carbonyloxy}phenylalanine;

N-[2-diethylamino-5-{N-ethyl-N-(piperidin-1-ylcarbonyl)amino}pyrimidin-4-yl]-L-4'-{(pyrrolidin-1-yl)carbonyloxy}phenylalanine;

N-[2-diethylamino-5-{N-ethyl-N—(N-ethyl-N-iso-propylaminocarbonyl)amino}pyrimidin-4-yl]-L-4'-{(pyrrolidin-1-yl)carbonyloxy}phenylalanine;

N-[2-diethylamino-5-{N-ethyl-N-(thien-3-ylcarbonyl)amino}pyrimidin-4-yl]-L-4'-{(pyrrolidin-1-yl)carbonyloxy}phenylalanine;

N-[2-diethylamino-5-{N-ethyl-N-(thien-2-ylcarbonyl)amino}pyrimidin-4-yl]-L-4'-{(pyrrolidin-1-yl)carbonyloxy}phenylalanine;

N-[2-diethylamino-5-{N-ethyl-N-(furan-3-ylcarbonyl)amino}pyrimidin-4-yl]-L-4'-{(pyrrolidin-1-yl)carbonyloxy}phenylalanine;

N-[2-diethylamino-5-{N-ethyl-N-(3-thiapyrrolidin-1-ylcarbonyl)amino}pyrimidin-4-yl]-L-4'-{(pyrrolidin-1-yl)carbonyloxy}phenylalanine;

N-[2-diethylamino-5-{N-ethyl-N-(thien-2-ylcarbonyl)amino}pyrimidin-4-yl]-L-4'-{(pyrrolidin-1-yl)carbonyloxy}-phenylalanine t-butyl ester;

N-[2-diethylamino-5-{N-ethyl-N-trifluoromethylcarbonyl)amino}pyrimidin-4-yl]-L-4'-{(pyrrolidin-1-yl)carbonyloxy}-phenylalanine t-butyl ester;

N-[2-diethylamino-5-{N-ethyl-N-t-butylcarbonyl)amino}pyrimidin-4-yl]-L-4'-{(pyrrolidin-1-yl)carbonyloxy}-phenylalanine t-butyl ester; and N-[2-diethylamino-5-{N-ethyl-N-furan-3-ylcarbonyl)amino}pyrimidin-4-yl]-L-4'-{(pyrrolidin-1-yl)carbonyloxy}-phenylalanine t-butyl ester;

or a pharmaceutically acceptable salt, ester, or prodrug thereof.

The following terms used in the specification and claims with reference to the above formulae III-V have the meanings given below:

"Alkyl" refers to straight, branched and cyclic alkyl groups preferably having from 1 to 4 carbon atoms and more preferably 1 to 3 carbon atoms. This term is exemplified by groups such as methyl, ethyl, n-propyl, iso-propyl, n-butyl, iso-butyl, sec-butyl, t-butyl, cyclopropyl, cyclobutyl, and methylenecyclopropyl.

"Alkenyl" refers to straight and branched alkenyl group having from 2 to 4 carbon atoms and preferably 2 to 3 carbon atoms and having at least 1 and preferably 1 site of alkenyl unsaturation. Examples of such alkenyl groups include vinyl (—CH=CH$_2$), allyl (—CH$_2$CH=CH$_2$), n-propen-1-yl (—CH=CHCH$_3$), n-buten-2-yl (—CH$_2$CH=CHCH$_3$), and the like. Included within this term are the cis and trans isomers or mixtures of these isomers.

"Alkynyl" refers to straight and branched alkynyl group having from 2 to 4 carbon atoms and preferably 2 to 3 carbon atoms and having at least 1 and preferably 1 site of alkynyl unsaturation. Examples of such alkynyl groups include acetylenyl (—C≡CH), propargyl (—CH$_2$C≡CH), n-propyn-1-yl (—CH=CHCH$_3$), and the like.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is at an aromatic carbon atom. Preferred aryls include phenyl and naphthyl.

"Substituted aryl" refers to aryl groups which are substituted with from 1 to 3 substituents, and preferably 1 to 2 substituents, selected from the group consisting of hydroxyl, acyl, acylamino, acyloxy, alkyl, substituted alkyl, alkoxy, substituted alkoxy, alkenyl, substituted alkenyl, alkynyl, substituted alkynyl, amino, substituted amino, aminoacyl, aryl, substituted aryl, aryloxy, substituted aryloxy, carboxyl, carboxyl esters, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, halo, nitro, heteroaryl, substituted heteroaryl, heterocyclic, substituted heterocyclic, heteroaryloxy, substituted heteroaryloxy, heterocyclyloxy, substituted heterocyclyloxy, amino sulfonyl (NH$_2$—SO$_2$—), and substituted amino sulfonyl.

"Halo" or "halogen" refers to fluoro, chloro, bromo and iodo and preferably is either fluoro or chloro.

"Haloalkyl" refers to alkyl groups having from 1 to 5 halo groups. Preferably, such groups have from 1 to 3 halo groups and 1 to 2 carbon atoms. Particularly preferred haloalkyl groups include trihalomethyl (e.g., trifluoromethyl) and trihaloethyl (e.g., 2,2,2-trifluoroeth-1-yl).

"Heteroaryl" refers to an aromatic carbocyclic group of from 2 to 10 carbon atoms and 1 to 4 heteroatoms selected from oxygen, nitrogen and sulfur within the ring. Such heteroaryl groups can have a single ring (e.g., pyridyl or furyl) or multiple condensed rings wherein the condensed ring may be aryl or heteroaryl. Examples of such heteroaryls include, for instance, furan-2-yl, furan-3-yl, thien-2-yl, thien-3-yl, pyrrol-2-yl, pyrrol-3-yl, pyridyl (2-, 3-, and 4-pyridyls) and the like. In one embodiment, the sulfur and/or nitrogen atoms of the heteroaryl are optionally oxidized (i.e., —S(O)— or —S(O)$_2$—, and/or N-oxides).

"Heterocycle" or "heterocyclic" refers to a saturated or unsaturated non-heteroaromatic group having a single ring or multiple condensed rings, from 1 to 10 carbon atoms and from 1 to 4 hetero atoms selected from nitrogen, sulfur or oxygen within the ring wherein, in fused ring systems, one or more the rings can be aryl or heteroaryl. In one embodiment, the sulfur and/or nitrogen atoms of the heterocycle are optionally oxidized (i.e., —S(O)— or —S(O)$_2$—, and/or N-oxides).

Compound Preparation

The compounds of the above formulae III-V can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, *Protecting Groups in Organic Synthesis*, Second Edition, Wiley, New York, 1991, and references cited therein.

Furthermore, the compounds of the above formulae III-V will typically contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of the above formulae III-V, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

In one embodiment, the compounds of the above formulae III-V can be prepared as described below in Scheme 4:

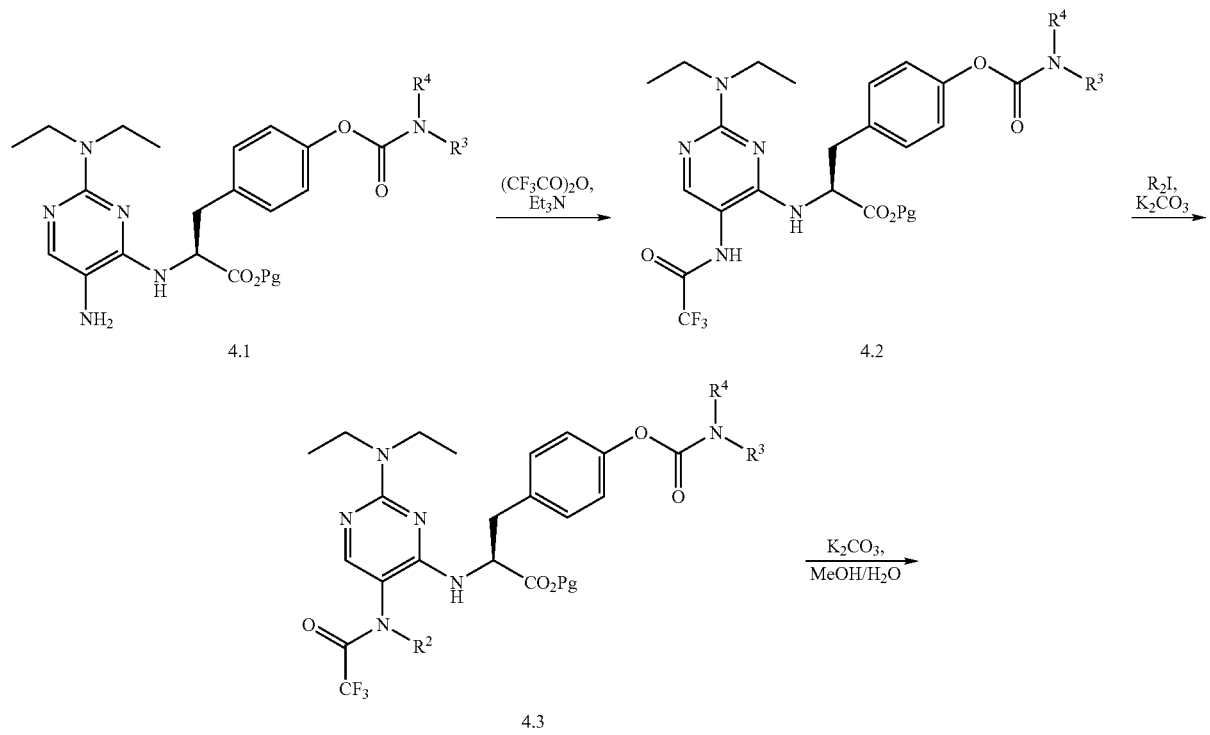

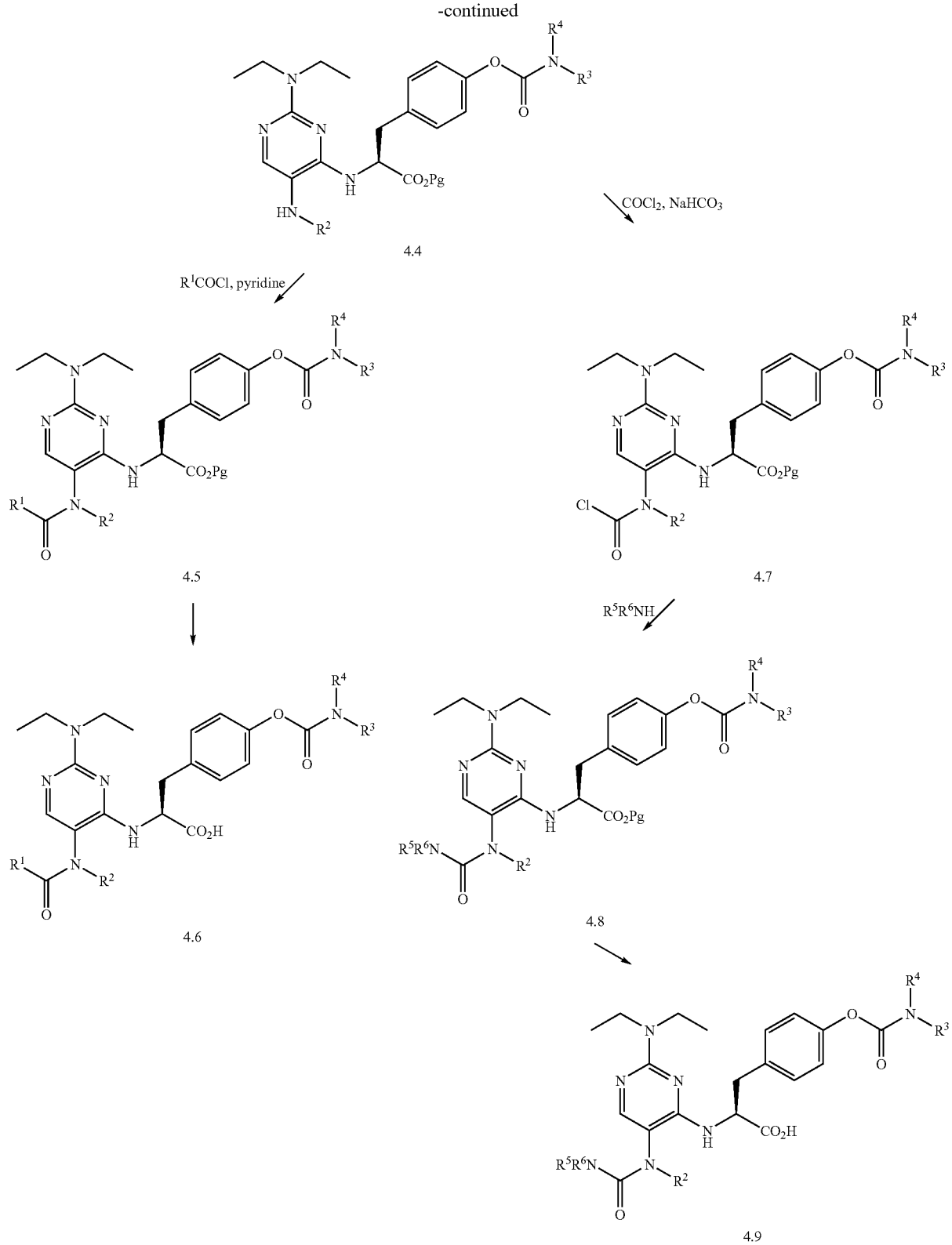
where $R^1$, $R^2$, $R^3$, $R^4$, $R^5$ and $R^6$ are as defined above and Pg is a carboxyl protecting group such as benzyl, t-butyl, and the like.
In Scheme 4, the starting 5-aminopyrimidine intermediates, compound 4.1, are described in detail in WO 03/099809, herein incorporated by reference in its entirety, and, for the sake of illustration only, are shown in this scheme as 4-substituted phenylalanine derivatives. It is understood, of course, that 2- and 3-substituted phenylalanine derivatives would follow a similar reaction pathway.

Specifically, in Scheme 4,5-amino-2-diethylamino-4-substituted pyrimidine, compound 4.1 (prepared from by corresponding 5-nitro-pyrimidine by reduction with 5% Pd/C or 5% $PtO_2$ by weight) is converted to the corresponding trifluoroacetamide, compound 4.2, by conventional methods. For example, a slight excess of trifluoroacetic anhydride is combined with compound 4.1 in a suitable inert diluent such as tetrahydrofuran, methylene chloride, pyridine, and the like. The reaction is maintained at from about 0° C. to about 30° C. until the reaction is substantially complete which typically occurs within about 0.5 to 24 hours. Upon completion of the reaction, the compound 4.2 is recovered by conventional methods including neutralization, evaporation, extraction, precipitation, chromatography, filtration, and the like or, alternatively, is employed in the next step without purification and/or isolation.

Conversion of compound 4.2 to the corresponding $N(R^2)$, N-trifluoroacetamidopyrimidine, compound 4.3, again proceeds via conventional techniques. For example, an excess of the halide, $R^2$—I, is combined with compound 4.2 in a suitable inert diluent such as DMF in the presence of an excess of a suitable base such as potassium carbonate. In a preferred embodiment, approximately two equivalents of $R^2$—I and potassium carbonate are employed. The reaction is maintained under ambient conditions in a sealed container and is continued until the reaction is substantially complete which typically occurs in 20-72 hours. Upon completion of the reaction, the compound 4.3 is recovered by conventional methods including neutralization, evaporation, extraction, precipitation, chromatography, filtration, and the like or, alternatively, is employed in the next step without purification and/or isolation.

The carboxyl protecting group of compound 4.3 can be removed by conventional conditions to provide for a compound of formula III (not shown). In one embodiment, a t-butyl protecting group can be removed by contact with formic acid. In another embodiment, a benzyl protecting group can be removed by contact with hydrogen in the presence of a palladium/carbon catalyst typically in a protic solvent such as methanol under elevated hydrogen pressures.

Alternatively, the trifluoroacetyl group can be removed to provide for the corresponding amine, compound 4.4. In this embodiment, the trifluoroacetyl group acts as an amine protecting group. As above, this reaction conventionally proceeds, for example, by contacting compound 4.3 with a large excess of a suitable base such as potassium carbonate in a mixture of water and a protic solvent such as methanol. The reaction is conducted at elevated temperatures such as 40° to 60° C. and is continued until the reaction is substantially complete. Upon completion of the reaction, the compound 4.4 is recovered by conventional methods including neutralization, evaporation, extraction, precipitation, chromatography, filtration, and the like or, alternatively, is employed in the next step without purification and/or isolation.

In Scheme 4, compound 4.4 can be used to prepare either urea derivatives where $R^1$=—$NR^5R^6$ or acylamino derivatives where $R^1$ is $C_1$ to $C_4$ alkyl, $C_1$ to $C_4$ haloalkyl or heteroaryl bound to the carbonyl group other than through a nitrogen atom. In the first embodiment, urea derivatives are prepared by conventional methods such as by first preparing the amido chloride, compound 4.7. This compound is prepared by contacting compound 4.4 with an excess of phosgene in the presence of a suitable base such as potassium carbonate, potassium bicarbonate, sodium carbonate, and the like. Upon completion of the reaction, compound 4.7 can be recovered by conventional methods including neutralization, evaporation, extraction, precipitation, chromatography, filtration, and the like but preferably is employed in the next step without purification and/or isolation.

Amido chloride, compound 4.7, is then converted to the corresponding urea derivative, compound 4.8, by reaction with a suitable amine, $R^5R^6NH$, under conventional conditions. Preferably, the reaction an equimolar amount or excess of the amine is contacted with compound 4.7 in a suitable solvent such tetrahydrofuran, dioxane, chloroform and the like. Upon completion of the reaction, compound 4.8 can be recovered by conventional methods including neutralization, evaporation, extraction, precipitation, chromatography, filtration, and the like or, alternatively, is employed in the next step without purification and/or isolation.

The carboxyl protecting group of compound 4.8 can be removed by conventional conditions to provide for compound 4.9, a compound of formula III. In one embodiment, a t-butyl protecting group can be removed by contact with formic acid. In another embodiment, a benzyl protecting group can be removed by contact with hydrogen in the presence of a palladium/carbon catalyst typically in a protic solvent such as methanol under elevated hydrogen pressures. Upon completion of the reaction, compound 4.9 can be recovered by conventional methods including neutralization, evaporation, extraction, precipitation, chromatography, filtration, and the like.

In the second embodiment, acylamino derivatives, compound 4.5, are prepared by contacting compound 4.4 with a slight excess of an acyl halide in the presence of a suitable base such as triethylamine, diisopropylethylamine and the like in order to scavenge the acid generated. The reaction is preferably conducted in a suitable inert solvent such as tetrahydrofuran, dioxane, chloroform and the like. The reaction is preferably conducted at from about 0° to 30° C. and is continued until the reaction is substantially complete which typically occurs in 2-48 hours. Upon completion of the reaction, compound 4.5 can be recovered by conventional methods including neutralization, evaporation, extraction, precipitation, chromatography, filtration, and the like or, alternatively, is employed in the next step without purification and/or isolation.

The carboxyl protecting group of compound 4.5 can be removed by conventional conditions to provide for compound 4.6, a compound of formula III. In one embodiment, a t-butyl protecting group can be removed by contact with formic acid. In another embodiment, a benzyl protecting group can be removed by contact with hydrogen in the presence of a palladium/carbon catalyst typically in a protic solvent such as methanol under elevated hydrogen pressures. Upon completion of the reaction, compound 4.6 can be recovered by conventional methods including neutralization, evaporation, extraction, precipitation, chromatography, filtration, and the like.

Further description of the above listed compounds and the compounds of the above formulae III-V and procedures and reaction conditions for preparing these compounds are also described in U.S. Patent Application Publication No. 2007/0142416 A1, entitled Pyrimidinyl Amide Compounds which Inhibit Leukocyte Adhesion Mediated by VLA-4, filed Sep. 28, 2006, incorporated in its entirety by reference.

In another aspect, the compounds that can be utilized are compounds of formula B below

B

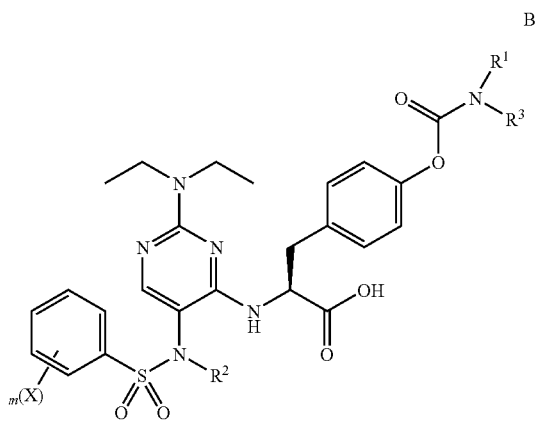

wherein each X is independently selected from the group consisting of fluoro and chloro;
m is an integer equal to 1 or 2;
$R^2$ is selected from the group consisting of lower alkyl, lower alkenyl, lower alkynyl and lower alkylenecycloalkyl;
$R^1$ and $R^3$ are each independently H or lower alkyl, or $R^1$ and $R^3$ together with the nitrogen atom to which they are bound form an azetidinyl, pyrrolidinyl, or piperidinyl group;
and pharmaceutically acceptable salts thereof.

Further description of the compounds of the above formula B and procedures and reaction conditions for preparing these compounds are described herein below and in U.S. Patent Application Publication No. 2004/0138243 entitled Heterocyclic Compounds Which Inhibit Leukocyte Adhesion Mediated By Alpha4Integrins, published Jul. 15, 2004, incorporated in its entirety by reference, and U.S. Patent Application Publication No. 2004/0142954 entitled Heteroaryl Compounds Which Inhibit Leukocyte Adhesion Mediated By Alpha4Integrins, published Jul. 22, 2004, incorporated in its entirety by reference.

In another aspect, the compounds that can be utilized are compounds of formula VI below

VI

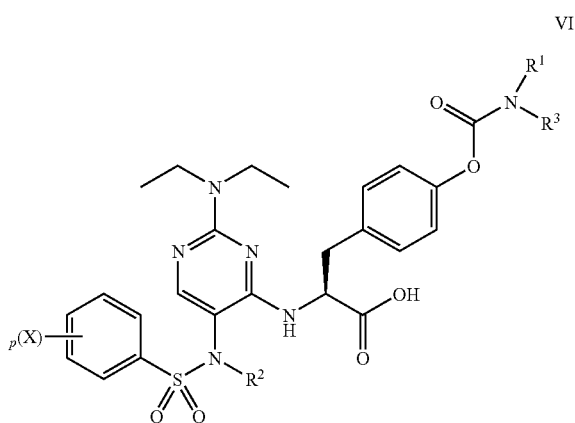

wherein each X is independently fluoro, chloro or bromo;
p is an integer from 0 to 3;
$R^1$ and $R^3$ together with the nitrogen atom to which they are bound form an azetidinyl, pyrrolidinyl, pyrrolyl, 2,5-dihydro-pyrrol-1-yl, piperidinyl, or 1,2,3,6-tetrahydro-pyridin-1-yl;
$R^2$ is selected from the group consisting of lower alkyl lower alkenyl, and lower alkylenecycloalkyl;

and pharmaceutically acceptable salts thereof.

In a preferred embodiment, $R^1$ and $R^3$ together with the nitrogen atom to which they are bound form an azetidinyl, pyrrolidinyl, or piperidinyl group.

In another aspect, the compounds that can be utilized are compounds of formula VII below

VII

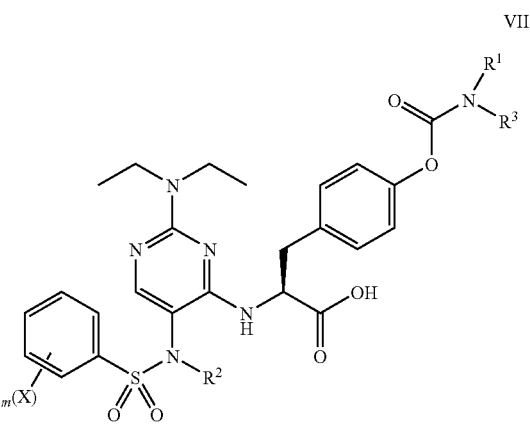

wherein each X is independently selected from the group consisting of fluoro and chloro;
m is an integer equal to 1 or 2;
$R^2$ is selected from the group consisting of lower alkyl, lower alkenyl, and lower alkylenecycloalkyl;
$R^1$ and $R^3$ together with the nitrogen atom to which they are bound form an azetidinyl, pyrrolidinyl, or piperidinyl group;
and pharmaceutically acceptable salts thereof.

In another aspect, the compounds that can be utilized are compounds of formula VIII below

VIII

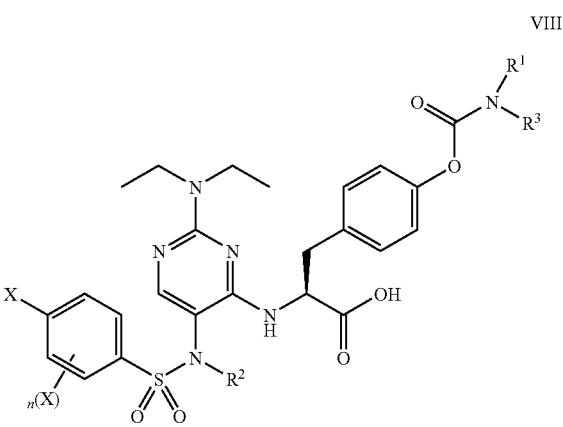

wherein each X is independently fluoro or chloro;
n is zero or one;
$R^2$ is —$CH_2$—R' where R' is selected from the group consisting of hydrogen, methyl or —CH=$CH_2$;
$R^1$ and $R^3$ together with the nitrogen atom to which they are bound form an azetidinyl, pyrrolidinyl, or piperidinyl group;
and pharmaceutically acceptable salts thereof.

In another aspect, the compounds that can be utilized are compounds of formula IX below

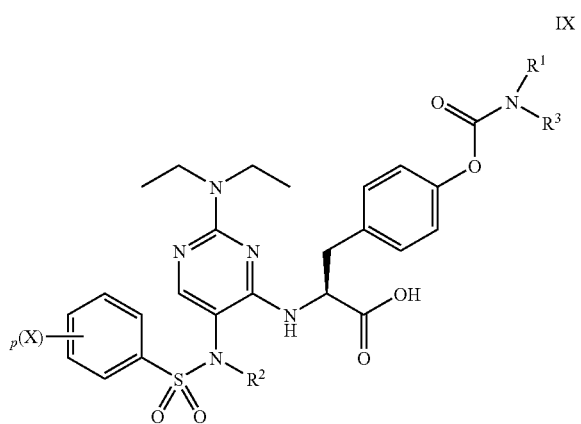

IX

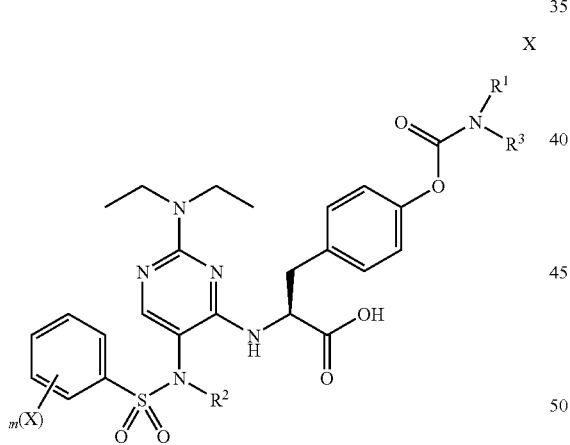

X

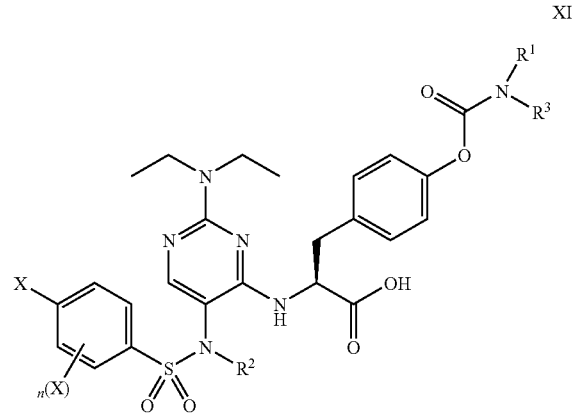

XI wherein each X is independently fluoro, chloro or bromo;
p is an integer from 0 to 3;
$R^1$ and $R^3$ together with the nitrogen atom to which they are bound form an azetidinyl, pyrrolidinyl, pyrrolyl, 2,5-dihydropyrrol-1-yl, piperidinyl, or 1,2,3,6-tetrahydropyridin-1-yl;
$R^2$ is lower alkynyl;
and pharmaceutically acceptable salts thereof.

In a preferred embodiment, $R^1$ and $R^3$ together with the nitrogen atom to which they are bound form an azetidinyl, pyrrolidinyl, or piperidinyl group and $R^2$ is propargyl.

In another aspect, the compounds that can be utilized are compounds of formula X below wherein each X is independently selected from the group consisting of fluoro and chloro;
m is an integer equal to 1 or 2;
$R^2$ is lower alkynyl;
$R^1$ and $R^3$ together with the nitrogen atom to which they are bound form an azetidinyl, pyrrolidinyl, or piperidinyl group;
and pharmaceutically acceptable salts thereof.

In the compounds of formula X, preferably $R^2$ is —$CH_2$—C≡CH.

In another aspect, the compounds that can be utilized are compounds of formula XI below wherein each X is independently fluoro or chloro;
n is zero or one;
$R^2$ is lower alkynyl;
$R^1$ and $R^3$ together with the nitrogen atom to which they are bound form an azetidinyl, pyrrolidinyl, or piperidinyl group;
and pharmaceutically acceptable salts thereof.

N-[2-N',N'-diethylamino-5-aminosulfonylphenylpyrimidin-4-yl]-p-carbonyloxy-phenylalanine compounds within the scope of the above formulae VI-XI include those set forth in Table 6 as follows:

TABLE 6

| $R^1$ and $R^3$ | $R^2$ | $(X)_p$ |
|---|---|---|
| pyrrolidinyl | Ethyl | 4-fluorophenyl |
| pyrrolidinyl | methyl | 4-fluorophenyl |
| pyrrolidinyl | methyl | 4-chlorophenyl |
| pyrrolidinyl | Ethyl | 4-chlorophenyl |
| piperidinyl | methyl | 4-fluorophenyl |
| azetidinyl | Ethyl | 4-fluorophenyl |
| azetidinyl | methyl | 4-fluorophenyl |
| azetidinyl | methyl | 4-chlorophenyl |
| azetidinyl | Ethyl | 4-chlorophenyl |
| piperidinyl | Ethyl | 4-fluorophenyl |
| azetidinyl | Ethyl | 2,4-difluorophenyl |
| pyrrolidinyl | methyl | 2,4-difluorophenyl |
| pyrrolidinyl | Ethyl | 2,4-difluorophenyl |
| azetidinyl | methyl | 2,4-difluorophenyl |
| pyrrolidinyl | propargyl | 4-fluorophenyl |
| pyrrolidinyl | progargyl | 2,4-difluorophenyl |
| azetidinyl | propargyl | 2,4-difluorophenyl |

TABLE 6-continued

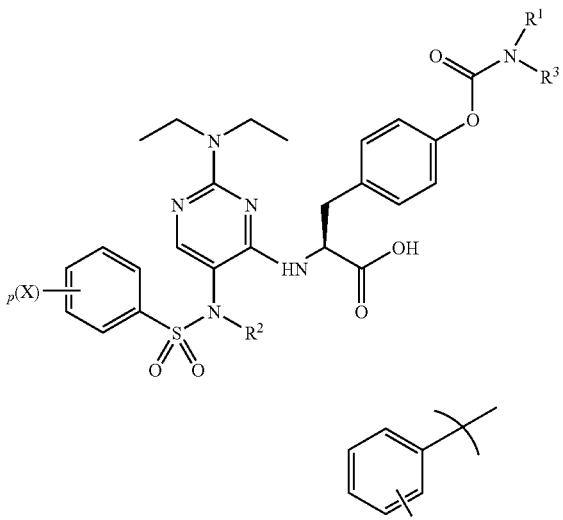

| R¹ and R³ | R² | (X)ₚ |
|---|---|---|
| azetidinyl | propargyl | 4-fluorophenyl |
| pyrrolidinyl | progargyl | 4-chlorophenyl |

Specific compounds within the scope of the above formulae VI-XI include the following compounds. As used below, these compounds are named based on phenylalanine derivatives but, alternatively, these compounds could have been named based on N-[2-N',N'-diethylamino-5-aminosulfonylphenyl-pyrimidin-4-yl]-p-carbonyloxyphenylalanine derivatives or 2-{2-diethylamino-5-[(benzenesulfonyl)methylamino]-pyrimidin-4-ylamino}-p-carbamoyloxy-phenyl) propionic acid derivatives.

N-(2-[N',N'-diethylamino]-5-[N"-(4-chlorophenylsulfonyl)-N"-ethylamino]pyrimidin-4-yl)-4'-(pyrrolidin-1-ylcarbonyloxy)-L-phenylalanine;

N-(2-[N',N'-diethylamino]-5-[N"-(4-fluorophenylsulfonyl)-N"-ethylamino]pyrimidin-4-yl)-4'-(pyrrolidin-1-ylcarbonyloxy)-L-phenylalanine;

N-(2-[N',N'-diethylamino]-5-[N"-(4-fluorophenylsulfonyl)-N'-methylamino]pyrimidin-4-yl)-4'-(pyrrolidin-1-ylcarbonyloxy)-L-phenylalanine;

N-(2-[N',N'-diethylamino]-5-[N"-(4-chlorophenylsulfonyl)-N"-methylamino]pyrimidin-4-yl)-4'-(pyrrolidin-1-ylcarbonyloxy)-L-phenylalanine;

N-(2-[N',N'-diethylamino]-5-[N"-(4-fluorophenylsulfonyl)-N"-methylamino]pyrimidin-4-yl)-4'-(piperidin-1-ylcarbonyloxy)-L-phenylalanine;

N-(2-[N',N'-diethylamino]-5-[N"-(4-fluorophenylsulfonyl)-N"-ethylamino]pyrimidin-4-yl)-4'-(piperidin-1-ylcarbonyloxy)-L-phenylalanine;

N-(2-[N',N'-diethylamino]-5-[N"-(4-fluorophenylsulfonyl)-N"-ethylamino]pyrimidin-4-yl)-4'-(azetidin-1-ylcarbonyloxy)-L-phenylalanine;

N-(2-[N',N'-diethylamino]-5-[N"-(4-fluorophenylsulfonyl)-N"-methylamino]pyrimidin-4-yl)-4'-(azetidin-1-ylcarbonyloxy)-L-phenylalanine;

N-(2-[N',N'-diethylamino]-5-[N"-(4-chlorophenylsulfonyl)-N"-methylamino]pyrimidin-4-yl)-4'-(azetidin-1-ylcarbonyloxy)-L-phenylalanine;

N-(2-[N',N'-diethylamino]-5-[N"-(4-chlorophenylsulfonyl)-N"-ethylamino]pyrimidin-4-yl)-4'-(azetidin-1-ylcarbonyloxy)-L-phenylalanine;

N-(2-[N',N'-diethylamino]-5-[N"-(2,4-difluorophenylsulfonyl)-N"-methylamino]pyrimidin-4-yl)-4'-(pyrrolidin-1-ylcarbonyloxy)-L-phenylalanine;

N-(2-[N',N'-diethylamino]-5-[N"-(2,4-difluorophenylsulfonyl)-N"-ethylamino]pyrimidin-4-yl)-4'-(pyrrolidin-1-ylcarbonyloxy)-L-phenylalanine;

N-(2-[N',N'-diethylamino]-5-[N"-(2,4-difluorophenylsulfonyl)-N"-methylamino]pyrimidin-4-yl)-4'-(azetidin-1-ylcarbonyloxy)-L-phenylalanine;

N-(2-[N',N'-diethylamino]-5-[N"-(2,4-difluorophenylsulfonyl)-N"-ethylamino]pyrimidin-4-yl)-4'-(azetidin-1-ylcarbonyloxy)-L-phenylalanine;

N-(2-[N',N'-diethylamino]-5-[N"-(4-fluorophenylsulfonyl)-N"-propargylamino]pyrimidin-4-yl)-4'-(pyrrolidin-1-ylcarbonyloxy)-L-phenylalanine;

N-(2-[N',N'-diethylamino]-5-[N"-(2,4-difluorophenylsulfonyl)-N"-propargylamino]pyrimidin-4-yl)-4'-(pyrrolidin-1-ylcarbonyloxy)-L-phenylalanine;

N-(2-[N',N'-diethylamino]-5-[N"-(2,4-difluorophenylsulfonyl)-N"-propargylamino]pyrimidin-4-yl)-4'-(azetidin-1-ylcarbonyloxy)-L-phenylalanine;

N-(2-[N',N'-diethylamino]-5-[N"-(4-fluorophenylsulfonyl)-N"-propargylamino]pyrimidin-4-yl)-4'-(azetidin-1-ylcarbonyloxy)-L-phenylalanine;

N-(2-[N',N'-diethylamino]-5-[N"-(4-chlorophenylsulfonyl)-N"-propargylamino]pyrimidin-4-yl)-4'-(pyrrolidin-1-ylcarbonyloxy)-L-phenylalanine; and pharmaceutically acceptable salts thereof.

The following terms used in the specification and claims with reference to the above formulae VI-XI have the meanings given below:

"Lower alkyl" refers to monovalent alkyl groups having from 1 to 5 carbon atoms including straight and branched chain alkyl groups. This term is exemplified by groups such as methyl, ethyl, iso-propyl, n-propyl, n-butyl, iso-butyl, sec-butyl, t-butyl, n-pentyl and the like.

The term "lower alkylene" refers to divalent alkylene groups of from 1 to 4 carbon atoms including straight and branched chain alkylene groups. This term is exemplified by groups such as methylene, ethylene, n-propylene, iso-propylene (—CH₂CH(CH₃)— and —CH(CH₃)CH₂—) and the like.

The term "lower alkenyl" refers to an alkenyl group preferably having from 2 to 6 carbon atoms and having at least 1 site and preferably only 1 site of alkenyl unsaturation (i.e., >C=C<). This term is exemplified by groups such as allyl, ethenyl, propenyl, butenyl, and the like.

The term "lower alkynyl" refers to an alkynyl group preferably having from 2 to 6 carbon atoms and having at least 1 site and preferably only 1 site of alkynyl unsaturation (i.e., —C≡C—). This term is exemplified by groups such as acetyl (—C≡CH), propargyl (—CH₂—C≡CH), 3-butynyl (—CH₂CH₂C≡CH₃) and the like.

The term "lower cycloalkyl" refers to cyclic alkyl groups of from 3 to 6 carbon atoms having a single cyclic ring including, by way of example, cyclopropyl, cyclobutyl, cyclopentyl and cyclohexyl.

The term "lower alkylenecycloalkyl" refers to the group consisting of a lower alkylene-lower cycloalkyl, as defined herein. Such groups are exemplified by methylenecyclopropyl (—CH₂-cyclopropyl), ethylenecyclopropyl and the like.

Compound Preparation

The compounds of the above formulae VI-XI can be prepared from readily available starting materials using the methods and procedures set forth in Scheme C and Examples 17-35 below. These methods and procedures outline specific reaction protocols for preparing N-[2-N',N'-diethylamino-5-aminosulfonylphenyl-pyrimidin-4-yl]-p-carbonyloxy-phenylalanine compounds. Compounds within the scope not exemplified in Examples 17-35 and methods are readily prepared by appropriate substitution of starting materials which are either commercially available or well known in the art.

Other procedures and reaction conditions for preparing the compounds of the above formulae VI-XI are described in Examples 17-35 set forth below. Additionally, other procedures for preparing compounds useful in certain aspects of the above formulae VI-XI are disclosed in U.S. Pat. No. 6,492,372, issued Dec. 10, 2002; the disclosure of which is incorporated herein by reference in its entirety.

Further description of the compounds of the above formulae VI-XI and procedures and reaction conditions for preparing these compounds are described in U.S. Patent Application Publication No. 2004/0138243 entitled Heterocyclic Compounds Which Inhibit Leukocyte Adhesion Mediated By Alpha4Integrins, published Jul. 15, 2004, incorporated in its entirety by reference.

In yet another aspect, the compounds that can be utilized are compounds of formula XII below

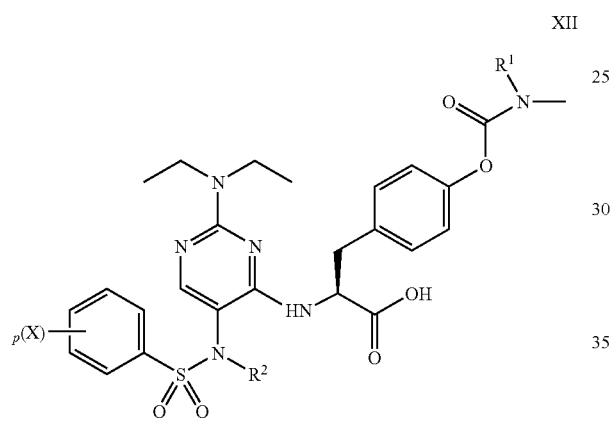

XII wherein each X is independently fluoro, chloro or bromo;
p is 0 or an integer from 1-3;
$R^1$ is selected from the group consisting of methyl and ethyl;
$R^2$ is selected from the group consisting of lower alkyl, lower alkenyl, and lower alkylenecycloalkyl;
and pharmaceutically acceptable salts thereof.

In another aspect, the compounds that can be utilized are compounds of formula XIII below

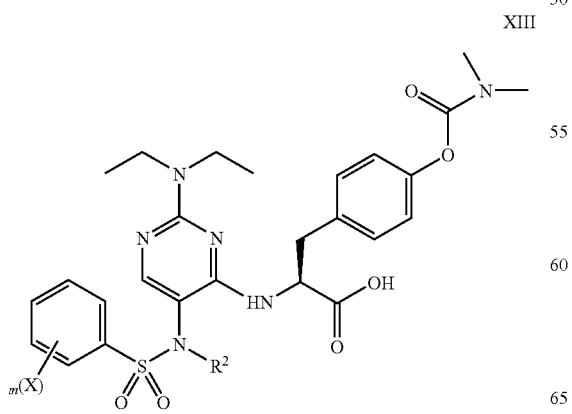

XIII wherein each X is independently selected from the group consisting of fluoro and chloro,
m is an integer equal to 1 or 2;
$R^2$ is selected from the group consisting of lower alkyl, lower alkenyl, and lower alkylenecycloalkyl;
and pharmaceutically acceptable salts thereof.

In another aspect, the compounds that can be utilized are compounds of formula XIV below

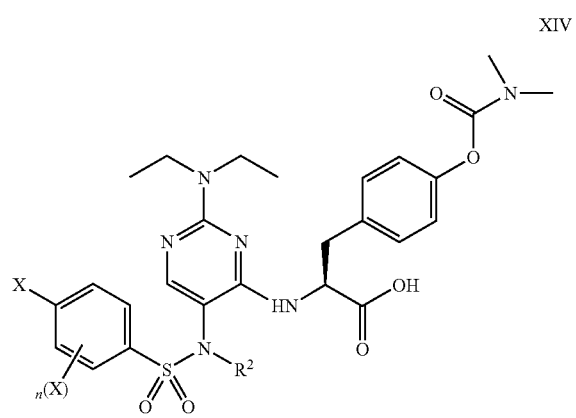

XIV wherein each X is independently fluoro or chloro;
n is zero or one;
$R^2$ is —$CH_2$—R' where R' is selected from the group consisting of hydrogen, methyl or —CH=$CH_2$;
and pharmaceutically acceptable salts thereof.

In another aspect, the compounds that can be utilized are compounds of formula XV below

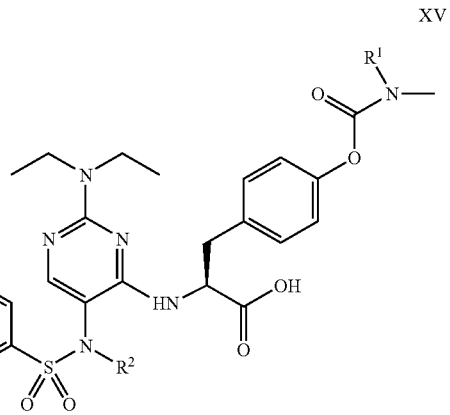

XV wherein each X is independently fluoro, chloro or bromo;
p is 0 or an integer from 1-3;
$R^1$ is selected from the group consisting of methyl and ethyl;
$R^2$ is lower alkynyl;
and pharmaceutically acceptable salts thereof.

In the compounds of formula XV, preferably $R^2$ is —$CH_2$—C≡CH.

In another aspect, the compounds that can be utilized are compounds of formula XVI below

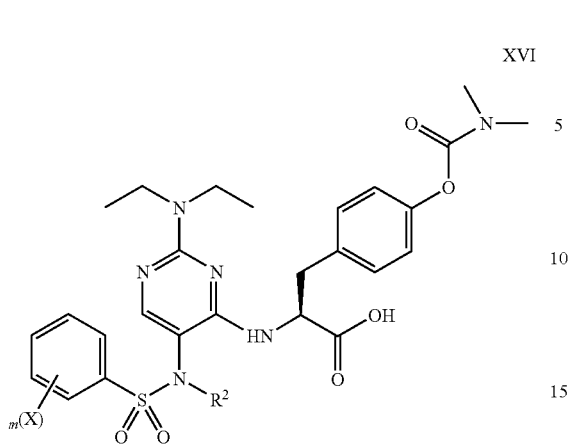

XVI wherein each X is independently selected from the group consisting of fluoro and chloro, m is an integer equal to 1 or 2;

$R^2$ is lower alkynyl;

and pharmaceutically acceptable salts thereof.

In another aspect, the compounds that can be utilized are compounds of formula XVII below

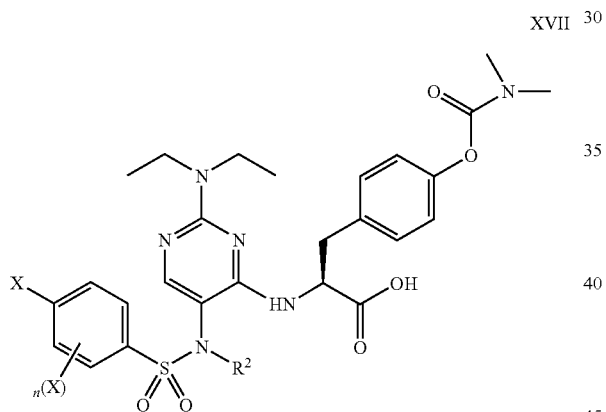

XVII wherein each X is independently fluoro or chloro;

n is zero or one;

$R^2$ is lower alkynyl;

and pharmaceutically acceptable salts thereof.

N-[2-N',N'-diethylamino-5-aminosulfonylphenylpyrimidin-4-yl]-p-carbonyloxyphenylalanine compounds within the scope of the above formulae XII-XVII include those set forth in Table 7 as follows:

TABLE 7

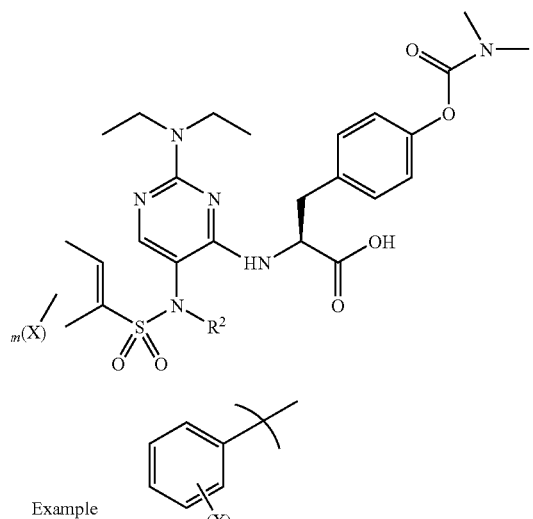

| Example No. | $(X)_m$ | $R^2$ |
|---|---|---|
| 36 | 4-fluorophenyl | methyl |
| 37 | 4-chlorophenyl | methyl |
| 38 | 3,4-difluorophenyl | methyl |
| 39 | 3,4-dichlorophenyl | methyl |
| 40 | Phenyl | methyl |
| 41 | 2-fluorophenyl | methyl |
| 42 | 3-fluorophenyl | methyl |
| 43 | 4-fluorophenyl | isopropyl |
| 44 | 4-fluorophenyl | ethyl |
| 45 | 3,4-difluorophenyl | isopropyl |
| 46 | 4-chlorophenyl | isopropyl |
| 47 | 3,4-difluorophenyl | ethyl |
| 48 | 4-chlorophenyl | ethyl |
| 49 | 4-fluorophenyl | cyclopropylmethyl |
| 50 | 3,5-difluorophenyl | methyl |
| 51 | 3,5-difluorophenyl | ethyl |
| 52 | 2,4-difluorophenyl | methyl |
| 53 | 2,4-difluorophenyl | ethyl |
| 54 | 3,5-dichlorophenyl | methyl |
| 55 | 3,5-dichlorophenyl | ethyl |
| 56 | 4-fluorophenyl | n-propyl |
| 57 | 4-fluorophenyl | allyl |
| 58 | 4-fluorophenyl | isobutyl |
| 59 | 4-fluorophenyl | n-butyl |
| 60 | 2,6-difluorophenyl | methyl |
| 61 | 2,3-difluorophenyl | methyl |
| 62 | 4-fluorophenyl | propargyl |
| 63 | 2,4-difluorophenyl | propargyl |
| 64 | 4-fluorophenyl | 2-trisfluoroethyl |

Specific compounds within the scope of the above formulae XII-XVII include the following. As used below, these compounds are named based on propionic acid derivatives but, alternatively, these compounds could have been named based on N-[2-N',N'-diethylamino-5-aminosulfonylphenylpyrimidin-4-yl]-p-carbonyloxy-phenylalanine derivatives.

2-{2-diethylamino-5-[(4-chlorobenzenesulfonyl)methylamino]-pyrimidin-4-ylamino}-3-(4-dimethylcarbamoyloxyphenyl)propionic acid;

2-{2-diethylamino-5-[(4-fluorobenzenesulfonyl)methylamino]-pyrimidin-4-ylamino}-3-(4-dimethylcarbamoyloxyphenyl)propionic acid;

2-{2-diethylamino-5-[(3,4-difluorobenzenesulfonyl)methylamino]-pyrimidin-4-ylamino}-3-(4-dimethylcarbamoyloxyphenyl)propionic acid;

2-{2-diethylamino-5-[(3,4-dichlorobenzenesulfonyl)methylamino]-pyrimidin-4-ylamino}-3-(4-dimethylcarbamoyloxyphenyl)propionic acid;

2-{2-diethylamino-5-[(benzenesulfonyl)methylamino]-pyrimidin-4-ylamino}-3-(4-dimethylcarbamoyloxyphenyl)propionic acid;

2-{2-diethylamino-5-[(2-fluorobenzenesulfonyl)methylamino]-pyrimidin-4-ylamino}-3-(4-dimethylcarbamoyloxyphenyl)propionic acid;

2-{2-diethylamino-5-[(3-fluorobenzenesulfonyl)methylamino]-pyrimidin-4-ylamino}-3-(4-dimethylcarbamoyloxyphenyl)propionic acid;

2-{2-diethylamino-5-[(4-fluorobenzenesulfonyl)isopropylamino]-pyrimidin-4-ylamino}-3-(4-dimethylcarbamoyloxyphenyl)propionic acid;

2-{2-diethylamino-5-[(4-fluorobenzenesulfonyl)ethylamino]-pyrimidin-4-ylamino}-3-(4-dimethylcarbamoyloxyphenyl)propionic acid;

2-{2-diethylamino-5-[(3,4-difluorobenzenesulfonyl)isopropylamino]-pyrimidin-4-ylamino}-3-(4-dimethylcarbamoyloxyphenyl)propionic acid;

2-{2-diethylamino-5-[(4-chlorobenzenesulfonyl)isopropylamino]-pyrimidin-4-ylamino}-3-(4-dimethylcarbamoyloxyphenyl)propionic acid;

2-{2-diethylamino-5-[(3,4-difluorobenzenesulfonyl)ethylamino]-pyrimidin-4-ylamino}-3-(4-dimethylcarbamoyloxyphenyl)propionic acid;

2-{2-diethylamino-5-[(4-chlorobenzenesulfonyl)ethylamino]-pyrimidin-4-ylamino}-3-(4-dimethylcarbamoyloxyphenyl)propionic acid;

2-{2-diethylamino-5-[(4-fluorobenzenesulfonyl)cyclopropylmethylamino]pyrimidin-4-ylamino}-3-(4-dimethylcarbamoyloxyphenyl)propionic acid;

2-{2-diethylamino-5-[(3,5-difluorobenzenesulfonyl)methylamino]-pyrimidin-4-ylamino}-3-(4-dimethylcarbamoyloxyphenyl)propionic acid;

2-{2-diethylamino-5-[(3,5-difluorobenzenesulfonyl)ethylamino]-pyrimidin-4-ylamino}-3-(4-dimethylcarbamoyloxyphenyl)propionic acid;

2-{2-diethylamino-5-[(2,4-difluorobenzenesulfonyl)methylamino]-pyrimidin-4-ylamino}-3-(4-dimethylcarbamoyloxyphenyl)propionic acid;

2-{2-diethylamino-5-[(2,4-difluorobenzenesulfonyl)ethylamino]-pyrimidin-4-ylamino}-3-(4-dimethylcarbamoyloxyphenyl)propionic acid;

2-{2-diethylamino-5-[(3,5-dichlorobenzenesulfonyl)methylamino]-pyrimidin-4-ylamino}-3-(4-dimethylcarbamoyloxyphenyl)propionic acid;

2-{2-diethylamino-5-[(3,5-dichlorobenzenesulfonyl)ethylamino]-pyrimidin-4-ylamino}-3-(4-dimethylcarbamoyloxyphenyl)propionic acid;

2-{2-diethylamino-5-[(4-fluorobenzenesulfonyl)-n-propylamino]-pyrimidin-4-ylamino}-3-(4-dimethylcarbamoyloxyphenyl)propionic acid;

2-{2-diethylamino-5-[(4-fluorobenzenesulfonyl)allylamino]-pyrimidin-4-ylamino}-3-(4-dimethylcarbamoyloxyphenyl)propionic acid;

2-{2-diethylamino-5-[(4-fluorobenzenesulfonyl)isobotylamino]-pyrimidin-4-ylamino}-3-(4-dimethylcarbamoyloxyphenyl)propionic acid;

2-{2-diethylamino-5-[(4-fluorobenzenesulfonyl)-n-butylamino]-pyrimidin-4-ylamino}-3-3-(4-dimethylcarbamoyloxyphenyl)propionic acid;

2-{2-diethylamino-5-[(2,6-difluorobenzenesulfonyl)methylamino]-pyrimidin-4-ylamino}-3-(4-dimethylcarbamoyloxyphenyl)propionic acid;

2-{2-diethylamino-5-[(2,3-difluorobenzenesulfonyl)ethylamino]-pyrimidin-4-ylamino}-3-(4-dimethylcarbamoyloxyphenyl)propionic acid;

2-{2-Diethylamino-5-[(4-fluorobenzenesulfonyl)propargylamino]pyrimidin-4-ylamino}-3-(4-dimethylcarbamoyloxyphenyl)propionic acid;

2-{2-Diethylamino-5-[(2,4-difluorobenzenesulfonyl)propargylamino]pyrimidin-4-ylamino}-3-(4-dimethylcarbamoyloxyphenyl)propionic acid;

2-{2-Diethylamino-5-[(4-fluorobenzenesulfonyl)-(2-trisfluoroethyl)-amino]pyrimidin-4-ylamino}-3-(4-dimethylcarbamoyloxyphenyl)propionic acid;

and pharmaceutically acceptable salts thereof.

The following terms used in the specification and claims with reference to the above formulae XII-XVII have the meanings given below:

"Lower alkyl" refers to monovalent alkyl groups having from 1 to 5 carbon atoms including straight and branched chain alkyl groups. This term is exemplified by groups such as methyl, ethyl, iso-propyl, n-propyl, n-butyl, iso-butyl, sec-butyl, t-butyl, n-pentyl and the like. "Lower alkyl" may be optionally substituted with a halogen, such as chloro, fluoro, bromo and the like.

The term "lower alkylene" refers to divalent alkylene groups of from 1 to 4 carbon atoms including straight and branched chain alkylene groups. This term is exemplified by groups such as methylene, ethylene, n-propylene, iso-propylene (—CH$_2$CH(CH$_3$)— and —CH(CH$_3$)CH$_2$—) and the like.

The term "lower alkynyl" refers to an alkynyl group preferably having from 2 to 6 carbon atoms and having at least 1 site and preferably only 1 site of alkynyl unsaturation (i.e., —C≡C). This term is exemplified by groups such as acetyl (—C≡CH), propargyl (—CH$_2$—C≡CH), 3-butynyl (—CH$_2$CH$_2$C≡CH$_3$) and the like.

The term "lower cycloalkyl" refers to cyclic alkyl groups of from 3 to 6 carbon atoms having a single cyclic ring including, by way of example, cyclopropyl, cyclobutyl, cyclopentyl and cyclohexyl.

The term "lower alkylenecycloalkyl" refers to the group consisting of a lower alkylene-lower cycloalkyl, as defined herein. Such groups are exemplified by methylenecyclopropyl (—CH$_2$-cyclopropyl), ethylenecyclopropyl and the like.

Compound Preparation

The compounds of the above formulae XII-XVII can be prepared from readily available starting materials using the methods and procedures set forth in Examples 36-64 below. These methods and procedures outline specific reaction protocols for preparing N-[2-N',N'-diethylamino-5-aminosulfonylphenyl-pyrimidin-4-yl]-p-carbonyloxy-phenylalanine compounds. Compounds within the scope not exemplified in Examples 36-64 and methods are readily prepared by appropriate substitution of starting materials which are either commercially available or well known in the art.

Other procedures and reaction conditions for preparing the compounds of the above formulae XII-XVII are described in Examples 36-64 set forth below. Additionally, other procedures for preparing compounds useful in certain aspects of the above formulae XII-XVII are disclosed in U.S. Pat. No. 6,492,372 the disclosure of which is incorporated herein by reference in its entirety.

Further description of the compounds of the above formulae XII-XVII and procedures and reaction conditions for preparing these compounds are described in U.S. Patent Application Publication No. 2004/0142954 entitled Heteroaryl Compounds Which Inhibit Leukocyte Adhesion Mediated By Alpha4Integrins, published Jul. 22, 2004, incorporated in its entirety by reference.

In yet another aspect, the compositions that can be utilized are conjugates of formula XVIII below:

$$\boxed{B} - (A)_q \qquad \text{XVIII}$$

wherein:
B is a bio-compatible polymer moiety optionally covalently attached to a branched-arm hub molecule;
q is from about 2 to about 100;
A at each occurrence is independently a compound of formula XIX $$\text{XIX}$$

(structure: J—NH—CH(CH$_2$—Ar$^2$—T)—C(O)—R$^{55}$)

or a pharmaceutically acceptable salt thereof, wherein
J is selected from:
  a) a group of formula (a):

(a) (pyrimidine-type ring with R$^{31}$ and R$^{32}$ substituents)

wherein R$^{31}$ is a covalent bond to the polymer moiety which optionally comprises a linker, or R$^{31}$ is —H, R$^{31'}$, —NH$_2$, —NHR$^{31'}$ or —N(R$^{31'}$)$_2$, —NC$_3$-C$_6$cyclic, —OR$^{31'}$, —SR$^{31'}$, wherein each R$^{31'}$ is independently an optionally substituted straight or branched C$_1$-C$_6$alkyl, optionally substituted C$_3$-C$_6$cycloalkyl, optionally substituted aryl, optionally substituted heteroaryl,
and R$^{32}$ is a covalent bond to the polymer moiety which optionally comprises a linker, or R$^{32}$ is —H, —NO$_2$, haloalkyl or the group —N(MR$^{41}$)R$^{42}$ wherein M is a covalent bond, —C(O)— or —SO$_2$—, R$^{41}$ is R$^{41'}$, N(R$^{41'}$)$_2$, or —OR$^{41'}$,
wherein each R$^{41'}$ is independently hydrogen, an optionally substituted straight or branched C$_1$-C$_6$alkyl, optionally substituted cycloalkyl, optionally substituted aryl, optionally substituted heterocyclic or an optionally substituted heteroaryl, wherein optional substitutions are halide, C$_1$-C$_6$alkyl, or —OC$_1$-C$_6$alkyl,
and R$^{42}$ is hydrogen or R$^{41'}$; and
b) a group of formula (b):

(b) (structure: Ar$^1$—SO$_2$—N within ring containing (—)$_m$, X, (R)$_n$, and attached C(O)—)

wherein R is selected from the group consisting of a covalent bond to the polymer moiety, amino, hydroxyl, substituted amino, alkyl, alkyloxy, aryloxy, heteroaryloxy, heterocyclyloxy, thiol, arylthio, heteroarylthio, heterocyclylthio and substituted alkyl wherein each amino, substituted amino, alkyl and substituted alkyl is optionally covalently bound to the polymer moiety wherein, in each case, the polymer moiety optionally comprises a linker which covalently links the polymer moiety;
Ar$^1$ is selected from the group consisting of aryl, substituted aryl, heteroaryl and substituted heteroaryl wherein each of aryl, substituted aryl, heteroaryl and substituted heteroaryl is optionally covalently bound to the polymer moiety wherein the polymer moiety optionally comprises a linker which covalently links the polymer moiety to Ar$^1$;
Ar$^2$ is selected from the group consisting of aryl, substituted aryl, heteroaryl and substituted heteroaryl wherein each of aryl, substituted aryl, heteroaryl and substituted heteroaryl is optionally covalently bound to the polymer moiety wherein the polymer moiety optionally comprises a linker which covalently links the polymer moiety to Ar$^2$;
X is selected from the group consisting of —NR$^1$—, —O—, —S—, —SO—, —SO$_2$ and optionally substituted —CH$_2$— where R$^1$ is selected from the group consisting of hydrogen and alkyl;
T is selected from:
  a) a group of formula (c)

(c) (structure: —Y—C(O)—W)

wherein Y is selected from the group consisting of —O— and —NR$^1$— wherein R$^1$ is selected from the group consisting of hydrogen and alkyl;
W is selected from the group consisting of a covalent bond to a polymer moiety which optionally comprises a linker and —NR$^2$R$^3$ wherein R$^2$ and R$^3$ are independently selected from the group consisting of hydrogen, alkyl, substituted alkyl, and where R$^2$ and R$^3$, together with the nitrogen atom bound thereto, form a heterocyclic ring or a substituted heterocyclic ring wherein each of alkyl, substituted alkyl, heterocyclic and substituted heterocyclic is optionally covalently bound to a polymer moiety which further optionally comprises a linker;
m is an integer equal to 0, 1 or 2;
n is an integer equal to 0, 1 or 2; and
b) a group of formula (d)

(d) (imidazolidinone ring with G substituent on one N and R$^6$ on other N, C=O)

wherein G is an optionally substituted aryl or optionally substituted heteroaryl 5 or 6 membered ring containing 0 to 3 nitrogens, wherein said aryl or heteroaryl optionally further comprises a covalent bond to a polymer moiety which optionally comprises a linker;

R$^6$ is a covalent bond to a polymer moiety which optionally comprises a linker, or R$^6$ is —H, alkyl, substituted alkyl, or —CH$_2$C(O)R$^{17}$, wherein R$^{17}$ is —OH, —OR$^{18}$, or —NHR$^{18}$, wherein R$^{18}$ is alkyl, substituted alkyl, aryl or substituted aryl;

R$^{55}$ is selected from the group consisting of amino, substituted amino, alkoxy, substituted alkoxy, cycloalkoxy, substituted cycloalkoxy, aryloxy and substituted aryloxy, and —OH;

provided that:

A. at least one of R, Ar$^1$, Ar$^2$, and T contains a covalent bond to the polymer moiety;

B. when R is covalently bound to the polymer moiety, n is one and X is not —O—, —S—, —SO—, or —SO$_2$—;

C. when X is —O— or —NR$^1$—, then m is two; and

D. the conjugate of formula XVIII has a molecular weight of no more than 100,000.

Preferably, the conjugate of formula XVIII has a molecular weight of about 10 to 60 kDa, and more preferably about 40 to 45 kDa.

In one preferred embodiment B is a polyalkyleneoxide polymer. The polyalkylene oxide is a [—O-alkylene-] repeating unit wherein the alkylene is divalent, straight, or branched C$_2$ to C$_4$ alkyl. In any one polymer, the polyalkylene oxide repeating units can be the same or different. The polyalkyleneoxide polymers are covalently attached to a branched-arm hub molecule. The polyalkyleneoxide polymers are present in an amount of repeating units such that the conjugate has a molecular weight of about 10 kDa to 60 kDa.

In one preferred embodiment, only one of R, Ar$^1$, Ar$^2$, W and —NR$^2$R$^3$ contains a covalent bond to a polymer moiety.

In another preferred embodiment, the polymer moiety is attached to the —NR$^2$R$^3$ group.

In yet another preferred embodiment, q is an integer of from 2 to about 20 and more preferably from 2 to about 8.

Preferred conjugates of formula XVIII include those of formula XVIIIa below:

  XVIIIa and pharmaceutically acceptable salts thereof, wherein

B is a di-valent, tri-valent, tetra-valent or higher valency bio-compatible polymer moiety or optionally more than one biocompatible polymers covalently joined by a functional group linkage or by a branched-arm hub molecule or both to form a di-valent, tri-valent, tetra-valent or higher valency polymer moiety;

q is from 2 to about 20;

A at each occurrence is independently a compound of formula XIXa

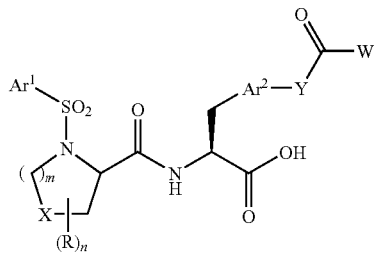  XIXa wherein

R is selected from the group consisting of a covalent bond to the polymer moiety, amino, substituted amino, alkyl and substituted alkyl wherein each amino, substituted amino, alkyl and substituted alkyl is optionally covalently bound to the polymer moiety wherein, in each case, the polymer moiety optionally comprises a linker which covalently links the polymer moiety;

Ar$^1$ is selected from the group consisting of aryl, substituted aryl, heteroaryl and substituted heteroaryl;

Ar$^2$ is selected from the group consisting of aryl, substituted aryl, heteroaryl and substituted heteroaryl wherein each of aryl, substituted aryl, heteroaryl and substituted heteroaryl is optionally covalently bound to the polymer moiety wherein the polymer moiety optionally comprises a linker which covalently links the polymer moiety to Ar$^2$;

X is selected from the group consisting of —NR$^1$—, —O—, —S—, —SO—, —SO$_2$ and optionally substituted —CH$_2$— where R$^1$ is selected from the group consisting of hydrogen and alkyl;

Y is selected from the group consisting of —O— and —NR$^1$— wherein R$^1$ is selected from the group consisting of hydrogen and alkyl;

W is selected from the group consisting of a covalent bond to the polymer moiety which optionally comprises a linker and —NR$^2$R$^3$ wherein R$^2$ and R$^3$ are independently selected from the group consisting of hydrogen, alkyl, substituted alkyl, and where R$^2$ and R$^3$, together with the nitrogen atom bound thereto, form a heterocyclic ring or a substituted heterocyclic ring wherein each of alkyl, substituted alkyl, heterocyclic and substituted heterocyclic is optionally covalently bound to the polymer moiety optionally through a linker;

m is an integer equal to 0, 1 or 2;

n is an integer equal to 0, 1 or 2; and pharmaceutically acceptable salts thereof;

provided that:

A. at least one of R, Ar$^2$, W and —NR$^2$R$^3$ contain a covalent bond to the polymer moiety;

B. when R is covalently bound to the polymer moiety, n is one and X is not —O—, —S—, —SO—, or —SO$_2$—;

C. when X is —O— or —NR$^1$—, then m is two; and

D. the conjugate of formula XVIIIa has a molecular weight of no more than 60,000.

Preferably, the conjugate of formula XVIIIa has a molecular weight of about 10 to 60 kDa, and more preferably about 40 to 45 kDa.

In one preferred embodiment B is a polyalkyleneoxide polymer. The polyalkylene oxide is a [—O-alkylene-] repeating unit wherein the alkylene is divalent, straight, or branched C$_2$ to C$_4$ alkyl. In any one polymer, the polyalkylene oxide repeating units can be the same or different. The polyalkyleneoxide polymers are covalently attached to a branched-arm hub molecule. The polyalkyleneoxide polymers are present in an amount of repeating units such that the conjugate has a molecular weight of about 10 kDa to 60 kDa.

Preferred conjugates of formula XVIII include those of formula XVIIIb below:

XVIIIb wherein each A is independently a compound of formula XIXb below:

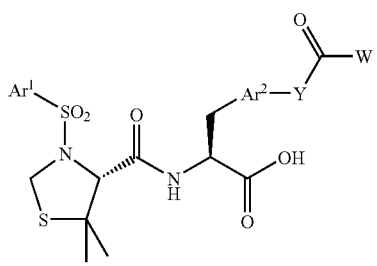

XIXb and wherein q is 2 to about 20;

B is as defined above;

$Ar^1$ is selected from the group consisting of aryl, substituted aryl, heteroaryl and substituted heteroaryl;

$Ar^2$ is selected from the group consisting of aryl, substituted aryl, heteroaryl and substituted heteroaryl wherein each of aryl, substituted aryl, heteroaryl and substituted heteroaryl is optionally covalently bound to a polymer moiety wherein the polymer moiety optionally comprises a linker which covalently links the polymer moiety to $Ar^2$;

Y is selected from the group consisting of —O— and —$NR^1$— wherein $R^1$ is selected from the group consisting of hydrogen and alkyl;

W is selected from the group consisting of a covalent bond to a polymer moiety which optionally comprises a linker and —$NR^2R^3$ wherein $R^2$ and $R^3$ are independently selected from the group consisting of hydrogen, alkyl, substituted alkyl, and where $R^2$ and $R^3$, together with the nitrogen atom bound thereto, form a heterocyclic ring or a substituted heterocyclic ring wherein each of alkyl, substituted alkyl, heterocyclic and substituted heterocyclic is optionally covalently bound to the polymer moiety which further optionally comprises a linker;

provided that at least one of $Ar^2$, W and —$NR^2R^3$ is covalently bound to a polymer moiety which optionally comprises a linker;

and further provided that the conjugate of formula XVIIIb has a molecular weight of no more than 60,000.

Preferred conjugates of formula XVIII include those of formula XVIII c below:

XVIIIc wherein each A is independently a compound of formula XIXc below:

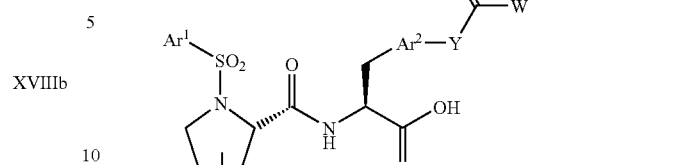

XIXc and wherein q is 2 to about 20;

B is as defined above;

R is selected from the group consisting of a covalent bond to a polymer moiety, amino, substituted amino, alkyl and substituted alkyl wherein each amino, substituted amino, alkyl and substituted alkyl is optionally covalently bound to the polymer moiety wherein, in each case, the polymer moiety optionally comprises a linker which covalently links the polymer moiety;

$Ar^1$ is selected from the group consisting of aryl, substituted aryl, heteroaryl and substituted heteroaryl;

$Ar^2$ is selected from the group consisting of aryl, substituted aryl, heteroaryl and substituted heteroaryl wherein each of aryl, substituted aryl, heteroaryl and substituted heteroaryl is optionally covalently bound to a polymer moiety wherein the polymer moiety optionally comprises a linker which covalently links the polymer moiety to $Ar^2$;

Y is selected from the group consisting of —O— and —$NR^1$— wherein $R^1$ is selected from the group consisting of hydrogen and alkyl;

W is selected from the group consisting of a covalent bond to a polymer moiety which optionally comprises a linker and —$NR^2R^3$ wherein $R^2$ and $R^3$ are independently selected from the group consisting of hydrogen, alkyl, substituted alkyl, and where $R^2$ and $R^3$, together with the nitrogen atom bound thereto, form a heterocyclic ring or a substituted heterocyclic ring wherein each of alkyl, substituted alkyl, heterocyclic and substituted heterocyclic is optionally covalently bound to a polymer moiety which further optionally comprises a linker;

n is an integer equal to 0, 1 or 2; and pharmaceutically acceptable salts thereof;

provided that at least one of R, $Ar^2$, W and —$NR^2R^3$ is covalently bound to a polymer moiety which optionally comprises a linker;

and further provided that the conjugate of formula XVIIIc has a molecular weight of no more than 60,000.

Preferred conjugates of formula XVIII include those of formula XVIIId below:

XVIIId wherein each A is independently a compound of formula XIXd below:

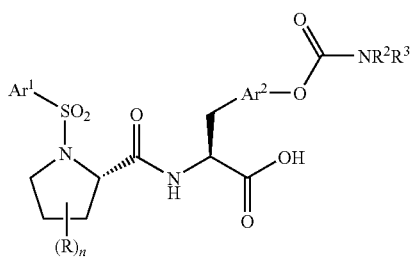

XIXd

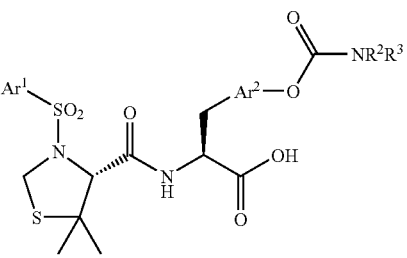

XIXe and wherein q is 2 to about 20;

B is as defined above;

R is selected from the group consisting of a covalent bond to a polymer moiety, amino, substituted amino, alkyl and substituted alkyl wherein each amino, substituted amino, alkyl and substituted alkyl is optionally covalently bound to a polymer moiety wherein, in each case, the polymer moiety optionally comprises a linker which covalently links the polymer moiety;

$Ar^1$ is selected from the group consisting of aryl, substituted aryl, heteroaryl and substituted heteroaryl;

$Ar^2$ is selected from the group consisting of aryl, substituted aryl, heteroaryl and substituted heteroaryl wherein each of aryl, substituted aryl, heteroaryl and substituted heteroaryl is optionally covalently bound to a polymer moiety wherein the polymer moiety optionally comprises a linker which covalently links the polymer moiety to $Ar^2$;

$R^2$ and $R^3$ are independently selected from the group consisting of hydrogen, alkyl, substituted alkyl, and where $R^2$ and $R^3$, together with the nitrogen atom bound thereto, form a heterocyclic ring or a substituted heterocyclic ring wherein each of alkyl, substituted alkyl, heterocyclic and substituted heterocyclic is optionally covalently bound to a polymer moiety which further optionally comprises a linker;

n is an integer equal to 0, 1 or 2; and pharmaceutically acceptable salts thereof;

provided that at least one of R, $Ar^2$, and $-NR^2R^3$ is covalently bound to a polymer which optionally comprises a linker;

and further provided that the conjugate of formula XVIIId has a molecular weight of no more than 100,000.

Preferred conjugates of formula XVIII include those of formula XVIIIe below:

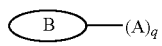

XVIIIe wherein each A is independently a compound of formula XIXe below:

and wherein q is 2 to about 20;

B is as defined above;

$Ar^1$ is selected from the group consisting of aryl, substituted aryl, heteroaryl and substituted heteroaryl;

$Ar^2$ is selected from the group consisting of aryl, substituted aryl, heteroaryl and substituted heteroaryl wherein each of aryl, substituted aryl, heteroaryl and substituted heteroaryl is optionally covalently bound to a polymer moiety wherein the polymer moiety optionally comprises a linker which covalently links the polymer moiety to $Ar^2$;

$R^2$ and $R^3$ are independently selected from the group consisting of hydrogen, alkyl, substituted alkyl, and where $R^2$ and $R^3$, together with the nitrogen atom bound thereto, form a heterocyclic ring or a substituted heterocyclic ring wherein each of alkyl, substituted alkyl, heterocyclic and substituted heterocyclic is optionally covalently bound to a polymer moiety which further optionally comprises a linker; and pharmaceutically acceptable salts thereof;

provided that at least one of $Ar^2$ and $-NR^2R^3$ is covalently bound to a polymer moiety which optionally comprises a linker;

and further provided that the conjugate of formula XVIIIe has a molecular weight of not more than 60,000.

Preferred conjugates of formula XVIII include those of formula XVIIIf below:

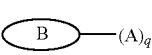

XVIIIf wherein each A is independently a compound of formula XIXf below:

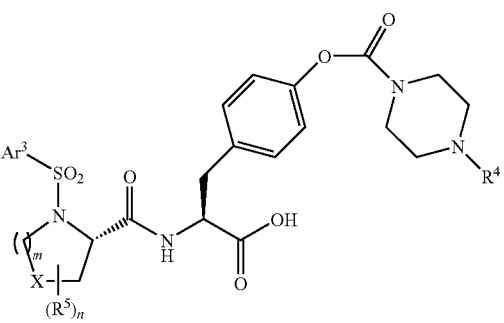

XIXf and wherein q is 2 to about 20;

B is as defined above;

$R^4$ is covalently bound to a polymer moiety which optionally comprises a linker;

$R^5$ is selected from the group consisting of alkyl and substituted alkyl;

$Ar^3$ is selected from the group consisting of aryl, substituted aryl, heteroaryl and substituted heteroaryl;

X is selected from the group consisting of —$NR^1$—, —O—, —S—, —SO—, —$SO_2$— and optionally substituted —$CH_2$— where $R^1$ is selected from the group consisting of hydrogen and alkyl;

m is an integer equal to 0, 1 or 2;

n is an integer equal to 0, 1 or 2; and pharmaceutically acceptable salts thereof;

provided that:

A. when R is covalently bound to the polymer moiety, n is one and X is not —O—, —S—, —SO—, or —$SO_2$—;

B. when X is —O— or —$NR^1$—, then m is two; and

C. the conjugate of formula XVIIIf has a molecular weight of no more than 60,000.

Preferred conjugates of formula XVIII include those of formula XVIIIg below:

XVIIIg wherein each A is independently a compound of formula XIXg below:

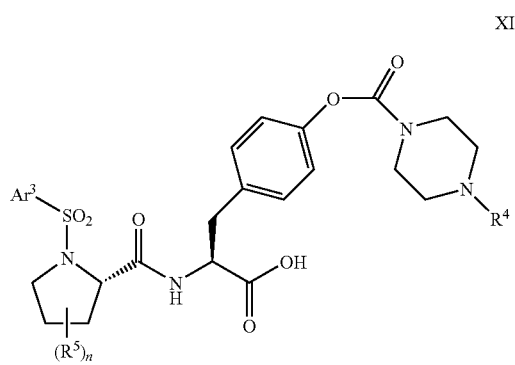

XIXg and wherein q is 2 to about 20;

B is as defined above;

$R^4$ is covalently bound to a polymer moiety which optionally comprises a linker;

$R^5$ is selected from the group consisting of alkyl and substituted alkyl;

$Ar^3$ is selected from the group consisting of aryl, substituted aryl, heteroaryl and substituted heteroaryl;

n is an integer equal to 0, 1 or 2; and pharmaceutically acceptable salts thereof;

provided that the conjugate of formula XVIIIg has a molecular weight of not more than 60,000.

Preferred conjugates of formula XVIII include those of formula XVIIIh below:

XVIIIh wherein each A is independently a compound of formula XIXh below:

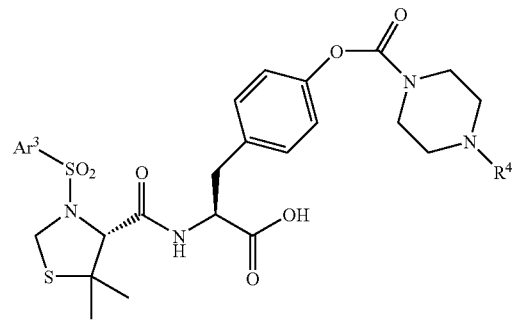

XIXh and wherein q is 2 to about 20;

$R^4$ is covalently bound to a polymer moiety which optionally comprises a linker;

$Ar^3$ is selected from the group consisting of aryl, substituted aryl, heteroaryl and substituted heteroaryl;

pharmaceutically acceptable salts thereof;

provided that the conjugate of formula XVIIIh has a molecular weight of not more than 60,000.

Preferred conjugates of formula XVIII include those of formula XVIIIi below:

XVIIIi wherein each A is independently a compound of formula XIXi below:

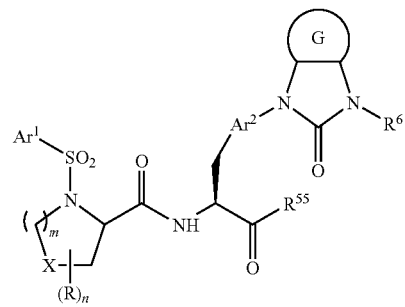

XIXi or a pharmaceutically acceptable salt thereof, and wherein q is 2 to about 20;

and provided that the conjugate of formula XVIIIi has a molecular weight of no more than 60,000.

Preferred conjugates of formula XVIII include those of formula XVIIIj below:

XVIIIj wherein each A is independently a compound of formula XIXj below:

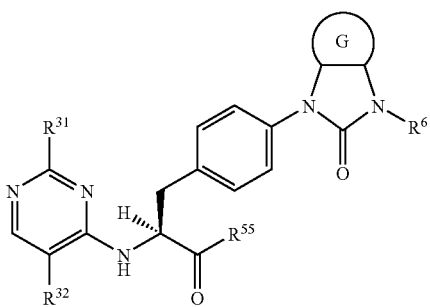

or a pharmaceutically acceptable salt thereof,
and wherein q is about 2 to about 20;

and provided that the conjugate of formula XVIIIj has a molecular weight of no more than 100,000.

Preferably, $Ar^1$ in formulae XIXa-XIXe and $Ar^3$ in formulae XIXf-XIXh are independently selected from the group consisting of:

phenyl,
4-methylphenyl,
4-t-butylphenyl,
2,4,6-trimethylphenyl,
2-fluorophenyl,
3-fluorophenyl,
4-fluorophenyl,
2,4-difluorophenyl,
3,4-difluorophenyl,
3,5-difluorophenyl,
2-chlorophenyl,
3-chlorophenyl,
4-chlorophenyl,
3,4-dichlorophenyl,
3,5-dichlorophenyl,
3-chloro-4-fluorophenyl,
4-bromophenyl,
2-methoxyphenyl,
3-methoxyphenyl,
4-methoxyphenyl,
3,4-dimethoxyphenyl,
4-t-butoxyphenyl,
4-(3'-dimethylamino-n-propoxy)-phenyl,
2-carboxyphenyl,
2-(methoxycarbonyl)phenyl,
4-($H_2NC(O)$-)phenyl,
4-($H_2NC(S)$-)phenyl,
4-cyanophenyl,
4-trifluoromethylphenyl,
4-trifluoromethoxyphenyl,
3,5-di-(trifluoromethyl)phenyl,
4-nitrophenyl,
4-aminophenyl,
4-($CH_3C(O)NH$—)phenyl,
4-(phenylNHC(O)NH—)phenyl,
4-amidinophenyl,
4-methylamidinophenyl,
4-[$CH_3SC(=NH)$-]phenyl,
4-chloro-3-[$H_2NS(O)_2$-]phenyl,
1-naphthyl,
2-naphthyl,
pyridin-2-yl,
pyridin-3-yl,
pyridin-4-yl,
pyrimidin-2-yl,
quinolin-8-yl,
2-(trifluoroacetyl)-1,2,3,4-tetrahydroisoquinolin-7-yl,
2-thienyl,
5-chloro-2-thienyl,
2,5-dichloro-4-thienyl,
1-N-methylimidazol-4-yl,
1-N-methylpyrazol-3-yl,
1-N-methylpyrazol-4-yl,
1-N-butylpyrazol-4-yl,
1-N-methyl-3-methyl-5-chloropyrazol-4-yl,
1-N-methyl-5-methyl-3-chloropyrazol-4-yl,
2-thiazolyl and
5-methyl-1,3,4-thiadiazol-2-yl.

Preferably, when A is of the formulae XIXa, XIXb, XIXc, XIXd, and XIXe, and $Ar^1$ is bound to a polymer moiety, then $Ar^1$ is of the formula:

wherein $Ar^1$ is selected from the group consisting of aryl, substituted aryl, heteroaryl, and substituted heteroaryl, Z is selected from the group consisting of a covalent bond, a linking group of from 1 to 40 atoms, —O—, and —$NR^9$—, where $R^9$ is selected from the group consisting of hydrogen and alkyl, $R^7$ is selected from the group consisting of hydrogen and methyl;

$R^8$ is selected from the group consisting of -$(L)_w$-A when p is greater than about 300 and $(L)$-B-$(A)_{q-1}$, wherein A is represented by any of formulae XIXa through XIXh above, L is a linking group of from 1 to 40 atoms and w is zero or one: and p is an integer of from about 200 to 1360.

When A is of the Formulae XIXa or XIXf, and R is not bound to a polymer moiety, the substituent of the following formula:

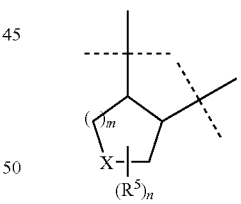

where $R^5$, X, m and n are as defined above, is preferably selected from the group consisting of azetidinyl, thiazolidinyl, piperidinyl, piperazinyl, morpholino, thiomorpholinyl, pyrrolidinyl, 4-hydroxypyrrolidinyl, 4-oxopyrrolidinyl, 4-fluoropyrrolidinyl, 4,4-difluoropyrrolidinyl, 4-(thiomorpholin-4-yl$C(O)O$—)pyrrolidinyl, 4-[$CH_3S(O)_2O$—]pyrrolidinyl, 3-phenylpyrrolidinyl, 3-thiophenylpyrrolidinyl, 4-amino-pyrrolidinyl, 3-methoxypyrrolidinyl, 4,4-dimethylpyrrolidinyl, 4-N-Cbz-piperazinyl, 4-[$CH_3S(O)_2$-]piperazinyl, 5,5-dimethylthiazolindin-4-yl, 1,1-dioxo-thiazolidinyl, 1,1-dioxo-5,5-dimethylthiazolidin-2-yl and 1,1-dioxothiomorpholinyl.

Preferably, when A is of the formulae XIXa and the substituent of the formula:

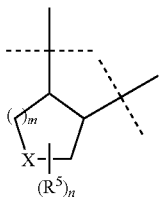

is bound to the polymer moiety, then preferably the substituent is of the formula:

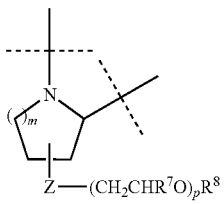

wherein m is an integer equal to zero, one or two;

Z is selected from the group consisting of a covalent bond, a linking group of from 1 to 40 atoms, —O—, —NR$^9$—, where R$^9$ is selected from the group consisting of hydrogen and alkyl, R$^7$ is selected from the group consisting of hydrogen and methyl;

p is an integer of from 0 to about 1360;

R$^8$ is selected from the group consisting of —B-(A)$_{q-1}$, and A when p is greater than about 300, and A is represented by any of formulae XIXa through XIXh above.

When A is of the formula XIXa, XIXb, XIXc, XIXd, XIXe and when Ar$^2$ is not bound to a polymer moiety, then preferably Ar$^2$ is selected from the group consisting of phenyl, substituted phenyl, 2-pyridinyl, 3-pyridinyl, 4-pyridinyl, and 4-pyridin-2-onyl.

When A is of the formula XIXa, XIXb, XIXc, XIXd, XIXe and when Ar$^2$ is bound to a polymer moiety, then Ar$^2$ is preferably represented by the formula:

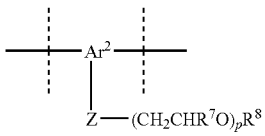

where Ar$^2$ is selected from the group consisting of aryl, substituted aryl, heteroaryl and substituted heteroaryl;

Z is selected from the group consisting of a covalent bond, a linking group of from 1 to 40 atoms, —O—, —NR$^9$—, amide, carbamate and urea, where R$^9$ is selected from the group consisting of hydrogen and alkyl, R$^7$ is selected from the group consisting of hydrogen and methyl;

p is an integer of from 0 to about 1360;

R$^8$ is selected from the group consisting of —B-(A)$_{q-1}$, and A when p is greater than about 300, and A is represented by any of formulae XIXa through XIXh above.

In one preferred embodiment, —YC(O)W is —OC(O)NR$^2$R$^3$.

When A is of the formulae XIXa, XIXb, or XIXc, —YC(O)W is —OC(O)NR$^2$R$^3$ and neither R$^2$ nor R$^3$ are bound to a polymer moiety, then preferably —OC(O)NR$^2$R$^3$ is selected from the group consisting of:
(CH$_3$)$_2$NC(O)O—,
(piperidin-1-yl)-C(O)O—,
(piperidin-4-yl)-C(O)O—,
(1-methylpiperidin-4-yl)-C(O)O—,
(4-hydroxypiperidin-1-yl)-C(O)O—,
(4-formyloxypiperidin-1-yl)-C(O)O—,
(4-ethoxycarbonylpiperidin-1-yl)-C(O)O—,
(4-carboxylpiperidin-1-yl)-C(O)O—,
(3-hydroxymethylpiperidin-1-yl)-C(O)O—,
(4-hydroxymethylpiperidin-1-yl)-C(O)O—,
(4-phenyl-1-Boc-piperidin-4-yl)-C(O)O—,
(4-piperidon-1-yl ethylene ketal)-C(O)O—,
(piperazin-4-yl)-C(O)O—,
(1-Boc-piperazin-4-yl)-C(O)O—,
(4-methylpiperazin-1-yl)-C(O)O—,
(4-methylhomopiperazin-1-yl)-C(O)O—,
(4-(2-hydroxyethyl)piperazin-1-yl)-C(O)O—,
(4-phenylpiperazin-1-yl)-C(O)O—,
(4-(pyridin-2-yl)piperazin-1-yl)-C(O)O—,
(4-(4-trifluoromethylpyridin-2-yl)piperazin-1-yl)-C(O)O—,
(4-(pyrimidin-2-yl)piperazin-1-yl)-C(O)O—,
(4-acetylpiperazin-1-yl)-C(O)O—,
(4-(phenyl-C(O)-)piperazin-1-yl)-C(O)O—,
(4-(pyridin-4'-yl-C(O)-)piperazin-1-yl)-C(O)O—,
(4-(phenyl-N H C(O)-)piperazin-1-yl)-C(O)O—,
(4-(phenyl-N H C(S)-)piperazin-1-yl)-C(O)O—,
(4-methanesulfonylpiperazin-1-yl)-C(O)O—,
(4-trifluoromethanesulfonylpiperazin-1-yl)-C(O)O—,
(morpholin-4-yl)-C(O)O—,
(thiomorpholin-4-yl)-C(O)O—,
(thiomorpholin-4'-yl sulfone)-C(O)O—,
(pyrrolidin-1-yl)-C(O)O—,
(2-methylpyrrolidin-1-yl)-C(O)O—,
(2-(methoxycarbonyl)pyrrolidin-1-yl)-C(O)O—,
(2-(hydroxymethyl)pyrrolidin-1-yl)-C(O)O—,
(2-(N,N-dimethylamino)ethyl)(CH$_3$)NC(O)O—,
(2-(N-methyl-N-toluene-4-sulfonylamino)ethyl)(CH$_3$)N—C(O)O—,
(2-(morpholin-4-yl)ethyl)(CH$_3$)NC(O)O—,
(2-(hydroxy)ethyl)(CH$_3$)NC(O)O—,
bis(2-(hydroxy)ethyl)NC(O)O—,
(2-(formyloxy)ethyl)(CH$_3$)NC(O)O—,
(CH$_3$OC(O)CH$_2$)HNC(O)O—, and
2-(phenylNHC(O)O—)ethyl-]HNC(O)O—.

When A is of the formulae XIXa, XIXb, or XIXc, —YC(O)W is —OC(O)NR$^2$R$^3$ and R$^2$ and/or R$^3$ are/is bound to the polymer moiety, the polymer moiety is preferably represented by the formula:

Z is selected from the group consisting of a covalent bond, a linking group of from 1 to 40 atoms, —O—, —NR$^9$—, amide, carbamate and urea, where R$^9$ is selected from the group consisting of hydrogen and alkyl, R$^7$ is selected from the group consisting of hydrogen and methyl;

p is an integer of from 0 to about 1360;

R$^8$ is selected from the group consisting of —B-(A)$_{q-1}$, and A when p is greater than about 300, and A is represented by any of formulae XIXa through XIXh above.

In the compounds of formulae XIXi and XIXj, it is preferred that that the group of

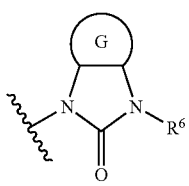

is of the formula:

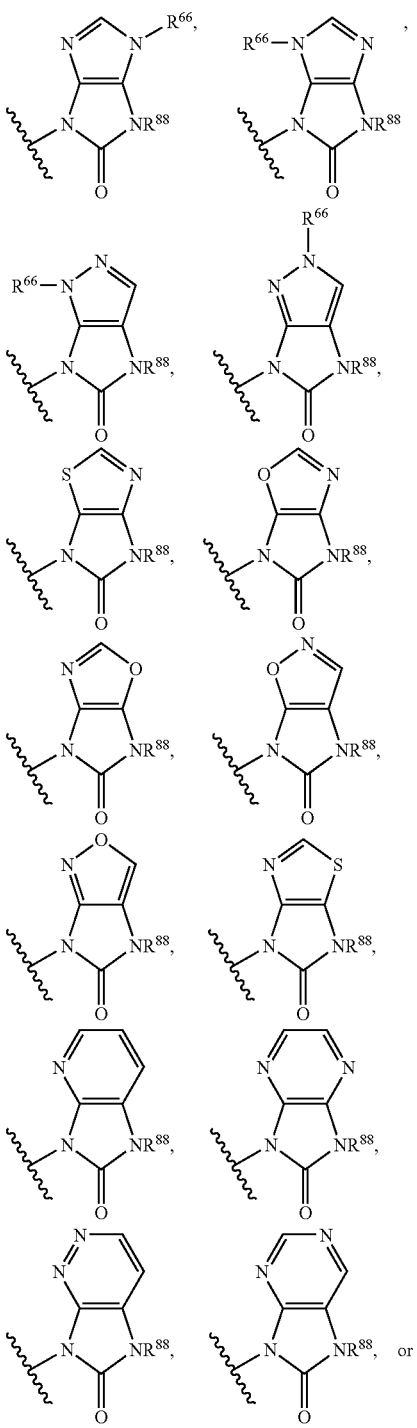

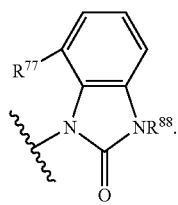

wherein $R^{66}$ is a covalent bond to the polymer moiety which optionally comprises a linker, or $R^{66}$ is hydrogen or straight or branched $C_1$-$C_6$alkyl; $R^{77}$ is a covalent bond to a polymer moiety which optionally comprises a linker, or $R^{77}$ is hydrogen, halogen or straight or branched $C_1$-$C_6$alkoxy; and $R^{88}$ is a covalent bond to the polymer moiety which optionally comprises a linker, or $R^{88}$ is hydrogen or straight or branched $C_1$-$C_6$alkyl Preferably, one of $R^{66}$, $R^{77}$, and $R^{88}$ is a covalent bond to the polymer moiety which optionally comprises a linker.

Preferred compounds of formula XIXi are also those of the formula XIXi-a:

XIXi-a

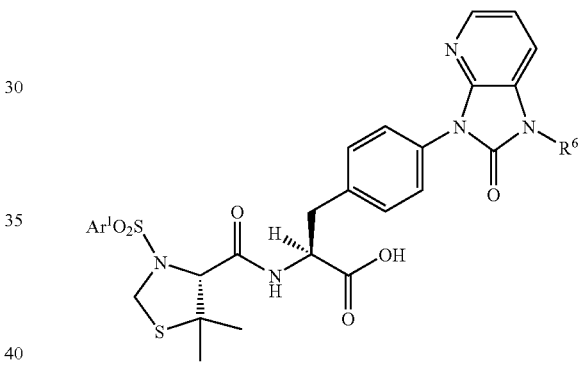

and pharmaceutically acceptable salts thereof, wherein $Ar^1$ is selected from the group consisting of alkyl, substituted alkyl, aryl, substituted aryl, cycloalkyl, substituted cycloalkyl, heterocyclic, substituted heterocyclic, heteroaryl and substituted heteroaryl; and $R^6$ is a covalent bond to a polymer moiety which optionally comprises a linker.

Preferred compounds of formula XIXi-a include those wherein $Ar^1$ is phenyl or a 5- or 6-membered heteroaryl group having at least one nitrogen atom, each of which is optionally substituted with halogen, hydroxy, $C_1$-$C_6$ alkoxy, $C_1$-$C_6$ alkyl, nitro, trifluoromethyl, amino, mono- or di($C_1$-$C_6$)alkylamino, amino($C_1$-$C_6$)alkyl, $C_2$-$C_6$ acyl, $C_2$-$C_6$ acylamino, or amino($C_1$-$C_6$)acyl. $Ar^1$ is pyridyl optionally substituted with halogen, hydroxy, $C_1$-$C_6$ alkyl, $C_1$-$C_6$ alkoxy, nitro, trifluoromethyl, amino, mono- or di($C_1$-$C_6$)alkylamino, amino($C_1$-$C_6$)alkyl, $C_2$-$C_6$ acyl, $C_2$-$C_6$ acylamino, or amino($C_1$-$C_6$)acyl. Particularly preferred compounds of Formula XIXi-a include those where $Ar^1$ is pyridyl optionally substituted with $C_1$-$C_6$ alkyl, hydroxy, halogen, $C_1$-$C_6$ alkoxy, nitro, trifluoromethyl, amino, or mono- or di($C_1$-$C_6$)alkylamino.

Preferred compounds of formula XIXj are also those of the formula XIXj-a:

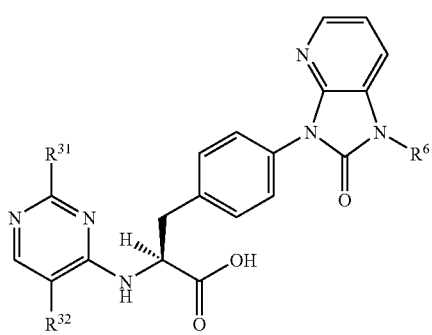

XIXj-a and pharmaceutically acceptable salts thereof, wherein
$R^6$ is a covalent bond to a polymer moiety which optionally comprises a linker.

Preferred compounds of Formula XIXj-a include those where $R^{31}$ is amino or mono- or di($C_1$-$C_6$)alkylamino; and $R^{32}$ is —H, —$NO_2$ or haloalkyl, more preferably trifluoromethylethyl.

Still other preferred compounds of Formula XIXj-a are those where
$R^{31}$ is amino or mono- or di($C_1$-$C_6$)alkylamino; and
$R^{32}$ is —N($MR^{41}$)$R^{42}$; where M is —$SO_2$— or —CO—;
$R^{41}$ is $C_1$-$C_6$ alkyl optionally substituted with halogen, hydroxy, $C_1$-$C_6$ alkoxy, amino, or mono- or di($C_1$-$C_6$)alkylamino; or
phenyl or a 5- or 6-membered heteroaryl containing at least one nitrogen, each of which is optionally substituted with halogen, hydroxy, $C_1$-$C_6$ alkyl, $C_1$-$C_6$ alkoxy, $C_3$-$C_7$ cycloalkyl, amino, nitro, trifluoromethyl, or mono- or di($C_1$-$C_6$)alkylamino; and
$R^{42}$ is hydrogen, $C_1$-$C_6$alkyl, or $C_3$-$C_7$cycloalkyl.

Further preferred compounds of formula XIXj-a include those wherein
$R^{41}$ groups within formula XIXj-a are $C_1$-$C_4$ alkyl optionally substituted with halogen, hydroxy, $C_1$-$C_6$ alkoxy, amino, or mono- or di($C_1$-$C_6$)alkylamino; or pyridyl or pyrimidinyl, each of which is optionally substituted with halogen, hydroxy, $C_1$-$C_3$ alkyl, $C_1$-$C_3$ alkoxy, amino, or mono- or di($C_1$-$C_4$)alkylamino; and
$R^{42}$ is hydrogen, $C_1$-$C_4$alkyl, or $C_3$-$C_7$cycloalkyl.

In one example, the conjugates of formula XVIII are divalent and are represented by formula XX:

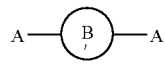

XX where each A is independently as defined above and B' is —Z'—($CH_2CHR^7O$)$_p$—Z'—where each Z' is independently a covalent bond or a linking group, $R^7$ is hydrogen or methyl and p is an integer of from about 100 to 1360. Preferably p provides a conjugate with a molecular weight of from about 10 to 60 kDa, more preferably from about 40-45 kDa.

In another example, the conjugates of formula XVIII are trivalent to decavalent and are preferably represented by formula XXI:

XXI where each A is independently as defined above and t is an integer from 3 to 10. Preferably t provides a conjugate with a molecular weight of from about 10 to 60 kDa, more preferably from about 40 to 45 kDa.

In a further aspect, the compounds that can be utilized are conjugates of the following formula XXII

XXII

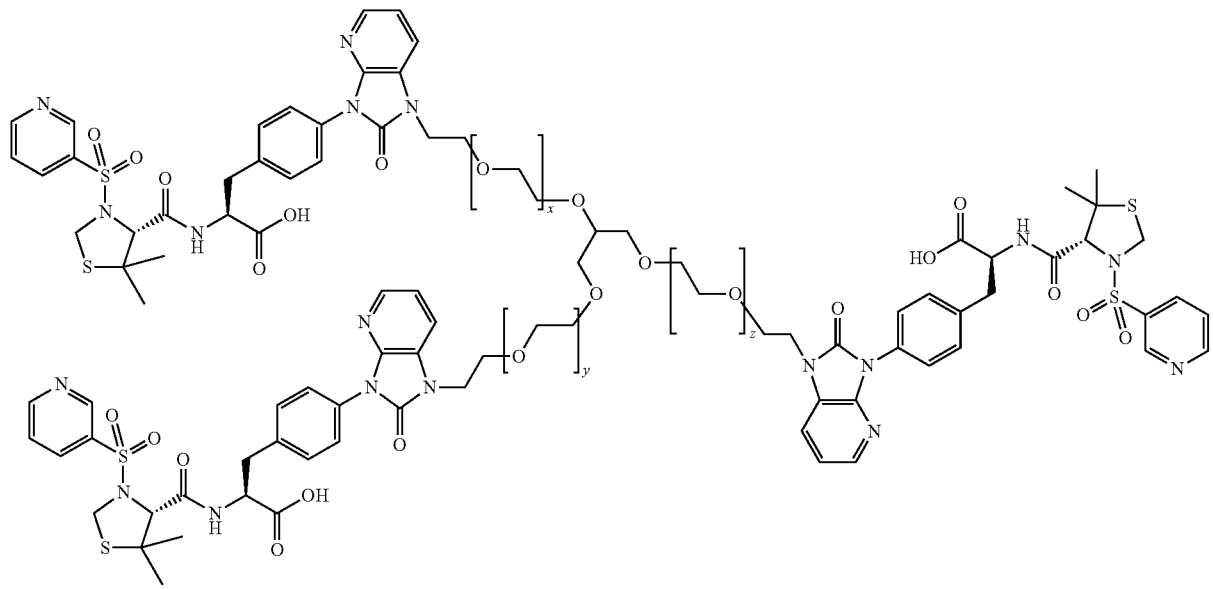

wherein x, y, and z are independently an integer such that the aggregate of x, y, and z is about 100 to 1360.

In an embodiment, x, y, and z are independently an integer such that there are a sufficient number of [—O—CH$_2$—CH$_2$—] repeating units that the conjugate of formula XXII has a molecular weight of about 10-60 kDa, preferably about 40-45 kDa.

The following terms used in the specification and claims with reference to the above formulae XVIII-XXII have the meanings given below:

"Alkyl" refers to monovalent saturated aliphatic hydrocarbyl groups having from 1 to 5 carbon atoms and more preferably 1 to 3 carbon atoms. This term is exemplified by groups such as methyl, ethyl, n-propyl, iso-propyl, n-butyl, t-butyl, n-pentyl and the like.

"Substituted alkyl" refers to an alkyl group having from 1 to 3, and preferably 1 to 2, substituents selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, spirocycloalkyl, heteroaryl, substituted heteroaryl, heterocyclic, and substituted heterocyclic.

"Alkylene" refers to divalent saturated aliphatic hydrocarbyl groups preferably having from 1 to 5 and more preferably 1 to 3 carbon atoms which are either straight-chained or branched. This term is exemplified by groups such as methylene (—CH$_2$—), ethylene (—CH$_2$CH$_2$—), n-propylene (—CH$_2$CH$_2$CH$_2$—), iso-propylene (—CH$_2$CH(CH$_3$)—) and the like.

"Alkoxy" refers to the group "alkyl-O—" which includes, by way of example, methoxy, ethoxy, n-propoxy, iso-propoxy, n-butoxy, t-butoxy, sec-butoxy, n-pentoxy and the like.

"Substituted alkoxy" refers to the group "substituted alkyl-O—".

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)-cycloalkyl-C(O)—, substituted cycloalkyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminoacyl" refers to the group —C(O)NR$^{10}$R$^{10}$ where each R$^{10}$ is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where each R10 is joined to form together with the nitrogen atom a heterocyclic or substituted heterocyclic ring wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Alkenyl" refers to alkenyl groups having from 2 to 6 carbon atoms and preferably 2 to 4 carbon atoms and having at least 1 and preferably from 1 to 2 sites of alkenyl unsaturation. Such groups are exemplified by vinyl, allyl, but-3-en-1-yl, and the like.

"Substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic with the proviso that any hydroxyl substitution is not attached to a vinyl (unsaturated) carbon atom.

"Alkynyl" refers to alkynyl groups having from 2 to 6 carbon atoms and preferably 2 to 3 carbon atoms and having at least 1 and preferably from 1 to 2 sites of alkynyl unsaturation.

"Substituted alkynyl" refers to alkynyl groups having from 1 to 3 substituents, and preferably 1 to 2 substituents, selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic.

"Amino" refers to the group —NH$_2$.

"Cyano" refers to the group —CN.

"Substituted amino" refers to the group —NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where R' and R" are joined, together with the nitrogen bound thereto to form a heterocyclic or substituted heterocyclic group provided that R' and R" are both not hydrogen. When R' is hydrogen and R" is alkyl, the substituted amino group is sometimes referred to herein as alkylamino. When R' and R" are alkyl, the substituted amino group is sometimes referred to herein as dialkylamino. When referring to a monosubstituted amino, it is meant that either R' or R" is hydrogen but not both. When referring to a disubstituted amino, it is meant that neither R' or R" is hydrogen.

"Nitro" refers to the group —NO$_2$.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is at an aromatic carbon atom. Preferred aryls include phenyl and naphthyl.

"Substituted aryl" refers to aryl groups which are substituted with from 1 to 3 substituents, and preferably 1 to 2 substituents, selected from the group consisting of hydroxy, acyl, acylamino, acyloxy, alkyl, substituted alkyl, alkoxy, substituted alkoxy, alkenyl, substituted alkenyl, alkynyl, substituted alkynyl, amino, substituted amino, aminoacyl, aryl, substituted aryl, aryloxy, substituted aryloxy, carboxyl, carboxyl esters, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, halo, nitro, heteroaryl, substituted heteroaryl, heterocyclic, substituted heterocyclic, heteroaryloxy, substituted heteroaryloxy, heterocyclyloxy, substituted heterocyclyloxy, amino sulfonyl (NH$_2$—SO$_2$—), and substituted amino sulfonyl.

"Aryloxy" refers to the group aryl-O— that includes, by way of example, phenoxy, naphthoxy, and the like.

"Substituted aryloxy" refers to substituted aryl-O— groups.

"Carboxyl" refers to —COOH or salts thereof.

"Carboxyl ester" refers to the groups —C(O)O-alkyl, —C(O)O-substituted alkyl, —C(O)-aryl, and —C(O)O-substituted aryl wherein alkyl, substituted alkyl, aryl and substituted aryl are as defined herein.

"Cycloalkyl" refers to cyclic alkyl groups of from 3 to 10 carbon atoms having single or multiple cyclic rings including, by way of example, adamantyl, cyclopropyl, cyclobutyl, cyclopentyl, cyclooctyl and the like.

"Cycloalkenyl" refers to cyclic alkenyl groups of from 4 to 10 carbon atoms having single or multiple cyclic rings and further having at least 1 and preferably from 1 to 2 internal sites of ethylenic or vinyl (>C=C<) unsaturation.

"Substituted cycloalkyl" and "substituted cycloalkenyl" refers to an cycloalkyl or cycloalkenyl group, having from 1 to 5 substituents selected from the group consisting of oxo (=O), thioxo (=S), alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic.

"Cycloalkoxy" refers to —O-cycloalkyl groups.

"Substituted cycloalkoxy" refers to —O-substituted cycloalkyl groups.

"Halo" or "halogen" refers to fluoro, chloro, bromo and iodo and preferably is fluoro or chloro.

"Hydroxy" refers to the group —OH.

"Heteroaryl" refers to an aromatic group of from 1 to 10 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. Preferred heteroaryls include pyridinyl, pyrrolyl, indolyl, thiophenyl, and furanyl.

"Substituted heteroaryl" refers to heteroaryl groups that are substituted with from 1 to 3 substituents selected from the same group of substituents defined for substituted aryl.

"Heteroaryloxy" refers to the group —O-heteroaryl and "substituted heteroaryloxy" refers to the group —O-substituted heteroaryl.

"Heterocycle" or "heterocyclic" or "heterocycloalkyl" or "heterocyclyl" refers to a saturated or unsaturated group having a single ring or multiple condensed rings, from 1 to 10 carbon atoms and from 1 to 4 hetero atoms selected from the group consisting of nitrogen, sulfur or oxygen within the ring wherein, in fused ring systems, one or more the rings can be cycloalkyl, aryl or heteroaryl provided that the point of attachment is through the heterocyclic ring.

"Substituted heterocyclic" or "substituted heterocycloalkyl" or "substituted heterocyclyl" refers to heterocyclyl groups that are substituted with from 1 to 3 of the same substituents as defined for substituted cycloalkyl.

Examples of heterocyclyls and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydro-isoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), piperidinyl, pyrrolidine, tetrahydrofuranyl, and the like.

"Polyalkylene oxide" is a [—O-alkylene-] repeating unit wherein the alkylene is divalent, straight or branched $C_2$ to $C_4$ alkyl. In any one polymer, the polyalkylene oxide repeating units can be the same or different.

"Thiol" refers to the group —SH.

"Thioalkyl" or "alkylthioether" or "thioalkoxy" refers to the group —S-alkyl.

"Substituted thioalkyl" or "substituted alkylthioether" or "substituted thioalkoxy" refers to the group —S-substituted alkyl.

"Thioaryl" refers to the group —S-aryl, where aryl is defined above.

"Substituted thioaryl" refers to the group —S-substituted aryl, where substituted aryl is defined above.

"Thioheteroaryl" refers to the group —S-heteroaryl, where heteroaryl is as defined above.

"Substituted thioheteroaryl" refers to the group —S-substituted heteroaryl, where substituted thioheteroaryl is defined above.

"Thioheterocyclic" refers to the group —S-heterocyclic and "substituted thioheterocyclic" refers to the group —S-substituted heterocyclic, where heterocyclic and substituted heterocyclic.

"Heterocyclyloxy" refers to the group heterocyclyl-O— and "substituted heterocyclyl-O—" refers to the group substituted heterocyclyl-O— where heterocyclyl and substituted heterocyclyl are as defined above.

"Thiocycloalkyl" refers to the group —S-cycloalkyl and "substituted thiocycloalkyl" refers to the group —S-substituted cycloalkyl, where cycloalkyl and substituted cycloalkyl are as defined above.

As used with regard to the conjugates, the terms "compound" and "active compound" are used to refer to the VLA-4 antagonist portion of a conjugate of formulae XVIII and XX-XXII and or to a VLA-4 antagonist as it exists prior to conjugation to a polymer.

The terms "Linker", "linking group" or "linker of from 1 to 40 atoms" refer to a group or groups that (1) covalently links the polymer to the active compound and/or (2) covalently link the polyalkylene oxide moieties of a polymer one to another. Within any particular conjugate, the linker connecting the polyalkylene oxide moieties of a polymer together, and the linker bonding a polymer to an active compound may be the same or different (i.e., may have the same or different chemical structures).

The linker that covalently links the polyalkylene oxide moieties of a polymer one to another is also referred to as a "branched-arm hub", or "branched-arm hub molecule". Branched-arm hubs are molecules that covalently bond three or more polyalkylene oxide chains to them, providing trivalent or higher valent polymer moieties for conjugation with the active compound. Non-limiting examples of such hub molecules are glycerol (1,2,3-propanetriol), pentaerythitol, lysine, 1,2,4-benzenetriol, glucose (in its pyranose form), ethylenediamine tetraacetic acid, amino acids, 3- or 4-aminosalicylic acid, 1,3-diamino-2-hydroxypropane, glucosamine, and sialic acid.

Representative functional group linkages, of which a linking group may have one or more, are amides (—C(O)NR$^3$—), ethers (—O—), thioethers (—S—), carbamates (—OC(O)NR$^3$—), thiocarbamates (—OC(S)NR$^3$—), ureas (—NR$^3$C(O)NR$^3$—), thioureas(—NR$^3$C(S)NR$^3$—), amino groups (—NR$^3$—), carbonyl groups (—C(O)—), alkoxy groups (—O-alkylene-), etc. The linker may be homogeneous or heterogeneous in its atom content (e.g., linkers containing only carbon atoms or linkers containing carbon atoms as well as one or more heteroatoms present on the linker. Preferably, the linker contains 1 to 25 carbon atoms and 0 to 15 heteroatoms selected from oxygen, NR$^3$, sulfur, —S(O)— and —S(O)$_2$—, where R$^3$ is hydrogen, alkyl or substituted alkyl. The linker may also be chiral or achiral, linear, branched or cyclic.

Intervening between the functional group linkages or bonds within the linker, the linker may further contain spacer groups including, but not limited to, spacers selected from alkyl, substituted alkyl, aryl, substituted aryl, cycloalkyl, substituted cycloalkyl, heteroaryl, substituted heteroaryl, heterocyclic, substituted heterocyclic, and combinations thereof. The spacer may be homogenous or heterogeneous in its atom content (e.g., spacers containing only carbon atoms or spacers containing carbon atoms as well as one or more heteroatoms present on the spacer. Preferably, the spacer contains 1 to 25 carbon atoms and 0 to 15 heteroatoms selected from oxygen, NR$^3$, sulfur, —S(O)— and —S(O)$_2$—, where R$^3$ is as defined above. The spacer may also be chiral or achiral, linear, branched or cyclic.

Non-limiting examples of spacers are straight or branched alkylene chains, phenylene, biphenylene, etc. rings, all of which are capable of carrying one or more than one functional group capable of forming a linkage with the active compound and one or more polyalkylene oxide moieties. One particular example of a polyfunctional linker-spacer group is lysine, which may link any of the active compounds to two polymer moieties via the two amino groups substituted on a $C_4$ alkylene chain. Other non-limiting examples include p-aminobenzoic acid and 3,5-diaminobenzoic acid which have 2 and 3 functional groups respectively available for linkage formation. Other such polyfunctional linkage plus spacer groups can be readily envisaged by one of skill in the art.

The terms "polymer" and "polymer moiety" refers to biocompatible, water-soluble, substantially non-immunogenic, polymers which are capable of being coupled to more than one VLA-4 antagonist of formula XIX. Preferably the polymer is non-ionic and biocompatible as measured by lack of toxicity at the molecular weights and dosages used. The terms also encompass molecules in which 3 or more polymers are connected to a branched-arm hub molecule, as discussed above.

Examples of suitable polymers include, but are not limited to: polyoxyalkylene polymers such as polyethylene glycol (PEG), polyvinylpyrrolidone (PVP), polyacrylamide (PAAm), polydimethylacrylamide (PDAAm), polyvinyl alcohol (PVA), dextran, poly (L-glutamic acid) (PGA), styrene maleic anhydride (SMA), poly-N-(2-hydroxypropyl) methacrylamide (HPMA), polydivinylether maleic anhydride (DIVEMA) (Kameda, Y. et al., Biomaterials 25: 3259-3266, 2004; Thanou, M. et al, Current Opinion in Investigational Drugs 4(6): 701-709, 2003; Veronese, F. M., et al., Il Farmaco 54: 497-516, 1999).

Preferred polymers are polyoxyalkylene polymers. By "polyoxyalkylene polymers" is meant macromolecules that include at least one polyalkylene oxide portion that is optionally covalently bonded to one or more additional polyalkylene oxides, wherein the polyalkylene oxides are the same or different. Non-limiting examples include polyethylene glycol (PEG), polypropylene glycol (PPG), polyisopropylene glycol (PIPG), PEG-PEG, PEG-PPG, PPG-PIPG, and the like. Also included within the definition of polyoxyalkylenes are macromolecules wherein the polyalkylene oxide portions are optionally connected to each other by a linker. Illustrative examples are PEG-linker-PEG, PEG-linker-PIPG, and the like. More specific examples include the commercially available poly[di(ethylene glycol)adipates, poly[di(ethylene glycol)phthalate diols, and the like. Other examples are block copolymers of oxyalkylene, polyethylene glycol, polypropylene glycol, and polyoxyethylenated polyol units.

At least one of its termini, the polymer is covalently attached to non-polymer substituted compound of formula XIX optionally through a linker using conventional chemical techniques providing for covalent linkage of the polymer to the non-polymer substituted compound of formula XIX.

When a linker is employed, the linker is covalently bonded to at least one of the polymer termini which, in turn, is covalently attached to the otherwise, non-polymer substituted compound of formula XIX. Reaction chemistries resulting in such linkages are well known in the art. Such reaction chemistries involve the use of complementary functional groups on the linker, the non-polymer substituted compound of formula XIX and the polymer. Preferably, the complementary functional groups on the linker are selected relative to the functional groups available on the polymer for bonding or which can be introduced onto the polymer for bonding. Again, such complementary functional groups are well known in the art. For example, reaction between a carboxylic acid of either the linker or the polymer and a primary or secondary amine of the polymer or the linker in the presence of suitable, well-known activating agents results in formation of an amide bond covalently linking the polymer moiety to the linker; reaction between an amine group of either the linker or the polymer group and a sulfonyl halide of the polymer or the linker results in formation of a sulfonamide bond covalently linking the polymer moiety to the linker; and reaction between an alcohol or phenol group of either the linker or the polymer and an alkyl or aryl halide of the polymer or the linker results in formation of an ether bond covalently linking the polymer group to the linker.

It is understood, of course, that if the appropriate substituents are found on the non-polymer substituted compound of formula XIX then the optional linker may not be needed as there can be direct linkage of the polymer to the non-polymer substituted compound of formula XIX.

Table 8 below illustrates numerous complementary reactive groups and the resulting bonds formed by reaction there between. One of ordinary skill in the art can select the appropriate solvents and reaction conditions to effect these linkages.

TABLE 8

Representative Complementary Binding Chemistries

| First Reactive Group | Second Reactive Group | Linkage |
| --- | --- | --- |
| Hydroxyl | Isocyanate | Urethane |
| Amine | Epoxide | β-hydroxyamine |
| sulfonyl halide | Amine | Sulfonamide |
| Carboxyl | Amine | Amide |
| Hydroxyl | alkyl/aryl halide | Ether |
| Aldehyde (under reductive amination conditions) | Amine | Amine |

Preferred linkers include, by way of example, the following —O—, —NR³—, —NR³C(O)O—, —OC(O)NR³—, —NR³C(O)—, —C(O)NR³—, —NR³C(O)NR³—, -alkylene-NR³C(O)O—, -alkylene-NR³C(O)NR³—, -alkylene-OC(O)NR³—, -alkylene-NR³—, -alkylene-O—, -alkylene-NR³C(O)—, -alkylene-C(O)NR³—, —NR³C(O)O-alkylene-, —NR³C(O)NR³-alkylene-, —OC(O)NR³-alkylene-, —NR³-alkylene-, —O-alkylene-, —NR³C(O)-alkylene-, —C(O)NR³-alkylene-, -alkylene-NR³C(O)O-alkylene-, -alkylene-NR³C(O)NR³-alkylene-, -alkylene-OC(O)NR³-alkylene-, -alkylene-NR³-alkylene-, alkylene-O-alkylene-, -alkylene-NR³C(O)-alkylene-, —C(O)NR³-alkylene-, —NR³C(O)O-alkyleneoxy-, —NR³C(O)NR³-alkyleneoxy-, —OC(O)NR³-alkyleneoxy, —NR³-alkyleneoxy-, —O-alkyleneoxy-, —NR³C(O)-alkyleneoxy-, —C(O)NR³-alkyleneoxy-, -alkyleneoxy-NR³C(O)O-alkyleneoxy- where R³ is as defined above and

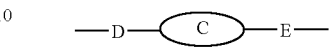

where

is selected from the group consisting of aryl, substituted aryl, cycloalkyl, substituted cycloalkyl, heteroaryl, substituted heteroaryl, heterocyclic and substituted heterocyclic, and D and E are independently selected from the group consisting of a bond, —O—, CO, —NR³—, —NR³C(O)O—, —OC(O) NR³—, —NR³C(O)—, —C(O)NR³—, —NR³C(O)NR³—, -alkylene-NR³C(O)O—, -alkylene-NR³C(O)NR³—, -alkylene-OC(O)NR³—, -alkylene-NR³—, -alkylene-O—, -alkylene-NR³C(O)—, alkylene-C(O)NR³—, —NR³C(O)O-alkylene-, —NR³C(O)NR³-alkylene-, —OC(O)NR³-alkylene-, —NR³-alkylene-, —O-alkylene-, —NR³C(O)-alkylene-, —NR³C(O)O-alkyleneoxy-, —NR³C(O)NR³-alkyleneoxy-, —OC(O)NR³-alkyleneoxy, —NR³-alkyleneoxy-, —O-alkyleneoxy-, —NR³C(O)-alkyleneoxy-, —C(O)NR³-alkyleneoxy-, -alkyleneoxy-NR³C(O)O-alkyleneoxy-, —C(O)NR³-alkylene-, -alkylene-NR³C(O)O-alkylene-, -alkylene-NR³C(O)NR³-alkylene-, -alkylene-OC(O) NR³-alkylene-, -alkylene-NR³-alkylene-, alkylene-O-alkylene-, -alkylene-NR³C(O)-alkylene-, and —C(O)NR³-alkylene-, where R³ is as defined above.

Preferred alkylene groups in the above linkers include $C_1$-$C_{15}$ alkylene groups, more preferably $C_1$-$C_6$ alkylene groups, and most preferably $C_1$-$C_3$ alkylene groups. Preferred heterocyclic groups include piperazinyl, piperidinyl, homopiperazinyl, homopiperidinyl, pyrrolidinyl, and imidazolidinyl. Preferred alkoxy groups are —(CH₂—CH₂—O)₁₋₁₅.

The term "oxyalkylene" refers to —OCH₂CHR$^d$— where R$^d$ is alkyl. Polymerized oxyalkylenes are referred to as polyoxyalkylenes, polyalkylene oxides or polyalkylene glycols, non-limiting examples of which include PEG, polypropylene glycol, polybutylene glycol, polyisopropylene glycol, and the like.

Such polymers are optionally mono-capped with a substituent preferably selected from alkyl, aryl, substituted alkyl, substituted aryl and a branched-arm hub molecule as described above. Inclusive of such polymers are those diamino capped polyoxyalkylene polymers which are known in the art as Jeffamines®. Still further, such polymers can optionally contain one or more non-oxyalkylene units such as the commercially available poly[di(ethylene glycol)adipates, poly[di(ethylene glycol)phthalate diols, and the like. Also included are block copolymers of oxyalkylene, polyethylene glycol, polypropylene glycol, and polyoxyethylenated polyol units.

Polyoxyalkylenes, such as PEG, are usually provided as a water soluble, waxy solid. Generally, as the polymer's molecular weight increases, its viscosity and freezing point also increase. Commercial preparations are usually characterized by the "average molecular weight" of the constituent polymers.

Typically, the average molecular weight of the total amount of polymer arising from single or multiple polymer moieties in the conjugates of formulae XVIII and XX-XXII is between about 100 to 100,000; preferably from about 10,000 to 60,000; preferably from about 20,000 to 60,000; more preferably from about 30,000 to about 50,000; and more preferably about 40,000 to 45,000.

It is apparent to those skilled in the art that polymers of this type will be polydisperse. Polydispersity refers to the fact that polymer molecules, even ones of the same type, come in different sizes (chain lengths, for linear or multi-armed polymers). Therefore average molecular weight will depend on the method of averaging. The polydispersity index, a common measure of the variability of molecular weights is the ratio of the weight average molecular weight to the number average molecular weight. It indicates the distribution of individual molecular weights in a batch of polymers. The number average molecular weight is a way of determining the molecular weight of a polymer. The number average molecular weight is the common average of the molecular weights of the individual polymers. It is determined by measuring the molecular weight of n polymer molecules, summing the weights, and dividing by n. The number average molecular weight of a polymer can be determined by osmometry, end-group titration, and colligative properties.

The weight average molecular weight can be determined by light scattering, small angle neutron scattering (SANS), X-ray scattering, and sedimentation velocity. The ratio of the weight average to the number average is called the polydispersity index. A theoretical sample of polymer having no dispersity would have a polydispersity index of 1. Preferred range of polydispersity index for the present invention is from about 1.10 to about 1.05. More preferred is a range from about 1.05 to the upper limit of commercially feasible synthesis, which to date is about 1.02.

Other suitable polymers such as polyvinylpyrrolidone (PVP), polyacrylamide (PAAm), polydimethylacrylamide (PDAAm), polyvinyl alcohol (PVA), dextran, poly (L-glutamic acid) (PGA), styrene maleic anhydride (SMA), poly-N-(2-hydroxypropyl) methacrylamide (HPMA), polydivinylether maleic anhydride (DIVEMA) are well known in the art and have molecular weights of from about 100 to 100,000; preferably from about 10,000 to 80,000; more preferably from about 20,000 to about 70,000.

Compound Preparation

The conjugates of formulae XVIII and XX-XXII can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, *Protecting Groups in Organic Synthesis*, Second Edition, Wiley, New York, 1991, and references cited therein.

Furthermore, the compounds will typically contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

The conjugates of formulae XVIII and XX-XXII preferably comprise a polymer moiety/optional branched-arm hub molecule containing 2 to about 20 substituents of formula XIX:

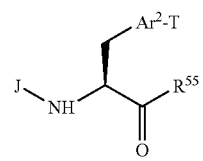

XIX

Specifically, the polymer moiety can be bound through a covalent bond to the $Ar^1$ substituent, the J substituent, the $Ar^2$ substituent and/or in the T substituent wherein the polymer moiety is either directly attached or is attached via a linker. In turn, the polymer moiety may optionally be bound to a branched-arm hub molecule.

In its simplest form, the compounds are divalent structures comprising a single polymer moiety having two substituents of formula XIX bound to both termini. In a representative case using a polymer moiety derived from PEG which is linked to a compound of formula XIX by a carbonyl linking group wherein the compound of formula XIX is represented by:

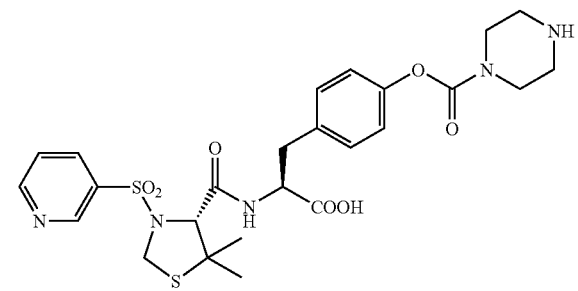

the resulting conjugate can be represented by the following formula:

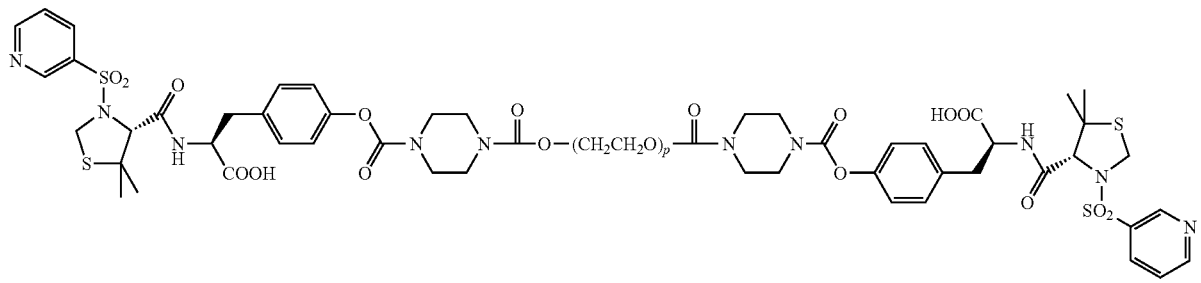

where p is preferably an integer of from about 100 to 1360.

In one example of a tetravalent form, the conjugate comprises four polymer moieties. In a representative case, one terminus of each polymer moiety is attached to a common a branched-arm hub molecule whereas the other terminus is attached to a compound of formula XIX optionally through a linker. Still further and again for illustrative purposes, each polymer moiety is derived from PEG and the common branched-arm hub molecule is pentaerythritol. In this exemplification, the other terminus of the PEG moiety is linked to a compound of formula XIX through a carbonyl linking group wherein the compound of formula XIX is represented by:

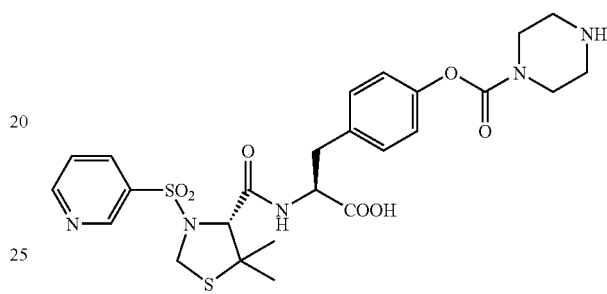

the resulting conjugate can be represented by the following formula:

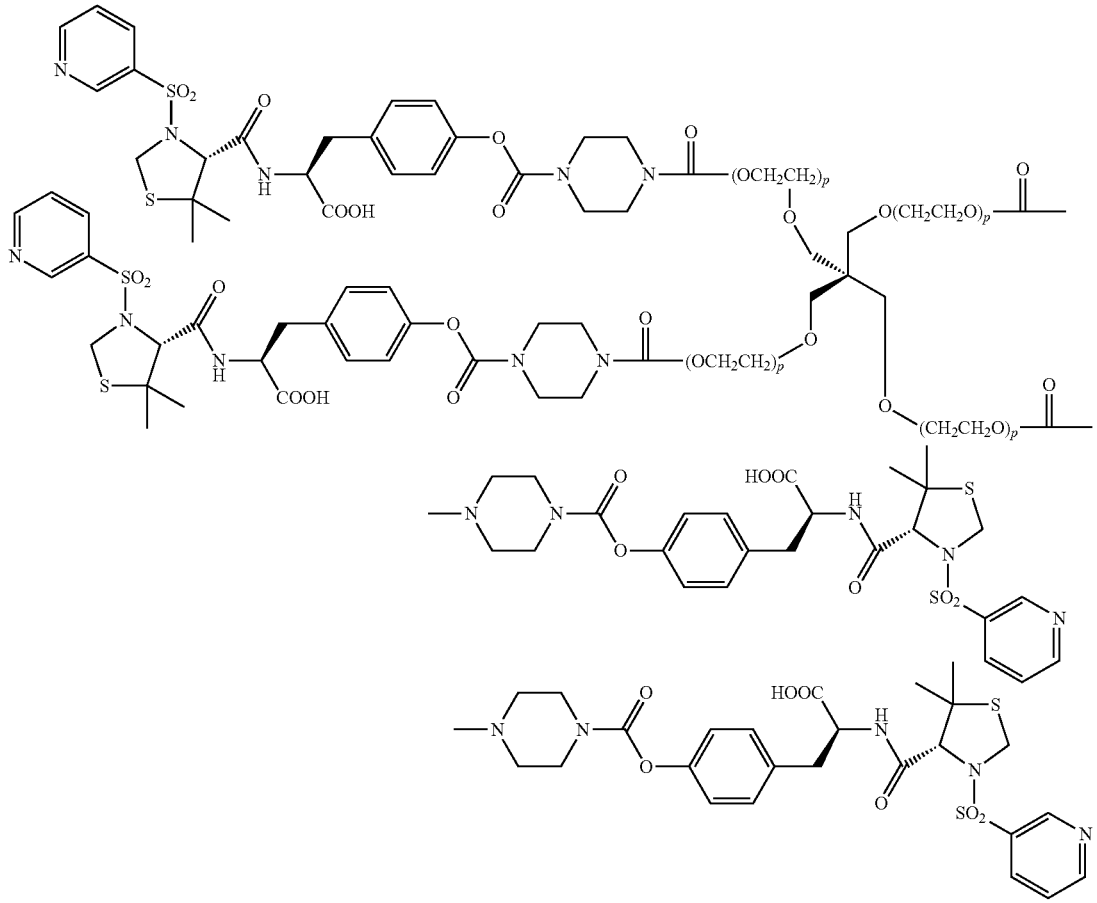

where the aggregate of the four p's is an integer preferably of from about 100 to 1360.

The synthetic protocol for forming the conjugates of formula XVIII entails reaction of a functional group on the polymer moiety with either a linking group or directly with a compound of formula XIX thereby covalently binding the polymer moiety to the compound of formula XIX.

Initially, non-PEG substituted compounds of formula XIXb-XIXh are well known in the art and are exemplified in a number of issued patents including, without limitation, U.S. Pat. Nos. 6,489,300 and 6,436,904 both of which are incorporated herein by reference in their entirety. Non-polymer variants of compounds of formula XIX include those having complementary functional groups or groups derivatizable to complementary functional groups on one or more of the $Ar^1$, R, $Ar^2$ and T moieties. For illustrative purposes, compounds having a complementary functional group (—OH) on the $Ar^2$ moiety (e.g., tyrosine) are recited below as a suitable starting point for addition of a polymer moiety to the molecule either directly or through a linker.

Such compounds can be prepared by first coupling a heterocyclic amino acid, 1, with an appropriate aryl sulfonyl chloride as illustrated in Scheme 5 below:

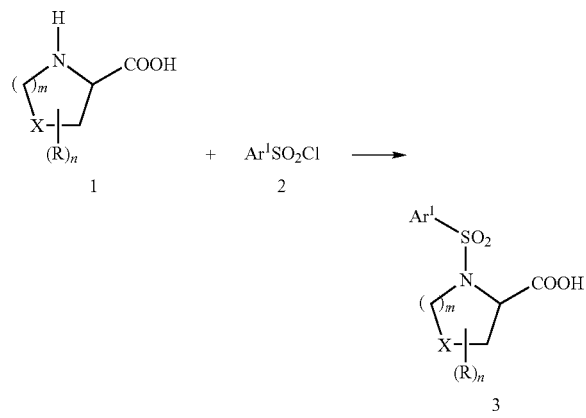

where R, $Ar^1$, X, m and n are as defined above.

Specifically, in Scheme 5 above, heterocyclic amino acid, 1, is combined with a stoichiometric equivalent or excess amount (preferably from about 1.1 to about 2 equivalents) of arylsulfonyl halide, 2, in a suitable inert diluent such as dichloromethane and the like. Generally, the reaction is conducted at a temperature ranging from about −70° C. to about 40° C. until the reaction is substantially complete, which typically occurs within 1 to 24 hours. Preferably, the reaction is conducted in the presence of a suitable base to scavenge the acid generated during the reaction. Suitable bases include, by way of example, tertiary amines, such as triethylamine, diisopropylethylamine, N-methyl-morpholine and the like. Alternatively, the reaction can be conducted under Schotten-Baumann-type conditions using an aqueous alkali solution such as an aqueous solution of sodium hydroxide, an aqueous phosphate solution buffered to pH 7.4, and the like. The resulting product, 3, can be recovered by conventional methods, such as chromatography, filtration, evaporation, crystallization, and the like or, alternatively, used in the next step without purification and/or isolation.

Heterocyclic amino acids, 1, employed in the above reaction are either known compounds or compounds that can be prepared from known compounds by conventional synthetic procedures. Examples of suitable amino acids for use in this reaction include, but are not limited to, L-proline, trans-4-hydroxyl-L-proline, cis-4-hydroxyl-L-proline, trans-3-phenyl-L-proline, cis-3-phenyl-L-proline, L-(2-methyl)proline, L-pipecolinic acid, L-azetidine-2-carboxylic acid, L-thiazolidine-4-carboxylic acid, L-(5,5-dimethyl)thiazolidine-4-carboxylic acid, L-thiamorpholine-3-carboxylic acid. If desired, the corresponding carboxylic acid esters of the amino acids, 1, such as the methyl esters, ethyl esters, t-butyl esters, and the like, can be employed in the above reaction with the arylsulfonyl chloride. Subsequent hydrolysis of the ester group to the carboxylic acid using conventional reagents and conditions, i.e., treatment with an alkali metal hydroxide in an inert diluent such as methanol/water, then provides the N-sulfonyl amino acid, 3.

Similarly, the arylsulfonyl chlorides, 2, employed in the above reaction are either known compounds or compounds that can be prepared from known compounds by conventional synthetic procedures. Such compounds are typically prepared from the corresponding sulfonic acid, i.e., from compounds of the formula $Ar^1SO_3H$ where $Ar^1$ is as defined above, using phosphorous trichloride and phosphorous pentachloride. This reaction is generally conducted by contacting the sulfonic acid with about 2 to 5 molar equivalents of phosphorous trichloride and phosphorous pentachloride, either neat or in an inert solvent, such as dichloromethane, at temperature in the range of about 0° C. to about 80° C. for about 1 to about 48 hours to afford the sulfonyl chloride. Alternatively, the arylsulfonyl chlorides, 2, can be prepared from the corresponding thiol compound, i.e., from compounds of the $Ar^1$—SH where $Ar^1$ is as defined herein, by treating the thiol with chlorine ($Cl_2$) and water under conventional reaction conditions.

Alternatively, arylsulfonyl chlorides, 2, employed in the above reaction may be prepared by chlorosulfonylation of substituted benzene or heterocycloalkyl group using Cl—$SO_3H$.

Examples of arylsulfonyl chlorides include, but are not limited to, benzenesulfonyl chloride, 1-naphthalenesulfonyl chloride, 2-naphthalenesulfonyl chloride, p-toluenesulfonyl chloride, o-toluenesulfonyl chloride, 4-acetamidobenzenesulfonyl chloride, 4-tert-butylbenzenesulfonyl chloride, 4-bromobenzenesulfonyl chloride, 2-carboxybenzenesulfonyl chloride, 4-cyanobenzenesulfonyl chloride, 3,4-dichlorobenzenesulfonyl chloride, 3,5-dichlorobenzenesulfonyl chloride, 3,4-dimethoxybenzenesulfonyl chloride, 3,5-ditrifluoromethylbenzenesulfonyl chloride, 4-fluorobenzenesulfonyl chloride, 4-methoxybenzenesulfonyl chloride, 2-methoxycarbonylbenzenesulfonyl chloride, 4-methylamido-benzenesulfonyl chloride, 4-nitrobenzenesulfonyl chloride, 4-trifluoromethyl-benzenesulfonyl chloride, 4-trifluoromethoxybenzenesulfonyl chloride, 2,4,6-trimethylbenzenesulfonyl chloride, 2-thiophenesulfonyl chloride, 5-chloro-2-thiophenesulfonyl chloride, 2,5-dichloro-4-thiophenesulfonyl chloride, 2-thiazolesulfonyl chloride, 2-methyl-4-thiazolesulfonyl chloride, 1-methyl-4-imidazolesulfonyl chloride, 1-methyl-4-pyrazolesulfonyl chloride, 5-chloro-1,3-dimethyl-4-pyrazolesulfonyl chloride, 3-pyridinesulfonyl chloride, 2-pyrimidinesulfonyl chloride and the like. If desired, a sulfonyl fluoride, sulfonyl bromide or sulfonic acid anhydride may be used in place of the sulfonyl chloride in the above reaction to form the N-sulfonyl amino acid, 3.

The N-arylsulfonyl amino acid, 3, is then coupled to commercially available tyrosine esters as shown in Scheme 6 below:

Scheme 6

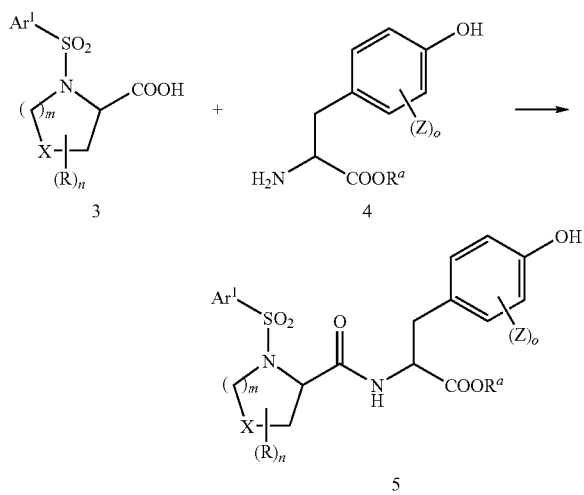

where R, Ar¹, X, m and n are as defined above, $R^a$ is hydrogen or alkyl but preferably is an alkyl group such as t-butyl, Z represents optional substitution on the aryl ring and o is zero, one or two.

This coupling reaction is typically conducted using well-known coupling reagents such as carbodiimides, BOP reagent (benzotriazol-1-yloxy-tris(dimethylamino)-phosphonium hexafluorophosphonate) and the like. Suitable carbodiimides include, by way of example, dicyclohexylcarbodiimide (DCC), 1-(3-dimethylaminopropyl)-3-ethylcarbodiimide (EDC) and the like. If desired, polymer supported forms of carbodiimide coupling reagents may also be used including, for example, those described in *Tetrahedron Letters*, 34(48), 7685 (1993). Additionally, well-known coupling promoters, such as N-hydroxysuccinimide, 1-hydroxybenzotriazole and the like, may be used to facilitate the coupling reaction.

This coupling reaction is typically conducted by contacting the N-sulfonylamino acid, 3, with about 1 to about 2 equivalents of the coupling reagent and at least one equivalent, preferably about 1 to about 1.2 equivalents, of tyrosine derivative, 4, in an inert diluent, such as dichloromethane, chloroform, acetonitrile, tetrahydrofuran, N,N-dimethylformamide and the like. Generally, this reaction is conducted at a temperature ranging from about 0° C. to about 37° C. for about 12 to about 24 hours. Upon completion of the reaction, the compound 5 is recovered by conventional methods including neutralization, evaporation, extraction, precipitation, chromatography, filtration, and the like.

Alternatively, the N-sulfonyl amino acid, 3, can be converted into an acid halide which is then coupled with compound, 4, to provide compound 5. The acid halide can be prepared by contacting compound 3 with an inorganic acid halide, such as thionyl chloride, phosphorous trichloride, phosphorous tribromide or phosphorous pentachloride, or preferably, with oxalyl chloride under conventional conditions. Generally, this reaction is conducted using about 1 to 5 molar equivalents of the inorganic acid halide or oxalyl chloride, either neat or in an inert solvent, such as dichloromethane or carbon tetrachloride, at temperature in the range of about 0° C. to about 80° C. for about 1 to about 48 hours. A catalyst, such as DMF, may also be used in this reaction.

The acid halide of N-sulfonyl amino acid, 3, is then contacted with at least one equivalent, preferably about 1.1 to about 1.5 equivalents, of the tyrosine derivative, 4, in an inert diluent, such as dichloromethane, at a temperature ranging from about −70° C. to about 40° C. for about 1 to about 24 hours. Preferably, this reaction is conducted in the presence of a suitable base to scavenge the acid generated during the reaction. Suitable bases include, by way of example, tertiary amines, such as triethylamine, diisopropylethylamine, N-methylmorpholine and the like. Alternatively, the reaction can be conducted under Schotten-Baumann-type conditions using aqueous alkali, such as sodium hydroxide and the like. Upon completion of the reaction, compound 5 is recovered by conventional methods including neutralization, evaporation, extraction, precipitation, chromatography, filtration, and the like.

Alternatively, compound 5 can be prepared by first forming a diamino acid derivative and then coupling the diamino acid to the arylsulfonyl halide, 2, as shown in Scheme 7 below:

Scheme 7

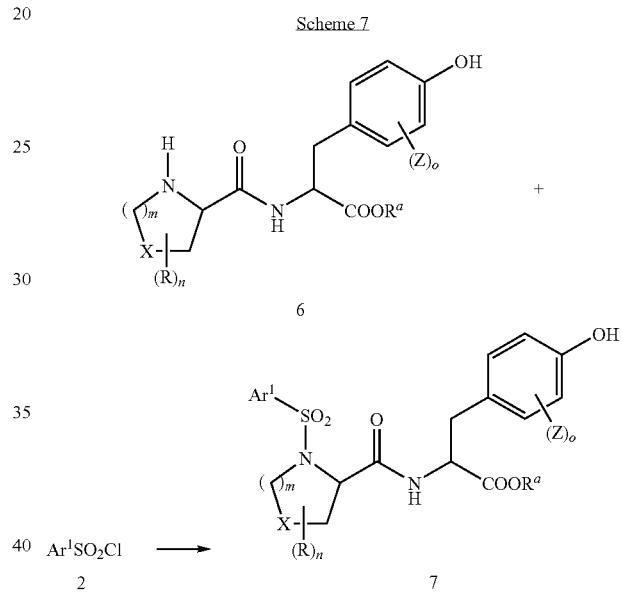

where R, $R^a$, Ar¹, X, Z, m, n and o are as defined above.

The diamino acid, 6, can be readily prepared by coupling amino acid, 1, with amino acid, 4, using conventional amino acid coupling techniques and reagents, such carbodiimides, BOP reagent and the like, as described above. Diamino acid, 6, can then be sulfonated using sulfonyl chloride, 2 and using the synthetic procedures described above to provide compound 7.

The tyrosine derivatives, 4, employed in the above reactions are either known compounds or compounds that can be prepared from known compounds by conventional synthetic procedures. For example, tyrosine derivatives, 4, suitable for use in the above reactions include, but are not limited to, L-tyrosine methyl ester, L-tyrosine t-butyl ester, L-3,5-diiodotyrosine methyl ester, L-3-iodotyrosine methyl ester, β-(4-hydroxy-naphth-1-yl)-L-alanine methyl ester, β-(6-hydroxy-naphth-2-yl)-L-alanine methyl ester, and the like. If desired, of course, other esters or amides of the above-described compounds may also be employed.

The N-arylsulfonyl-heterocyclic amino acid-tyrosine derivative, 7, can be used as a starting point to attach a polymer moiety at the $Ar^2$ group by coupling reactions shown in Schemes 8-18 below which coupling reactions are illustrative only in demonstrating how polymer moieties can be introduced. In Schemes 8-18, PEG is used as the polymer moiety for illustrative purposes only. It is understood that other suitable polymers could be used in place of PEG and that one of ordinary skill in the art would readily be able to modify the reaction schemes below to incorporate such other polymers.

In some cases, the PEG moiety can be directly introduced onto the phenoxy group and, in other cases, the PEG moiety can be introduced by linkage through a linker moiety.

Specifically, Scheme 8 illustrates the following:

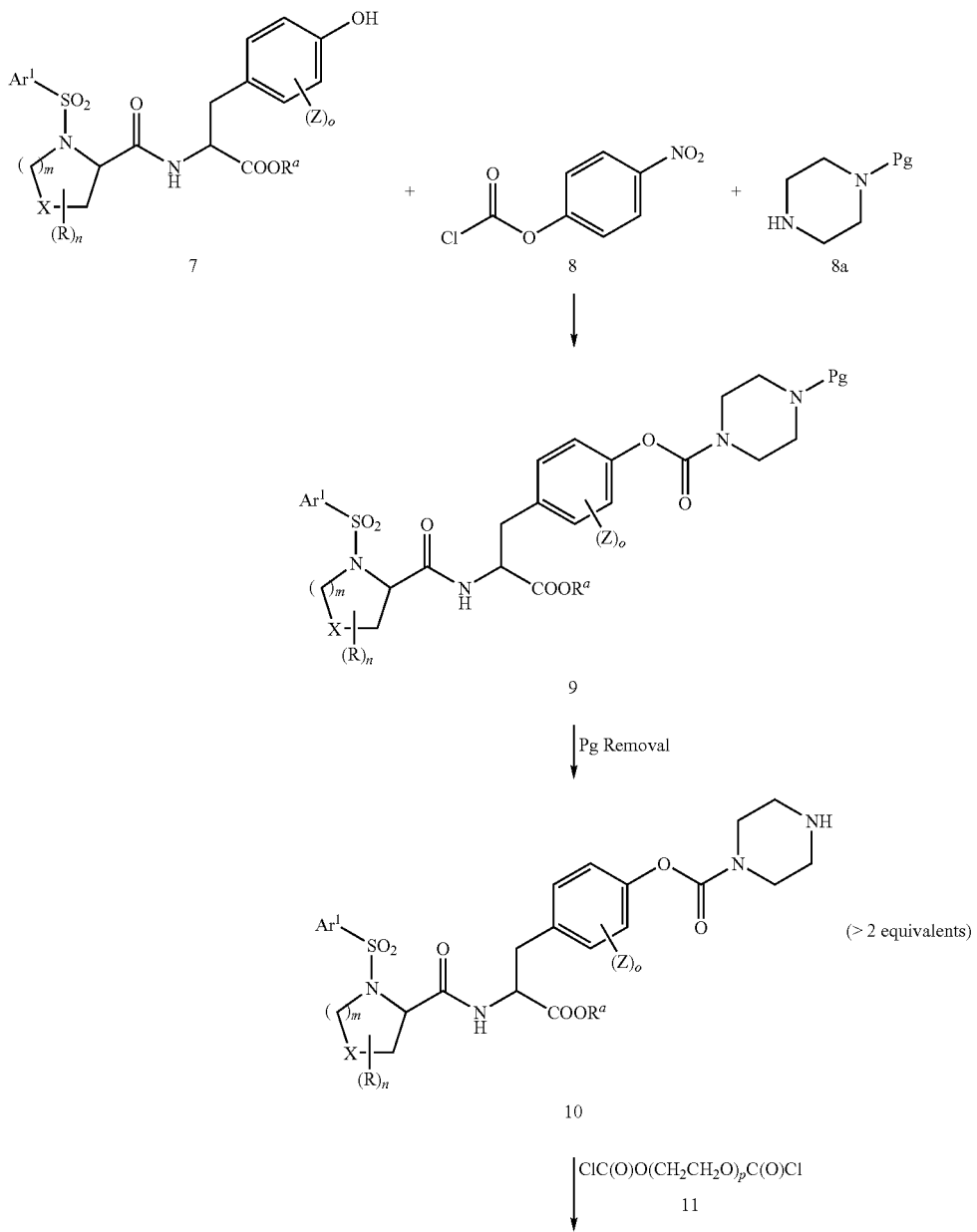

-continued

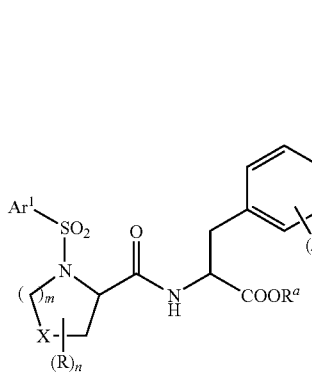

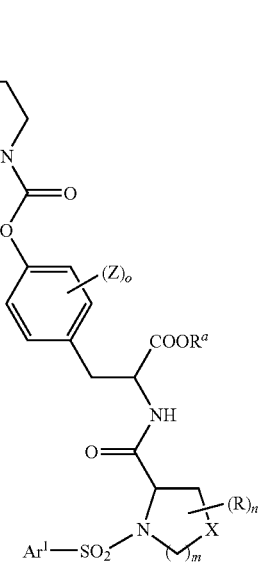

12 wherein Ar¹, R, R$^a$, m, n, o, X, and Z are as defined above, Pg is an amine protecting group such as CBZ, Boc, etc, which is preferably orthogonally removable as compared to the R$^a$ carboxyl protecting group and p is an integer preferably of from about 100 to 1360.

Specifically, in Scheme 8, compound 7, prepared as above, is combined with at least an equivalent and preferably an excess of 4-nitrophenyl chloroformate, 8, in a suitable solvent such as methylene chloride, chloroform and the like and preferably under an inert atmosphere. The reaction is preferably conducted at a temperature of from about −40° to about 0° C. in the presence of a suitable base to scavenge the acid generated. Suitable bases include, by way of example, triethylamine, diisopropylethylamine, and the like. After formation of the intermediate mixed carbonate (not shown), at least an approximately equimolar amount of N-Pg piperazine, 8a, is added to the reaction solution. This reaction is allowed to continue at room temperature for about 1 to 24 hours. Upon completion of the reaction, compound 9 is recovered by conventional methods including neutralization, evaporation, extraction, precipitation, chromatography, filtration, and the like, or, alternatively, is used in the next reaction without purification and/or isolation.

Conventional removal of the protecting group provides for the free piperazine derivative, 10. Removal is accomplished in accordance with the blocking group employed. For example, a trifluoromethylcarbonyl protecting group is readily removed via an aqueous solution of potassium carbonate. Further, suitable protecting groups for various functional groups as well as suitable conditions for protecting and deprotecting particular functional groups are well known in the art. See, for example, T. W. Greene and G. M. Wuts, *Protecting Groups in Organic Chemistry*, Second Edition, Wiley, New York, 1991, and references cited therein.

The free piperazine derivative, 10, is then combined with an α,ω-dichloroformate polyoxyethylene, compound 11, in a suitable inert diluent such as methylene chloride, chloroform, and the like and preferably under an inert atmosphere. Typically, at least 2 equivalents and preferably from about 2.5 to 10 equivalents of compound 10 per chloroformate entity are employed in combination with compound 11. The reaction is optionally conducted in the presence of a catalytic amount of DMAP and a base to scavenge the acid generated during reaction. The reaction is continued under ambient conditions until substantially complete which typically occurs within 4 to 24 hours. When R$^a$ is alkyl, subsequent hydrolysis of the ester derivative provides for the free carboxyl group or a salt thereof. The resulting dimer, 12, is recovered by conventional procedures such as neutralization, evaporation, extraction, precipitation, chromatography, filtration, and the like.

The α,ω-dichloroformate polyoxyethylene, compound 11, is readily prepared from commercially available polyoxyethylene by reaction with an excess of phosgene, typically from at least 2 to about 20 equivalents, in a suitable inert solvent such as methylene chloride, chloroform and the like. The reaction is preferably conducted under an inert atmosphere at ambient conditions until the reaction is substantially complete which typically occurs in from about 2 to 24 hours. Afterwards, the resulting α,ω-dichloroformate polyoxyethylene, compound 11, is recovered by convention procedures such as neutralization, evaporation, extraction, precipitation, chromatography, filtration, and the like.

A specific example of this reaction scheme up to formation of the piperazine derivative 28 is illustrated in Scheme 9 below:

Scheme 9
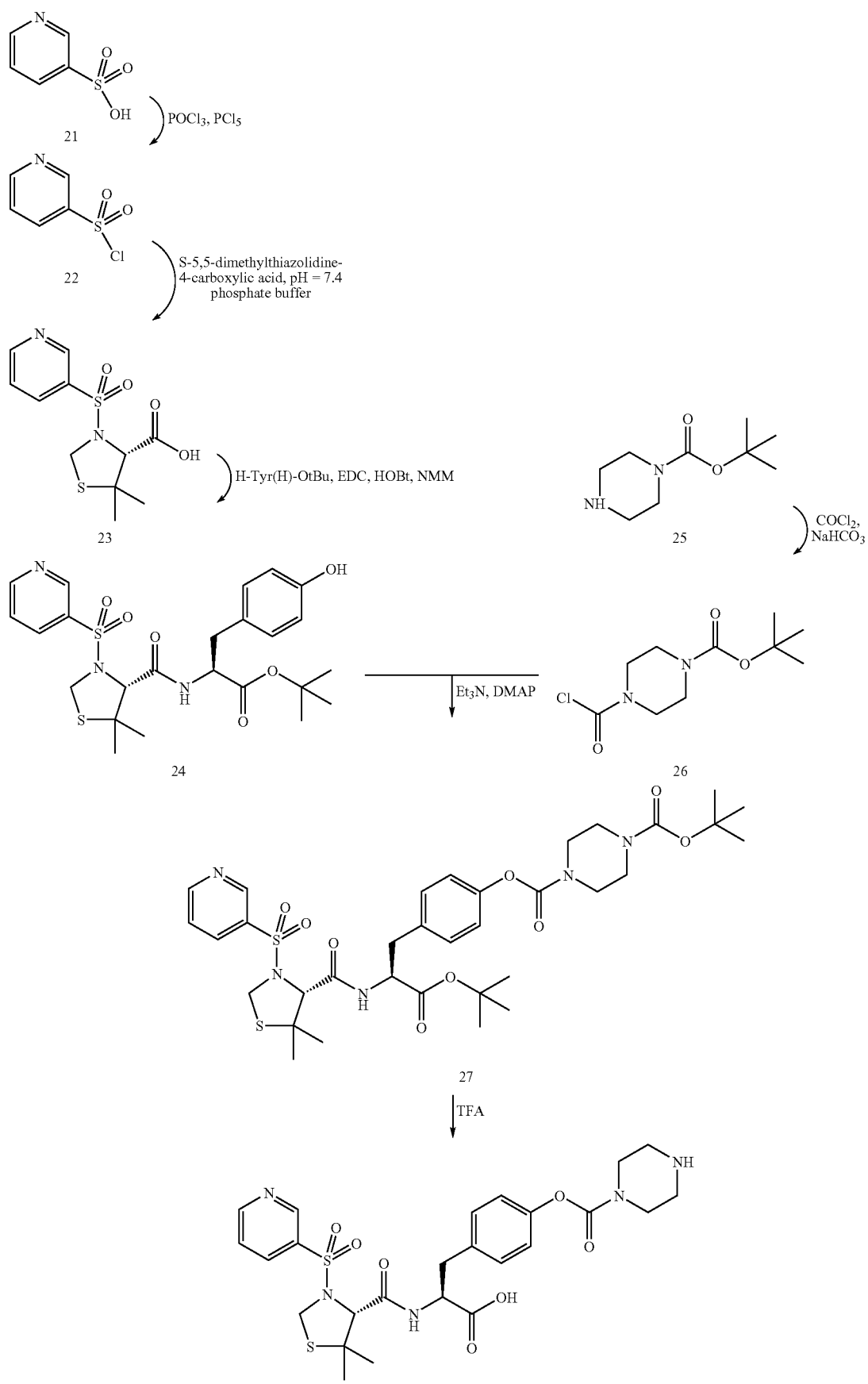

Specifically, commercially available 3-pyridinesulfonic acid, 21, is converted under conventional conditions to the corresponding sulfonyl chloride, 22, by contact with $POCl_3$/$PCl_5$ using conditions well known in the art. Coupling of sulfonyl chloride, 22, with commercially available S-5,5-dimethylthiazolidine-4-carboxylic acid, 23, is accomplished under conventional conditions preferably in the presence of a phosphate buffer (pH 7.4) using an excess of sulfonyl chloride. The reaction is preferably conducted at a temperature of from about −10 to 20° C. until the reaction is substantially complete, which typically occurs within 0.5 to 5 hours. The resulting product, 24, can be recovered by conventional methods, such as chromatography, filtration, evaporation, crystallization, and the like or, alternatively, used in the next step without purification and/or isolation.

The N-pyridinyl sulfonyl-5,5-dimethylthiazolidine-4-carboxylic acid compound, 23, is next coupled to t-butyl tyrosine using conventional amino acid coupling conditions. Specifically, this coupling reaction is conducted using well known coupling reagents such as 1-(3-dimethylaminopropyl)-3-ethylcarbodiimide (EDC), 1-hydroxy-benzotriazole (HOBt) and N-methylmorpholine to facilitate the coupling reaction.

This coupling reaction is typically conducted by contacting the N-sulfonylamino acid, 23, with about 1 to about 2 equivalents of the coupling reagent and at least one equivalent, preferably about 1 to about 1.2 equivalents, of tyrosine t-butyl ester in an inert diluent, such as dichloromethane, chloroform, acetonitrile, tetrahydrofuran, N,N-dimethylformamide and the like. Generally, this reaction is conducted at a temperature ranging from about 0° C. to about 22° C. for about 12 to about 24 hours. Upon completion of the reaction, the compound 24 is recovered by conventional methods including neutralization, evaporation, extraction, precipitation, chromatography, filtration, and the like or, alternatively, is employed in the next step without purification and/or isolation.

Separately, mono-N-Boc-piperazine, 25, is converted to the corresponding carbamyl chloride, 26, by reaction with phosgene in the manner described above. Upon completion of the reaction, the compound 26 is recovered by conventional methods including neutralization, evaporation, extraction, precipitation, chromatography, filtration, and the like or, alternatively, is employed in the next step without purification and/or isolation.

Coupling of compound 24 with compound 26 to provide for compound 27 proceeds under conventional conditions in an inert diluent such as dichloromethane, with a catalytic amount of DMAP and preferably in the presence of a base to scavenge the acid generate. The reaction is run at a temperature of about −20 to about 22° C. for about 2 to about 24 hours. Upon completion of the reaction, compound 27 is recovered by conventional methods including neutralization, evaporation, extraction, precipitation, chromatography, filtration, and the like or, alternatively, is employed in the next step without purification and/or isolation.

Removal of both the amino Boc protecting group and the t-butyl ester proceeds in the presence of trifluoroacetic acid to provide for compound 28 which can be recovered by conventional methods including neutralization, evaporation, extraction, precipitation, chromatography, filtration, and the like.

Scheme 10 below illustrates the preparation of a piperazine compound orthogonally protected on one of the amine groups relative to the carboxyl protecting group found on the phenylalanine compound such that after coupling, the piperazine protecting group can be removed differentially from that of the carboxyl protecting group. Such orthogonal protection is necessary if subsequent reactions on the resulting compound require a carboxyl protecting group to avoid undesired side reactions.

Scheme 10

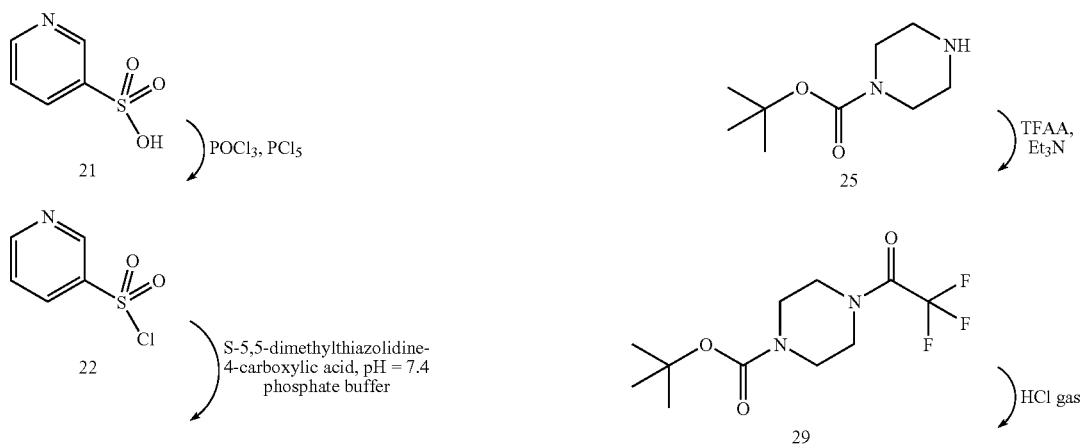

-continued

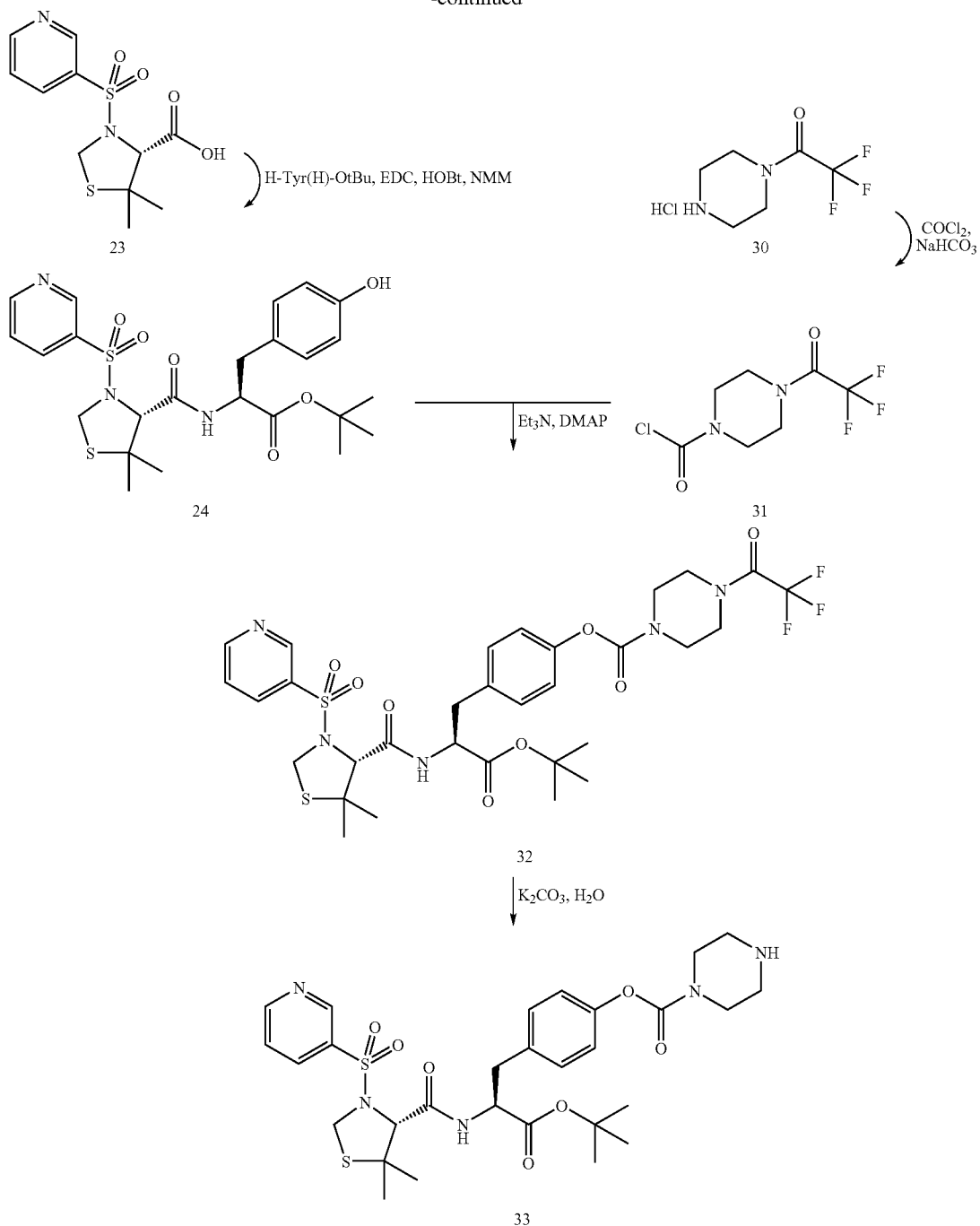

Specifically, in Scheme 10, compound 24 is prepared in the manner described above. N-t-Boc-piperazine, 25, is conventionally converted to N-t-Boc-N'-trifluoromethyl-carbonylpiperazine, 29, by contact with an excess of trifluoroacetic anhydride in the presence of a suitable amine such as triethylamine to scavenge the acid generated during reaction in a suitable solvent such as dichloromethane. Generally, this reaction is conducted at a temperature ranging from about −20° C. to about 22° C. for about 1 to about 24 hours. Upon completion of the reaction, compound 29 can be recovered by conventional methods including neutralization, evaporation, extraction, precipitation, chromatography, filtration, and the like or, alternatively and preferably, is employed in the next step without purification and/or isolation.

In turn, removal of the t-Boc protecting group on the N-t-Boc-N'-trifluoromethyl-carbonylpiperazine, 29, proceeds under conventional conditions using gaseous HCl bubbled through an inert solvent such as methylene chloride, EtOAc, EtO$_2$, and the like under ambient conditions to provide for the hydrochloride salt of N'-trifluoromethylcarbonylpiperazine, 30. Generally, this reaction is conducted at a temperature ranging from about −20° C. to about 22° C. for about 0.5 to about 4 hours. Upon completion of the reaction, compound 30 can be recovered by conventional methods including neutralization, evaporation, extraction, precipitation, chromatography, filtration, and the like or, alternatively and preferably, is employed in the next step without purification and/or isolation.

Conversion of N'-trifluoromethylcarbonylpiperazine, 30, to the N-carbamyl chloride derivative, 31, conventionally proceeds by contact with phosgene in the manner described above. Upon completion of the reaction, compound 31 can be recovered by conventional methods including neutralization, evaporation, extraction, precipitation, chromatography, filtration, and the like or, alternatively and preferably, is employed in the next step without purification and/or isolation.

Compounds 31 and 24 are coupled under conditions similar to those described above to provide for compound 32 which is orthogonally protected at the amino moiety of the piperazine group as well as the carboxyl moiety of the phenylalanine group. Selective removal of the trifluoromethylcarbonyl amino protecting group proceeds under conventional conditions using an aqueous solution of potassium carbonate to provide for compound 33.

Scheme 11 below illustrates modification of the polymer moiety prior to covalently binding the compound of formula XIX. For illustrative purposes only, the polymer moiety is a tetravalent PEG bound to a pentaerythritol. Scheme 11 illustrates that the length of the polymer moiety can be readily adjusted by conventional chemistry to provide for optimal lengths.

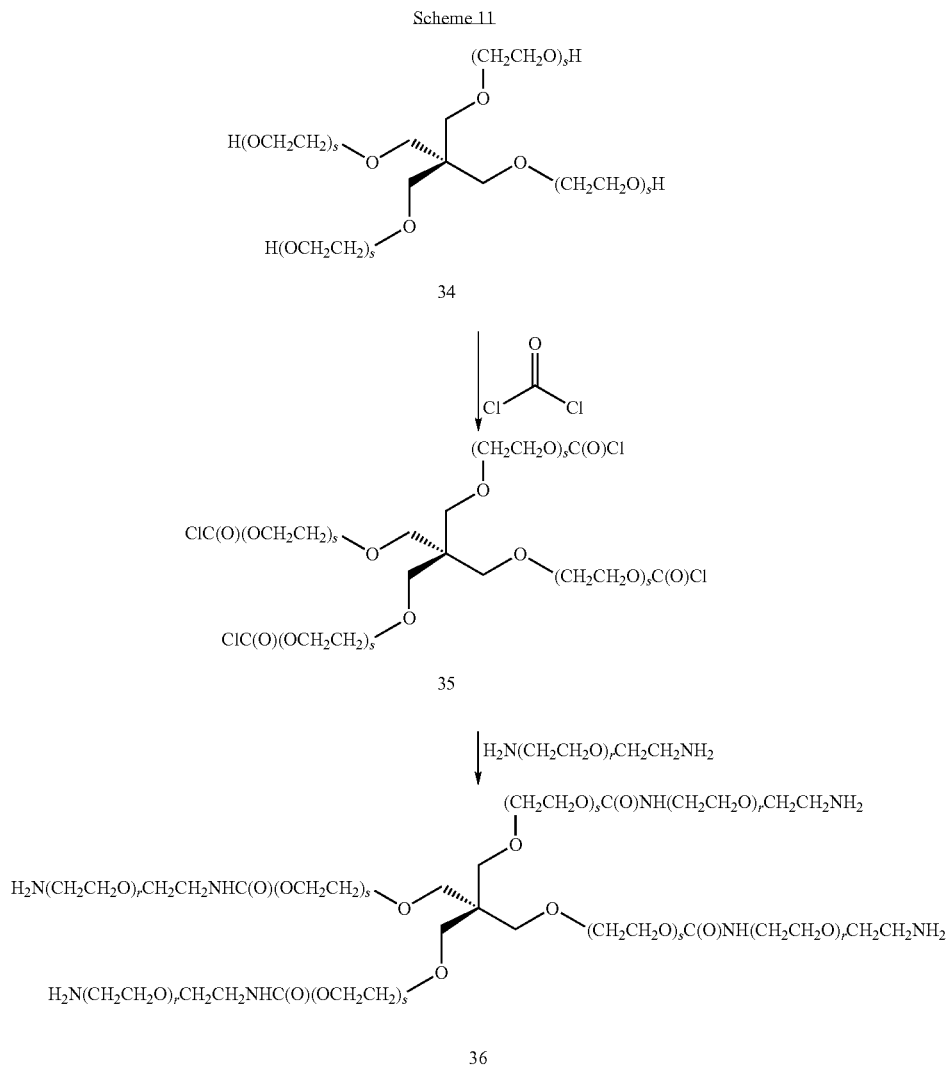

Specifically, wherein in Scheme 1 the aggregate of the four r's and s's is an integer preferably from about 100 to 1360.

Specifically, commercially available tetra-pegylated pentaerythritol, compound 34, (e.g., a compound having a total molecular weight of approximately 20 kD and available from Sun Bio, Orinda, Calif., USA, as catalog no. P40H-20), is reacted with an excess of phosgene, typically from at least 4 to about 40 equivalents, in a suitable inert solvent such as methylene chloride, chloroform and the like. The reaction is preferably conducted under an inert atmosphere at ambient conditions until the reaction is substantially complete which typically occurs in from about 2 to 24 hours. Afterwards, the resulting tetrachloroformate polyoxyethylene, compound 35, is recovered by convention procedures such as neutralization, evaporation, extraction, precipitation, chromatography, filtration, and the like or is used in the next reaction step without purification and/or isolation.

Tetrachloroformate, compound 35, is then combined with an excess (typically 2.5 to 10 equivalents per chloroformate entity) of an α,ω-diaminopolyoxyethylene compound (e.g., a compound having a molecular weight of approximately 6 kD and available from Sun Bio, as catalog no. P2AM-6), under conventional conditions in an inert diluent such as dichloromethane, optionally in the presence of a catalytic amount of DMAP and a base to scavenge the acid generate. The reaction is typically conducted at a temperature of about −20 to about 22° C. for about 2 to about 24 hours or until substantial completion of the reaction. Upon completion, compound 36 is recovered by conventional methods including neutralization, evaporation, extraction, precipitation, chromatography, filtration, and the like or, alternatively, is employed in the next step without purification and/or isolation.

When the specific tetra-pegylated pentaerythritol from Sun Bio and the diamine from Sun Bio are employed, the resulting product, compound 36, has a molecular weight of approximately 45 kD. α,ω-Diaminopolyoxyethylenes are commercially available under the tradename Jeffamines® and typically have molecular weights of up to 10,000 or higher.

It is understood that a mono-amino protected α,ω-diaminopolyoxyethylene may be used in Scheme 11 in order to minimize cross-linking as well as cyclization. Upon reaction completion, the mono-amino protecting group is removed by conventional means well known in the art.

Scheme 12 illustrates a second route for derivatization to provide for polymer substitution. In this scheme, the amino moiety of the piperazine group is employed as a complementary functional group to an in situ formed activated carboxyl groups of an α,ω-dicarboxylic acid polymer. Again for the sake of illustration only, the α,ω-dicarboxylic acid polymer is an α,ω-dicarboxylic acid polyoxyethylene. In this embodiment, the dicarboxyl-PEG compound is represented by the formula HOOCCH$_2$(OCH$_2$CH$_2$)$_p$OCH$_2$COOH where p is as defined above and the resulting linker to the PEG group is represented by —C(O)CH$_2$—.

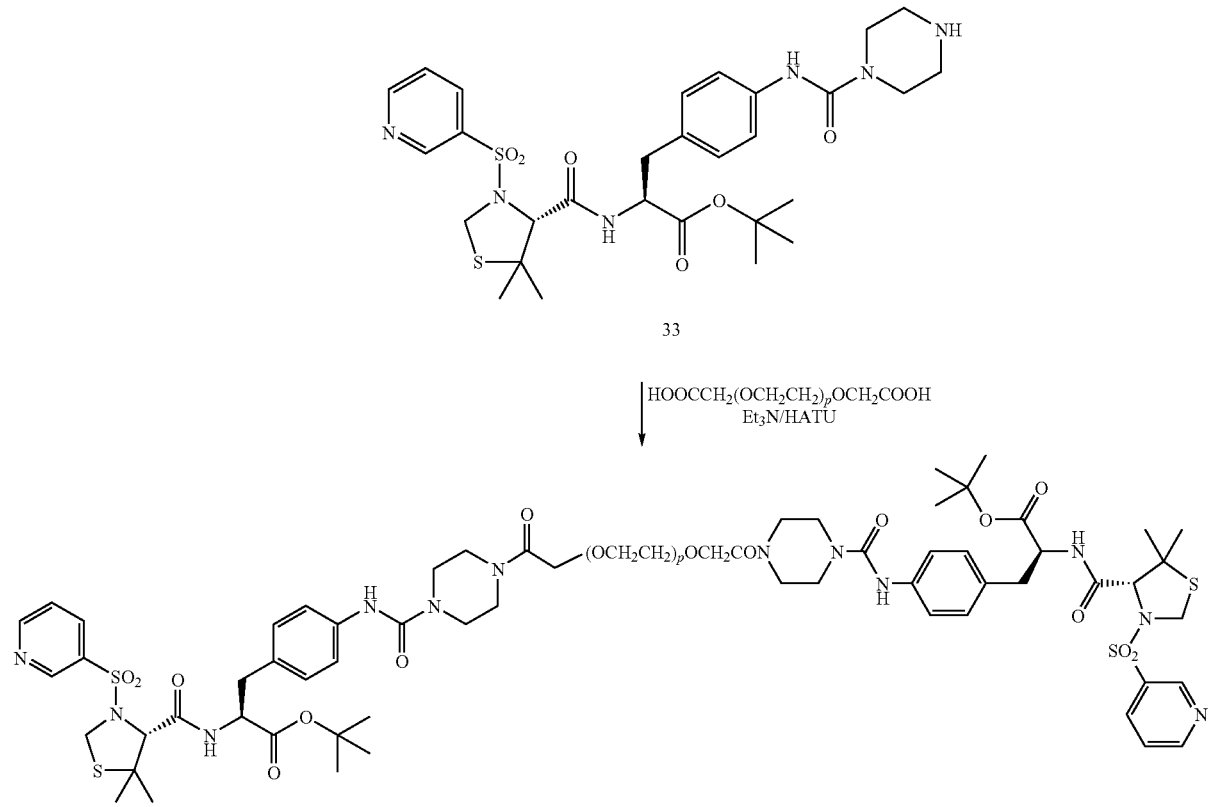

Specifically, in Scheme 12, an excess of compound 33 (e.g., 2.5 to 10 equivalents of compound 33 per carboxyl group), prepared as above, is added to the dicarboxyl-PEG compound which is converted in situ to an activated ester (not shown) by contact with at least two equivalents and preferably an excess of HATU [O-(7-azabenzotriazol-1-yl)-1,1,3,3-tetramethyluronium hexafluorophosphate] in the presence of a suitable amine such as triethylamine. Coupling of the dicarboxyl-PEG compound to compound 33 preferably proceeds at a temperature of from about 0 to about 22° C. for about 2 to about 24 hours. Upon completion of the reaction, the compound 39 is recovered by conventional methods including neutralization, evaporation, extraction, precipitation, chromatography, filtration, and the like or, alternatively, is employed in the next step without purification and/or isolation.

Conventional removal of the t-butyl carboxyl protecting group with an excess of formic acid provides for a compound of formula XVIIIA.

Scheme 13 illustrates still another route for derivatization to provide for polymer addition to compound A. In this scheme, the amino moiety of the piperazine group is employed as a complementary functional group to an in situ formed chloroformate of a polymer comprising an α,ω-diol. Again for illustrative purposes, the polymer comprising an α,ω-diol is PEG which is represented by the formula $HOCH_2CH_2(OCH_2CH_2)_pOH$ where p is as defined above and the resulting linker is represented by —C(O)—.

ture of from about 0 to about 22° C. for about 2 to about 4 hours. Upon completion of the reaction, the compound 44 is recovered by conventional methods including neutralization, evaporation, extraction, precipitation, chromatography, filtration, and the like or, alternatively, is employed in the next step without purification and/or isolation.

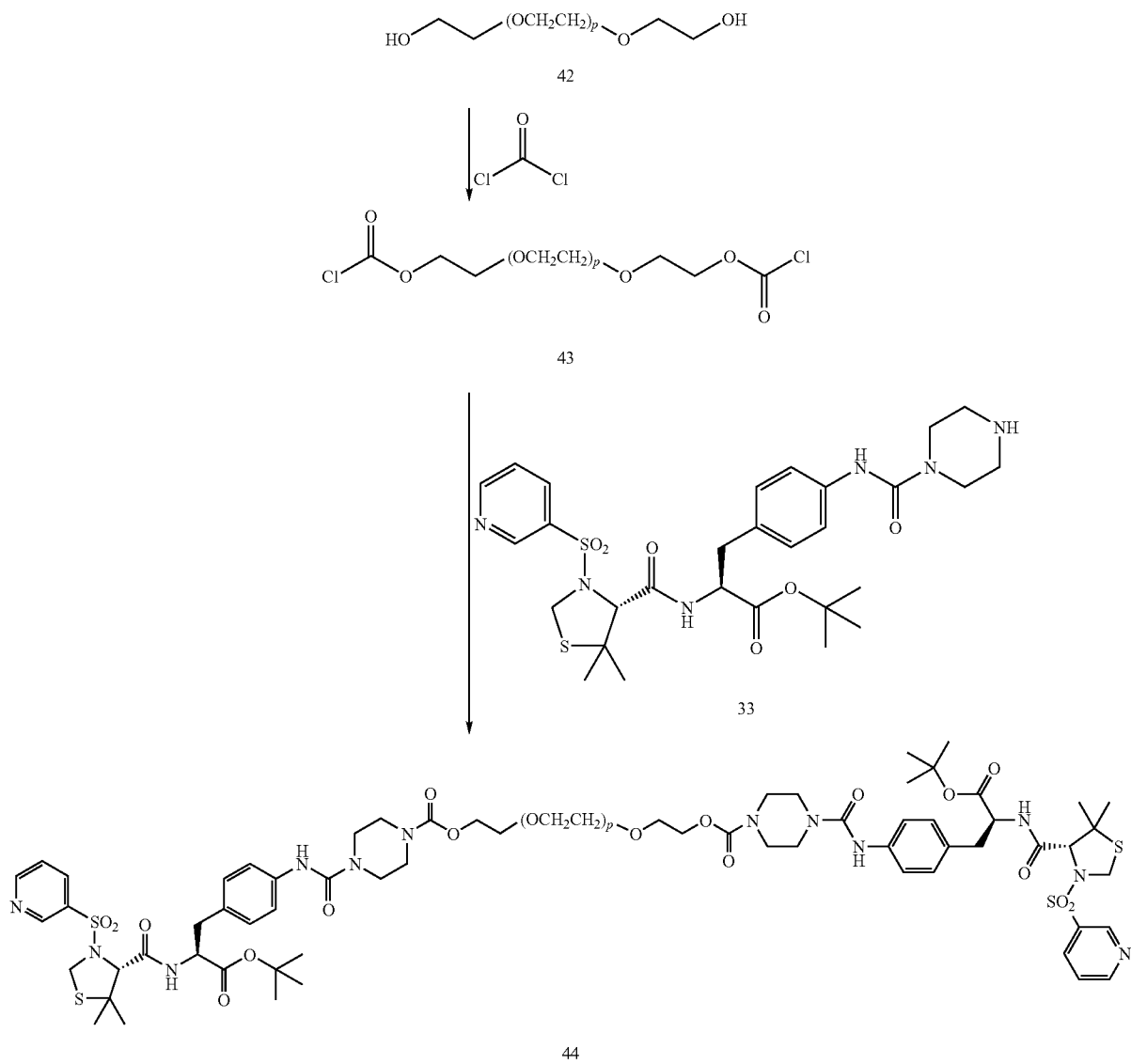

Specifically, in Scheme 13, the hydroxyl group of a commercially available dihydroxy PEG, 42, is converted to the corresponding chloroformate, 37 by reaction with phosgene in toluene (Fluka), in dichloromethane. The product is isolated by evaporation and is employed in the next step without further purification.

An excess of compound 33 (e.g., 2.5 to 10 equivalent of compound 33 per chloroformate entity) is contacted with dichloroformate, compound 43, prepared as above, in the presence of a suitable base such as triethylamine to scavenge the acid generated. Coupling of the dichloroformate-PEG compound to compound 33 preferably proceeds at a tempera- Conventional removal of the t-butyl carboxyl protecting group with an excess of formic acid provides for a compound of formula XVIII.

The reactions depicted in Schemes 12 and 13 are simultaneously conducted at either end of the dicarboxylic acid (Scheme 12) or the dichloroformate (Scheme 13) thereby providing a one pot synthesis of a homomeric divalent or higher multivalent conjugate. It is understood, however, that these reactions can be conducted sequentially by use of protecting groups.

In the case of a dicarboxylic acid, one of the carboxyl groups can be protected while the other undergoes coupling to the amino group of the piperazine. Upon completion, the protecting group can be removed and then reacted with either the same or preferably a different compound A to provide for a heterodivalent structure. Still further, heterotrivalent, heterotetravalent and higher heteromultivalent structures can be prepared by use of orthogonal protecting groups on the carboxylic functionality. In the case of a diol (Scheme 13), one of the hydroxyl groups can be protected while the other undergoes reaction with phosgene to form a chloroformate for subsequent addition to the amino group of the piperazine. Upon completion, the protecting group can be removed and then reacted with phosgene and subsequently with either the same or preferably a different compound A to provide for a heterodivalent structure. Still further, heterotrivalent, heterotetravalent and higher heteromultivalent structures can be prepared by use of orthogonal protecting groups on the alcohol functionality.

Scheme 14 illustrates the synthesis of N-carbamyl chloride and isocyanate intermediates useful for subsequent polymer addition. In this scheme, the amino moiety of the piperazine group is derivatized for subsequent polymer addition.

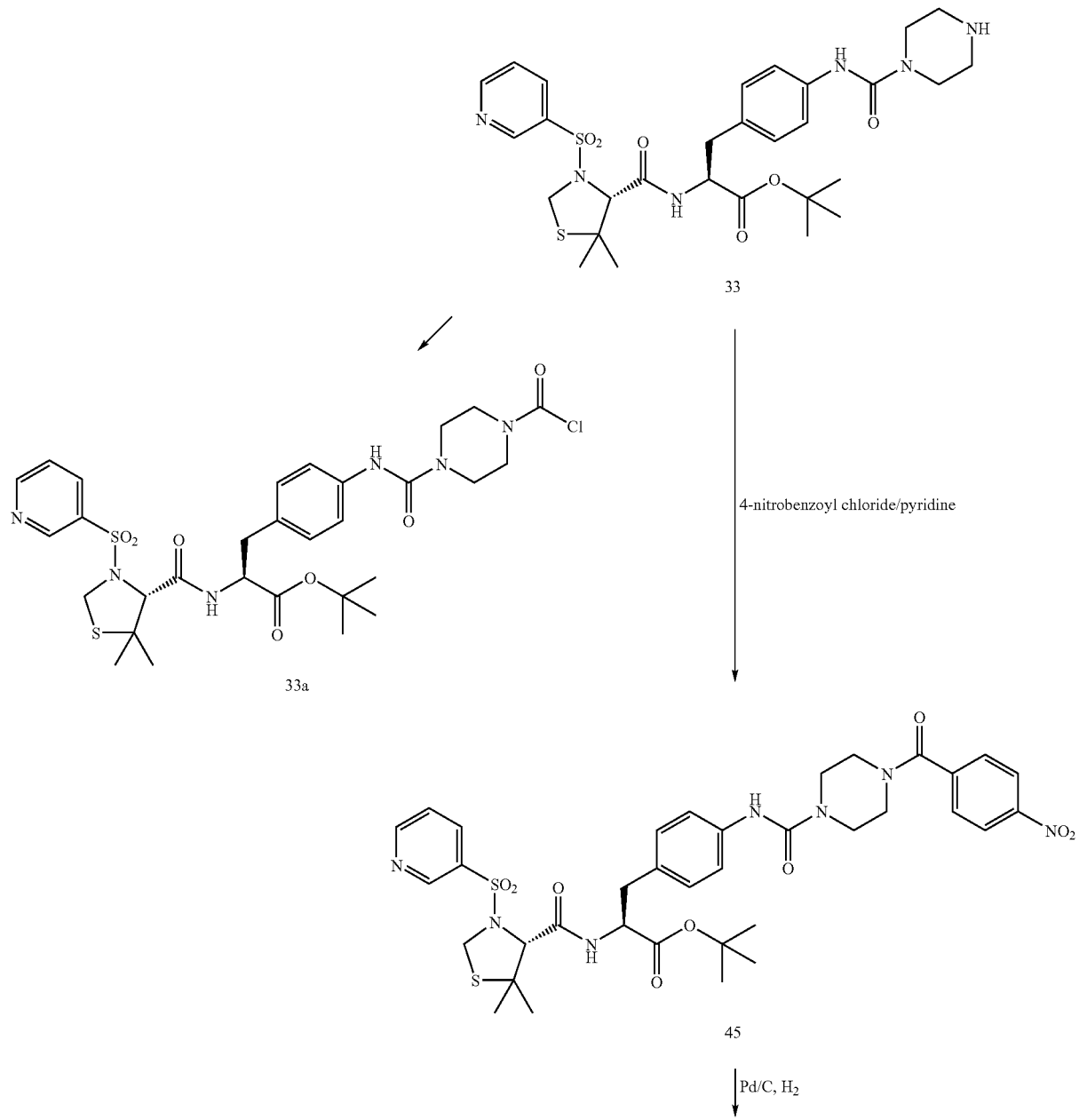

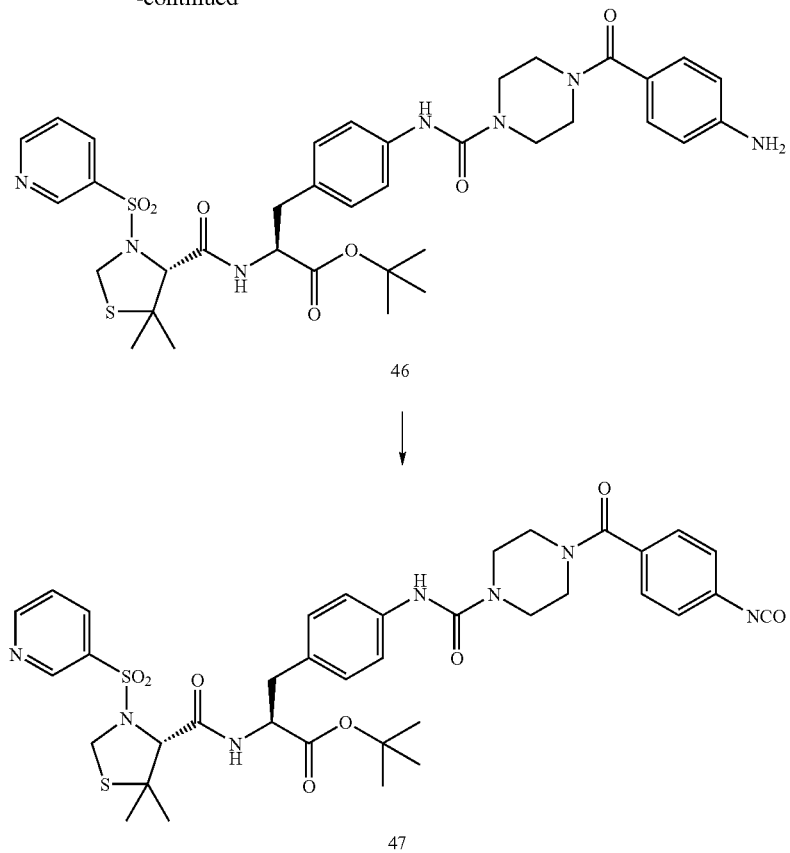

46

47

Specifically, in Scheme 14, conversion of the amino moiety of the piperazine group of compound 33, to the corresponding N-carbamyl chloride, compound 33a, proceeds by contact with an excess of phosgene in the presence of a suitable base such as sodium bicarbonate to scavenge the acid generated during reaction. Upon completion of the reaction, compound 33a can be recovered by conventional methods such as neutralization, evaporation, extraction, precipitation, chromatography, filtration, and the like or, alternatively and preferably is employed in the next (illustrated in Scheme 15) without purification and/or isolation.

Alternatively, the amino moiety of the piperazine group of compound 33 can be converted to the corresponding amide, compound 45, by reaction with at least an equivalent and preferably an excess of 4-nitrobenzoyl chloride in the presence of a base such as pyridine (which can also act as a solvent) to scavenge the acid generated during reaction. The reaction preferably proceeds at a temperature of from about 0 to about 22° C. for about 1 to about 24 hours. Upon completion of the reaction, compound 45 is recovered by conventional methods including neutralization, evaporation, extraction, precipitation, chromatography, filtration, and the like or, alternatively, is employed in the next step without purification and/or isolation.

Subsequent reduction of the para-nitro substituent of the phenyl group provides for the amine substituent in compound 46. Reduction is conventionally conducted using palladium/carbon under a hydrogen atmosphere typically at elevated pressures in a suitable diluent such as methanol. The reaction proceeds until substantial completion which typically occurs within about 24 to about 72 hours. During the reaction, additional catalyst is added as required to affect reaction completion. Upon completion of the reaction, the compound 46 is recovered by conventional methods including neutralization, evaporation, extraction, precipitation, chromatography, filtration, and the like or, alternatively, is employed in the next step without purification and/or isolation.

Conversion of the para-amino substituent of the phenyl group of compound 46 to the corresponding isocyanate, 47, occurs by reaction with an excess of phosgene in the presence of a suitable base such as sodium bicarbonate which scavenges the acid generated. The reaction proceeds until substantial completion which typically occurs within about 0.5 to about 5 hours at about 0° C. to about 22° C. Upon completion of the reaction, the compound 47 is recovered by conventional methods including neutralization, evaporation, extraction, precipitation, chromatography, filtration, and the like or, alternatively, is employed in the next step without purification and/or isolation.

Scheme 15 illustrates still a further route for derivatization to provide for polymer substitution. In this scheme, the carbamyl chloride moiety of the piperazine group of compound 33a is employed as a complementary functional group to form a carbamate or urea bond. For illustrative purposes only, the polymer employed is an α,ω-diol or diamine of a PEG and is represented by the formula $HQCH_2CH_2(OCH_2CH_2)_pQH$ where Q is NH or O.

Scheme 15

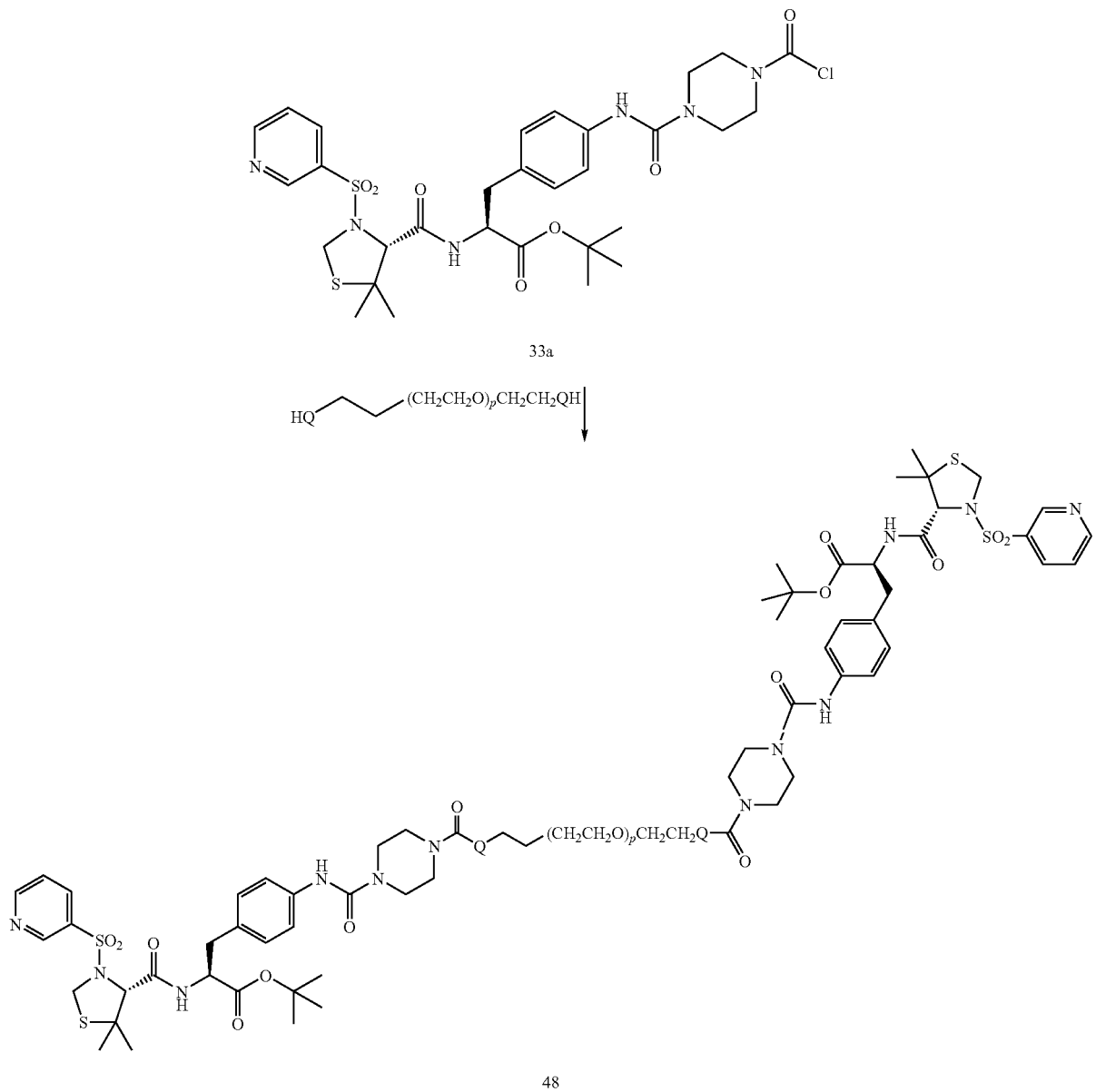

Specifically, in Scheme 15, an excess (e.g., 2.5 to 10 equivalents of carbamyl chloride per each HQ moiety) of compound 33a, is contacted in an inert solvent such as dichloromethane with a suitable dihydroxy- or diamino-PEG compound preferably in the presence of a suitable base such as triethylamine and/or catalytic amounts of 4-N,N-dimethylaminopyridine (DMAP). The reaction proceeds until substantial completion which typically occurs within about 4 to about 48 hours. Upon completion of the reaction, the compound 48 is recovered by conventional methods including neutralization, evaporation, extraction, precipitation, chromatography, filtration, and the like or, alternatively, is employed in the next step without purification and/or isolation.

When Q is a hydroxyl group, the product contains a carbamate functionality covalently linking the PEG group to the VLA-4 antagonist through a linker represented by —C(O)—.

When Q is an amino group, the product contains a urea functionality covalently linking the PEG group to the VLA-4 antagonist through a linker represented by —C(O)—. The t-butyl carboxyl protecting group can be conventionally removed with an excess of formic acid.

Scheme 16 illustrates yet another route for derivatization to provide for polymer substitution. In this scheme, the isocyanate of compound 47 is employed as a complementary functional group to form a carbamate or urea bond. For illustrative purposes only, the polymer employed is an α,ω-diol or diamine of a PEG and is represented by the formula $HQCH_2CH_2(OCH_2CH_2)_pQH$ where Q is NH or O.

Scheme 16

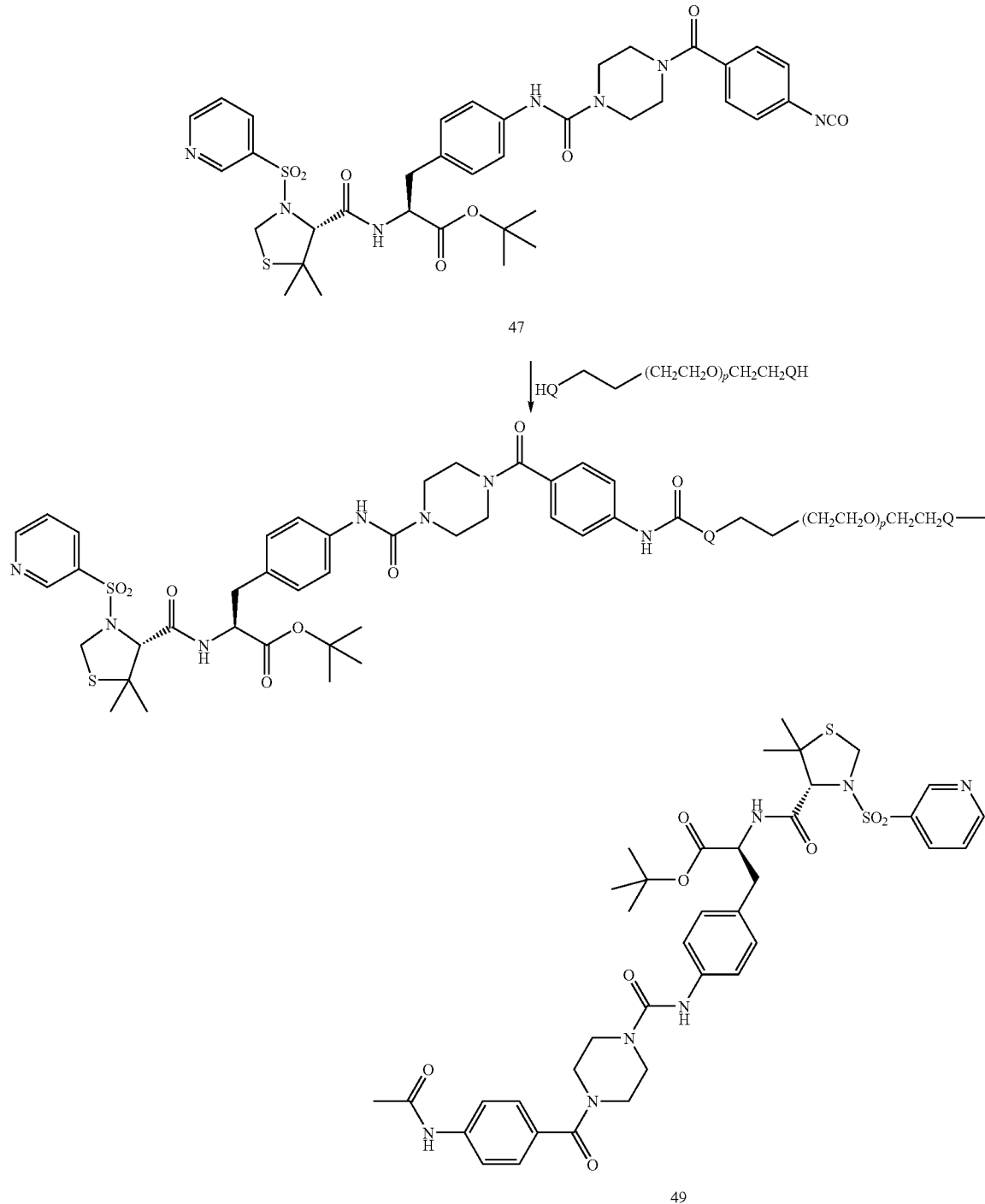

Specifically, in Scheme 16, an excess of isocyanate 47 (e.g., 2.5 to 10 equivalents of isocyanate 47 per each HQ moiety) is contacted with a suitable dihydroxy- or diamino-PEG compound in a suitable inert diluent such as dichloromethane or toluene. The reaction is preferably maintained at a temperature of from about 0° to about 105° C. until substantial completion which typically occurs within about 1 to about 24 hours. Upon completion of the reaction, compound 49 is recovered by conventional methods including neutralization, evaporation, extraction, precipitation, chromatography, filtration, and the like or, alternatively, is employed in the next step without purification and/or isolation.

When Q is a hydroxyl group, the resulting product contains a carbamate functionality covalently linking the PEG group to the VLA-4 antagonist through a —C(O)— linking group. When Q is an amino group, the resulting product contains a urea functionality covalently linking the PEG group to the VLA-4 antagonist through a —C(O)— linking group.

Conventional removal of the t-butyl carboxyl protecting group with an excess of formic acid provides for a mono-PEG compound, 47, of formula XVIII.

The reactions depicted in Schemes 15 and 16 are simultaneously conducted at both ends of the polymer (for dimer formation) thereby providing a one pot synthesis of a homomeric divalent or higher multivalent conjugate. It is understood, however, that these reactions can be conducted sequentially by use of protecting groups.

In the case of a diamine, one of the amine groups can be protected while the other undergoes coupling to either the carbamyl chloride of compound 33a or the isocyanate of compound 47. Upon completion, the protecting group can be removed and then reacted with either the same or preferably a different compound A to provide for a heterodivalent structure. Still further, heterotrivalent, heterotetravalent and higher heteromultivalent structures can be prepared by use of orthogonal protecting groups on one or more of the amine functionalities.

In the case of a diol, one of the hydroxyl groups can be protected while the other undergoes coupling to either the carbamyl chloride of compound 33a or the isocyanate of compound 47. Upon completion, the protecting group can be removed and then reacted with either the same or preferably a different compound A to provide for a heterodivalent structure. Still further, heterotrivalent, heterotetravalent and higher heteromultivalent structures can be prepared by use of orthogonal protecting groups on one or more of the hydroxyl functionalities.

In Schemes 5-16 above, amine moieties located on other portions of the molecule can be employed in the manner described above to covalently link a polymer group to the molecule. For example, amines located on $Ar^1$, on the heterocyclic amino acid or on $Ar^2$ can be similarly derivatized to provide for PEG substitution. The amine moieties can be included in these substituents during synthesis and appropriately protected as necessary. Alternatively, amine precursors can be employed. For example, as shown in Scheme 14, reduction of a nitro group provides for the corresponding amine. Similarly, reduction of a cyano group provides for a $H_2NCH_2$— group. Nitro and cyano substituted $Ar^1$ groups are provided in U.S. Pat. No. 6,489,300 as is an amino substituted $Ar^1$ group.

Further, the amino substitution can be incorporated into the heterocyclic amino acid functionality and then derivatized to include a polymer moiety. For example, the heterocyclic amino acid functionality can be 2-carboxylpiperazine depicted in U.S. Pat. No. 6,489,300. Alternatively, commercially available 3- or 4-hydroxyproline can be oxidized to the corresponding ketone and then reductively aminated with ammonia in the presence of sodium cyanoborohydride to form the corresponding amine moiety. Still further, 4-cyanoproline can be reduced to provide for a substituted alkyl group of the formula —$CH_2NH_2$ which can be derivatized through the amine.

Still further, the amine moiety can be incorporated into the $Ar^2$ functionality. Preferably, the amine moiety is present as an amine precursor such as a nitro or cyano group bound to $Ar^2$.

In Schemes 5-16 above, the reactions of the amine with a complementary functional group can be reversed such that the carboxyl or hydroxyl group is on the VLA-4 antagonist of formula XIX (without any polymer substituents) and the amine group could be part of the polymer moiety. In such cases, the amine group, preferably terminating the polymer moiety, can be converted to an isocyanate, using phosgene and $Et_3N$, and reacted with the hydroxyl group to form a carbamate as illustrated in Scheme 17 below:

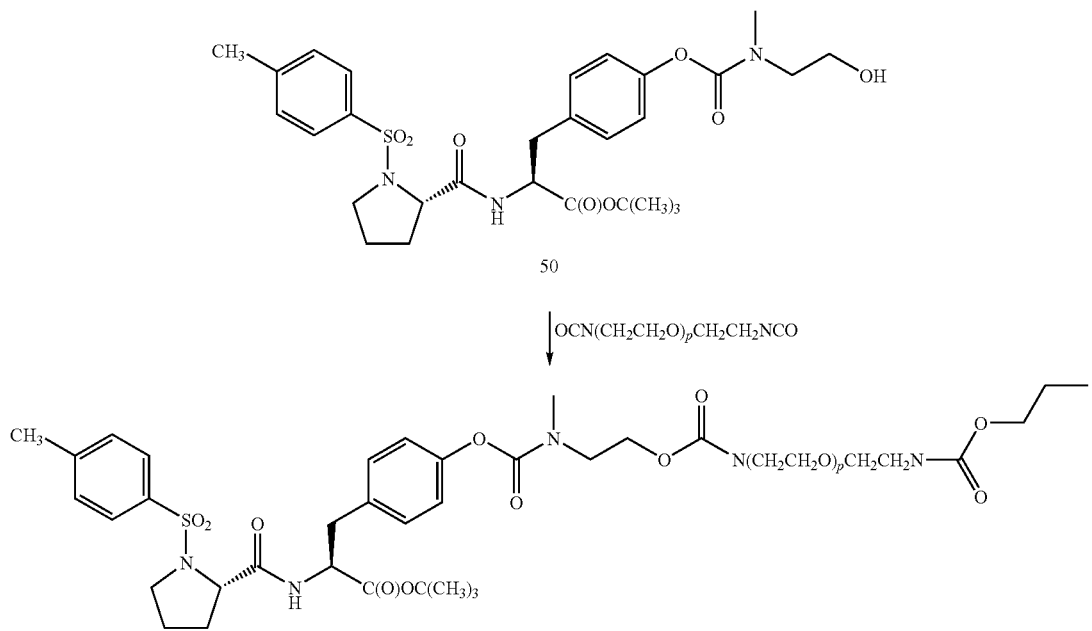

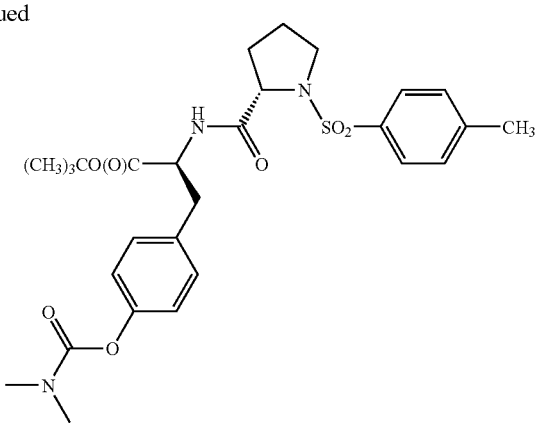

Specifically, an excess of compound 50 described in U.S. Pat. No. 6,489,300, is contacted with in the manner described above to provide for the corresponding carbamate, 51. Preferably, from about 2.5 to 10 equivalents of compound 50 per each isocyanate moiety is employed. Deprotection, as described above, then provides for the corresponding diacid (not shown).

Alternatively, in Scheme 17, the hydroxyl functionality can be reacted with phosgene to provide for the chlorocarbonyloxy derivative which reacts with an amine group of a diamine compound to provide for the carbamate.

Carboxyl functionality, for example on the $Ar^1$ moiety, can be converted to the corresponding amide by reaction with a di- or higher-aminopolymer in the manner described above in Scheme 12. Alternatively, Scheme 18 below illustrates one method for the generation of an amine functionality from the corresponding cyano group on the $Ar^1$ moiety.

Scheme 18

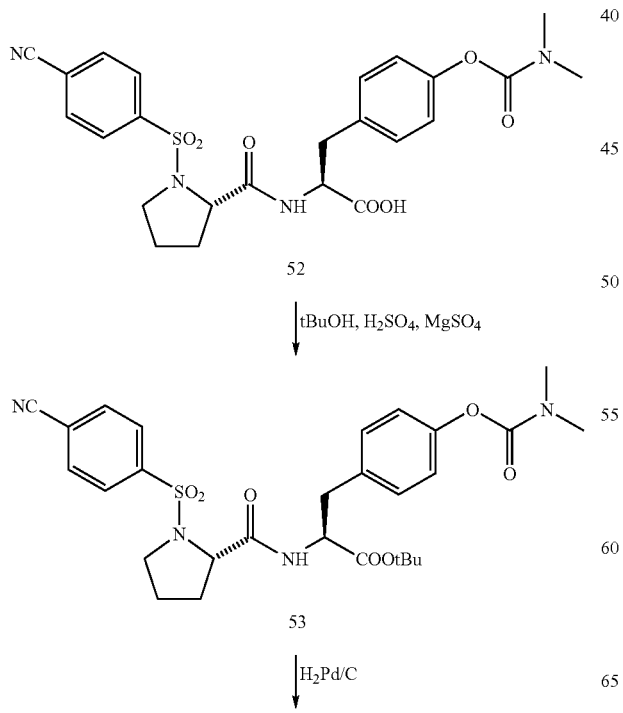

-continued

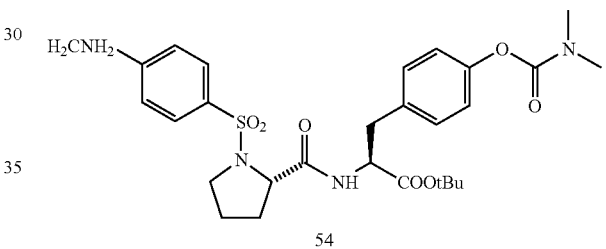

54

Specifically, in Scheme 18, known compound 52, described in U.S. Pat. No. 6,489,300, is t-butyl protected under convention conditions to provide the cyano compound 53, which is hydrogenated under conventional conditions to provide the aminomethyl compound 54. The aminomethyl group of compound 54 is available for coupling of a polymer moiety thereto in one on any of Schemes 5-18 illustrated above.

Scheme 19 below illustrates an alternative synthesis of 3-aminopyrrolidinyl derivatives useful for coupling a polymer moiety thereto in any one of Schemes 5-18 illustrated above.

Scheme 19

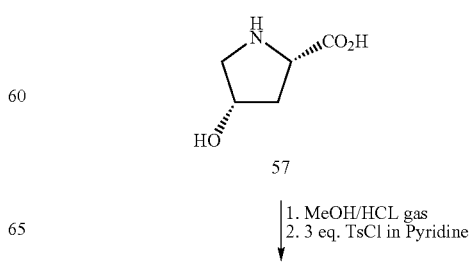

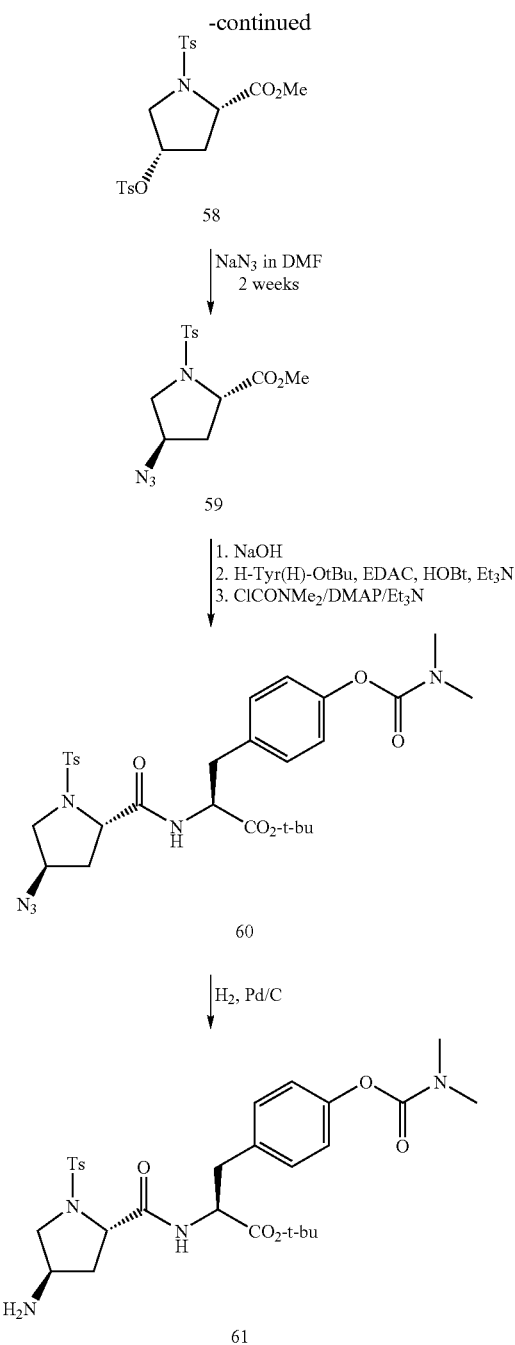

solvent such as EtOAc. The product 59 may be purified by crystallization, flash chromatography, or more preferably be used in subsequent steps without purification.

Compound 59 is treated with sodium hydroxide, in a mixture of water and methanol, thus hydrolyzing the methyl ester and generating a carboxylic acid, which is isolated by acidification and extraction with an organic solvent such as EtOAc. The carboxylic acid is treated with L-tyrosine t-butyl ester[H-Tyr(H)-OtBu], EDAC, HOBt, and $Et_3N$ in DMF, generating a dipeptide, which is isolated by dilution with water and extraction with an organic solvent such as EtOAc. The dipeptide is treated with $ClCONMe_2$, $Et_3N$, and DMAP in DCM at reflux for 24 hours, generating the carbamate, 60, which is isolated by dilution with EtOAc, sequential washing with weak aqueous acid and base, and then evaporation. Compound 60 is rigorously purified by flash chromatography.

Finally, compound 61 is prepared by shaking of a solution of 60 in methanol, with a Pd/C catalyst under an atmosphere of hydrogen. The product, 61, is isolated by removal of the catalyst by filtration and evaporation.

Other methods for coupling of a compound of formula XIX with a polymer (optionally bound to a branched-arm hub molecule) are well known in the art.

Other polymers suitable for conjugation to a compound of formula XIX include, without limitation, polyvinylpyrrolidone (PVP), polyacrylamide (PAAm), polydimethylacrylamide (PDAAm), polyvinyl alcohol (PVA), dextran, poly(L-glutamic acid) (PGA), styrene maleic anhydride (SMA), poly-N-(2-hydroxypropyl)methacrylamide (HPMA), polydivinylether maleic anhydride (DIVEMA). By way of example, PVP, PAAm and PDAAm may be functionalized by introduction of co-monomers during radical polymerization. PVA and dextran each contain primary hydroxyl (OH) groups suitable for conjugation. Methods for synthesis of these biopolymers and for conjugating them to biological materials are well known in the art (see, for example, published U.S. Patent Application 20040043030; U.S. Pat. No. 5,177,059; U.S. Pat. No. 6,716,821; U.S. Pat. No. 5,824,701; U.S. Pat. No. 6,664,331; U.S. Pat. No. 5,880,131; Kameda, Y. et al., Biomaterials 25: 3259-3266, 2004; Thanou, M. et al, Current Opinion in Investigational Drugs 4(6): 701-709, 2003; Veronese, F. M., et al., Il Farmaco 54: 497-516, 1999, all of which are incorporated herein in their entireties).

Pharmaceutical Formulations of the Polymer Conjugates

When employed as pharmaceuticals, the conjugates are usually administered in the form of pharmaceutical compositions. These conjugates can be administered by a variety of routes including oral, rectal, transdermal, subcutaneous, intravenous, intramuscular, sublingual, ophthalmic, or inhalation including administration by nasal or oral inhalation. Preferred administration routes include subcutaneous, intravenous, and intramuscular. Such compositions are prepared in a manner well known in the pharmaceutical art and comprise at least one conjugate.

The invention also provides pharmaceutical compositions comprising a conjugate according to the invention, e.g., a conjugate of Formula I, in combination with a separate compound which is an $\alpha_4\beta_7$ inhibitor. Such compositions also comprise a pharmaceutically acceptable carrier or excipient and may be administered as discussed elsewhere herein.

The conjugate is effective over a wide dosage range and is generally administered in a pharmaceutically effective amount. It, will be understood, however, that the amount of the conjugate actually administered will be determined by a physician, in the light of the relevant circumstances, including the condition to be treated, the chosen route of adminis- Using conventional methods, commercially available cis-4-hydroxy L-proline, 57, is treated with methanolic hydrogen chloride for several hours at reflux, followed by evaporation, and the so generated methyl ester hydrochloride is treated with excess tosyl chloride in pyridine for two days at room temperature, giving the product, 58. Compound 58 is isolated by neutralizing the pyridine using weak aqueous acid and extracting the product with an organic solvent such as EtOAc. The product 58 may be purified by crystallization, flash chromatography, or more preferably be used in subsequent steps without purification.

Reaction of 58 with a saturated solution of excess sodium azide in DMF at room temperature for 15 days affords compound 59. Compound 59 is isolated by dilution of the reaction mixture with water, followed by extraction with an organic tration, the actual compound administered, the age, weight, and response of the individual patient, the severity of the patient's symptoms, and the like.

Polymer Conjugates

As described with reference to the conjugates, compounds are formulated and administered are polymer conjugates. Polymer conjugates are anticipated to provide benefits over non-conjugated compounds, such as improved solubility and in vivo stability.

As such, single polymer molecule may be employed for conjugation with the compounds, although it is also contemplated that more than one polymer molecule can be attached as well, typically through a carrier. Additionally, it will be recognized that the conjugating polymer may utilize any other groups, moieties, or other conjugated species, as appropriate to the end use application. As an example, it may be advantageous in some applications to functionalize the polymer to render it reactive and enable it to conjugate to a compound of formula XIX and to enhance various properties or characteristics of the overall conjugated material. Accordingly, the polymer may contain any functionality, repeating groups, linkages, or other constituent structures which do not preclude the efficacy of the conjugated compounds for its intended purpose.

Illustrative polymers that are usefully employed to achieve these desirable characteristics are described supra, as well as in WO 01/54690 (to Zheng et al.) incorporated by reference herein in its entirety. The polymer may be coupled to the compounds (preferably via a linker moiety) to form stable bonds that are not significantly cleavable by human enzymes. Generally, for a bond to be not "significantly" cleavable requires that no more than about 20% of the bonds connecting the polymer and the compounds to which the polymer is linked, are cleaved within a 24 hour period, as measured by standard techniques in the art including, but not limited to, high pressure liquid chromatography (HPLC).

Generally, the compounds contain at least about 2 compounds of formula XIX bound to a polymer. The final amount is a balance between maximizing the extent of the reaction while minimizing non-specific modifications of the product and, at the same time, defining chemistries that will maintain optimum activity, while at the same time optimizing the half-life of the compounds. Preferably, at least about 50% of the biological activity of the compounds is retained, and most preferably 100% is retained.

As noted above, in an embodiment, polyalkylene glycol residues of $C_2$-$C_4$ alkyl polyalkylene glycols, preferably polyethylene glycol (PEG), or poly(oxy)alkylene glycol residues of such glycols are advantageously incorporated in the polymer systems of interest. Thus, the polymer to which the compounds are attached may be a homopolymer of polyethylene glycol (PEG) or is a polyoxyethylated polyol, provided in all cases that the polymer is soluble in water at room temperature. Non-limiting examples of such polymers include polyalkylene oxide homopolymers such as PEG or polypropylene glycols, polyoxyethylenated glycols, copolymers thereof and block copolymers thereof, provided that the water solubility of the block copolymer is maintained.

Examples of polyoxyethylated polyols include, but are not limited to, polyoxyethylated glycerol, polyoxyethylated sorbitol, polyoxyethylated glucose, or the like. The glycerol backbone of polyoxyethylated glycerol is the same backbone occurring naturally in, for example, animals and humans in mono-, di-, and triglycerides. Therefore, this branching would not necessarily be seen as a foreign agent in the body.

Those of ordinary skill in the art will recognize that the foregoing list is merely illustrative and that all polymer materials having the qualities described herein are contemplated. The polymer need not have any particular molecular weight, but it is preferred that the molecular weight be between about 100 and 100,000, preferably from about 10,000 to 80,000; preferably about 10,000 to 60,000; more preferably from about 20,000 to about 60,000; and more preferably about 40,000 to 45,000. In particular, sizes of 20,000 or more are most effective at preventing loss of the product due to filtration in the kidneys.

By PEG derivative is meant a polyethylene glycol polymer in which one or both of the terminal hydroxyl groups found in polyethylene glycol itself has been modified. Examples of suitable modifications include replacing one or both hydroxyl group(s) with alternative functional groups, which may be protected or unprotected, with low molecular weight ligands, or with another macromolecule or polymer. Modification of the terminal hydroxyl groups in the polyethylene glycol may be achieved by reacting the polyethylene glycol with compounds comprising complementary reactive functional groups, including functional groups which are able to undergo a reaction with the hydroxyl groups in polyethylene glycol. The PEG derivatives of the compounds may contain one or more polyethylene glycol (PEG) substituents covalently attached thereto by a linking group.

Further description of the conjugates of the above formulae XVIII and XX-XXII and procedures and reaction conditions for preparing these compounds are described in WO 2006/010054 entitled Multivalent VLA-4 Antagonists Comprising Polymer Moieties, published Jan. 26, 2006, incorporated in its entirety by reference.

Combination Therapies

The compositions as disclosed herein may be utilized in combination therapies. Many treatments exist for cancers. The particular cancer therapy or combination of therapy modalities used to treat a cancer depend greatly on the type of cancer, its stage, the patient (e.g., weight, sex, age, health, prior cancers, and the like), and where the patient is in therapy (e.g., first treatment, in blast crisis, refractive to initial treatments, cancer relapse, or a second cancer perhaps induced by the treatment of the first cancer months or years before). Accordingly, physicians will frequently have to combine a variety of treatment modalities that will best suit the needs of the patient in combating the disease and the patient's self-determination of quality of life. Treatments may include surgery, radiation therapy, chemotherapy, biologic therapy (e.g., cytokines, immunotherapy, and interferons), hormone therapies, and hyperthermia.

Conventional chemotherapy can be further broken down into hormone therapies (e.g., antiestrogens, aromatase inhibitors, gonadotropin-releasing hormone analogues, and anti-androgens), anti-tumor alkylating agents (e.g., mustards, nitrosoureas, tetrazines, and aziridines), cisplatin and its analogues, anti-metabolites (e.g., methotrexate, antifolates, 5-fluoropyrimidines, cytarabine, azacitidine, gemcitabine, 6-thipurines, and hydroxyurea), topoisomerase interactive agents, antimicrotubule agents (e.g., vinca alkaloids, taxanes, and estramustine), differentiating agents (e.g., retinoids, vitamin D3, polar-apolar compounds, butyrate and phenylactetate, cytotoxic drugs, cytokines, and combinations thereof), and other chemotherapeutic agents such as fludarabine, 2-chlorodeoxyadenosine, 2'-deoxycoformycin, homoharringtonine (HHT), suramin, bleomycin, and L-asparaginase.

The compositions of the present invention may be administered in conjunction with chemotherapeutic agents. For example, the compounds of the present invention may be administered with acute chemotherapy when the cancer is characterized by alpha-4 positive tumors, such as leukemia and myeloma. The chemotherapy drug may include, but is not limited to, melphalan, vincristine, cyclophosphamide, doxorubicin, idarubicin, or carmustine.

The compositions of the present invention may be administered with one or more therapies, active agents, or treatments utilized in treating liquid tumor cancers. As such, the compositions of the present invention may be administered with alkylating agents, including for example, melphalan, cyclophosphamide, nitrosoureas, and the like. The compositions of the present invention may be administered with anti vascular endothelial growth factor (anti-VEGF) agents, including for example, Avastin and VEGF-trap. The compositions of the present invention may be administered with bis-phosphonates, including for example zoledronic acid. The compositions of the present invention may be administered with interferon alpha agents. The compositions of the present invention may be administered with Temsirolimus. The compositions of the present invention may be administered with anti-CD20 agents, including for example rituximab. The compositions of the present invention may be administered with clarithromycin. The compositions of the present invention may be administered with stem cell transplants, both autologous and allogeneic. The compositions of the present invention may be administered with histone deacetylase (HDAC) inhibitors, including for example Vorinostat.

The compositions of the present invention may be administered with any single or multiple combination of velcade, revlimid, dexamethaonse, thaliodmide, doxorubicin, cyclophosphamide, vincristine, and prednisolone. In certain embodiments, the compositions of the present invention may be administered in conjunction with velcade and doxil. In other embodiments, the compositions of the present invention may also be administered in conjunction with revlimid and dexamethasone.

When utilized in combination therapies, the compositions of the present invention may be utilized with one or more of the therapies, active agents, or treatments utilized in treating liquid tumor cancers.

The combined use of the agents of the present invention with these other therapies or treatment modalities may be concurrent, or the two treatments may be divided up such that the agent of the present invention may be given prior to or after the other therapy or treatment modality.

Combination Therapy for Ameliorating Conditions Associated with Treating Cancer

Cancer treatments often use radiation or chemotherapy to poison cancer cells, as cancer cells proliferate faster than normal cells, making them more susceptible to the chemotherapy and radiation. Treating a patient with radiation and chemotherapy or even with some of the newer cancer treatment modalities, however, does have adverse side effects to the patient.

Thus, one aspect of the invention contemplates the use of compounds and compositions which ameliorate the negative effects produced by the combination of the treatment modalities used to treat the patients. For example, drugs can be administered to the patient in conjunction with the anti-cancer therapy that would treat adverse effects, such as but not limited to, nausea, vomiting, mucositis and other oral complications, cystitis, pulmonary toxicity, cardiac toxicity, hair loss, and gonadal dysfunction. Accordingly, the reagents and combination treatments discussed herein can be further combined with drug treatments that ameliorate these adverse effects, as well as in combination with any conventional cancer treatment modalities. For details regarding methods of ameliorating the adverse effects of cancer therapies, see generally CANCER: PRINCIPLES & PRACTICE OF ONCOLOGY (Vincent T. DeVita et al., editors, 5th ed., 1997).

Pharmaceutical Formulations and Methods of Administration of the Compositions

In general, the compositions of the subject invention will be administered in a therapeutically effective amount by any of the accepted modes of administration for these compounds. The compositions can be administered by a variety of routes, including, but not limited to, oral, parenteral (e.g., subcutaneous, subdural, intravenous, intramuscular, intrathecal, intraperitoneal, intracerebral, intraarterial, or intralesional routes of administration), topical, intranasal, localized (e.g., surgical application or surgical suppository), rectal, and pulmonary (e.g., aerosols, inhalation, or powder). Accordingly, these compounds are effective as both injectable and oral compositions. The compositions can be administered continuously by infusion or by bolus injection.

Preferably, the compositions are administered by parenteral routes. More preferably, the compositions are administered by intravenous, subcutaneous, and intramuscular routes. Such compositions are prepared in a manner well known in the pharmaceutical art.

For example, the pegylated conjugates may be administered via an injectable route, including subcutaneous, subdural, intravenous, intramuscular, intrathecal, intraperitoneal, intracerebral, intraarterial, or intralesional routes. The conjugates can be administered continuously by infusion or by bolus injection. Such compositions are prepared in a manner well known in the pharmaceutical art. For pegylated compounds administered as an injectable formulation, the dose may be in the range of about 0.01 mg to about 20 mg per kilogram body weight, preferably about 0.02 mg to about 15 mg per kilogram body weight and more preferably about 0.05 mg to about 10 mg per kilogram of body weight. Effective doses can be extrapolated from dose-response curves derived from in vitro or animal model test systems. Typically, the clinician will administer the compound until a dosage is reached that achieves the desired effect.

The compositions of the present invention may be administered in dosing intervals. These intervals can be once a day, once a week, once every two weeks, monthly, or as otherwise appropriate. The clinician will know how to adapt the dosing to be compatible with the dosing interval.

The actual amount of the composition of the subject invention, i.e., the active ingredient, will depend on a number of factors, such as the severity of the tumor and/or malignancy, the age and relative health of the subject, the potency of the compound used, the route and form of administration, and other factors.

Toxicity and therapeutic efficacy of such compositions can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$ Compounds that exhibit large therapeutic indices are preferred.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any composition used in the method of the invention, the therapeutically effective dose can be estimated initially from cell culture assays. A dose may be formulated in animal models to achieve a circulating plasma concentration range which includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The amount of the pharmaceutical composition administered to the patient will vary depending upon what is being administered, the purpose of the administration, such as prophylaxis or therapy, the state of the patient, the manner of administration, and the like. In therapeutic applications, compositions are administered to a patient already suffering from a disease in an amount sufficient to cure or at least partially arrest the symptoms of the disease and its complications. An amount adequate to accomplish this is defined as "therapeutically effective dose." Amounts effective for this use will depend on the disease condition being treated as well as by the judgment of the attending clinician depending upon factors such as the severity of the inflammation, the age, weight and general condition of the patient, and the like.

The compositions administered to a patient are in the form of pharmaceutical compositions described herein. These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The active composition is effective over a wide dosage range and is generally administered in a pharmaceutically or therapeutically effective amount. The therapeutic dosage of the compounds of the present invention will vary according to, for example, the particular use for which the treatment is made, the manner of administration of the compound, the health and condition of the patient, and the judgment of the prescribing physician. For example, for intravenous administration, the dose may be in the range of about 0.01 mg to about 20 mg per kilogram body weight, preferably about 0.02 mg to about 15 mg per kilogram body weight and more preferably about 0.05 mg to about 10 mg per kilogram of body weight. Effective doses can be extrapolated from dose-response curves derived from in vitro or animal model test systems. Typically, the clinician will administer the compound until a dosage is reached that achieves the desired effect.

Administration may be carried out continuously or periodically within the maximum tolerated dose. The administration may be conducted, for example, hourly, once every two hours, once every six hours, once every twelve hours, daily, weekly, every two weeks, every three weeks, or monthly, as needed. Administration may be conducted, for example, weekly or in single or double daily doses.

When employed as pharmaceuticals, the compositions of the subject invention are usually administered in the form of pharmaceutical compositions. This invention also includes pharmaceutical compositions, which contain as the active ingredient, one or more of the compositions of the subject invention above, associated with one or more pharmaceutically acceptable carriers or excipients. The excipient employed is typically one suitable for administration to human subjects or other mammals. In making the compositions of this invention, the active ingredient is usually mixed with an excipient, diluted by an excipient or enclosed within a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active composition to provide the appropriate particle size prior to combining with the other ingredients. If the active composition is substantially insoluble, it ordinarily is milled to a particle size of less than 200 mesh. If the active composition is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The quantity of active composition in the pharmaceutical formulation and unit dosage form thereof may be varied or adjusted widely depending upon the particular application, the manner or introduction, the potency of the particular composition, and the desired concentration. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Preferably, the composition is formulated for parenteral administration in a suitable inert carrier, such as a sterile physiological saline solution. The dose administered will be determined by route of administration. Preferred routes of administration include parenteral or intravenous administration.

By way of example, for preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above.

The dosage per day for oral dosage forms may include, for example, 10 mg to about 2900 mg per day of the active ingredient of the present invention. Preferably, the oral dosage form may contain about 50 mg to about 1200 mg of the active ingredient per day.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer, which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compositions of the present invention may be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described herein. The compositions may be administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices which deliver the formulation in an appropriate manner.

The compositions of this invention can be administered in a sustained release form. Suitable examples of sustained-release preparations include semipermeable matrices of solid hydrophobic polymers containing the protein, which matrices are in the form of shaped articles, e.g., films, or microcapsules. Examples of sustained-release matrices include polyesters, hydrogels (e.g., poly(2-hydroxyethyl-methacrylate) as described by Langer et al., J. Biomed. Mater. Res. 15: 167-277 (1981) and Langer, Chem. Tech. 12: 98-105 (1982) or poly(vinyl alcohol)), polylactides (U.S. Pat. No. 3,773, 919), copolymers of L-glutamic acid and gamma ethyl-L-glutamate (Sidman et al., Biopolymers 22: 547-556, 1983), non-degradable ethylene-vinyl acetate (Langer et al., supra), degradable lactic acid-glycolic acid copolymers such as the LUPRON DEPOT™ (i.e. injectable microspheres composed of lactic acid-glycolic acid copolymer and leuprolide acetate), and poly-D-(−)-3-hydroxybutyric acid (EP 133,988).

The compositions of this invention can be administered in a sustained release form, for example a depot injection, implant preparation, or osmotic pump, which can be formulated in such a manner as to permit a sustained release of the active ingredient. Implants for sustained release formulations are well-known in the art. Implants may be formulated as, including but not limited to, microspheres, slabs, with biodegradable or non-biodegradable polymers. For example, polymers of lactic acid and/or glycolic acid form an erodible polymer that is well-tolerated by the host. The implant is placed in proximity to the site of protein deposits (e.g., the site of formation of amyloid deposits associated with neurodegenerative disorders), so that the local concentration of active agent is increased at that site relative to the rest of the body.

The following formulation examples illustrate the pharmaceutical compositions of the present invention.

Formulation Example 1

A subcutaneous formulation may be prepared as follows:

| Ingredient | Quantity |
| --- | --- |
| Active Ingredient | 50 mg · mL mg |
| Phosphate buffered saline | 1.0 ml |

Formulation Example 2

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules in 340 mg quantities.

Formulation Example 3

A tablet formula is prepared using the ingredients below:

| Ingredient | Quantity (mg/tablet) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Example 4

Tablets, each containing 30 mg of active ingredient, are prepared as follows:

| Ingredient | Quantity (mg/tablet) |
| --- | --- |
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° C. to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Formulation Example 5

Capsules, each containing 40 mg of medicament are made as follows:

| Ingredient | Quantity (mg/capsule) |
|---|---|
| Active Ingredient | 40.0 mg |
| Starch | 109.0 mg |
| Magnesium stearate | 1.0 mg |
| Total | 150.0 mg |

The active ingredient, starch and magnesium stearate are blended, passed through a No. 20 mesh U.S. sieve, and filled into hard gelatin capsules in 150 mg quantities.

Formulation Example 6

Suppositories, each containing 25 mg of active ingredient are made as follows:

| Ingredient | Amount |
|---|---|
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Example 7

Suspensions, each containing 50 mg of medicament per 5.0 ml dose are made as follows:

| Ingredient | Amount |
|---|---|
| Active Ingredient | 50.0 mg |
| Xanthan gum | 4.0 mg |
| Sodium carboxymethyl cellulose (11%) | 50.0 mg |
| Microcrystalline cellulose (89%) | |
| Sucrose | 1.75 g |
| Sodium benzoate | 10.0 mg |
| Flavor and Color | q.v. |
| Purified water to | 5.0 ml |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Example 8

An intravenous formulation may be prepared as follows:

| Ingredient | Quantity |
|---|---|
| Active Ingredient | 250 mg |
| Isotonic saline | 100 ml |

Other suitable formulations for use in the present invention can be found in Remington's Pharmaceutical Sciences, Mace Publishing Company, Philadelphia, Pa., 17th ed. (1985).

As noted above, the compositions described herein are suitable for use in a variety of drug delivery systems described above. Additionally, in order to enhance the in vivo serum half-life of the administered composition, the compositions may be encapsulated, introduced into the lumen of liposomes, prepared as a colloid, or other conventional techniques may be employed which provide an extended serum half-life of the compounds. A variety of methods are available for preparing liposomes, as described in, e.g., Szoka, et al., U.S. Pat. Nos. 4,235,871, 4,501,728 and 4,837,028 each of which is incorporated herein by reference.

Efficacy

The efficacy of the compositions of the present invention in inhibiting liquid tumor growth, malignancies thereof and/or development of metastases thereof may be assayed. The compositions are assayed for their ability to inhibit liquid tumor growth, reduce liquid tumor mass, effect the loss of metastatic lesions, inhibit development of new metastatic lesions after treatment has started, or reduce tumors such that there is no detectable disease. The presence of liquid tumors and malignant diseases such as leukemias or myelomas may be assessed by radiologic imaging, biological fluid analysis, cytogenetics, fluorescence in situ hybridization, immunocytochemistry, colony assays, multiparameter flow cytometry, or polymerase chain reaction, as well as other assays methods known in the art.

For example, human tumor cell lines may be screened for expression of alpha-4 and alpha-9 by immunohistochemistry (IHC) and flow cytometry. Functionality of the alpha-4 and alpha-9 may be confirmed by an in vitro binding assay. Any cytotoxicity or induction of cell proliferation in human tumor cells may be evaluated by thymidine incorporation. Evaluation of positive or negative effects on proliferation of the tumors may be performed, for example, using $^3$H-thymidine incorporation assays.

EXAMPLES

The following synthetic and biological examples are offered to illustrate this invention and are not to be construed in any way as limiting the scope of this invention. Unless otherwise stated, all temperatures are in degrees Celsius. In the examples below, the following abbreviations have the following meanings. If an abbreviation is not defined, it has its generally accepted meaning.

| | |
|---|---|
| Å = | Angstroms |
| ACN = | acetonitrile |
| AUC = | Area under the curve |
| br s OR bs = | broad singlet |
| bd = | broad doublet |
| BSA = | bovine serum albumin |

-continued

| | |
|---|---|
| d = | doublet |
| dd = | doublet of doublets |
| dq = | doubet of quartets |
| dsextet = | doublte of sextets |
| DMF = | dimethylformamide |
| DMAP = | 4-N,N-dimethylaminopyridine ethylcarbodiimide hydrochloride |
| $EC_{50}$ = | The dosage at which the desired response is present for 50 percent of the population |
| EDTA = | ethylenediamine tetraacetic acid |
| EtOAc = | ethyl acetate |
| EtOH = | ethanol |
| $Et_3N$ = | triethylamine |
| EM = | wavelength of emission (in nm) |
| EX = | wavelength of excitation (in nm) |
| Dq. = | equivalent |
| FACS = | Fluoresence activated Cell Sorter |
| FITC = | Fluorescein isothiocyanate |
| g = | gram |
| Hct = | hematocrit, or measurement of packed red blood cells obtained by centrifugation in a volume of a blood sample |
| HB or Hb = | hemoglobin |
| HBSS = | Hank's balanced salt solution |
| HEPES = | 4-(2-hydroxyethyl)-1-piperazineethanesulfonic acid |
| HPLC = | high performance liquid chromatography |
| hr or h = | hours |
| $IC_{50}$ = | the concentration of an inhibitor that is required for 50% inhibition of an enzyme in vitro |
| IgG Fc = | a binding domain of the immunoglobulin |
| in. = | inch |
| i.p. = | intraperitoneally |
| i-PrOH = | iso-propanol |
| kDa = | kilodalton |
| kg = | kilogram |
| L = | liters |
| LC/MS = | liquid chromatography/mass spectroscopy |
| m = | multiplet (when used with NMR data) |
| $m^2$ = | square meters |
| M = | molar |
| mbar = | millibar |
| mg = | milligram |
| MHz = | megahertz |
| min. = | minutes |
| MCH = | Mean Corpuscular Hemoglobin; Hb/RBC |
| MCHC = | mean corpuscular hemoglobin count expressed as a percentage; HB/Hct. |
| MCV = | mean corpuscular volume; the avg. volume of erythrocytes, conventionally expressed in cubic micrometers per red cell. |
| MeOH = | methanol |
| mg = | milligrams |
| mL = | milliliters |
| mm = | millimeters |
| mM = | millimolar |
| mol = | moles |
| mmol = | millimoles |
| mOsm = | milliosmol |
| mpk = | milligrams per kilogram |
| MTBE = | methyl tert-butylether |
| m/z or M/Z = | mass to charge ratio |
| N = | normal |
| ng = | nanograms |
| nm = | nanometers |
| NMR = | nuclear magnetic resonance |
| PBS = | phosphate buffered saline |
| PBS++ = | PBS with calcium and magnesium |
| ppm = | parts per million |
| psi = | pounds per square inch |
| p.o. = | per os, literally "by mouth", includes oral gavage |
| q = | quartet |
| q.s. = | sufficient amount |
| $R_f$ = | retention factor (ratio of distance traveled by substance/distance traveled by solvent front) |
| rpm = | rotations per minute |
| rt or RT = | room temperature |
| $R_t$ = | retention time |
| s = | singlet |
| sat. = | saturated |
| t = | triplet |
| TFA = | trifluoroacetic acid |
| THF = | tetrahydrofuran |
| TLC or tlc = | thin layer chromatography |
| Ts = | Tosyl |
| UV = | ultraviolet |
| $V_t$ = | Total Volume |
| WBC = | White Blood Cells |
| wt/wt = | weight to weight ratio |
| w/v = | weight to volume ratio |
| µg = | micrograms |
| µL = | microliter |
| µm = | microns |
| µM = | micromolar |

Example 1

Preparation of (S)-2-(2-(diethylamino)-5-(N-isopropylmethylsulfonamido)pyrimidin-4-ylamino)-3-(4-(pyrrolidine-1-carbonyloxy)phenyl)propanoic acid The synthetic protocol employed in Example 1 is summarized in Scheme A illustrated below:

Scheme A

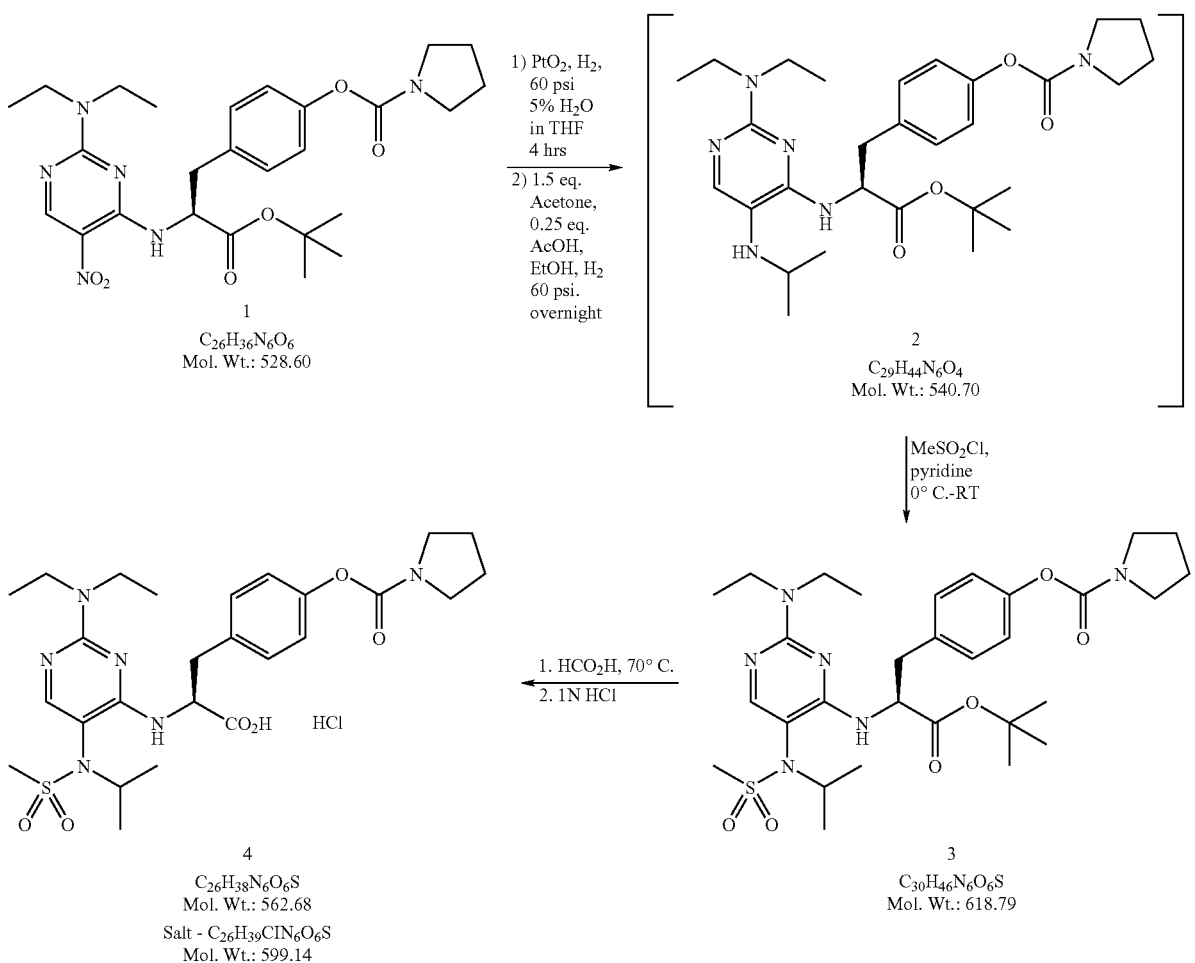

In Scheme A, compound 4 was prepared in a three pot sequence from the 5-nitropyridine compound 1. The synthetic protocol of Scheme A significantly simplifies the preparation of this compound by one or more of the following:

1) a substantially accelerated nitro group reduction step;
2) a streamlined reduction/reductive amination sequence that is performed in the same flask with the same solvent and the same catalyst, so manipulations are reduced and exposure of the oxygen sensitive products to air is minimized;
3) the conditions for the reductive amination step minimizes generation of a bis-isopropylamino pyrimidine side product thereby eliminating the need for a chromatographic purification of compound 3;
4) conditions are described whereby it is possible to purify the mono-isopropylaminopyrimidine intermediate, compound 2, by trituration of the corresponding L-tartaric acid salt (though the need for this discrete purification of compound 2 also has been rendered unnecessary by the improvements in the reductive amination step), and
5) conditions for the discrete purification of compound 3 by crystallization from MTBE-hexane or MTBE-cyclohexane have been identified.

In the reaction steps of Scheme A, flash chromatography was performed using a Biotage Flash 75L, using 800 g KP-Sil silica cartridges (32-63 μM, 60 angstrom, 500-550 m$^2$/g). $R_f$s are reported for analytical thin layer chromatography, using EM Sciences Silica Gel 60 F(254), 250 μM thick plates for normal phase. NMR spectra were obtained on a Varian Gemini 300 MHz spectrometer (300 MHz for $^1$H spectra and 75 MHz for $^{13}$C spectra). Analytical HPLC was performed on an Agilent 1100 Series HPLC with a Phenomenex Luna, 3 μm, C-18, 30×4.6 mm column. The detector was UV at 210 nm. Solvents were 0.1% TFA in water and 0.1% TFA in acetonitrile. The standard flow rate was 1.5 mL/min. and the standard method was named M1 with the solvent gradient changing from 20% CH$_3$CN to 70% CH$_3$CN over 2.33 minutes. An alternate method was named M2 with a flow rate of 2 mL/min. and a gradient changing from 20% CH$_3$CN to 70% CH$_3$CN over 1.75 minutes. Method M15 had a flow rate of 1.5 ml/min. with the solvent composition changing from 20% CH$_3$CN to 70% CH$_3$CN over 10 min., holding at 70% for 2 min., then ramping to 95% over 1 min. and holding at 95% for 2 minutes. LC/MS was performed on an Agilent 1100 Series HPLC with a Series 1100 MSD with electrospray ionization (unless otherwise indicated as chemical ionization). The column and conditions were matched to the free standing HPLC.

Step 1: Preparation of (S)-4-(3-tert-butoxy-2-(2-(diethylamino)-5-(isopropylamino)pyrimidin-4-ylamino)-3-oxopropyl)phenyl pyrrolidine-1-carboxylate

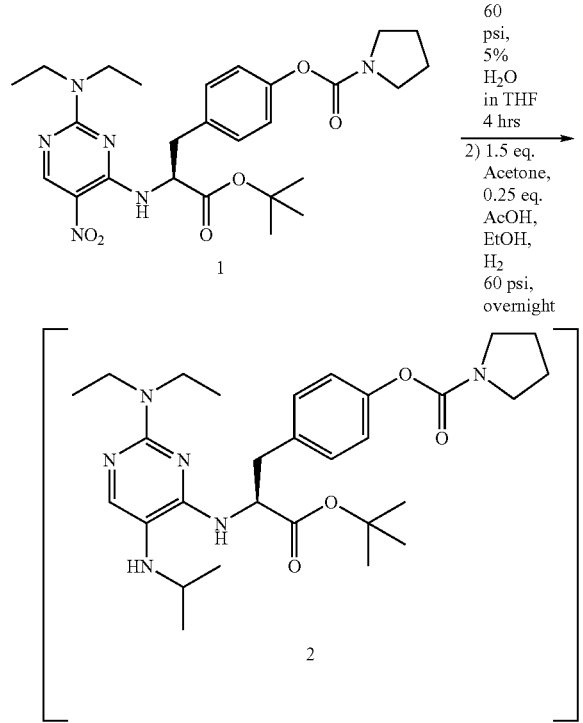

Nitropyrimidine-carbamate 1 (100 g, 189 mmol) and $PtO_2$ (6.33 g, 27.85 mmol) were suspended in 360 mL of wet THF (5% $H_2O$). The mixture was stirred at room temperature under hydrogen (60 psi). After 3 hours, TLC (50% EtOAc/hexanes on silica gel) indicated complete reduction of the nitro group (TLC analysis on silica with EtOAc showed $R_f$=0.2 (streaky) for the amino-pyrimidine and $R_f$=0.86 for the starting nitropyrimidine-carbamate.) In this regard, the use of $PtO_2$ for both steps in this two-step process permitted a one-pot reaction with that added feature that the rate of reduction of the nitro group was dramatically accelerated. In any event, care be taken to minimize exposure to air/oxygen as the aminopyrimidine product is prone to oxidation.

Ethanol (200 mL), acetone (21 mL, 1.5 eq.), and glacial acetic acid (3.0 mL, 0.28 eq.) were added to the aminopyrimidine solution in the hydrogenation flask. After evacuating and purging, the flask was pressurized with $H_2$ (60 psi). The reductive amination was allowed to proceed overnight. TLC on silica using EtOAc as the eluant gave an $R_f$=0.41 (streaky) for the isopropylamino-pyrimidine and an $R_f$=0.11 for the starting aminopyrimidine carbamate. Both TLC and LC/MS confirmed complete reaction with virtually no bis-isopropylaminopyrimidine produced. If necessary, HPLC can be used as an alternative means to monitor progress of the reaction. The crude reaction solution was diluted with EtOAc (1 L) and filtered through a pad of basic alumina (400 mL). The alumina was rinsed with EtOAc (200 mL) and EtOH (200 mL) and the combined organic solutions were concentrated in vacuo. The flask was vented under $N_2$. The viscous oil was redissolved in anhydrous toluene (700 mL) and concentrated. After venting the flask under nitrogen, the product was dried again by azeotropic removal of another 400 mL of toluene. A viscous reddish-brown oil was obtained.

As evidenced by the LC/MS, very little bis-isopropylaminopyrimidine carbamate impurity was produced with this procedure as compared to prior methods wherein the bis-isopropylamino pyrimidine carbamate impurity required removal by chromatography.

If a formal purification of the mono-isopropylamino pyrimidine 2 step is required, it can be precipitated from THF/ether as the (L)-tartaric acid salt and triturated. A small-scale example follows: (5.09 g, 99.6% yield) L-Tartaric acid (1.42 g) was dissolved in hot THF (45 mL). The hot tartaric acid solution was added to the gum of the isopropylamino-pyrimidine 2 (5.1 g). The mixture was swirled and warmed until homogeneous. The solution changed from pink-purple in color to tan. The solution was concentrated in vacuo to give a tan gum. Ether (~150 mL) was added whereupon oiling was observed. The ether mixture was concentrated in vacuo. Acetone (~20 mL) and then ether (~200 mL) was added, and the formation of a gummy oil was again observed. The mixture was concentrated for a third time. Methylene chloride (5-10 mL) was added followed by ether (~80 mL). A tan precipitate was observed to form underneath a bright orange-pink supernatant. The mixture was filtered. The precipitate was rinsed with ether (50 mL) and then again with a mixture (~60 mL) of acetone and ether (1:1). The precipitate was dried under vacuum overnight to give a cream colored solid (4.9 g, 76% yield). A small aliquot of the solid tartaric acid salt was dissolved in i-PrOH and EtOH and passed through a small plug of basic alumina to give the free base. The aliquot of free base was analyzed by TLC and LC/MS. The remaining salt was suspended in a mixture of $CH_2Cl_2$ (250 mL) and 1N $NaHCO_3$ (150 mL). With mixing and some bubbling, the solid dissolved and the free base amine was extracted into the organic layer. The aqueous layer was extracted once more with EtOAc (150 mL) and the organic extracts were combined and dried over $MgSO_4$ (~150 g). The dried organic solution was passed through a plug of basic alumina (~100 g) to give a light pink solution that was concentrated in vacuo to give a tan/pink gum (3.28 g, 64% yield from starting nitro-carbamate).

Several other acids were investigated in an attempt to form salts with the mono-isopropylaminopyrimidine carbamate 2. p-Toluenesulfonic acid and methanesulfonic acid gave oils. Solid salts could be formed with HCl and $H_3PO_4$, but tartaric acid appeared to give the most favorable solubility characteristics. The HCl and phosphoric acid salts seemed to dissolve readily in a $CH_2Cl_2$, i-PrOH, and acetone, whereas the tartaric acid salt seemed to be mostly insoluble in $CH_2Cl_2$ and only partially soluble in the other solvents.

Step 2: Preparation of (S)-4-(3-tert-butoxy-2-(2-(diethylamino)-5-(N-isopropylmethylsulfonamido)pyrimidin-4-ylamino)-3-oxopropyl)phenyl pyrrolidine-1-carboxylate (3)

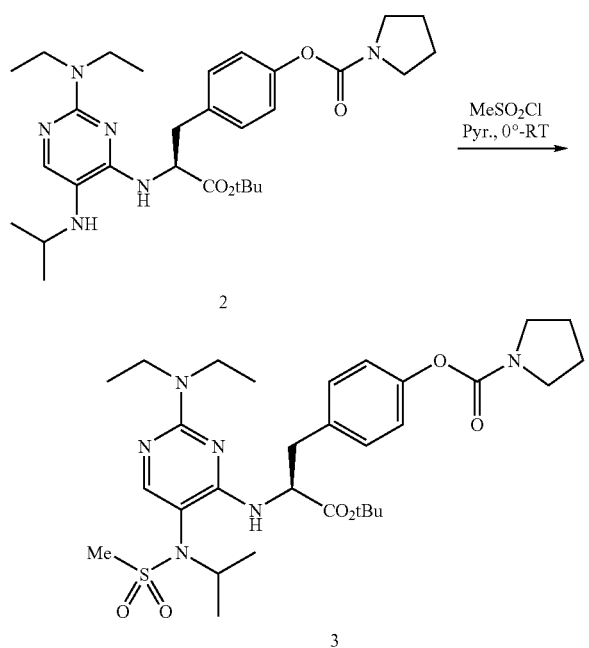

Isopropylaminopyrimidine carbamate 2 from Step 1 (assume 189 mmol) was dissolved in pyridine (680 mL) and the solution was cooled to 0° C. under $N_2$. Methanesulfonyl chloride (44 mL, 3.0 eq.) was added via syringe pump over 20 min. to the cold pyridine solution of the isopropylaminopyrimidine carbamate. The ice bath was removed and the solution was allowed to warm to RT. The solution was allowed to stir for six hours. A small aliquot was removed and a mini-workup was performed (diluted with EtOAc, washed with 5% $KH_2PO_4$, brine, and then dried over $MgSO_4$). Analysis by TLC showed the reaction to be complete and generally clean (only one spot besides a baseline spot from residual pyridine. The bulk reaction solution was concentrated. When 650 mL of distillate had been collected, the blood red oil was diluted with EtOAc (2 L). The organic solution was washed with 5% $KH_2PO_4$ (1 L and 750 mL), 0.2 N citric acid (1 L), and brine (1 L). The organic solution was dried over $MgSO_4$ (150 g). The dried organic solution was filtered through a pad of silica gel (1 L) to give a green-black solution. The flask and silica gel were rinsed with EtOAc (1.5 L) to bring the total volume of organic solution to 3.5 L. The solution was filtered through a pad of basic alumina (300 mL) to give a deep green solution. The solution was concentrated in vacuo. A reddish gum (150 g) was obtained.

The flask was flushed with nitrogen, capped and placed in the refrigerator whereupon a red-brown solid formed. LC/MS indicated acceptable purity, but TLC analysis indicated a bright red baseline spot as well as two to three very faint impurities. The odor of pyridine was still present. The red-brown solid was dissolved in a mixture of $CH_2Cl_2$ (100 mL), THF (200 mL), and ether (800 mL). The solution was filtered/eluted through a pad of silica gel (1 L) and the silica was rinsed with ether (3 L). Most of the colored baseline impurity was retained on the silica gel. The solution was concentrated to give a red oil that dried to a pink foamy solid (100 g) that analyzed to be 94.7% pure by LC/MS. The material was then chromatographed on silica gel (2 L) eluted with $CH_2Cl_2$ (3 L), $CH_2Cl_2$ and ether (1:1; 4 L), ether (4 L), ether:THF (1:1; 4 L), and EtOAc with 5% $Et_3N$ and 2% EtOH (4 L). The $CH_2Cl_2$:ether eluent gave a red oil of mixed fractions (12.4 g; Fraction A) and the ether eluent gave a tan oil (13 g; Fraction B) that was generally pure. The bulk of the material remained on the column and it was realized that the desired product had crystallized on the column. Elution with ether:THF and EtOAc (with 5% $Et_3N$ and 2% EtOH) allowed the product to redissolve and elute in concentrated plug (Fraction C) Fraction A and Fraction B were combined and concentrated together. Fraction C was concentrated separately. Upon concentrating and drying, crystals formed in both fractions. Further investigations found that the solid could be recrystallized from methyl tert-butyl ether (MTBE), cyclohexane, ether-hexane (1:1), MTBE-hexanes, or cyclohexane-hexanes. Combined Fractions A and B and Fraction C were each recrystallized from MTBE-hexanes to give the tert-butyl ester 3 as a white solid (57.75 g total with a purity >99%) and red filtrate/mother liquors. The mother liquors were concentrated to give a red oil (24 g). The mother liquor oil was chromatographed on a Biotage 75 and eluted with 4% THF in $CH_2Cl_2$ (12 L) to give enriched fractions that were then concentrated and re-crystallized to give an additional 14 g of purified tert-butyl ester.

LC/MS by method M2 gave $t_R$=1.97 min. with M/Z=619 for $[M+1]^+$ for the desired product.

LC/MS by method M15 gave $t_R$=6.09 min. with M/Z=619 for $[M+1]^+$ for the desired product.

$^1$H NMR (CDCl$_3$, 300 MHz) δ, ppm: 0.88 (d, j=6 Hz, 1.4H), 1.04 (d, j=6 Hz, 2H), 1.20 (m, 10H), 1.37 (s, 4.8H), 1.39 (s, 4.8H), 1.93 (AA'BB', 4H), 2.80 (s, 1.7H), 2.9 (s, 1.6H), 3.18 (m, 2.4H), 3.4-3.7 (m overlapping two apparent triplets, 8.3H), 4.40 (sextet, j=6 Hz, 1.1H), 4.8 (sextet, 1H), 5.64 (d, j=6.5 Hz, 0.5H), 5.70 (d, j=6.5 Hz, 0.5H), 7.03 (m, 2H), 7.18 (apparent dd, 2H), 7.80 (d, j=4 Hz, 1H). The $^1$H NMR shows rotamers.

It is contemplated that treatment with the methanesulfonyl chloride be done in THF with little or no additional base. If base is used, a base such as triethylamine or diisopropylethylamine should be employed.

Step 3: Preparation of (S)-2-(2-(diethylamino)-5-(N-isopropylmethyl-sulfonamido)pyrimidin-4-ylamino)-3-(4-(pyrrolidine-1-carbonyloxy)phenyl)propanoic acid (4)

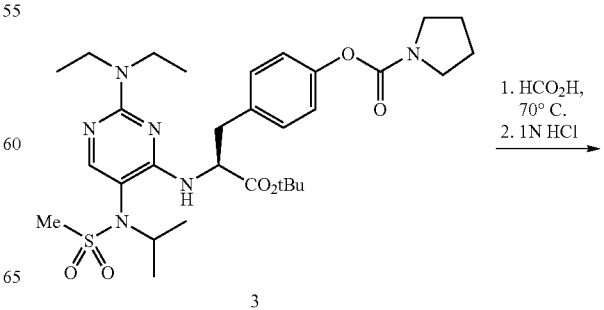

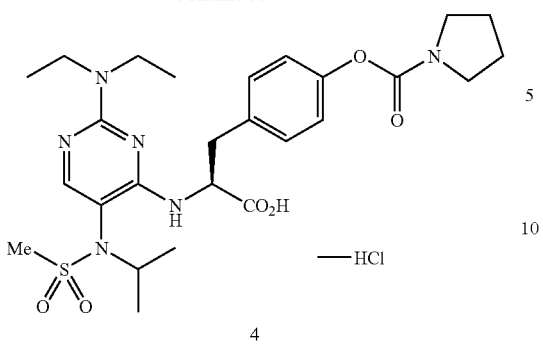

4

A formic acid (1.5 L) solution of the t-butyl ester from Step 2 (57.75 g, 0.093 mol) was heated to 50° C. overnight and then concentrated in vacuo. Alternatively, the reaction can also be performed at 70° or 80° for 60-90 minutes.

Water (~100 mL) was added to the crude product and the mixture was concentrated to dryness. The residue was dried under high vacuum. The crude product was dissolved and concentrated twice from 1.0N HCl (250 mL and 200 mL). The product was twice dissolved in hot THF and concentrated to dryness to yield a foamy solid. The foamy solid was dried under high vacuum at 65° for two hours. This solid was scraped from the flask and dried in the vacuum oven overnight (60° C., 28 in. Hg) to give the hydrochloride salt of (S)-2-(2-(diethylamino)-5-(N-isopropylmethylsulfonamido)pyrimidin-4-ylamino)-3-(4-(pyrrolidine-1-carbonyloxy)phenyl) propanoic acid –5 (50.9 g; 98.3% pure).

LC/MS by method M15 gave $t_R$=1.96 min. with M/Z=563.

LC/MS by method M2 gave $t_R$=1.43 min. with M/Z=563.

$^1$H NMR (CD$_3$OD, 300 MHz) δ, ppm: 0.80 (d, j=6 Hz, 1.4H), 1.02 (d, j=6 Hz, 1.6H), 1.23 (m, 9.2H), 1.80-2.0 (AA'BB'+m, 5.2H), 2.99 (d, 3.2H), 3.2-3.45 (m, 4.5H), 3.45-3.8 (m, 7.6H), 4.40 (sextet, 1H), 4.90 (m, 3H), 7.00 (d, 2H), 7.23 (d, 2H), 7.60 (d, 0.25H), 7.75 (d, 1H), 7.83 (d, 0.25H).

$^{13}$C NMR (CD$_3$OD, 75 MHz) δ, ppm: 6.5, 14.7, 14.8, 15.4, 15.5, 19.4, 20.0, 20.2, 29.91, 30.44, 33.95, 34.15, 41.03, 41.08, (41.71, 41.99, 42.28, 42.6, 42.8, 43.1—solvent peaks), 47.21, 47.36, 50.01, 50.42, 62.43, 102.11, 102.23, 116.78, 124.9, 125.19, 128.54, 129.01, 138.49, 139.02, 145.53, 145.60, 145.78, 148.68, 156.77, 156.86, 166.91, 167.07.

Example 2

Preparation of (S)-2-(2-(diethylamino)-5-(N-ethylmethylsulfonamido)pyrimidin-4-ylamino)-3-(4-(pyrrolidine-1-carbonyloxy)phenyl)propanoic acid (7)

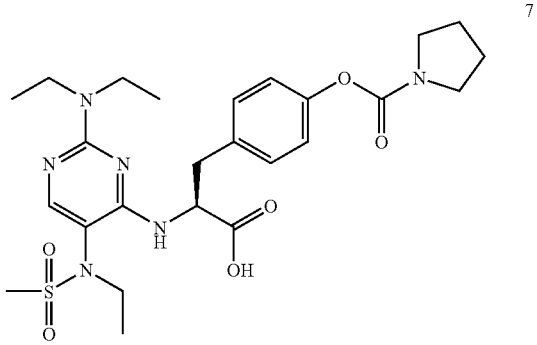

7

Step 1: One-pot reduction/reductive ethylation of (S)-4-(3-tert-butoxy-2-(2-(diethylamino)-5-nitropyrimidin-4-ylamino)-3-oxopropyl)phenyl pyrrolidine-1-carboxylate (6)

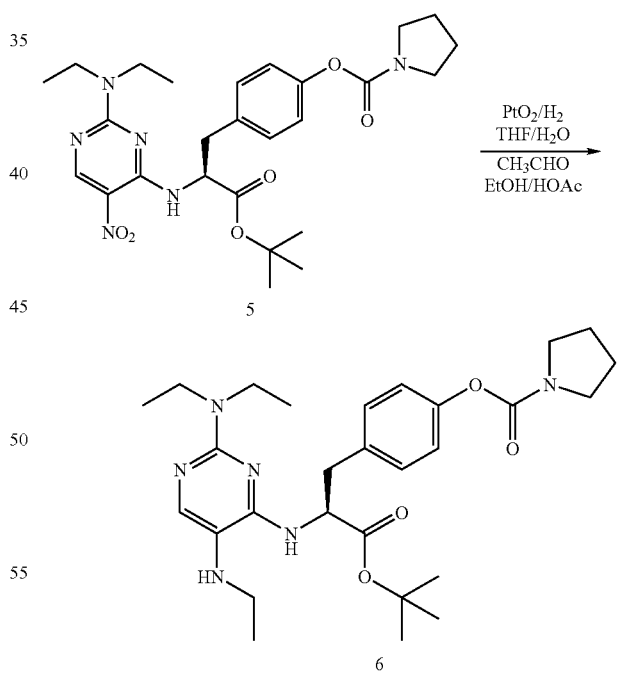

Nitro-carbamate (compound 5, 10.8 g, 20 mmol) was slurried in THF (35 mL) and water (1 mL, 3 vol %) was added. The solution was stirred, Adams catalyst (0.360 g, 6 mole %) was added and the solution was de-oxygenated by three cycles of evacuation (50 mm Hg) and refilling with dry nitrogen (10 psi). Finally, the reaction vessel was pressurized with hydrogen (60 psi) and reaction mixture was vigorously stirred for 90 min. If necessary or desired, progress of the hydrogenation reaction can be monitored by TLC (silica gel, eluting with dichloromethane:methanol (95:5)). $R_f$ of nitrocarbamate is 0.95, primary amine=0.16.

The hydrogen was replaced by dry nitrogen (three cycles of evacuation and refilling with nitrogen). The ethanol (25 mL), acetic acid (0.3 mL) and acetaldehyde (1.2 mL, 21 mmol, 1.05 eq) were added, vessel was partially evacuated at low pressures (ca. 150 mm Hg) in order to minimize loss of the volatile acetaldehyde, refilled with nitrogen (10 psi) and reaction mixture was stirred vigorously for 50 min. At the end of this time, nitrogen was replaced by hydrogen (60 psi) by partial evacuation and re-pressurizing with hydrogen two times. The mixture was stirred for another 45 min. Progress of reductive amination may be monitored by TLC (silica gel, eluting with dichloromethane:methanol (95:5). $R_f$ of primary amine=0.16, secondary amine–0.32 and tertiary amine=0.43. At the end of process, hydrogen was flushed out by three cycles of evacuation and refilling with nitrogen, the catalyst was filtered off on a bed of Celite using methanol to rinse, the filtrates were stripped to dryness to give amber oil (11.9 g). The product is sensitive to oxygen, resulting in considerable darkening and appearance of low $R_f$ material in TLC. All handling should be done with appropriate precautions.

The reaction product was purified by flash chromatography using dichloro-methane:methanol mixture (97:3), containing 0.3% of ammonium hydroxide. Fractions containing N-ethyl product were combined to give 7.9 g of compound 6 as an amber oil (98.5% pure; 73% yield). The purity of the crude product appears to be adequate for many purposes, especially if product of the subsequent anticipated reactions is known to be crystalline.

$^1$H-NMR, CDCl$_3$, (δ): 7.60 (s, 1H), 7.17 (d, J=8.4 Hz, 2H), 7.05 (d, J=8.4 Hz, 2H), 5.75 (d, J=7.5 Hz, 1H), 4.84 (q, J=6.6 Hz, 1H), 3.64-3.46 (m, 8H), 3.19 (d, J=6.3 Hz, 2H), 2.86 (q, J=7.2 Hz, 2H), 1.94 (m, 4H), 1.39 (s, 9H), 1.20-1.11 (m, 9H).

$^{13}$C-NMR, CDCl$_3$, (δ): 171.7, 157.7, 157.5, 153.1, 150.3, 145.8, 133.7, 130.2, 121.5, 117.4, 81.8, 54.7, 46.4, 46.3, 42.4, 41.7, 37.4, 28.0, 25.8, 24.9, 15.5, 13.5.

MS (m/z): 527.3 [M+1].

Steps 2 and 3: (S)-2-(2-(diethylamino)-5-(N-ethylmethylsulfonamido)-pyrimidin-4-ylamino)-3-(4-(pyrrolidine-1-carbonyloxy)phenyl)propanoic acid 7

Following the procedures of Steps 2 and 3 of Example 1, compound 6 was converted to the corresponding (S)-2-(2-(diethylamino)-5-(N-ethylmethylsulfonamido)pyrimidin-4-ylamino)-3-(4-(pyrrolidine-1-carbonyloxy)phenyl)propanoic acid 7 which was characterized as follows:

$^1$H-NMR, CDCl$_3$, (δ): 8.17 (s, 1H), 7.77 (s, 1H), 7.26-7.23 (m, 2H), 7.00-6.98 (d, 2H), 4.85-4.82 (m, 1H), 3.58-3.51 (m, 6H), 3.43-3.39 (m, 3H), 2.96-2.84 (m, 3H), 2.01-1.91 (m, 4H), 1.29-0.97 (m, 9H);

$^{13}$C-NMR, CDCl$_3$, (δ): 175.6, 165.7, 157.2, 155.2, 152.0, 151.8, 151.7, 151.3, 136.0, 135.9, 131.5, 123.0, 110.5, 56.7, 43.8, 39.4, 39.2, 37.4, 26.7, 25.8, 14.4, 13.3; and

MS: M(+H) 549

Example 3

Preparation of (S)-2-(5-(N-cyclopentylmethylsulfonamido)-2-(diethylamino)pyrimidin-4-ylamino)-3-(4-(pyrrolidine-1-carbonyloxy)phenyl)propanoic acid (8)

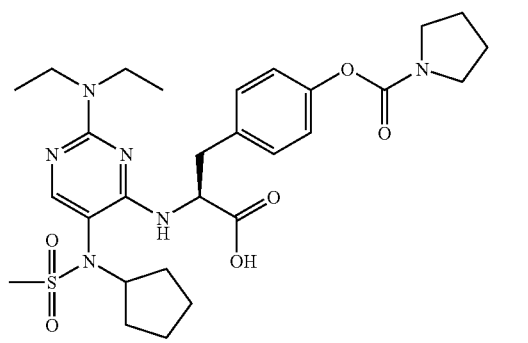

Following the procedures of Example 1 and employing cyclopentanone in place of acetone (Example 1) or acetaldehyde (Example 2), (S)-2-(5-(N-cyclopentylmethylsulfonamido)-2-(diethylamino)pyrimidin-4-ylamino)-3-(4-(pyrrolidine-1-carbonyloxy)phenyl)propanoic acid 8 was prepared and characterized as follows:

$^1$H-NMR, CDCl$_3$, (δ): 7.74-7.71 (d, 1H), 7.28-7.24 (m, 2H), 7.04-7.00 (m, 2H), 5.00-4.95 (m, 1H), 4.37-4.27 (m, 1H), 3.60-3.37 (m, 9H), 3.00-2.97 (d, 3H), 2.03-1.78 (m, 6H), 1.67-1.40 (m, 6H), 1.31-1.23 (m, 6H);

$^{13}$C-NMR, CDCl$_3$, (δ): 173.6, 173.4, 163.1, 155.1, 152.4, 152.0, 145.3, 144.7, 135.5, 135.1, 131.6, 131.4, 123.2, 109.6, 109.4, 62.5, 62.3, 56.7, 56.5, 48.1, 40.3, 40.1, 36.8, 36.4, 31.2, 30.5, 26.7, 25.8, 23.2, 23.1, 12.7; and

MS: M(+H) 589.

Example 4

Preparation of (S)-2-(2-(diethylamino)-5-(N-(prop-2-ynyl)methylsulfonamido)pyrimidin-4-ylamino)-3-(4-(pyrrolidine-1-carbonyloxy)phenyl)propanoic acid (13)

The synthetic protocol employed in Example 4 is summarized in Scheme B illustrated below:

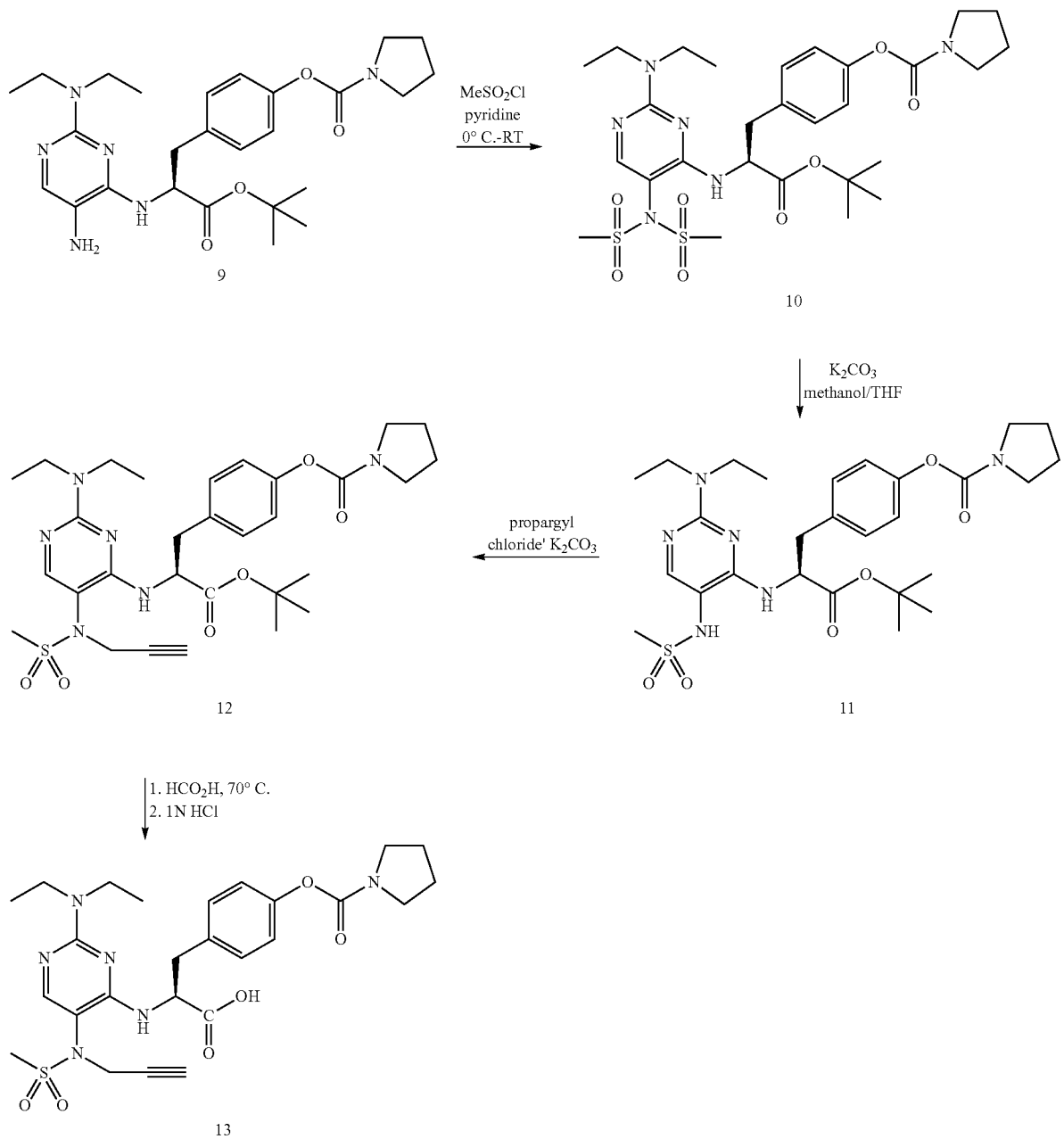

Scheme B

Step 1: (S)-4-(3-tert-butoxy-2-(2-(diethylamino)-5-(N-(methylsulfonyl)-methylsulfonamido)pyrimidin-4-ylamino)-3-oxopropyl)phenyl pyrrolidine-1-carboxylate (10)

Aminopyrimidine (2.0 g, 4.0 mmol-compound 2) (prepared by reduction of compound 1) was dissolved in dichloromethane (10 mL). THF (10 mL) and triethylamine (2.8 mL, 20 mmol) were added and the reaction cooled in an ice bath. Methanesulfonyl chloride (1.1 mL, 14 mmol) was added and the reaction warmed to room temperature over 18 hours. The reaction mixture was concentrated in vacuo and the residue taken up in ethyl acetate. The solution was washed with 0.2 N citric acid, water, sat. NaHCO$_3$, and brine. The organic layer was dried over Na$_2$SO$_4$, filtered, and concentrated in vacuo to yield crude product as a brown foam. The residue was purified by flash chromatography (2:3 ethyl acetate/hexanes) to yield 2.2 g (73%) of the di-sulfonylated material as a yellow foam (compound 10).

Step 2: (S)-4-(3-tert-butoxy-2-(2-(diethylamino)-5-(methylsulfonamido)-pyrimidin-4-ylamino)-3-oxopropyl)phenyl pyrrolidine-1-carboxylate (11)

Compound 10 (2.2 g, 3.4 mmol) was dissolved in methanol (5 mL) and THF (5 mL). 1.0 M K$_2$CO$_3$ (10 mL) was added and the reaction mixture was heated at 40° C. for 96 hours. The reaction mixture was acidified to pH 3 with 2N HCl and extracted with ethyl acetate. The organic layer was washed with brine, dried over $Na_2SO_4$, filtered, and concentrated in vacuo to yield 1.68 g (86%) product as a beige foam, compound 11. The crude material was used without purification.

Step 3: (S)-4-(3-tert-butoxy-2-(2-(diethylamino)-5-(N-(prop-2-ynyl)methyl-sulfonamido)pyrimidin-4-ylamino)-3-oxopropyl)phenyl pyrrolidine-1-carboxylate (12)

Compound 11 (0.20 g, 0.35 mmol), $K_2CO_3$ (0.073 g, 0.53 mmol), and acetone (3 mL) were placed in a sealed tube and stirred at room temperature for one hour. Propargyl chloride (0.26 mL, 3.5 mmol) was added and the reaction was sealed and heated at reflux for 48 hours. The reaction mixture was concentrated in vacuo and the residue taken up in ethyl acetate. The solution was washed with water and brine. The organic layer was dried over $Na_2SO_4$, filtered, and concentrated in vacuo to yield crude product as an orange film. The residue was purified by flash chromatography (1:1 ethyl acetate/hexanes) to yield 0.11 g (51%) of compound 12 as a transparent film.
MS (m/z) 615, $(M+H)^+$.

Step 4: (S)-2-(2-(diethylamino)-5-(N-(prop-2-ynyl) methylsulfonamido)-pyrimidin-4-ylamino)-3-(4-(pyrrolidine-1-carbonyloxy)phenyl)propanoic acid (13)

Formic acid (2 mL) was added to t-butyl ester (100 mg) and stirred at 40° C. over night. The formic acid was removed under reduced pressure to yield compound 13 in quantitative yield and characterized as follows:
$^1$H-NMR, $CDCl_3$, (δ): 8.13 (s, 1H), 7.97 (s, 1H), 7.26-7.24 (d, 2H), 7.02-6.99 (d, 2H), 4.59-4.44 (m, 1H), 4.04-3.79 (m, 1H), 3.64-3.53 (m, 6H), 3.45-3.39 (t, 3H), 3.08-2.84 (m, 4H), 2.84-1.89 (m, 4H) 1.22-1.17 (t, 6H);
$^{13}$C-NMR, $CDCl_3$, (δ): 165.3, 155.3, 151.8, 136.1, 131.5, 123.0, 76.1, 76.0, 56.8, 49.9, 48.1, 43.8, 41.2, 40.2, 37.4, 26.7, 25.9, 13.3; and
MS: M(+H) 559.

Example 5

Preparation of (S)-2-(2-(diethylamino)-5-(N-methyl-methylsulfonamido)-pyrimidin-4-ylamino)-3-(4-(pyrrolidine-1-carbonyloxy)phenyl)propanoic acid (14)

Following the procedures of Example 4 and employing dimethylsulfate in place of propargyl chloride, the title compound was prepared and was characterized as follows:
$^1$H-NMR, $CDCl_3$, (δ): 8.14 (s, 1H), 7.83 (s, 1H), 7.26-7.23 (d, 2H), 7.01-6.98 (d, 2H), 4.84-4.81 (m, 1H), 3.60-3.53 (m, 6H), 3.43-3.38 (m, 3H), 3.09 (s, 3H), 2.94 (s, 3H), 2.00-1.91 (m, 4H), 1.22-1.18 (t, 6H);
$^{13}$C-NMR, $CDCl_3$, (δ): 175.5, 165.4, 160.7, 156.3, 155.3, 151.8, 149.1, 136.0, 131.6, 123.0, 113.4, 56.9, 43.9, 38.8, 38.1, 37.4, 26.7, 25.8, 13.2; and
MS: M(+H) 535.

General Methods of Examples 6-16. Flash chromatography was performed using a Biotage Flash 75L, using 800 g KP-Sil silica cartridges (32-63 μM, 60 Å, 500-550 m$^2$/g). Rf's are reported for analytical TLC, using EM Sciences Silica Gel 60 F(254), 250 μM thick plates for normal phase. NMR spectra were obtained on a Varian Gemini 300 MHz spectrometer (300 MHz for $^1$H spectra and 75 MHz for $^{13}$C spectra). Analytical HPLC was performed on an Agilent 1100 Series HPLC with a Phenomenex Luna, 3 μm, C-18, 30×4.6 mm column. The detector was UV at 210 nm. Solvents were 0.1% TFA in water and 0.1% TFA in acetonitrile. The standard flow rate was 1.5 mL/min., and in the standard method the solvent gradient changed from 20% $CH_3CN$ to 70% $CH_3CN$ over 2.33 minutes. A second alternative method has a flow rate of 2 mL/min. and a gradient changing from 20% $CH_3CN$ to 70% $CH_3CN$ over 1.75 minutes. A third method has a flow rate of 1.5 ml/min. with the solvent composition changing from 20% $CH_3CN$ to 70% $CH_3CN$ over 10 min., holding at 70% for 2 min., then ramping to 95% over 1 min. and holding at 95% for 2 minutes. LC/MS was performed on an Agilent 1100 Series HPLC with a Series 1100 MSD with electrospray ionization (unless otherwise indicated as chemical ionization). The column and conditions were matched to the free standing HPLC.

$^1$H NMR of amides typically show rotamers and integration of some peaks are reported in fractional proton values.

Example 6

Preparation of N-[2-diethylamino-5-{N-ethyl-N-(furan-3-ylcarbonyl)amino}pyrimidin-4-yl]-L-4'-{(pyrrolidin-1-yl)carbonyloxy}phenylalanine

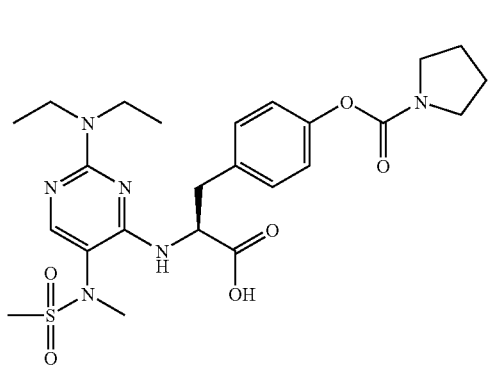

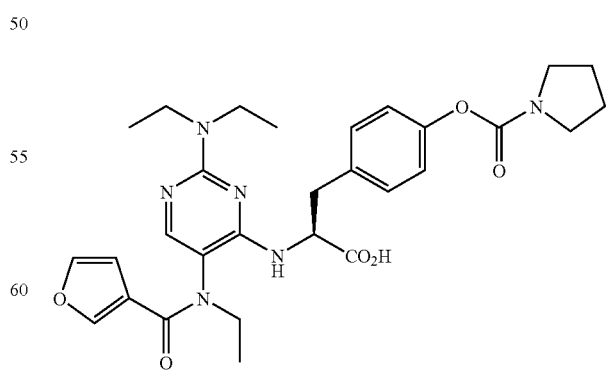

Step 1: Preparation of N-[2-diethylamino-5-{N-amino}pyrimidin-4-yl]-L-4'-{(pyrrolidin-1-yl)carbonyloxy}phenylalanine tert-butyl ester 2

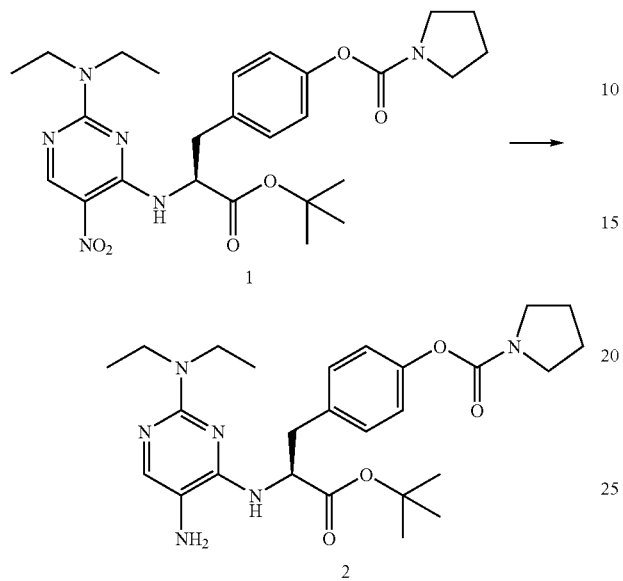

A mixture of nitropyrimidine-carbamate 1 (160.25 g, 0.3035 mol; prepared as in WO 03/099809) and 5% Pd/C (15 g, 50/50 wt/wt with $H_2O$, Degussa E 101 R/W) in THF-water solution (1 L THF and 50 mL $H_2O$) was stirred under 60 psi hydrogen at rt. After 22 hrs, TLC (50% EtOAc/hexanes on silica gel) showed 100% conversion to product. The reaction mixture was filtered through a Celite pad (200 mL). The hydrogenation flask and the celite pad were rinsed with fresh, anhydrous THF (500 mL) to give a green filtrate solution. The filtrate was concentrated in vacuo to give the crude product as a greenish-black gummy oil. The rotatory evaporator was vented under $N_2$ and fresh, anhydrous THF (600 mL) was added. The solution was concentrated in vacuo and vented under nitrogen. (The process of dissolving in fresh, anhydrous THF and concentrating was repeated twice more to azeotropically remove residual water.) This material is used immediately in Step 2 due to apparent air sensitivity. m/z=499.5 for $[M+1]^+$ for the desired product.

Step 2: Preparation of N-[2-diethylamino-5-{N-trifluoroacetylamino}pyrimidin-4-yl]-L-4'-{(pyrrolidin-1-yl)carbonyloxy}phenylalanine tert-butyl ester 3

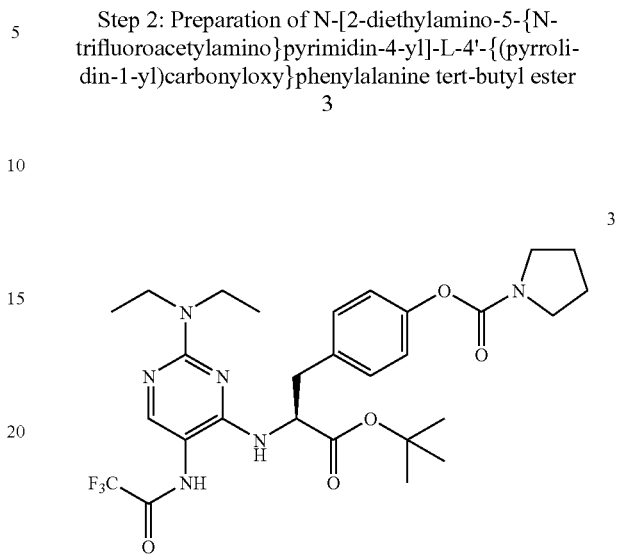

The crude aminopyrimidine carbamate 2 from Step 1 was dissolved in 600 mL anhydrous THF. The solution was cooled to 0° C. under nitrogen. Trifluoroacetic anhydride (45.5 mL, 1.51 g/mL, 327.3 mmol) was slowly added to the cold amine solution via syringe pump over 45 minutes. The solution was allowed to warm to room temperature and stirred overnight. TLC (40% EtOAc in Hexanes, silica gel) indicated the reaction was essentially complete. LC/MS analysis confirmed reaction and did not show any starting material. The reaction was diluted with ethyl acetate (1.4 L) and was washed with a mixture of water (400 mL) and saturated, aqueous $NaHCO_3$ (700 mL, 0° C.). The organic solution was washed with brine (700 mL) and dried over $MgSO_4$ (105 g) to give a tan-brown solution. The dried solution was filtered through a pad of silica gel (400 mL) to give a greenish-grey solution. (The tan colored impurity was retained on the silica gel.) The silica gel was rinsed with EtOAc (400 mL). The filtrate solution was concentrated in vacuo and the flask was vented under nitrogen to minimize exposure to oxygen. Anhydrous toluene (600 mL) was added. The solution was concentrated in vacuo and was azeotroped a second time from anhydrous toluene (400 mL) to give a green-black gummy oil. The flask was vented under $N_2$. This crude product m/z=595.5 for $[M+1]^+$ was carried forward to Step 3.

Step 3: Preparation of N-[2-diethylamino-5-{N-ethyl-N-trifluoroacetylamino}pyrimidin-4-yl]-L-4'-{(pyrrolidin-1-yl)carbonyloxy}phenylalanine tert-butyl ester 4

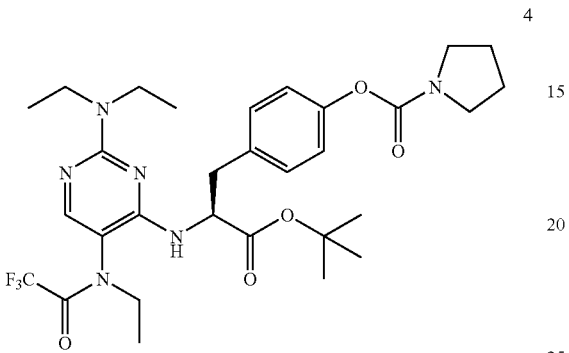

4

Crude trifluoroacetamidopyrimidine carbamate 3 from Step 2 was dissolved in DMF (350 mL). Solid anhydrous potassium carbonate (79.6 g, 575.7 mmol; ground to a fine powder with a mortar and pestle and then was placed in a vacuum oven at 110° C. under 28 in. Hg vacuum over night) was added. Ethyl iodide (46.5 mL, 89.8 g, 575.7 mmol) was added quickly at room temperature. The reaction flask was capped tightly and the slurry was stirred vigorously. After stirring at room temperature for 20 hours, the reaction was sampled (TLC, LC/MS). The reaction was stirred for an additional 18 hours to ensure complete reaction. Again, the reaction was sampled and a mini-workup was performed whereupon TLC analysis indicated the consumption of starting material. The reaction was diluted with 2.7 L of ethyl acetate and was stirred vigorously. The slurry was filtered through Whatman #1 filter paper to remove solid $K_2CO_3$. The organic solution was placed in a 6 L separatory funnel. Water (2.5 L) was added and vigorously mixed. The layers were slow to separate, then brine (200 mL) was added to break the emulsion. The organic layer was washed with another 1 L of water and then 2 L of brine.

The organic layer was dried over $MgSO_4$ (50 g) and $Na_2SO_4$ (200 g). The dried organic solution was filtered through a plug of silica gel (700 mL) to obtain an olive-drab green-tan smoky colored solution. (A purple/red baseline impurity was removed.) The silica gel was rinsed with EtOAc (800 mL). The organic solution was concentrated to give an olive drab green solid (194.3 g, 103% crude). Hexane (300 mL) was added. The sides of the flask were scrapped with a metal spatula to loosen the solid product and a magnetic stir bar was added to the flask. The mixture was rotated slowly for 30 minutes to break up the solid chunks and then quickly for 30 minutes until a fine slurry resulted. The slurry was filtered through Whatman #1 filter paper and the precipitate was rinsed with hexane (1.2 L) to give a white solid (141 g, 74% yield, 92% pure by LC/MS). The filtrate was concentrated to give a green-tan gum (33.3 g), which by TLC analysis contains some desired product.

$^1$H NMR (CDCl$_3$, 300 MHz) δ, ppm: 7.80 (apparent d, 1H), 7.18 (apparent d, AA'XX', 2H), 7.03 (apparent dd, AA'XX', 2H), 5.00 (apparent d, 1H), 4.80 (apparent dq, 1H), 3.95 (apparent dsextet, 1H), 3.4-3.7 (m, 8.5H), 3.0-3.3 (m, 3H), 2.78 (sextet, 0.7H), 1.93 (AA'BB', 4H), 1.38 (apparent d, 9H), 1.24-1.05 (m, 9H). The $^1$H NMR shows rotamers as is evidenced by the doubling of most peaks.

$^{13}$C NMR (CDCl$_3$, 75 MHz) δ, ppm: 166.5, 166.3, 155.6, 152.7, 150.9, 146.0, 145.9, 128.7, 128.3, 125.44, 125.39, 117.18, 77.66, (72.82, 72.28, 71.97—CDCl$_3$), 50.23, 49.74, 41.72, 41.64, 40.16, 39.90, 37.28, 32.60, 32.44, 23.24, 23.17, 21.05, 20.23, 8.50, 8.47, 7.32.

Step 4: Preparation of N-[2-diethylamino-5-{N-ethylamino}pyrimidin-4-yl]-L-4'-{(pyrrolidin-1-yl)carbonyloxy}phenylalanine tert-butyl ester 5

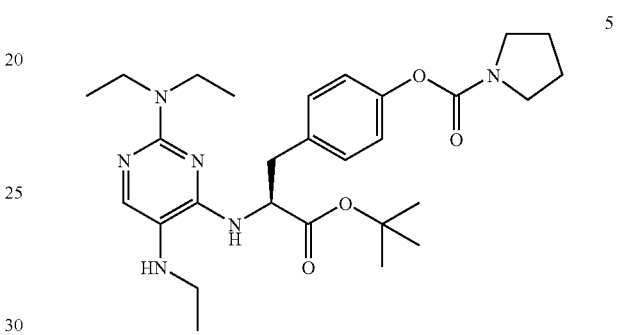

5

The trifluoroacetamide 4 (140 g) was suspended/dissolved in methanol (1.6 L). An aqueous solution of potassium carbonate (7% $K_2CO_3$) (480 mL) was added. (The trifluoroacetamide partially precipitated and formed a gel.) The reaction flask was lowered into a 55° C. water bath. The solution was mixed at 55° C., with monitoring by TLC, over 9 hours. The reaction was concentrated in vacuo very carefully until 1.2 L of methanol had been collected. The solution was diluted with water (200 mL) and brine (600 mL) and was extracted with EtOAc (2 L) to give an orange solution. The EtOAc layer was washed with water (1 L) and then brine (400 mL). Each of the three aqueous layers/washes was back extracted in sequential order with a single 1 L of EtOAc to obtain a bright yellow solution. The organic extracts were combined and dried over $MgSO_4$ (126 g). The dried organic solution was filtered through a pad of basic alumina (300 mL) and concentrated in vacuo to give a brown gum. After azeotroping from 600 mL toluene, a reddish solid (117.1 g) was obtained.

Step 5: Preparation of N-[2-diethylamino-5-{N-ethyl-N-(furan-3-ylcarbonyl)amino}pyrimidin-4-yl]-L-4'-{(pyrrolidin-1-yl)carbonyloxy}phenylalanine tert-butyl ester 6

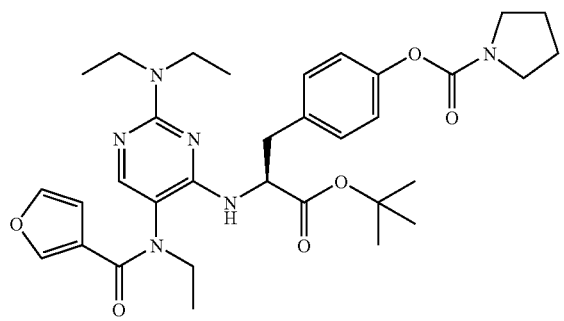

The amino-pyrimidine 5 (117.1 g, 222.2 mmol) was dissolved in anhydrous THF (1.5 L). Hunig's base, diisopropylethyl amine, (115 mL, 3 eq., 666.6 mmol) was added. The solution was cooled to 0° C. under $N_2$. The reaction flask was fitted with a pressure equalizing addition funnel and the addition funnel was charged with a solution of 3-furoyl chloride (32 g; Yamamoto & Maruoka; J. Am. Chem. Soc., 1981, 103, 6133-6136) in THF (90 mL). The furoyl chloride solution was added slowly to the cold amine solution over two hours. The reaction was allowed to slowly come to room temperature and was stirred for 36 hours. The reaction was diluted with EtOAc (2 L) and was washed twice with 0.2 N citric acid (1.2 L and 1.0 L), once with brine (1.8 L), and once with saturated aqueous $NaHCO_3$ (1.3 L). The bright orange-pink organic solution was dried over $Na_2SO_4$ (250 g) and $MgSO_4$ (51 g). The dried solution was filtered through a pad of silica gel (1 L) and the flask and silica were rinsed with EtOAc (1 L). The solution was concentrated in vacuo. During the evaporation process, a white solid crystallized. Once the solution was fully concentrated, an orange, pink, & white solid was obtained. Ether (400 mL) and hexanes (500 mL) were added. The slurry was mixed thoroughly and filtered through Whatman #1 filter paper to obtain a peach-pink solid and a bright red filtrate. The precipitate was rinsed with hexanes (500 mL), ether (800 mL), and again hexanes (400 mL) to get a light peach-orange solid. The filtrate and rinsings were combined, concentrated, and set aside for later use. The solid was dried in a vacuum oven at 60° C. for two days under a 28 in. Hg vacuum (49 Torr) to yield 100.0 g. LC/MS showed the solid to be 92% pure. The crude ester 6 was chromatographed on 2 L (1 kg) silica gel that had been slurry packed with 3 L of $CH_2Cl_2$. The peach colored product ester was dissolved in $CH_2Cl_2$ (200 mL) and was applied to the 2 L silica column. The column was eluted with $CH_2Cl_2$ (3 L), 50% EtOAc in hexanes (4 L), and 75% EtOAc in hexanes (4 L). Within a few minutes, desired product ester began crystallizing from several of the EtOAc-hexane fractions. Fractions that were shown to be pure by TLC were concentrated to give a white solid (82.5 g, purity >99% by LC/MS). This pure material was carried forward to the final deprotection step. Fractions that were shown by TLC to be contaminated were combined with the residue from the original filtrate/hexane & ether rinsings. This material was flash chromatographed in a manner similar to that described above to give a slight peach colored solid (13.2 g; m/z=621.5 for $[M+1]^+$).

$^1$H NMR (CDCl$_3$, 300 MHz) δ, ppm: 7.58 (apparent d, 1H), 7.35-6.90 (apparent AB overlapped with ABX, 6H), 6.45 (apparent d, 1H), 5.25 (apparent d, 1H), 4.85 (apparent dq, 1H), 4.05 (apparent octet, 1H), 3.7-3.4 (m, 8H), 3.0-3.3 (m, 2.5H), 2.90 (sextet, 0.5H), 1.93 (AA'BB', 4H), 1.38 (apparent d, 9H), 1.24-1.05 (m, 9H). The $^1$H NMR shows rotamers as is evidenced by the doubling of most peaks.

Step 6. Preparation of N-[2-diethylamino-5-{N-ethyl-N-(furan-3-ylcarbonyl)amino}pyrimidin-4-yl]-L-4'-{(pyrrolidin-1-yl)carbonyloxy}phenylalanine To the t-butyl ester 6 from Step 5 (82.5 g, 132.7 mmol) was added formic acid (2 L). The resulting solution was heated to 50° C. overnight. Analysis by TLC verified complete reaction and the solution was concentrated in vacuo. Water (~200 mL) was added to the crude product and the mixture was concentrated to dryness. Another 150 mL of water were added and the crude product was concentrated in vacuo again. The crude white solid product was concentrated from iPrOH, and twice from anhydrous THF, then dried on the rotary evaporator at 45° C. and 35-40 mbar (26-30 Torr) overnight to obtain 90 g of white solid. LC/MS showed the crude product to be 97.7% pure.

$^1$H NMR (CD$_3$OD, 300 MHz) δ, ppm: 7.65 (s, 0.55H), 7.45 (s, 0.45H), 7.38 (m, 2H), 7.25 (d, 1.3H), 7.18 (d, 1H), 7.05 (d, 1.2H), 6.90 (d, 1H), 6.55 (s, 0.55H), 6.22 (broad s, 0.45H), 4.9-4.8 residual solvent peak overlapped with sample peak, 4.10 (apparent septet, 1.1H), 3.7 (m, 3.3H), 3.58 (m, 7H), 3.45-2.9 (m, 6H), 2.78 (apparent sextet, 0.7H), 1.90 (AA'BB', 4.5H), 1.85 (m, 3.16H), 1.23-1.0 (m, 10.3H).

$^{13}$C NMR (CD$_3$OD, 75 MHz) δ, ppm: 169.6, 169.2, 160.8, 153.9, 153.6 148.8, 145.8, 145.2, 145.1, 140.7, 140.5, 138.0, 137.9, 130.3, 130.2, 124.7, 124.6, 116.5, 116.4, 116.2, 116.1, 106.9, 106.6, 105.1, 105.0, 62.4, 50.7, 50.1, 41.0, 37.9, 37.2, 30.5, 20.2, 20.0, 19.4, 6.9, 6.8, 6.1, 5.9.

Examples 7-12 below were prepared in a manner similar to Example 6.

Example 7

Preparation of (S)-2-(2-(diethylamino)-5-(N-ethyl-2,2,2-trifluoroacetamido)pyrimidin-4-ylamino)-3-(4-(pyrrolidine-1-carboxyloyloxy)phenyl)propanoic acid

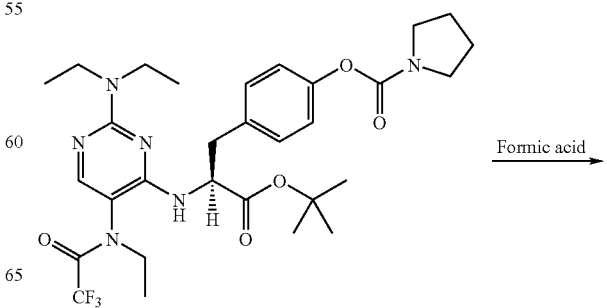

-continued

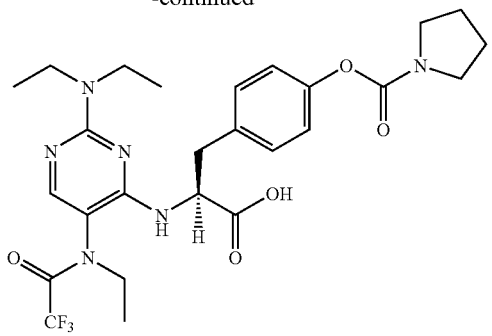

¹H NMR (300 MHz, CD₃OD) δ1.03 (1.5H, t, J=7.2 Hz), 1.10-1.28 (7.5H, m), 1.98 (4H, m), 2.67-2.85 (0.5H, m), 2.90-3.05 (0.5H, m), 3.05-3.38 (2H, m, overlap with CD₃OD), 3.41 (2H, m), 3.58 (6H, m), 3.90-4.11 (1H, m), 4.85-4.90 (1H, overlap with CD₃OD), 7.02 (2H, m), 7.26 (2H, m), 7.66 (1H, d, J=8.7 Hz)

HPLC/MS: MH⁺=567.1

Example 8

Preparation of N-[2-diethylamino-5-{N-ethyl-N-(thien-2-ylcarbonyl)amino}pyrimidin-4-yl]-L-4'-{(pyrrolidin-1-yl)carbonyloxy}phenylalanine Step 1:

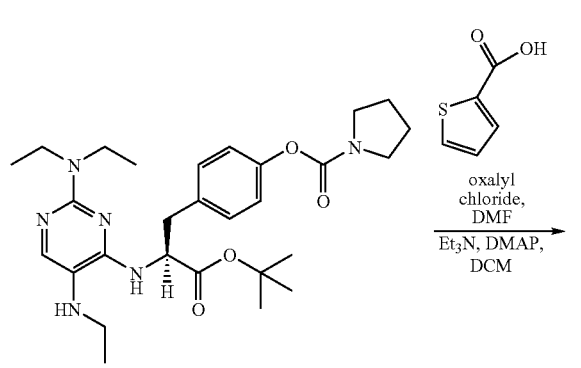

¹H NMR (300 MHz, CDCl₃) δ 1.09-1.17 (3H, m), 1.23-1.26 (3H, m), 1.47 (12H, m), 1.87-1.99 (4H, m), 2.80 (0.4H, br s), 3.10 (1.6H, m), 3.20 (1H, m), 3.44 (2H, t, J=6.0 Hz), 3.54 (2H, t, J=6.0 Hz), 3.88-4.15 (3H, m), 4.80-4.85 (1H, m), 6.48 (0.6H, br s), 6.75 (0.4H, s), 6.69-7.08 (5H, m), 7.41 (1H, s), 7.50 (1H, s), 7.78 (0.4H, br s), 7.85 (0.6H, br s)

HPLC/MS: MH⁺=637.2

Step 2:

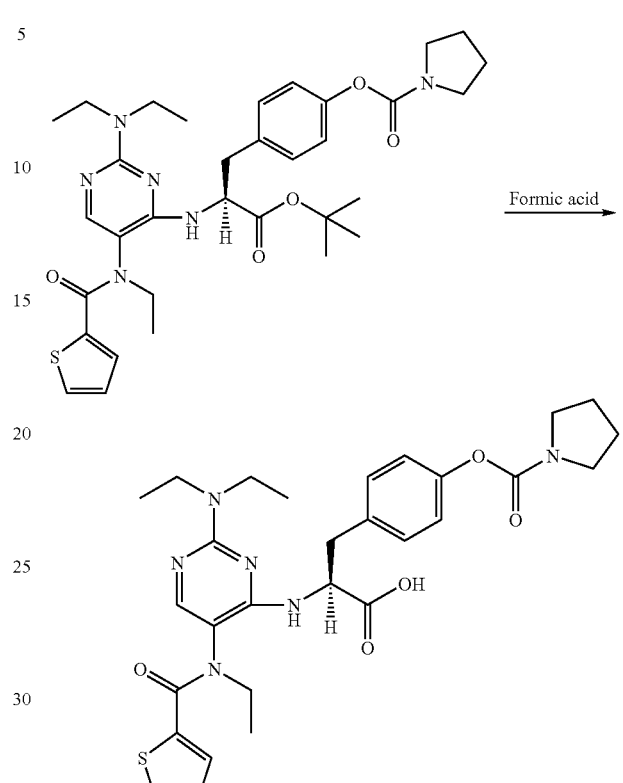

¹H NMR (300 MHz, CDCl₃) δ 0.90 (3H, t, J=6.9 Hz), 1.10-1.30 (6H, m), 1.85-1.94 (4H, m), 2.85-3.24 (2.4H, m), 3.35 (8.6H, m), 4.00-4.15 (1H, m), 4.55 (0.4H, br s), 4.73 (0.6H, br s), 5.85 (0.6H, d, J=5.7 Hz), 5.87 (0.4H, br s), 6.60-7.12 (5.4H, m), 7.39 (1H, m), 7.60-7.68 (1.6H, m)

HPLC/MS: MH⁺=581.2

Example 9

Preparation of N-[2-diethylamino-5-{N-ethyl-N-(thien-3-ylcarbonyl)amino}pyrimidin-4-yl]-L-4'-{(pyrrolidin-1-yl)carbonyloxy}phenylalanine Step 1:

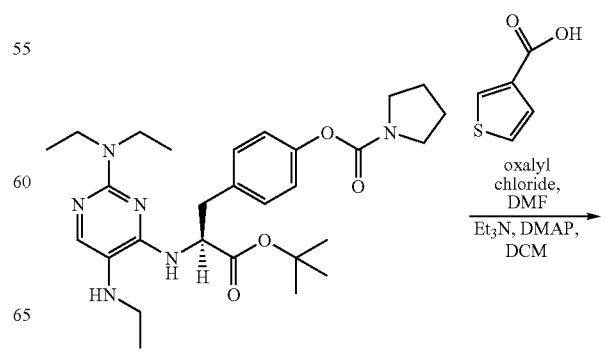

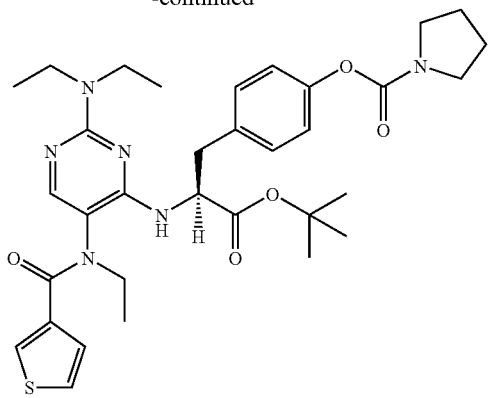

¹H NMR (300 MHz, CDCl₃) δ 1.07-1.27 (9H, m), 1.40 (9H, s), 1.90 (4H, m), 3.05-3.24 (3H, m), 3.43-3.64 (8H, m), 4.73-4.95 (1H, m), 5.22 (1H, m), 6.95-7.14 (7H, m), 7.41 (0.4H, s), 7.50 (0.6H, s)

HPLC/MS: M⁺=637.2

Step 2:

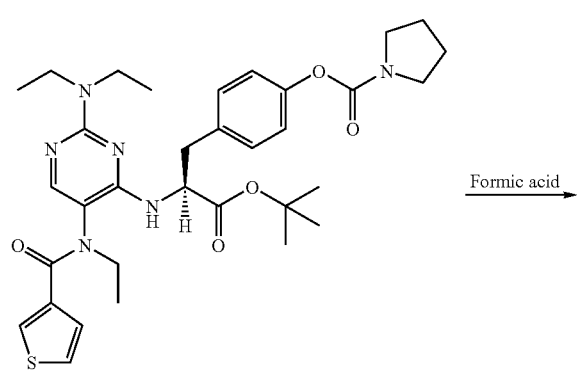

Formic acid →

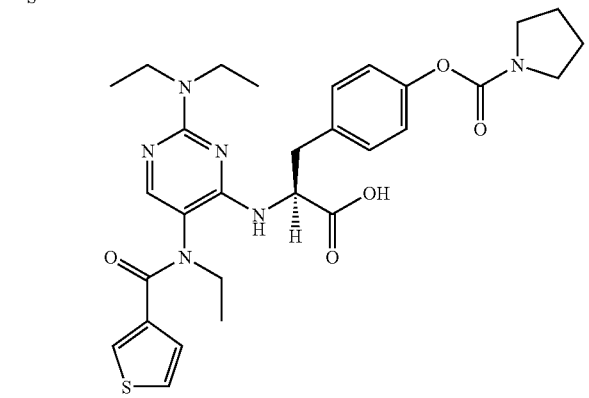

¹H NMR (300 MHz, CDCl₃), δ 0.70-1.4 (9H, m), 1.81-2.08 (4H, m), 2.62-4.10 (12H, m), 4.95 (1H, br s), 6.90-8.07 (8H, m)

HPLC/MS: MH⁺=581.2

Example 10

Preparation of N-[2-diethylamino-5-{N-ethyl-N-(furan-2-ylcarbonyl)amino}pyrimidin-4-yl]-L-4'-{(pyrrolidin-1-yl)carbonyloxy}phenylalanine Step 1:

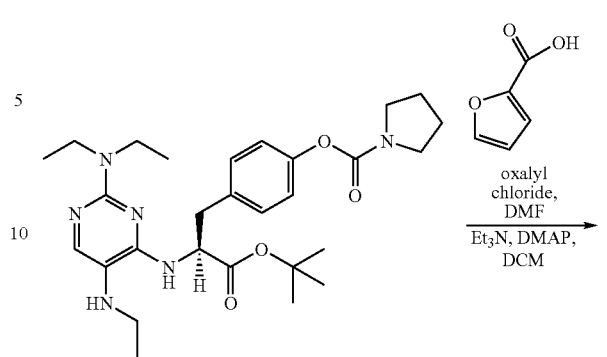

oxalyl chloride, DMF
Et₃N, DMAP, DCM →

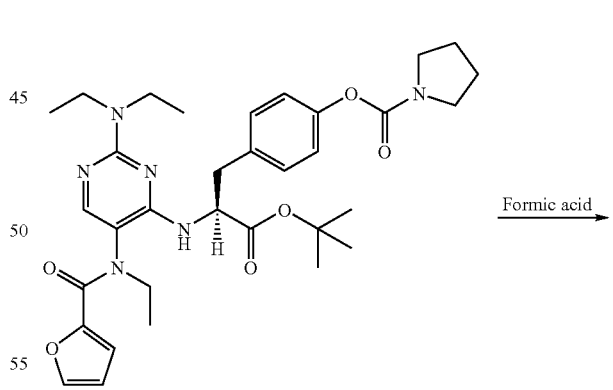

¹H NMR (300 MHz, CDCl₃) δ 1.15-1.28 (9H, m), 1.37 (3.6H, s), 1.42 (5.4H, s), 1.93-2.05 (4H, m), 2.85-3.15 (2H, m), 3.19-3.35 (1H, m), 3.45-3.75 (8H, m), 3.90-4.15 (1H, m), 4.76-4.85 (0.4H, m), 4.90-5.00 (0.6H, m), 5.15-5.22 (1H, m), 6.20-6.40 (2H, m), 6.91-7.18 (4H, m), 7.39 (1H, s), 7.58 (0.4H, s), 7.65 (0.6H, s)

HPLC/MS: MH⁺=621.3

Step 2:

Formic acid →

-continued

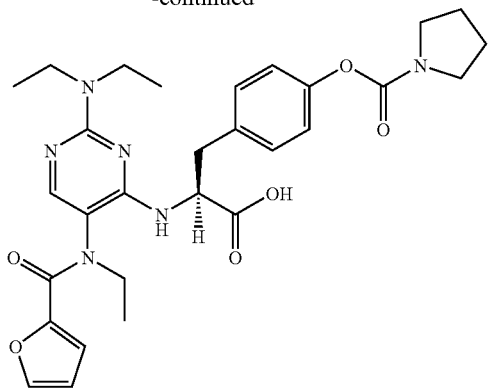

¹H NMR (300 MHz, CD₃OD) δ 0.84-1.25 (9H, m), 1.85-1.92 (4H, m), 2.70-2.81 (0.5H, m), 2.92-3.30 (2.5H, m, overlap with CD₃OD), 3.30-3.38 (2H, m), 3.45-3.59 (6H, m), 4.04-4.12 (1H, m), 4.80-4.89 (1H, overlap with CD₃OD), 6.18 (1H, m), 6.58 (0.5H, br s), 6.78 (0.5H, br s), 6.83 (1H, d, J=8.1 Hz), 6.92 (1H, d, J=8.1 Hz), 7.06 (1H, d, J=8.1 Hz), 7.19 (1H, d, J=8.1 Hz), 7.38 (0.5H, br s), 7.44 (0.5H, s), 7.47 (0.5H, br s), 7.48 (0.5H, s)

HPLC/MS: MH⁺=565.2

Example 11

Preparation of N-[2-diethylamino-5-{N-ethyl-N-(t-butylcarbonyl)amino}pyrimidin-4-yl]-L-4'-{(pyrrolidin-1-yl)carbonyloxy}phenylalanine Step 1:

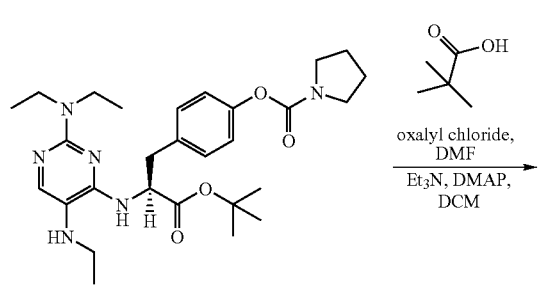

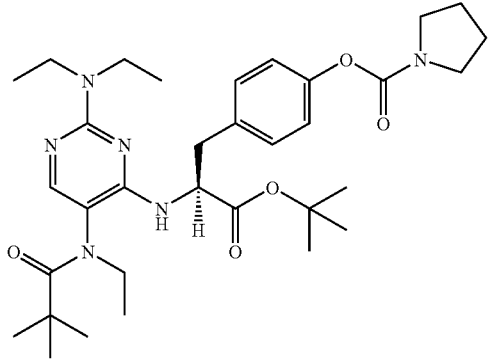

¹H NMR (300 MHz, CDCl₃) δ 1.04-1.11 (18H, m), 1.40 (4.5H, s), 1.42 (4.5H, s), 1.96 (4H, m), 2.46-2.59 (0.5H, m), 2.72-2.85 (0.5H, m), 3.00-3.32 (2H, m), 3.45-3.62 (8H, m), 3.82-4.15 (1H, m), 4.82-4.93 (1H, m), 5.05 (0.5H, d, J=7.2 Hz), 5.15 (0.5H, d, J=7.2 Hz), 7.08-7.18 (4H, m), 7.67 (1H, s)

HPLC/MS: MH⁺=611.3

Step 2:

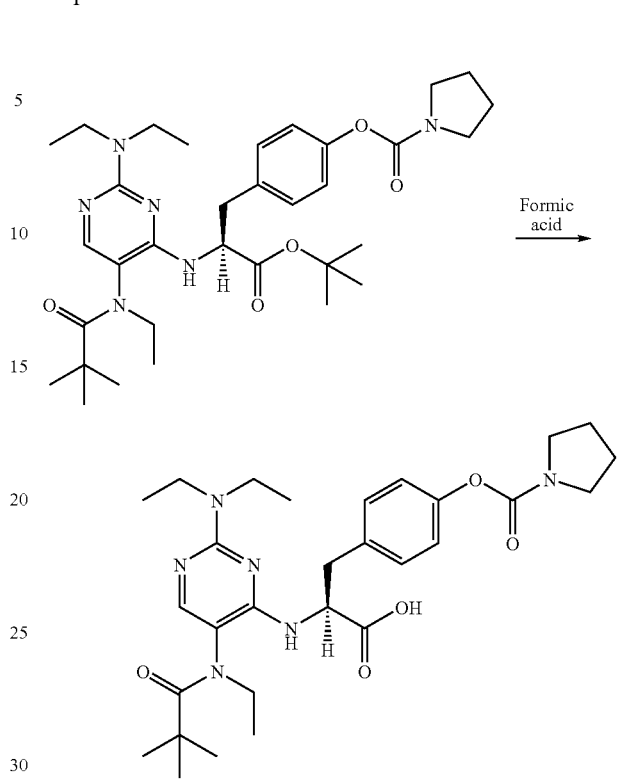

¹H NMR (300 MHz, CD₃OD) δ 0.86-1.20 (18H, m), 1.87 (4H, m), 2.32-2.45 (0.5H, m), 2.56-2.68 (0.6H, m), 3.05-3.20 (2H, m), 3.29-3.38 (2H, m), 3.43-3.52 (6H, m), 3.8-3.99 (1H, m), 4.75-4.82 (1H, overlap with CD₃OD), 6.90 (2H, d, J=9.0 Hz), 7.15 (2H, d, J=9.0 Hz), 7.43 (1H, s)

HPLC/MS: MH⁺=555.2

Example 12

Preparation of N-[2-diethylamino-5-{N-ethyl-N-(iso-propylcarbonyl)amino}pyrimidin-4-yl]-L-4'-{(pyrrolidin-1-yl)carbonyloxy}phenylalanine Step 1:

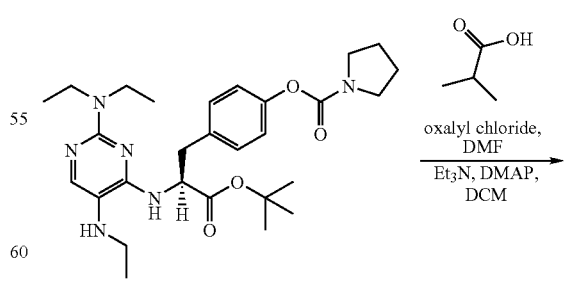

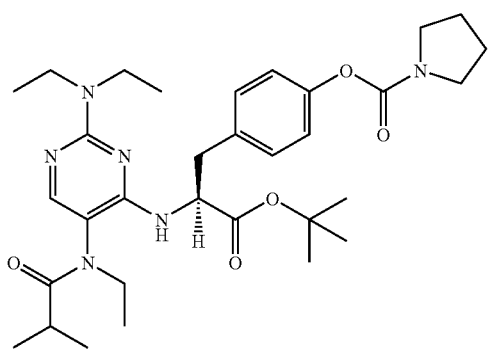

¹H NMR (300 MHz, CDCl₃) δ 0.90-1.21 (15H, m), 1.38 (9H, s), 1.92 (4H, m), 2.28-2.50 (1H, m), 2.80-3.16 (3H, m), 3.41-3.70 (8H, m), 3.80-3.95 (1H, m), 4.71-4.85 (1H, m), 5.05-5.11 (1H, m), 7.00-7.08 (2H, m), 7.08-7.16 (2H, m), 7.65 (1H, d, J=5.0 Hz)

HPLC/MS: MH⁺=597.3

Step 2:

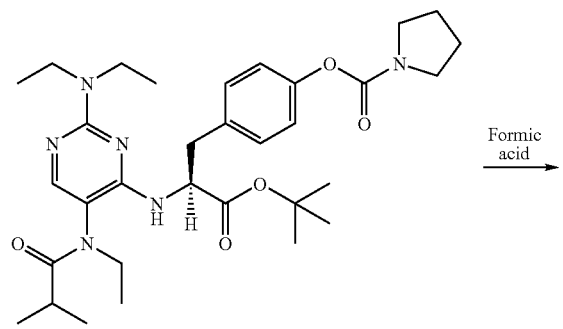

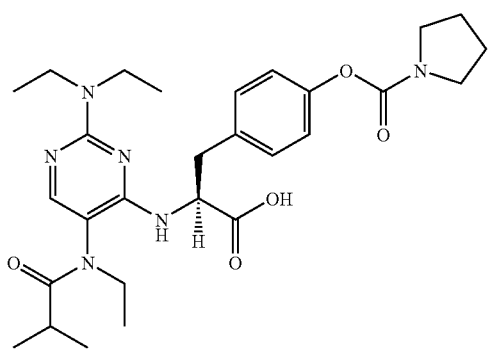

¹H NMR (300 MHz, CD₃OD) δ 0.80-0.98 (9H, m), 1.15-1.19 (6H, m), 1.88 (4H, m), 2.20-2.42 (1H, m), 2.65-2.83 (1H, m), 3.08-3.25 (2H, m), 3.26-3.59 (8H, m), 3.88-3.97 (1H, m), 4.70-5.05 (1H, overlap with CD₃OD), 6.92 (2H, d, J=7.8 Hz), 7.17 (2H, m), 7.63 (1H, d, J=5.0 Hz)

HPLC/MS: MH⁺=541.3

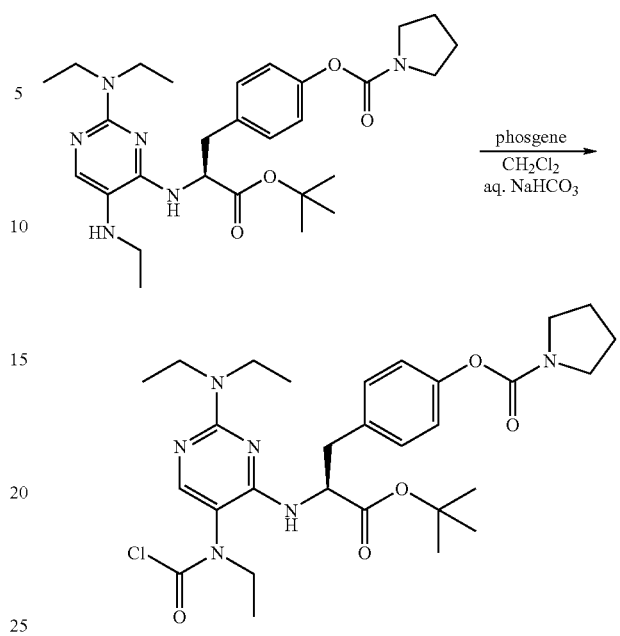

N-[2-diethylamino-5-{N-ethylamino}pyrimidin-4-yl]-L-4'-{(pyrrolidin-1-yl)carbonyloxy}phenylalanine tert-butyl ester (0.436 g, 0.83 mmol) was dissolved in CH₂Cl₂ (0.35 mL) and sat. NaHCO₃ (0.7 mL). The solution was cooled to zero degrees and vigorously stirred for 10 minutes. After 10 minutes the stirring was stopped and the immiscible layers were allowed to separate. Phosgene (0.52 mL, 4.97 mmol) was added to the bottom layer via syringe. The reaction mixture was stirred under N₂ for three hours. Upon completion, the organic layer was separated and it was concentrated in vacuo at rt. It was redissolved in EtOAc and washed with de-ionized water and back extracted two times. The organic layer was dried over Na₂SO₄ and concentrated in vacuo. The crude oil was taken forward to the next step without purification.

HPLC/MS: MH⁺=589.0

Step 2:

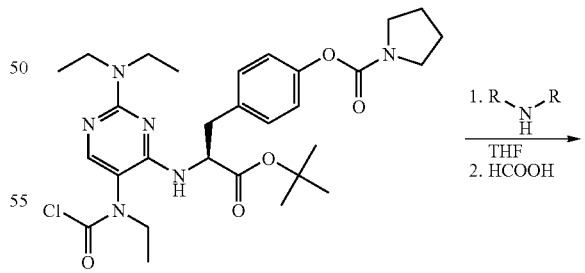

Example 13

General method for the preparation of pyrimidinyl ureas.

Step 1:

-continued

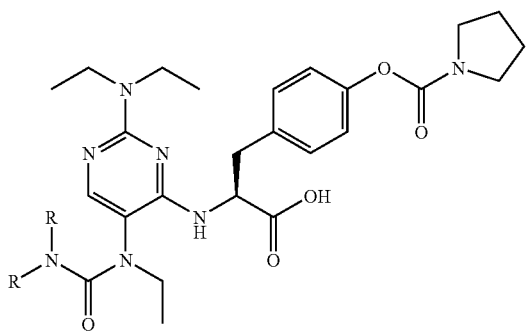

Crude carbamyl chloride (1 eq.) and amine (5 eq.) were dissolved in THF (0.2M) and stirred over night under N₂. The reaction mixture was concentrated in vacuo and redissolved in ethyl acetate. The organic layer was washed with water, dried over Na₂SO₄ and concentrated in vacuo. The products were purified by HPLC. The products were treated with HCOOH as solvent at 40° C. overnight. The solvent was removed under reduced pressure and the products were obtained.

Examples 14-16 were prepared according to example 13.

Example 14

Preparation of N-[2-diethylamino-5-{N-ethyl-N-(piperidin-1-ylcarbonyl)amino}pyrimidin-4-yl]-L-4'-{(pyrrolidin-1-yl)carbonyloxy}phenylalanine

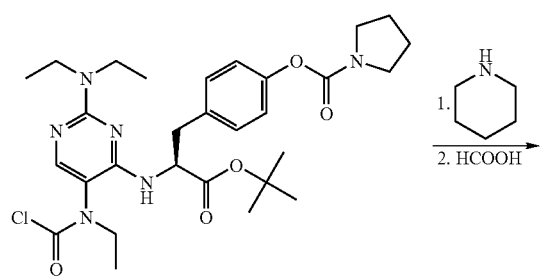

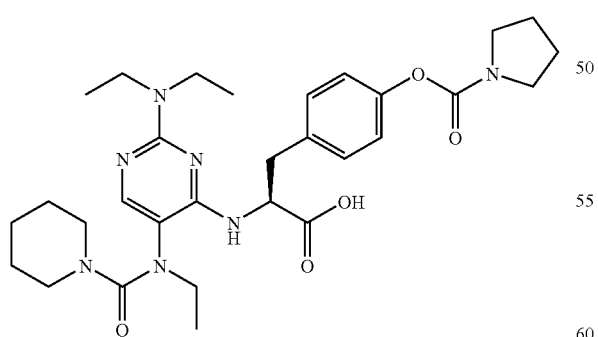

$^1$H NMR (300 MHz, CDCl$_3$) δ 1.01 (3H, t, J=7 Hz), 1.22 (6H, t, J=7 Hz), 1.36 (4H, m), 1.49 (2H, m), 1.95 (4H, m), 3.10-3.66 (16H, m), 4.86-4.92 (1H, m), 6.75 (1H, d, J=7.2 Hz), 7.25 (2H, d, J=8.4 Hz), 7.14 (2H, d, J=8.4 Hz), 7.64 (1H, s).

HPLC/MS: MH$^+$=582.3

Example 15

Preparation of N-[2-diethylamino-5-{N-ethyl-N—(N-ethyl-N-iso-propylaminocarbonyl)amino}pyrimidin-4-yl]-L-4'-{(pyrrolidin-1-yl)carbonyloxy}phenylalanine

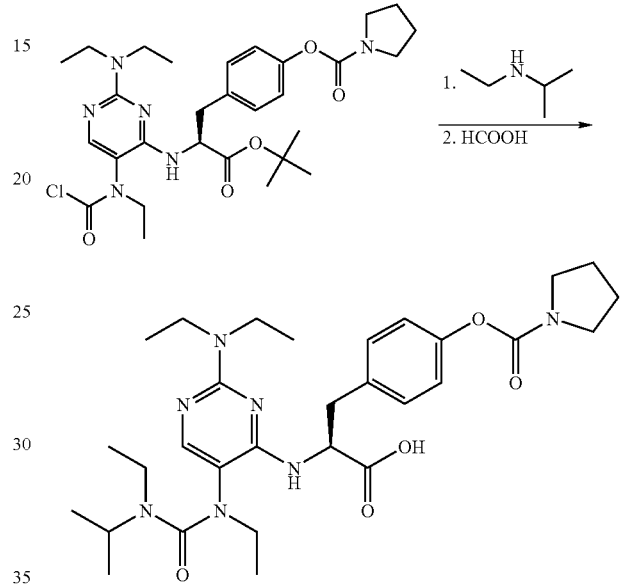

$^1$H NMR (300 MHz, CDCl$_3$) δ 1.01 (9H, br s), 1.21 (9H, m), 1.90-1.99 (4H, m), 2.98 (2H, m), 3.15 (3H, m), 3.33 (1H, m), 3.45 (2H, m), 3.52-3.60 (6H, m), 3.76 (1H, m), 4.91-4.97 (1H, br s), 6.64 (1H, br s), 7.04 (2H, d, J=8 Hz), 7.14 (2H, d, J=8 Hz), 7.66 (1H, s).

HPLC/MS: MH$^+$=584.4

Example 16

Preparation of N-[2-diethylamino-5-{N-ethyl-N-(3-thiapyrrolidin-1-ylcarbonyl)amino}pyrimidin-4-yl]-L-4'-{(pyrrolidin-1-yl)carbonyloxy}phenylalanine

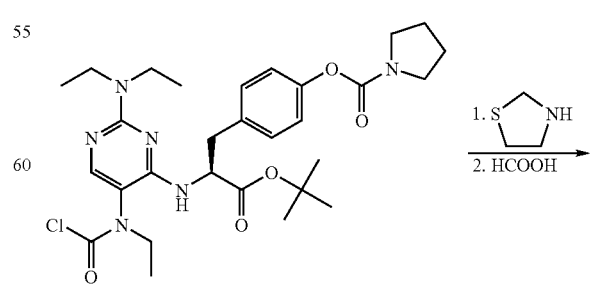

-continued
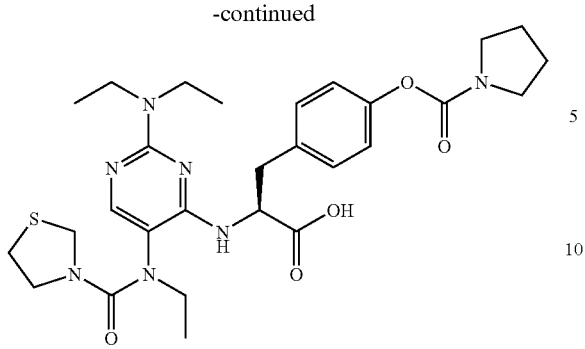
$^1$H NMR (300 MHz, CDCl$_3$) δ 1.03 (3H, t, J=6.6 Hz), 1.21 (6H, t, J=6.6 Hz), 1.90-1.99 (4H, m), 2.84 (2H, t, J=6 Hz), 3.09-3.63 (14H, m), 4.06-4.14 (2H, q, J=7.8 Hz), 4.91-4.97 (1H, m), 6.64 (1H, d, J=7 Hz), 7.04 (2H, d, J=8.4 Hz), 7.13 (2H, d, J=8.4 Hz), 7.75 (1H, s).
HPLC/MS: MH$^+$=586.2
Compounds of the above formulae VI-XI may be prepared as illustrated in Scheme C and as described in the methods below:
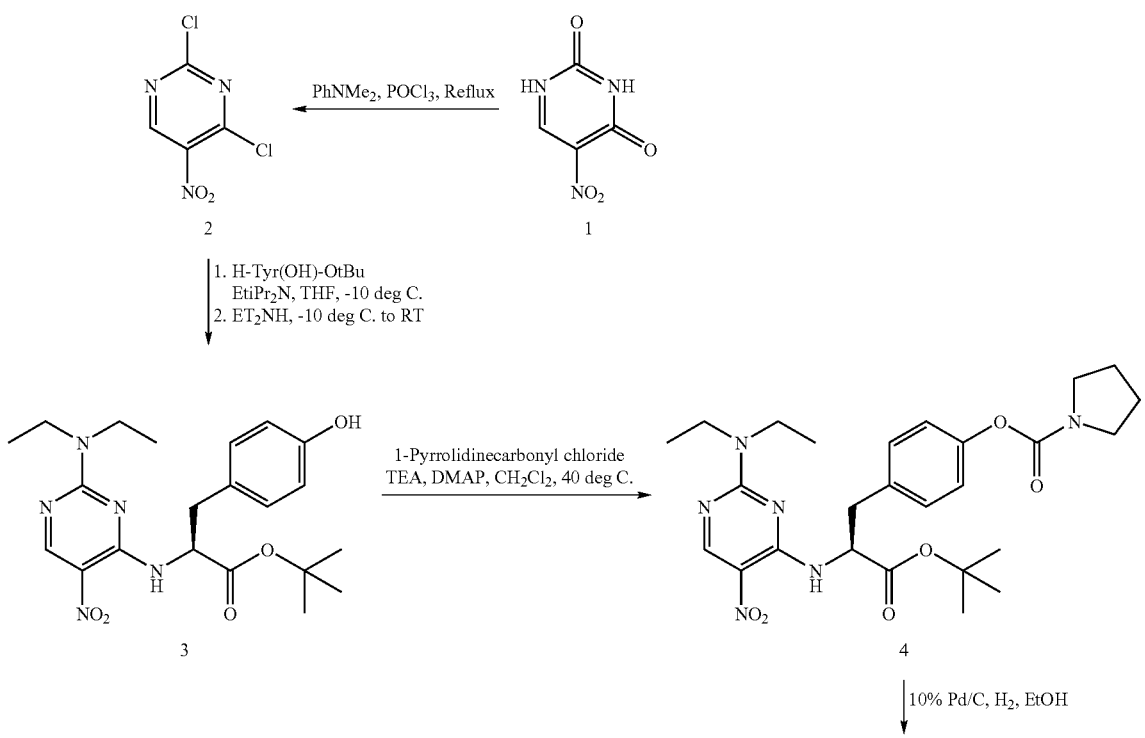

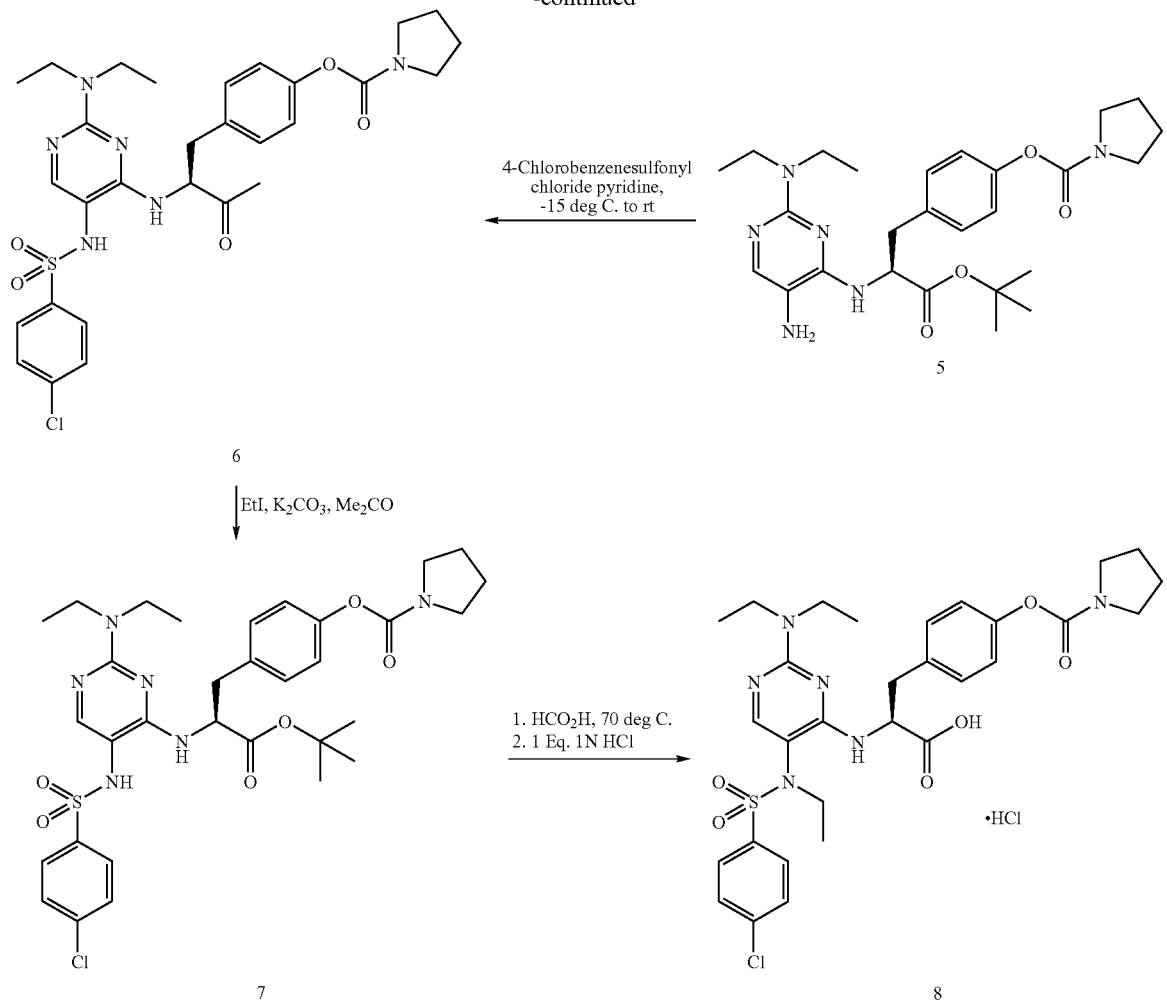

Example 17

Preparation of N-(2-[N',N'-diethylamino]-5-[N''-(4-chlorophenylsulfonyl)-N''-ethylamino]pyrimidin-4-yl)-4'-(pyrrolidin-1-ylcarbonyloxy)-L-phenylalanine Step 1: Preparation of 2,4-Dichloro-5-nitropyrimidine (2). 5-Nitrouracil, (1), was treated with phosphorous oxychloride ($POCl_3$) and N,N-dimethylaniline ($PhNMe_2$), according to the procedure of Whittaker (J. Chem. Soc. 1951, 1565), to give compound 2. Compound 2 is also available from City Chemical (West Haven, Conn.).

Step 2: Preparation of N-(2-[N',N'-diethylamino]-5-nitropyrimidin-4-yl)-L-tyrosine tert-butyl ester (3). To a solution of L-tyrosine tert-butyl ester (H-Tyr(OH)-OtBu) (30.6 g, 0.129 mol) in THF (250 mL) at −10° C. was added 2,4-dichloro-5-nitropyrimidine (25 g, 0.129 mol), keeping the temperature below 5° C. during the addition. Once the addition was complete, N,N-diisopropylethylamine ($EtiPr_2N$) (33.7 mL, 0.194 mol) was added dropwise. After stirring for 1 h at −10° C., diethylamine ($Et_2NH$) (66.73 mL, 0.645 mol) was added slowly, and then the reaction mixture was warmed to room temperature overnight. The reaction mixture was diluted with diethyl ether (500 mL), and the organic layer was washed with 0.2 N citric acid (3×150 mL), water (1×150 mL), and 10% $K_2CO_3$ (3×150 mL). The organic phase was dried ($Na_2SO_4$), filtered, and concentrated in vacuo to yield a yellow residue. The residue was purified by flash chromatography (20% EtOAc/hexanes on silica gel) to yield 37.39 g (67%) of compound 3 as a yellow foam. $R_f$=0.21 (25% EtOAc/hexanes on silica gel).

Step 3: Preparation of N-(2-[N',N'-diethylamino]-5-nitropyrimidin-4-yl)-4'-(pyrrolidin-1-ylcarbonyloxy)-L-phenylalanine tert-butyl ester (4). To a solution of N-(2-[N',N'-diethylamino]-5-nitropyrimidin-4-yl)-L-tyrosine tert-butyl ester (37.39 g, 0.087 mol) in $CH_2Cl_2$ (150 mL) was added DMAP (10.59 g, 0.087 mol). After 5 minutes triethylamine (TEA) (18.19 mL, 0.131 mol) was added dropwise.

1-Pyrrolidinecarbamoyl chloride (14.42 mL, 0.131 mol) was added dropwise, and the reaction was heated to reflux (40° C.) overnight. The reaction mixture was concentrated in vacuo and taken up in EtOAc (300 mL). The organic phase was washed with 0.2 N citric acid (3×150 mL), water (1×150 mL), sat. $NaHCO_3$ (3×150 mL), brine (1×150 mL), dried ($Na_2SO_4$), filtered, and concentrated in vacuo to yield 43.07 g (94%) of compound 4 as a yellow solid. $R_f$=0.5 (50% EtOAc/hexanes on silica gel).

Step 4: Preparation of N-(2-[N',N'-diethylamino]-5-aminopyrimidin-4-yl)-4'-(pyrrolidin-1-ylcarbonyloxy)-L-phenylalanine tert-butyl ester (5). A mixture of N-(2-[N',N'-diethylamino]-5-nitropyrimidin-4-yl)-4'-(pyrrolidin-1-ylcarbonyloxy)-L-phenylalanine tert-butyl ester (43.07 g, 0.081 mol) and 10% Pd/C (4.3 g, 10 wt % Pd) in EtOH (200 mL) was shaken under 45 psi hydrogen until TLC (50% EtOAc/hexanes on silica gel) showed 100% conversion to product (48 hours). The reaction mixture was then filtered through a Celite plug and concentrated in vacuo to yield 40.29 g (100%) of compound 5 as a purple foam. $R_f$=0.11 (6:1 EtOAc/hexanes on silica gel).

Step 5: Preparation of N-(2-[N',N'-diethylamino]-5-[N"-(4-chlorophenyl-sulfonyl)amino]pyrimidin-4-yl)-4'-(pyrrolidin-1-ylcarbonyloxy)-L-phenylalanine tert-butyl ester (6). A pyridine (160 mL) solution of N-(2-[N',N'-diethylamino]-5-aminopyrimidin-4-yl)-4'-(pyrrolidin-1-ylcarbonyloxy)-L-phenylalanine tert-butyl ester (40.29 g, 0.081 mol) was cooled to −20° C. with a dry ice/CH$_3$CN bath. The mixture stirred for 30 minutes, and then 4-chlorobenzenesulfonyl chloride (17.06 g, 0.081 mol) was added slowly. The reaction was stirred at −20° C. to −15° C. for 4 h and then allowed to warm to room temperature overnight. The reaction was diluted with EtOAc (400 mL), and the organic phase was washed with 0.2 N citric acid (3×150 mL), water (1×150 mL), sat. NaHCO$_3$ (3×150 mL), brine (1×150 mL), dried (Na$_2$SO$_4$), filtered, and concentrated in vacuo to yield a brown residue. The residue was purified by flash chromatography (50% EtOAc/hexanes on silica gel) to yield 43.49 g (80%) of compound 6 as a yellow foam. $R_f$=0.35 (50% EtOAc/hexanes on silica gel).

Step 6: Preparation of N-(2-[N',N'-diethylamino]-5-[N"-(4-chlorophenyl-sulfonyl)-N"-ethylamino]pyrimidin-4-yl)-4'-(pyrrolidin-1-ylcarbonyloxy)-L-phenylalanine tert-butyl ester (7). To a solution of N-(2-[N',N'-diethylamino]-5-[N"-(4-chlorophenyl-sulfonyl)amino]pyrimidin-4-yl)-4'-(pyrrolidin-1-ylcarbonyloxy)-L-phenylalanine tert-butyl ester (42.92 g, 0.064 mol) in acetone (Me$_2$CO) (600 mL) was added K$_2$CO$_3$ (12.75 g, 0.096 mol), and the mixture was stirred for 1 h at room temperature. Iodoethane (EtI) (7.73 mL, 0.096 mol) was then added slowly, and the reaction mixture was stirred overnight at room temperature. The reaction mixture was concentrated in vacuo, and the residue was taken up in EtOAc (300 mL). The organic phase was washed with water (2×300 mL), brine (1×100 mL), dried (Na$_2$SO$_4$), filtered, and concentrated in vacuo. The residue was purified by flash chromatography (2:1 hexanes/EtOAc on silica gel) to yield 37.36 g (85%) of compound 7 as a white solid. $R_f$=0.53 (50% EtOAc/hexanes on silica gel).

Step 7: Preparation of N-(2-[N',N'-diethylamino]-5-[N"-(4-chlorophenylsulfonyl)-N"-ethylamino]pyrimidin-4-yl)-4'-(pyrrolidin-1-ylcarbonyloxy)-L-phenylalanine hydrochloride (8). A formic acid (500 mL) solution of N-(2-[N',N'-diethylamino]-5-[N"-(4-chlorophenyl-sulfonyl)-N"-ethylamino]pyrimidin-4-yl)-4'-(pyrrolidin-1-ylcarbonyloxy)-L-phenylalanine tert-butyl ester (36.21 g, 0.052 mol) was heated to 70° C. for 2 h and then concentrated in vacuo. The residue was dissolved again in formic acid (500 mL) and heated again at 70° C. for 2 h. The solution was reduced in volume by 80% and then treated with at least 1 eq. of 1.0 N HCl (52 mL, 0.052 mol) followed by distilled water (100 mL). The resulting heterogeneous mixture was concentrated in vacuo. Distilled water (100 mL) was added, and the heterogeneous mixture was concentrated in vacuo. The latter steps were repeated twice to yield a wet white product. This was dried by placing under high vacuum at 40° C. (7 days) to yield 32.8 g (93%) of compound 8, as a free-flowing white solid. $R_f$=0.25 (7/3 MeOH/H$_2$O+0.1% TFA, reverse phase).

$^1$H NMR (CD$_3$OD) δ 8.22 (bs, 1H), 7.82-7.79 (m, 1H), 7.64-7.60 (m, 2H), 7.36-7.33 (m, 1H), 7.22-7.13 (m, 2H), 7.07-6.98 (m, 2H), 4.91-4.90 (m, 1H), 4.80-4.79 (m, 1H), 4.12-4.10 (m, 1H), 3.87-3.75 (m, 1H), 3.55-3.53 (m, 4H), 3.41-3.40 (m, 3H), 3.26-3.19 (m, 2H), 2.03 (bs, 1H), 1.97-1.89 (m, 3H), 1.27-1.15 (m, 6H), 1.10-1.05 (t, 1.5H), 0.97-0.92 (t, 1.5H)

$^{13}$C NMR (CD$_3$OD) δ 175.8, 175.7, 166.5, 162.7, 162.2, 155.8, 155.7, 155.7, 152.6, 148.1, 147.7, 142.0, 138.5, 136.2, 132.6, 132.3, 131.9, 131.7, 123.7, 111.8, 111.5, 62.3, 57.8, 44.9, 38.7, 38.0, 27.4, 26.6, 15.3, 14.9, 14.7, 14.0, 13.9

Example 18

Preparation of N-(2-[N',N'-diethylamino]-5-[N"-(4-fluorophenylsulfonyl)-N"-ethylamino]pyrimidin-4-yl)-4'-(pyrrolidin-1-ylcarbonyloxy)-L-phenylalanine Steps 1, 2, 3, 4, 6 and 7 were performed as for Example 17. Step 5 was performed using 4-fluorobenzenesulfonyl chloride in place of 4-chlorobenzenesulfonyl chloride.

$^1$H NMR (CD$_3$OD) δ 8.17 (bs, 1H), 7.90-7.87 (m, 2H), 7.40-7.34 (m, 2H), 7.20-7.16 (m, 1H), 7.08-7.00 (m, 3H), 5.52-5.51 (m, 1H), 4.96-4.93 (m, 2H), 5.78-5.70 (m, 1H), 3.85-3.75 (m, 1H), 3.59-3.53 (m, 4H), 4.47-4.43 (m, 2H), 3.44-3.24 (m, 2H), 2.02-1.94 (m, 3H), 1.24-1.16 (m, 6H), 1.10-1.05 (t, 1.5H), 0.99-0.94 (t, 1.5H)

$^{13}$C NMR (CD$_3$OD) δ 133.0, 132.9, 132.5, 132.2, 123.7, 123.6, 118.6, 57.1, 44.3, 38.3, 27.3, 26.6, 14.7, 14.1

MS m/z 629.5 (MH+)

Example 19

Preparation of N-(2-[N',N'-diethylamino]-5-[N"-(4-fluorophenylsulfonyl)-N"-methylamino]pyrimidin-4-yl)-4'-(pyrrolidin-1-ylcarbonyloxy)-L-phenylalanine Steps 1, 2, 3, 4, 5 and 7 were performed as for Example 18. Step 6 was performed using dimethyl sulfate in place of ethyl iodide.

$^1$H NMR (CD$_3$OD) δ 8.16 (bs, 1H), 7.89-7.88 (m, 1H), 7.39-7.35 (m, 3H), 7.20-7.13 (m, 1H), 7.05-7.00 (m, 2H), 4.85-4.84 (m, 1H), 4.14-4.12 (m, 1H), 3.59-3.54 (m, 5H), 3.45-3.44 (m, 2H), 3.45-3.33 (m, 3H), 3.13-3.12 (m, 1H), 3.02-3.01 (m, 1H), 2.04-1.95 (m, 4H), 1.29-1.18 (m, 6H)

$^{13}$C NMR (CD$_3$OD) δ 176.5, 169.8, 166.9, 166.4, 156.2, 152.7, 151.8, 150.4, 136.8, 133.3, 133.2, 132.5, 123.7, 118.8, 118.5, 57.8, 57.1, 48.3, 44.5, 41.0, 38.8, 27.5, 26.7, 14.1

MS m/z 615.2 (MH+)

Example 20

Preparation of N-(2-[N',N'-diethylamino]-5-[N"-(4-chlorophenylsulfonyl)-N"-methylamino]pyrimidin-4-yl)-4'-(pyrrolidin-1-ylcarbonyloxy)-L-phenylalanine Steps 1, 2, 3, 4, 5 and 7 were performed as for Example 17. Step 6 was performed using dimethyl sulfate in place of ethyl iodide.

$^1$H NMR (CD$_3$OD) δ 8.20 (bs, 1H), 7.83-7.80 (m, 2H), 7.67-7.64 (m, 2H), 7.37-7.34 (m, 1H), 7.21-7.18 (m, 1H), 7.10-7.03 (m, 2H), 4.88-4.87 (m, 1H), 4.13-4.10 (m, 1H), 3.55-3.45 (m, 6H), 3.42-3.40 (m, 2H), 3.24-3.23 (m, 2H), 3.11-3.10 (m, 1H), 3.02-3.01 (m, 1H), 2.04-2.03 (m, 1H), 1.98-1.90 (m, 3H), 1.28-1.18 (m, 6H)

¹³C NMR (CD₃OD) δ 176.0, 166.4, 161.8, 155.9, 155.4, 152.6, 146.5, 142.2, 137.6, 137.4, 136.4, 132.5, 131.9, 123.7, 114.6, 62.4, 58.1, 57.7, 45.0, 40.8, 38.6, 38.3, 27.4, 26.6, 15.3, 13.9

Example 21

Preparation of N-(2-[N',N'-diethylamino]-5-[N"-(4-fluorophenylsulfonyl)-N"'-methylamino]pyrimidin-4-yl)-4'-(piperidin-1-ylcarbonyloxy)-L-phenylalanine Steps 1, 2, 4, 5, 6 and 7 were performed as for Example 19. Step 3 was performed using 1-piperidinecarbonyl chloride in place of 1-pyrrolidinecarbonyl chloride.
¹H NMR (CD₃OD) δ 8.16 (bs, 1H), 7.90-7.88 (m, 2H), 7.40-7.35 (m, 2H), 7.21-7.20 (m, 1H), 7.14-7.13 (m, 1H), 7.02-7.01 (m, 2H), 5.51 (bs, 1H), 4.83-4.77 (m, 1H), 3.64-3.53 (m, 6H), 3.34-3.33 (m, 2H), 3.20-3.17 (m, 1H), 3.12-3.11 (m, 2H), 3.02-3.01 (m, 1H), 1.68-1.65 (m, 6H), 1.19-1.17 (m, 6H)
¹³C NMR (CD₃OD) δ 185.0, 169.7, 166.3, 152.7, 136.6, 135.0, 133.2, 133.0, 132.5, 131.8, 126.3, 123.6, 121.7, 118.6, 118.3, 57.6, 54.5, 46.9, 44.3, 39.6, 38.7, 27.6, 25.9, 14.0

Example 22

Preparation of N-(2-[N',N'-diethylamino]-5-[N"-(4-fluorophenylsulfonyl)-N"'-ethylamino]pyrimidin-4-yl)-4'-(piperidin-1-ylcarbonyloxy)-L-phenylalanine Steps 1, 2, 4, 5, 6 and 7 were performed as for Example 18. Step 3 was performed using 1-piperidinecarbonyl chloride in place of 1-pyrrolidinecarbonyl chloride.
¹H NMR (CD₃OD) δ 8.17 (bs, 1H), 7.91-7.85 (m, 2H), 7.39-7.31 (m, 3H), 7.20-7.16 (m, 1H), 7.05-6.97 (m, 2H), 4.88-4.69 (m, 2H), 4.71-4.69 (m, 1H), 3.80-3.75 (m, 1H), 3.62-3.39 (m, 6H), 3.34-3.32 (m, 2H), 3.30-3.16 (m, 3H), 1.68-1.65 (m, 4H), 1.23-1.17 (m, 6H), 1.10-1.05 (t, 1.5H), 0.99-0.94 (t, 1.5H)
¹³C NMR (CD₃OD) δ 199.9, 187.6, 183.1, 176.2, 169.7, 166.3, 163.0, 162.7, 153.9, 152.9, 136.5, 133.1, 133.0, 132.7, 132.4, 123.8, 118.8, 118.4, 111.1, 110.6, 102.8, 79.4, 57.3, 55.4, 44.4, 38.9, 38.4, 27.7, 26.1, 15.1, 14.8, 14.3, 14.2

Example 23

Preparation of N-(2-[N',N'-diethylamino]-5-[N"-(4-fluorophenylsulfonyl)-N"'-ethylamino]pyrimidin-4-yl)-4'-(azetidin-1-ylcarbonyloxy)-L-phenylalanine Steps 1, 2, 4, 5, 6 and 7 were performed as for Example 18. Step 3 was performed according to the following procedure.
¹H NMR (CD₃OD) δ 7.92-7.86 (m, 2H), 7.41-7.32 (m, 3H), 7.22 (d, 1H), 7.04-6.91 (m, 3H), 4.29-3.98 (m, 4H), 3.88-3.72 (m, 1H), 3.69-3.37 (m, 4H), 2.40-2.24 (m, 2H), 1.28-1.11 (m, 6H), 1.10-1.00 (t, 1.5H), 1.01-0.89 (t, 1.5H)
¹³C NMR (CD₃OD) δ 174.2, 169.7, 166.4, 163.2, 162.8, 157.0, 153.3, 153.2, 152.4, 144.3, 143.8, 136.1, 135.6, 135.5, 133.2, 133.1, 132.5, 132.2, 123.7, 118.9, 118.6, 112.9, 112.6, 57.5, 38.1, 37.7, 17.4, 14.7, 14.5, 13.8, 13.7
MS m/z 615 (MH⁺)
Alternative Preparation of N-(2-[N',N'-diethylamino]-5-nitropyrimidin-4-yl)-4'-(azetidin-1-ylcarbonyloxy)-L-phenylalanine tert-butyl ester. To a −15° C. stirred solution of compound 3 (24.9 g, 0.0578 mol) and 4-nitrophenyl chloroformate (11.7 g, 0.0578 mmol) in CH₂Cl₂ (300 mL) was added triethylamine (24.2 mL, 0.173 mol), at a rate such that the temperature of the reaction mixture did not exceed −10° C. After stirring for 20 min, azetidine (3.30 g, 0.0578 mmol) was added dropwise, and the reaction mixtures was warmed to room temperature and stirred overnight. The reaction mixture was diluted with EtOAc (100 mL) and hexanes (100 mL), and then was extracted repeatedly with 10% aqueous K₂CO₃, until no yellow color (4-nitrophenol) was seen in the aqueous phase. The organic layer was washed with brine (75 mL), dried with MgSO₄, filtered, and evaporated to yield 28.5 g (96%) of N-(2-[N',N'-diethylamino]-5-nitropyrimidin-4-yl)-4'-(azetidin-1-ylcarbonyloxy)-L-phenylalanine tert-butyl ester as a yellow solid, which was used without purification. Rf=0.17 (2:5 EtOAc/hexanes on silica gel).

Example 24

Preparation of N-(2-[N',N'-diethylamino]-5-[N"-(4-fluorophenylsulfonyl)-N"'-methylamino]pyrimidin-4-yl)-4'-(azetidin-1-ylcarbonyloxy)-L-phenylalanine Steps 1, 2, 3, 4, 5 and 7 were performed as for Example 23. Step 6 was performed using dimethyl sulfate in place of ethyl iodide.
¹H NMR (CD₃OD) δ 7.95-7.76 (m, 2H), 7.44-7.11 (m, 4H), 7.01-6.83 (m, 3H), 4.30-3.93 (m, 4H), 3.66-3.41 (m, 4H), 3.14-2.92 (m, 3H), 2.42-2.21 (m, 2H), 1.32-1.01 (m, 6H)
¹³C NMR (CD₃OD) δ 152.3, 136.3, 133.4, 133.2, 132.4, 123.6, 118.8, 118.5, 38.2, 17.4, 13.8
MS m/z 601 (MH⁺)

Example 25

Preparation of N-(2-[N',N'-diethylamino]-5-[N"-(4-chlorophenylsulfonyl)-N"'-methylamino]pyrimidin-4-yl)-4'-(azetidin-1-ylcarbonyloxy)-L-phenylalanine Steps 1, 2, 3, 4, 6 and 7 were performed as for Example 24. Step 5 was performed using 4-chlorobenzenesulfonyl chloride in place of 4-fluorobenzenesulfonyl chloride.
¹H NMR (CD₃OD) δ 7.83 (d, 2H), 7.67 (d, 2H), 7.36-7.18 (m, 2H), 7.06-6.86 (m, 3H), 4.29-3.97 (m, 4H), 3.66-3.34 (m, 5H), 3.15-2.95 (m, 4H), 2.41-2.22 (m, 2H) 1.26-1.06 (m, 6H)
¹³C NMR (CD₃OD) δ157.2, 153.0, 152.5, 142.9, 142.5, 136.4, 132.5, 132.1, 132.0, 123.8, 57.9, 52.2, 40.7, 38.0, 17.4, 13.6
MS m/z 617 (MH⁺)

Example 26

Preparation of N-(2-[N',N'-diethylamino]-5-[N"-(4-chlorophenylsulfonyl)-N"'-ethylamino]pyrimidin-4-yl)-4'-(azetidin-1-ylcarbonyloxy)-L-phenylalanine Steps 1, 2, 3, 4, 6 and 7 were performed as for Example 23. Step 5 was performed using 4-chlorobenzenesulfonyl chloride in place of 4-fluorobenzenesulfonyl chloride.
¹H NMR (CD₃OD) δ 7.86-7.76 (m, 2H), 7.70-7.60 (m, 2H), 7.32 (bd, 1H), 7.21 (bd, 1H), 7.03-6.97 (m, 2H), 6.90 (bs, 1H), 4.29-4.00 (m, 4H), 3.89-3.72 (m, 1H), 3.70-3.36 (m, 5H), 3.28-3.10 (m, 2H), 2.42-2.24 (m, 2H), 1.28-1.13 (m, 6H), 1.11-1.02 (t, 1.5H), 1.01-0.90 (t, 1.5H)

MS m/z 631 (MH+)

Example 27

Preparation of N-(2-[N',N'-diethylamino]-5-[N''-(2,4-difluorophenylsulfonyl)-N''-methylamino]pyrimidin-4-yl)-4'-(pyrrolidin-1-ylcarbonyloxy)-L-phenylalanine Steps 1, 2, 3, 4, 6 and 7 were performed as for Example 19. Step 5 was performed using 2,4-difluorobenzenesulfonyl chloride in place of 4-fluorobenzenesulfonyl chloride.

$^1$H NMR (CDCl$_3$) δ 1.16 (bs, 6H), 1.93 (bs, 4H), 2.50-3.75 (m, 13H), 4.83 (bs, 1H), 6.60-7.40 (m, 7H), 7.60 (bs, 1H), 7.77 (m, 1H), 9.41 (bs, 1H)

Example 28

Preparation of N-(2-[N',N'-diethylamino]-5-[N''-(2,4-difluorophenylsulfonyl)-N''-ethylamino]pyrimidin-4-yl)-4'-(pyrrolidin-1-ylcarbonyloxy)-L-phenylalanine Steps 1, 2, 3, 4, 6 and 7 were performed as for Example 18. Step 5 was performed using 2,4-difluorobenzenesulfonyl chloride in place of 4-fluorobenzenesulfonyl chloride.

$^1$H NMR (CDCl$_3$) δ 0.91 (t, J=6.9, 1.8H), 1.12 (m, 7.2H), 1.92 (bs, 4H), 2.50-4.00 (m, 13H), 4.78 (m, 0.6H), 4.88 (m, 0.4H), 6.55 (d, J=6.9, 0.4H), 6.77 (d, J=6.3, 0.6H), 6.80-7.38 (m, 6H), 7.51 (s, 0.4H), 7.58 (s, 0.6H), 7.74 (m, 1H), 9.33 (m, 1H)

Example 29

Preparation of N-(2-[N',N'-diethylamino]-5-[N''-(2,4-difluorophenylsulfonyl)-N''-methylamino]pyrimidin-4-yl)-4'-(azetidin-1-ylcarbonyloxy)-L-phenylalanine Steps 1, 2, 4, 5, 6 and 7 were performed as for Example 27. Step 3 was performed as for Example 23.

$^1$H NMR (CDCl$_3$) δ 1.14 (t, J=6.6, 6H), 2.32 (m, 2H), 2.50-3.80 (m, 9H), 4.13 (m, 4H), 4.62 (m, 0.6H), 4.81 (m, 0.4H), 5.81 (bd, 0.6H), 5.90 (bd, 0.4H), 6.90-7.40 (m, 7H), 7.77 (m, 1H)

MS m/z 619.2 (MH+)

Example 30

Preparation of N-(2-[N',N'-diethylamino]-5-[N''-(2,4-difluorophenylsulfonyl)-N''-ethylamino]pyrimidin-4-yl)-4'-(azetidin-1-ylcarbonyloxy)-L-phenylalanine Steps 1, 2, 4, 5, 6 and 7 were performed as for Example 28. Step 3 was performed as for Example 23.

$^1$H NMR (CDCl$_3$) δ 0.89 (t, J=6.7, 1.8H), 1.16 (m, 7.2H), 2.28 (m, 2H), 3.00-4.00 (m, 8H), 4.09 (bs, 4H), 4.79 (m, 0.6H), 4.88 (m, 0.4H), 6.80-7.30 (m, 7H), 7.57 (s, 0.4H), 7.62 (s, 0.6H), 7.75 (m, 1H), 11.9 (bs, 1H)

MS m/z 633.2 (MH+)

Example 31

Preparation of N-(2-[N',N'-diethylamino]-5-[N''-(4-fluorophenylsulfonyl)-N''-propargylamino]pyrimidin-4-yl)-4'-(pyrrolidin-1-ylcarbonyloxy)-L-phenylalanine Steps 1, 2, 3, 4, 5 and 7 were performed as for Example 18. Step 6 was performed using propargyl bromide in place of ethyl iodide.

$^1$H NMR (CDCl$_3$) δ 1.18 (m, 6H), 1.93 (bs, 4H), 2.37 (s, 1H), 3.00-3.70 (m, 10H), 3.80 (d, J=21.3, 0.6H), 3.98 (d, J=18.3, 0.4H), 4.51 (m, 1H), 4.88 (m, 1H), 6.75-7.35 (m, 7H), 7.58 (s, 0.6H), 7.63 (s, 0.4H), 7.86 (m, 2H), 9.71 (bs, 1H)

Example 32

Preparation of N-(2-[N',N'-diethylamino]-5-[N''-(2,4-difluorophenylsulfonyl)-N''-propargylamino]pyrimidin-4-yl)-4'-(pyrrolidin-1-ylcarbonyloxy)-L-phenylalanine Steps 1, 2, 3, 4, 5 and 7 were performed as for Example 27. Step 6 was performed using propargyl bromide in place of dimethyl sulfate.

$^1$H NMR (CDCl$_3$) δ 1.17 (m, 6H), 1.94 (m, 4H), 2.40 (m, 1H), 3.00-3.75 (m, 10H), 3.99 (d, J=18.0, 0.6H), 4.18 (d, J=18.0, 0.4H), 4.50 (m, 1H), 4.90 (m, 1H), 6.75-7.35 (m, 7H), 7.81 (m, 2H), 10.0 (bs, 1H)

Example 33

Preparation of N-(2-[N',N'-diethylamino]-5-[N''-(2,4-difluorophenylsulfonyl)-N''-propargylamino]pyrimidin-4-yl)-4'-(azetidin-1-ylcarbonyloxy)-L-phenylalanine Steps 1, 2, 4, 5, 6 and 7 were performed as for Example 32. Step 3 was performed as for Example 23.

$^1$H NMR (CDCl$_3$) δ 1.18 (m, 6H), 2.34 (m, 3H), 3.00-3.75 (m, 6H), 3.80-4.25 (m, 5H), 4.47 (m, 1H), 4.89 (m, 1H), 6.75-7.35 (m, 7H), 7.79 (m, 2H), 10.3 (bs, 1H)

MS m/z 643.2 (MH+)

Example 34

Preparation of N-(2-[N',N'-diethylamino]-5-[N''-(4-fluorophenylsulfonyl)-N''-propargylamino]pyrimidin-4-yl)-4'-(azetidin-1-ylcarbonyloxy)-L-phenylalanine Steps 1, 2, 3, 4, 5 and 7 were performed as for Example 23. Step 6 was performed using propargyl bromide in place of ethyl iodide.

$^1$H NMR (CDCl$_3$) δ 1.25 (m, 6H), 2.28 (m, 3H), 3.00-3.75 (m, 6H), 3.80-4.25 (m, 5H), 4.47 (m, 1H), 4.89 (m, 1H), 6.75-7.35 (m, 7H), 7.57 (s, 0.6H), 7.62 (s, 0.4H), 7.79 (m, 2H), 10.6 (bs, 1H)

MS m/z 625.2 (MH+)

Example 35

Preparation of N-(2-[N',N'-diethylamino]-5-[N''-(4-chlorophenylsulfonyl)-N''-propargylamino]pyrimidin-4-yl)-4'-(pyrrolidin-1-ylcarbonyloxy)-L-phenylalanine Steps 1, 2, 3, 4, 5 and 7 were performed as for Example 17. Step 6 was performed using propargyl bromide in place of ethyl iodide.

¹H NMR (CD₃OD) δ 8.13 (s, 1H), 7.86-7.82 (m, 2H), 7.62-7.58 (m, 2H), 7.32-7.28 (m, 2H), 7.19-7.17 (m, 1H), 7.04-6.98 (m, 2H), 4.83-4.5 (m, 2H), 4.12-3.82 (m, 1H), 3.63-3.37 (m, 8H), 3.27-3.08 (m, 2H), 2.72 (bs, 1H), 2.04-1.86 (m, 4H), 1.24-1.07 (m, 6H)

¹³C NMR (CD₃OD) δ 177.2, 176.5, 162.7, 156.7, 155.7, 154.5, 153.2, 142.6, 140.3, 137.4, 137.3, 133.1, 132.9, 132.8, 132.7, 132.2, 132.1, 124.3, 111.3, 80.5, 80.3, 77.7, 58.2, 57.7, 44.9, 43.4, 28.1, 27.3, 14.8, 14.7

MS m/z 655 (MH⁺)

Example 36

Preparation of 2-{2-diethylamino-5-[(4-fluorobenzenesulfonyl)methylamino]pyrimidin-4-ylamino}-3-(4-dimethylcarbamoyloxyphenyl)propionic acid General. Flash chromatography was performed using a Biotage Flash 75L, using 800 g KP-Sil silica cartridges (32-63 μM, 60 angstrom, 500-550 m²/g). R$_f$s are reported for analytical thin layer chromatography, using EM Science Silica Gel F(254) 250 μM thick plates for normal phase, and Watman MKC18F 200 μM thick plates for reverse phase.

Step 1: Preparation of 2,4-Dichloro-5-nitropyrimidine. 5-Nitrouracil, was treated with phosphorous oxychloride and N,N-dimethylaniline, according to the procedure of Whittaker (J. Chem. Soc. 1951, 1565), to give the title compound, which is also available from City Chemical (West Haven, Conn.).

Step 2: Preparation of 2-(2-diethylamino-5-nitropyrimidin-4-ylamino)-3-(4-hydroxyphenyl)propionic acid, t-butyl ester. To a solution of 2-amino-3-(4-hydroxyphenyl)propionic acid, (30.6 g, 0.129 mol) in THF (250 mL) at +10° C. was added 2,4-Dichloro-5-nitropyrimidine (25 g, 0.129 mol), keeping the temperature below 5° C. during the addition. Once the addition was complete, N,N-diisopropylethylamine (33.7 mL, 0.194 mol) was added dropwise. After stirring for 1 h at +10° C., diethylamine (66.73 mL, 0.645 mol) was added slowly, and then the reaction mixture was warmed to room temperature overnight. The reaction mixture was diluted with diethyl ether (500 mL), and the organic layer was washed with 0.2 N citric acid (3×150 mL), water (1×150 mL), and 10% K₂CO₃ (3×150 mL). The organic phase was dried (Na₂SO₄), filtered, and concentrated in vacuo to yield a yellow residue. The residue was purified by flash chromatography (20% EtOAc/hexanes on silica gel) to yield 37.39 g (67%) the title compound as a yellow foam. R$_f$=0.21 (25% EtOAc/hexanes on silica gel).

Step 3: Preparation of 2-(2-diethylamino-5-nitropyrimidin-4-ylamino)-3-(4-dimethylcarbamoyloxyphenyl)propionic acid t-butyl ester. To a solution of 2-(2-diethylamino-5-nitropyrimidin-4-ylamino)-3-(4-hydroxy-phenyl)propionic acid t-butyl ester (31.80 g, 0.074 mol) in CH₂Cl₂ (600 mL) was added DMAP (9.00 g, 0.074 mol). After 5 minutes triethylamine (10.23 mL, 0.074 mol) was added dropwise. N,N-dimethylcarbamyl chloride (13.83 mL, 0.110 mol) was added dropwise, and the reaction was heated to reflux overnight. The reaction mixture was concentrated in vacuo and taken up in EtOAc (1 L). The organic phase was washed with 0.5 M citric acid (3×250 mL), sat. NaHCO₃ (3×250 mL), brine (1×250 mL), dried (MgSO₄), filtered, and concentrated in vacuo to yield 37.0 g (99%) the title compound as a white solid.

Step 4: Preparation of 2-(2-diethylamino-5-aminopyrimidin-4-ylamino)-3-(4-dimethylcarbamoyloxyphenyl)propionic acid t-butyl ester. A mixture of 2-(2-diethylamino-5-nitropyrimidin-4-ylamino)-3-(4-dimethylcarbamoyloxyphenyl)propionic acid t-butyl ester (37.0 g, 0.073 mol) and 10% Pd/C (3.8 g, 10 wt % Pd) in EtOH (250 mL) was shaken under 60 psi hydrogen until TLC (50% EtOAc/hexanes on silica gel) showed 100% conversion to product (48 hours). The reaction mixture was then filtered through a Celite plug and concentrated in vacuo to yield 32.0 g (92%) the title compound as a violet foam.

Step 5: Preparation of 2-{2-diethylamino-5-[(4-fluorobenzenesulfonyl)amino]-pyrimidin-4-ylamino}-3-(4-dimethylcarbamoyloxyphenyl) propionic acid t-butyl ester. A pyridine (120 mL) solution of 2-(2-diethylamino-5-aminopyrimidin-4-ylamino)-3-(4-dimethylcarbamoyloxy-phenyl)propionic acid t-butyl ester (32.0 g, 0.067 mol) was cooled to −20° C. with a dry ice/CH₃CN bath. The mixture stirred for 30 minutes, and then p-fluorobenzenesulfonyl chloride (13.18 g, 0.067 mol) was added slowly. The reaction was stirred at −20° C. for 4.5 hrs, and then 3-dimethylaminopropyl amine (8.52 mL, 0.067 mol) was added, and then the mixture was allowed to warm to room temperature overnight. The reaction was concentrated in vacuo. The residue was taken up in EtOAc (1 L), and the organic phase was washed with 0.5 M citric acid (3×900 mL), water (1×900 mL), sat. NaHCO₃ (3×900 mL), brine (1×900 mL), dried (MgSO₄), filtered, and concentrated in vacuo to yield a brown residue. The residue was purified by flash chromatography (50% EtOAc/hexanes on silica gel) to yield 33.04 g (77%) the title compound as a yellow foam. R$_f$=0.54 (3:2 EtOAc/hexanes on silica gel).

Step 6: Preparation of 2-{2-diethylamino-5-[(4-fluorobenzenesulfonyl)methylamino]-pyrimidin-4-ylamino}-3-(4-dimethylcarbamoyloxyphenyl) propionic acid t-butyl ester. To a solution of 2-{2-diethylamino-5-[(4-fluorobenzenesulfonyl)amino]-pyrimidin-4-ylamino}-3-(4-dimethyl-carbamoyloxyphenyl)propionic acid t-butyl ester (33.04 g, 0.052 mol) in acetone (510 mL) was added K₂CO₃ (8.69 g, 0.063 mol), and the mixture was stirred for 10 min at room temperature. Dimethyl sulfate (5.95 mL, 0.063 mol) was then added slowly, and the reaction mixture was stirred overnight at room temperature. The reaction mixture was concentrated in vacuo, and the residue was taken up in EtOAc (600 mL). The organic phase was washed with water (2×400 mL), brine (2×400 mL), dried MgSO₄, filtered, and concentrated in vacuo. The residue was purified by flash:chromatography (2:1 hexanes/EtOAc on silica gel) to yield 28.69 g (85%) the title compound as a white solid.

Step 7: Preparation of 2-{2-diethylamino-5-[(4-fluorobenzenesulfonyl)methylamino]-pyrimidin-4-ylamino}-3-(4-dimethylcarbamoyloxyphenyl) propionic acid hydrochloride. A formic acid (500 mL) solution of 2-{2-diethylamino-5-[(4-fluorobenzenesulfonyl)methylamino]-pyrimidin-4-ylamino}-3-(4-dimethylcarbamoyloxyphenyl) propionic acid t-butyl ester (28.69 g, 0.044 mol) was heated to 70° C. for 2 h, and then concentrated in vacuo. The residue was dissolved again in formic acid (500 mL), and then heated again at 70° C. for 2 h, and then concentrated again in vacuo. The residue was dissolved again in formic acid (500 mL), and then heated again at 70° C. for 1 h. The solution was reduced in volume by 90%, and then treated with 1.0 M HCl (44 mL, 0.044 mol) and distilled water (490 mL). The resulting homogeneous solution was concentrated in vacuo, and then distilled water (100 mL) was added, and the homogenous solution was lyophilized over 14 days to yield 26.76 g (96%) the title compound, as a white solid.

¹H NMR (CD₃OD) d 7.96-7.92 (m, 2H), 7.45-7.25 (m, 4H), 7.06-6.95 (m, 3H), 5.00-4.93 (m, 1H), 3.55-3.40 (m, 5H), 3.34-3.20 (m, 2H), 3.15-3.05 (m, 5H), 3.07-3.00 (m, 3H), 1.22 (bs, 6H)

¹³C NMR (CD₃OD) d 171.6, 168.3, 154.5, 144.4, 137.9, 135.1, 135.0, 134.1, 125.5, 120.6, 120.3, 39.6, 39.2, 39.1, 15.2

MS m/z 589 (MH+)

Example 37

Preparation of 2-{2-diethylamino-5-[(4-chlorobenzenesulfonyl)methylamino]pyrimidin-4-ylamino}-3-(4-dimethylcarbamoyloxyphenyl)propionic acid Steps 1, 2, 3, 4, 6 and 7 were performed as for Example 36. Step 5 was performed using 4-chlorobenzenesulfonyl chloride in place of 4-fluorobenzenesulfonyl chloride.

¹H NMR (CD₃OD) d 7.88-7.85 (m, 2H), 7.72-7.69 (m, 2H), 7.39-7.25 (m, 2H), 7.14-6.92 (m, 3H), 5.00-4.85 (m, 1H), 3.60-3.50 (m, 1H), 3.37-3.28 (m, 6H), 3.15-3.07 (m, 6H), 3.01 (bs, 3H), 1.22 (bs, 6H)

¹³C NMR (CD₃OD) d 208.6, 145.3, 134.9, 128.8, 124.9, 124.5, 124.4, 116.3, 50.2, 30.4, 30.0, 6.0

MS m/z 605 (MH+)

Example 38

Preparation of 2-{2-diethylamino-5-[(3,4-difluorobenzenesulfonyl)methylamino] pyrimidin-4-ylamino}-3-(4-dimethylcarbamoyloxyphenyl) propionic acid Steps 1, 2, 3, 4, 6 and 7 were performed as for Example 36. Step 5 was performed using 3,4-difluorobenzenesulfonyl chloride in place of 4-fluorobenzenesulfonyl chloride.

¹H NMR (CD₃OD) d 7.84-7.77 (m, 1H), 7.67 (bs, 1H), 7.58-7.53 (m, 1H), 7.37-7.34 (m, 1H), 7.22-7.18 (m, 1H), 7.08-7.02 (m, 3H), 4.83-4.76 (m, 1H), 3.55-3.54 (m, 4H), 3.35-3.33 (m, 1H), 3.23-3.12 (m, 6H), 3.03-2.99 (m, 3H), 1.19 (bs, 6H)

¹³C NMR (CD₃OD) d 178.3, 177.8, 163.2, 162.6, 159.3, 159.1, 155.9, 155.7, 154.3, 153.0, 152.5, 152.4, 138.4, 138.1, 134.0, 129.5, 125.3, 122.4, 122.2, 121.7, 121.4, 115.3, 59.3, 46.0, 42.4, 41.9, 40.4, 39.9, 39.2, 39.1, 15.76

MS m/z 607.2 (MH+)

Example 39

Preparation of 2-{2-diethylamino-5-[(3,4-dichlorobenzenesulfonyl)methylamino]pyrimidin-4-ylamino}-3-(4-dimethylcarbamoyloxyphenyl) propionic acid Steps 1, 2, 3, 4, 6 and 7 were performed as for Example 36. Step 5 was performed using 3,4-dichlorobenzenesulfonyl chloride in place of 4-fluorobenzenesulfonyl chloride.

¹H NMR (CD₃OD) d 8.00-7.98 (m, 1H), 7.83-7.74 (m, 2H), 7.37-7.34 (m, 1H), 7.21-7.20 (m, 1H), 7.10-7.02 (m, 3H), 4.85-4.83 (m, 1H), 3.55-3.53 (m, 2H), 3.35-3.33 (m, 1H), 3.21-3.12 (m, 6H), 3.04-2.99 (m, 6H), 1.19 (bs, 6H)

¹³C NMR (CD₃OD) d 176.4, 166.2, 161.7, 161.2, 158.0, 157.8, 152.8, 151.8, 150.5, 140.2, 139.8, 139.5, 136.8, 135.8, 133.9, 132.6, 132.0, 129.8, 123.8, 113.7, 113.4, 57.8, 44.6, 40.8, 40.4, 38.7, 38.3, 37.7, 37.5, 14.1

MS m/z 639.1 (MH+)

Example 40

Preparation of 2-{2-diethylamino-5-[(benzenesulfonyl)methylamino]pyrimidin-4-ylamino}-3-(4-dimethylcarbamoyloxyphenyl)propionic acid Steps 1, 2, 3, 4, 6 and 7 were performed as for Example 36. Step 5 was performed using benzenesulfonyl chloride in place of 4-fluorobenzenesulfonyl chloride.

¹H NMR (CD₃OD) d 8.14 (bs, 1H), (7.85-7.84 (m, 1H), 7.8-7.78 (m, 1H), 7.69-7.66 (m, 2H), 7.40-7.37 (m, 1H), 7.21-7.195 (m, 1H), 7.04-7.03 (m, 2H), 7.95-7.90 (m, 1H), 5.52 (bs, 1H), 3.54-3.53 (m, 2H), 3.36-3.33 (m, 6H), 3.13-3.12 (m, 3H), 3.01-3.00 (m, 3H), 1.20-1.17 (m, 6H)

¹³C NMR (CD₃OD) d 165.9, 152.8, 136.7, 135.8, 132.6, 131.6, 130.2, 123.8, 44.7, 37.5, 14.0

MS m/z 571.2 (MH+)

Example 41

Preparation of 2-{2-diethylamino-5-[(2-fluorobenzenesulfonyl)methylamino] pyrimidin-4-ylamino}-3-(4-dimethylcarbamoyloxyphenyl)propionic acid Steps 1, 2, 3, 4, 6 and 7 were performed as for Example 36. Step 5 was performed using 2-fluorobenzenesulfonyl chloride in place of 4-fluorobenzenesulfonyl chloride.

¹H NMR (CD₃OD) d 8.31 (bs, 1H), 7.94-7.85 (m, 2H), 7.57-7.44 (m, 3H), 7.34-7.30 (m, 1H), 7.15-7.12 (m, 2H), 5.00-4.85 (1H), 3.63-3.62 (m, 4H), 3.50-3.42 (m, 1H), 3.34-3.30 (m, 4H), 3.29-3.22 (m, 4H), 3.11-3.10 (m, 2H), 1.28 (bs, 6H)

¹³C NMR (CD₃OD) d 176.5, 166.4, 163.1, 160.4, 159.7, 157.7, 152.8, 151.5, 150.7, 138.5, 138.3, 136.7, 133.7, 132.5, 132.2, 127.1, 123.7, 119.9, 119.6, 113.4, 57.8, 44.6, 40.6, 39.0, 38.4, 37.7, 37.5, 14.1

Example 42

Preparation of 2-{2-diethylamino-5-[(3-fluorobenzenesulfonyl)methylamino]pyrimidin-4-ylamino}-3-(4-dimethylcarbamoyloxyphenyl) propionic acid Steps 1, 2, 3, 4, 6 and 7 were performed as for Example 36. Step 5 was performed using 3-fluorobenzenesulfonyl chloride in place of 4-fluorobenzenesulfonyl chloride.

¹H NMR (CD₃OD) d 8.15-8.12 (bs, 1H), 7.72-7.68 (m, 1H), 7.63-7.60 (m, 1H), 7.53-7.52 (m, 1H), 7.38-7.35 (m, 1H), 7.21-7.20 (m, 1H), 7.10-6.99 (m, 3H), 4.87-4.86 (m, 1H), 3.54-3.53 (m, 4H), 3.35-3.34 (m, 3H), 3.15-3.12 (m, 4H), 3.05-3.00 (m, 4H), 1.20 (bs, 6H)

¹³C NMR (CD₃OD) d 166.1, 153.1, 136.9, 134.1, 132.8, 126.5, 124.1, 123.2, 122.9, 117.7, 117.4, 103.4, 45.0, 38.0, 14.3

MS m/z 589.2 (MH+)

Example 43

Preparation of 2-{2-diethylamino-5-[(4-fluorobenzenesulfonyl) isopropylamino]pyrimidin-4-ylamino}-3-(4-dimethylcarbamoyloxyphenyl) propionic acid Steps 1, 2 and 3 were performed as for Example 36. Thereafter, Steps 4 and 6 were accomplished in one pot, according to the following procedure. Thereafter, Steps 5 and 7 were performed as for Example 36.

¹H NMR (CD₃OD) d 8.20-8.16 (m, 1H), 7.95-7.84 (m, 2H), 7.36-7.25 (m, 3H), 7.24-7.15 (m, 3H), 7.07-6.98 (m, 3H), 5.07-5.05 (m, 1H), 4.90-4.86 (m, 1H), 4.65-4.62 (m, 1H), 4.49-4.41 (m, 1H), 3.63-3.56 (m, 3H), 3.38-3.31 (m, 2H), 3.27-3.11 (m, 2H), 3.00-2.99 (m, 3H), 1.27-1.21 (m, 6H), 1.05-0.99 (m, 6H)

¹³C NMR (CD₃OD) d 175.8, 175.5, 169.6, 166.3, 165.9, 163.5, 163.4, 157.7, 153.0, 152.9, 152.3, 138.1, 136.4, 136.1, 133.1, 133.0, 133.0, 132.9, 132.7, 132.3, 123.8, 118.8, 118.7, 118.5, 118.4, 107.5, 57.6, 57.2, 54.7, 44.7, 38.7, 38.1, 37.6, 37.5, 23.0, 22.9, 22.2, 22.0, 14.1, 14.0

Alternative one-pot procedure for the preparation of 2-(2-diethylamino-5-isopropylaminopyrimidin-4-yl)-3-(4-dimethylcarbamoyloxyphenyl) propionic acid t-butyl ester. A mixture of 2-(2-diethylamino-5-nitropyrimidin-4-ylamino)-3-(4-dimethylcarbamoyloxyphenyl)propionic acid t-butyl ester (5.0 g, 0.010 mol), glacial acetic acid (10 drops), acetone (2.19 mL, 0.030 mol), and platinum oxide (0.250 g, 5 wt %) in EtOH (15 mL) was hydrogenated at 45 psi hydrogen until TLC (50% EtOAc/hexanes) showed 100% conversion to product (20 hours). The reaction mixture was then filtered through a Celite plug and concentrated in vacuo to yield a brown residue. The residue was purified by flash chromatography (4:1 EtOAc/hexanes) to yield 3.54 g (70%) 9 as a purple foam.

Example 44

Preparation of 2-{2-diethylamino-5-[(4-fluorobenzenesulfonyl)ethylamino]pyrimidin-4-ylamino}-3-(4-dimethylcarbamoyloxyphenyl)propionic acid Steps 1, 2, 3, 4, 5 and 7 were performed as for Example 36. Step 6 was performed using ethyl iodide in place of dimethyl sulfate.

¹H NMR (CDCl₃) δ 0.89 (t, J=7.2, 1.8H), 1.06 (t, J=7.1, 1.2H), 1.10-1.30 (m, 6H), 2.97 (s, 3H), 3.05 (s, 3H), 3.10-3.90 (m, 8H), 4.82 (q, J=5.4, 0.6H), 4.91 (q, J=6.1, 0.4H), 6.80-7.45 (m, 8H), 7.77 (m, 2H), 12.44 (bs, 1H)

MS m/z 603.3 (MH⁺)

Example 45

Preparation of 2-{2-diethylamino-5-[(3,4-difluorobenzenesulfonyl) isopropylamino]pyrimidin-4-ylamino}-3-(4-dimethylcarbamoyloxyphenyl) propionic acid Steps 1, 2, 3, 4, 6 and 7 were performed as for Example 43. Step 5 was performed using 3,4-difluorobenzenesulfonyl chloride in place of 4-fluorobenzenesulfonyl chloride.

¹H NMR (CD₃OD) d 8.20-8.19 (m, 1H), 7.84-7.78 (m, 1H), 7.70-7.64 (m, 1H), 7.54-7.48 (m, 1H), 7.39-7.31 (m, 1H), 7.20-7.17 (m, 1H), 7.05-6.96 (m, 2H), 4.91-4.89 (m, 1H), 4.70-4.68 (m, 1H), 4.48-4.41 (m, 2H), 3.60-3.58 (m, 3H), 3.34-3.33 (m, 1H), 3.27-3.20 (m, 1H), 3.09-3.08 (m, 2H), 2.98-2.97 (m, 2H), 1.28-1.19 (m, 6H), 1.06-0.98 (m, 6H), 0.83-0.81 (m, 1H)

¹³C NMR (CD₃OD) d 177.6, 177.2, 167.9, 164.9, 164.8, 159.2, 159.1, 155.7, 154.5, 154.4, 152.4, 152.3, 140.4, 140.3, 137.8, 134.3, 133.9, 129.3, 129.2, 125.4, 122.6, 122.5, 122.4, 122.2, 121.5, 121.2, 109.1, 59.5, 59.1, 56.7, 56.6, 46.4, 46.3, 39.6, 39.3, 39.2, 24.7, 24.5, 23.9, 23.6, 15.7, 15.6

Example 46

Preparation of 2-{2-diethylamino-5-[(4-chlorobenzenesulfonyl) isopropylamino]pyrimidin-4-ylamino}-3-(4-dimethylcarbamoyloxyphenyl) propionic acid Steps 1, 2, 3, 4, 6 and 7 were performed as for Example 43. Step 5 was performed using 4-chlorobenzenesulfonyl chloride in place of 4-fluorobenzenesulfonyl chloride.

¹H NMR (CD₃OD) d 8.18-8.17 (m, 1H), 7.85-7.78 (m, 1H), 7.62-7.58 (m, 1H), 7.38-7.35 (m, 1H), 7.34-7.24 (m, 1H), 7.17-7.16 (m, 1H), 7.10-7.05 (m, 2H), 7.04-6.98 (m, 2H), 4.98-4.87 (m, 1H), 4.73-4.68 (m, 1H), 4.55-4.38 (m, 2H), 3.70-3.52 (m, 3H), 3.40-3.30 (m, 1H), 3.28-3.18 (m, 1H), 3.17-3.08 (m, 2H), 3.05-2.98 (m, 2H), 1.25-1.20 (m, 6H), 1.04-0.96 (m, 6H), 0.80-0.77 (m, 1H)

¹³C NMR (CD₃OD) d 175.7, 175.5, 166.2, 165.8, 169.6, 163.5, 163.4, 157.6, 152.9, 152.8, 138.0, 136.3, 136.1, 133.1, 133.0, 132.9, 132.7, 132.2, 123.8, 118.8, 118.6, 118.5, 118.5, 118.3, 107.5, 57.6, 57.2, 54.7, 44.6, 38.6, 38.1, 37.6, 37.5, 22.9, 22.8, 22.2, 21.9, 14.1, 13.9

Example 47

Preparation of 2-{2-diethylamino-5-[(3,4-difluorobenzenesulfonyl)ethylamino]pyrimidin-4-ylamino}-3-(4-dimethylcarbamoyloxyphenyl)propionic acid Steps 1, 2, 3, 4, 6 and 7 were performed as for Example 44. Step 5 was performed using 3,4-difluorobenzenesulfonyl chloride in place of 4-fluorobenzenesulfonyl chloride.

¹H NMR (CD₃OD) d 8.15-8.14 (m, 1H), 7.80-7.75 (m, 1H), 7.73-7.62 (m, 1H), 7.60-7.49 (m, 1H), 7.30-7.18 (m, 1H), 7.16-7.00 (m, 2H), 5.58-5.50 (m, 1H), 4.90-4.83 (m, 1H), 5.78-5.70 (m, 1H), 3.85-3.75 (m, 1H), 3.65-3.54 (m, 3H), 3.40-3.23 (m, 5H), 3.18-3.10 (m, 3H), 3.05-2.98 (m, 3H), 1.25-1.15 (m, 3H), 1.18-1.05 (t, 1.5H), 1.02-1.00 (t, 1.5H)

¹³C NMR (CD₃OD) d 165.8, 152.7, 145.7, 136.4, 136.3, 132.5, 132.2, 127.5, 123.6, 120.7, 120.4, 81.4, 57.0, 44.3, 38.5, 38.1, 37.4, 14.9, 14.6, 14.1, 14.0

MS m/z 621.5 (MH+)

Example 48

Preparation of 2-{2-diethylamino-5-[(4-chlorobenzenesulfonyl)ethylamino]pyrimidin-4-ylamino}-3-(4-dimethylcarbamoyloxyphenyl)propionic acid Steps 1, 2, 3, 4, 6 and 7 were performed as for Example 44. Step 5 was performed using 4-chlorobenzenesulfonyl chloride in place of 4-fluorobenzenesulfonyl chloride.

¹H NMR (CD₃OD) d 8.15-8.14 (m, 1H), 7.84-7.79 (m, 1H), 7.67-7.61 (m, 1H), 7.37-7.33 (m, 1H), 7.22-7.18 (m, 1H), 7.14-7.13 (m, 1H), 7.06-7.00 (m, 3H), 4.80-4.75 (m, 1H), 4.18-4.10 (m, 1H), 3.65-3.30 (m, 3H), 3.28-3.20 (m, 3H), 3.18-3.08 (m, 2H), 3.03-2.98 (m, 2H), 2.05-2.04 (m, 1H), 1.30-1.16 (m, 9H), 1.10-1.08 (t, 1.5H), 0.99-0.95 (t, 1.5H)

¹³C NMR (CD₃OD) d 176.2, 176.1, 166.7, 162.7, 162.3, 157.6, 152.9, 142.0, 138.8, 136.5, 132.8, 132.5, 132.0, 131.8, 123.8, 111.7, 111.4, 57.9, 57.8, 44.9, 38.9, 38.3, 37.8, 37.7, 15.1, 14.9, 14.3, 14.2

MS m/z 619.4 (MH+)

Example 49

Preparation of 2-{2-diethylamino-5-[(4-fluorobenzenesulfonyl) cyclopropylmethylamino]pyrimidin-4-ylamino}-3-(4-dimethylcarbamoyloxyphenyl)propionic acid Steps 1, 2, 3, 4, 5 and 7 were performed as for Example 36. Step 6 was performed using bromomethylcyclopropane and cesium carbonate in place of dimethyl sulfate and potassium carbonate.

$^1$H NMR (CDCl$_3$) d −0.2-0.2 (m, 2.4H), 0.2-0.45 (m, 1.6H), 0.54 (m, 0.6H), 0.85 (m, 0.4H), 1.00-1.40 (m, 6H), 2.80-3.80 (m, 14H), 4.79 (q, J=5.5, 0.6H), 4.91 (q, J=6.3, 0.4H), 6.70-7.40 (m, 8H), 7.77 (m, 2H), 10.26 (bs, 1H)

MS m/z 629.2 (MH$^+$)

Example 50

Preparation of 2-{2-diethylamino-5-[(3,5-difluorobenzenesulfonyl)methylamino]pyrimidin-4-ylamino}-3-(4-dimethylcarbamoyloxyphenyl) propionic acid Steps 1, 2, 3, 4, 6 and 7 were performed as for Example 36. Step 5 was performed using 3,5-difluorobenzenesulfonyl chloride in place of 4-fluorobenzenesulfonyl chloride.

$^1$H NMR (CD$_3$OD) d 7.68-7.67 (m, 1H), 7.67-7.56 (m, 2H), 7.42-7.40 (m, 2H), 7.31-7.30 (m, 1H), 7.26-7.23 (m, 2H), 5.20-4.90 (m, 1H), 4.35-4.33 (m, 1H), 3.78-3.74 (m, 4H), 3.57-3.54 (2H), 3.38-3.33 (m, 2H), 3.26-3.21 (m, 2H), 2.41-2.39 (m, 2H), 2.26-2.25 (m, 2H), 1.50-1.38 (m, 6H)

$^{13}$C NMR (CD$_3$OD) d 162.5, 162.3, 159.2, 159.0, 148.0, 146.1, 132.2, 127.8, 127.7, 127.6, 118.9, 109.1, 109.0, 108.7, 108.6, 106.2, 105.8, 52.5, 39.6, 34.1, 32.9, 9.5

Example 51

Preparation of 2-{2-diethylamino-5-[(3,5-difluorobenzenesulfonyl)ethylamino] pyrimidin-4-ylamino}-3-(4-dimethylcarbamoyloxyphenyl)propionic acid Steps 1, 2, 3, 4, 5 and 7 were performed as for example 50. Step 6 was performed using ethyl iodide in place of dimethyl sulfate.

$^1$H NMR (CD$_3$OD) d 7.45-7.43 (m, 1H), 7.42-7.18 (m, 2H), 7.21-7.16 (m, 2H), 7.07-7.06 (m, 1H), 7.04-6.97 (m, 2H), 5.51 (bs, 1H), 4.86-4.82 (m, 1H), 4.72-4.66 (m, 1H), 3.84-3.77 (m, 1H), 3.59-3.50 (m, 3H), 3.34-3.31 (m, 2H), 3.12-3.10 (m, 3H), 2.99-2.96 (m, 3H), 1.22-1.14 (m, 9H), 1.10-1.05 (t, 1.5H), 0.97-0.95 (t, 1.5H)

$^{13}$C NMR (CD$_3$OD) d 159.9, 150.9, 150.1, 134.0, 130.0, 129.7, 121.2, 107.9, 86.7, 42.0, 41.9, 36.3, 35.2, 35.1, 12.8, 12.5, 11.9, 11.8,

Example 52

Preparation of 2-{2-diethylamino-5-[(2,4-difluorobenzenesulfonyl)methylamino] pyrimidin-4-ylamino}-3-(4-dimethylcarbamoyloxyphenyl)propionic acid Steps 1, 2, 3, 4, 6 and 7 were performed as for Example 36. Step 5 was performed using 2,4-difluorobenzenesulfonyl chloride in place of 4-fluorobenzenesulfonyl chloride.

$^1$H NMR (CD$_3$OD) d 8.16-8.11 (m, 1H), 7.59-7.56 (m, 2H), 7.48-7.45 (m, 2H), 7.26-7.24 (m, 3H), 5.21-5.16 (m, 1H), 3.79-3.77 (m, 4H), 3.57-3.54 (m, 3H), 3.48-3.46 (m, 2H), 3.44-3.34 (m, 3H), 3.22-3.21 (m, 3H), 1.45-1.44 (m, 6H)

$^{13}$C NMR (CDCl) d 180.2, 170.3, 166.6, 150.3, 129.0, 128.9, 128.7, 125.9, 125.4, 117.5, 117.4, 116.5, 114.8, 107.7, 107.4, 95.5, 90.8, 68.0, 65.1, 55.7, 50.8, 37.6, 36.4, 31.9, 31.7, 31.6, 13.2, 9.4, 8.3, 7.8

Example 53

Preparation of 2-{2-diethylamino-5-[(2,4-difluorobenzenesulfonyl)ethylamino]pyrimidin-4-ylamino}-3-(4-dimethylcarbamoyloxyphenyl) propionic acid Steps 1, 2, 3, 4, 5 and 7 were performed as for Example 52. Step 6 was performed using ethyl iodide in place of dimethyl sulfate.

$^1$H NMR (CD$_3$OD) d 8.15 (bs, 1H), 7.91-7.76 (m, 1H), 7.32-7.30 (m, 2H), 7.20-7.19 (m, 2H), 7.04-7.00 (m, 2H), 4.84-4.83 (m, 1H), 4.74-4.67 (m, 1H), 4.14-4.07 (m, 1H), 3.92-3.82 (m, 1H), 3.51-3.49 (m, 3H), 3.34-3.31 (m, 3H), 3.12-2.99 (m, 2H), 2.98-2.97 (m, 2H), 2.03-2.02 (m, 1H), 1.26-1.17 (m, 6H), 1.10-1.06 (t, 1.5H), 1.03-0.98 (t, 1.5H)

$^{13}$C NMR (CD$_3$OD) d 173.6, 173.3, 171.4, 167.7, 164.3, 161.2, 159.9, 159.3, 157.1, 156.7, 155.2, 152.4, 151.0, 150.3, 134.0, 133.3, 133.1, 132.9, 130.0, 123.2, 122.9, 122.8, 121.3, 121.2, 112.0, 111.8, 111.6, 111.5, 107.7, 107.2, 106.0, 105.9, 105.6, 105.2, 60.0, 54.8, 42.0, 36.5, 35.9, 35.3, 35.1, 19.3, 13.0, 12.9, 12.7, 11.9, 11.8

Example 54

Preparation of 2-{2-diethylamino-5-[(3,5-dichlorobenzenesulfonyl)methylamino]pyrimidin-4-ylamino}-3-(4-dimethylcarbamoyloxyphenyl) propionic acid Steps 1, 2, 3, 4, 6 and 7 were performed as for Example 36. Step 5 was performed using 3,5-dichlorobenzenesulfonyl chloride in place of 4-fluorobenzenesulfonyl chloride.

$^1$H NMR (CD$_3$OD) d 7.84-7.82 (m, 1H), 7.76-7.75 (m, 3H), 7.34-7.32 (m, 1H), 7.19-7.10 (m, 1H), 7.03-7.00 (m, 2H), 5.50 (bs, 1H), 4.83-4.82 (m, 1H), 4.74-7.73 (m, 1H), 3.55-3.38 (m, 4H), 3.34-3.32 (m, 2H), 3.15-3.11 (m, 4H), 3.02-2.99 (m, 3H), 1.18-1.15 (m, 6H)

$^{13}$C NMR (CD$_3$OD) d 157.1, 155.2, 150.1, 149.7, 140.1, 135.9, 134.3, 132.9, 130.0, 129.9, 126.0, 121.2, 110.7, 55.2, 54.8, 42.0, 38.5, 38.1, 36.5, 35.9, 35.2, 35.1, 11.9

MS m/z 639.1 (MH+)

Example 55

Preparation of 2-{2-diethylamino-5-[(3,5-dichlorobenzenesulfonyl)ethylamino]pyrimidin-4-ylamino}-3-(4-dimethylcarbamoyloxyphenyl)propionic acid Steps 1, 2, 3, 4, 5 and 7 were performed as for Example 54. Step 6 was performed using ethyl iodide in place of dimethyl sulfate.

$^1$H NMR (CD$_3$OD) d 8.15 (bs, 1H), 7.84-7.84-7.79 (m, 1H), 7.76-7.74 (m, 2H), 7.33-7.30 (m, 1H), 7.22-7.11 (m, 2H), 7.04-6.98 (m, 1H), 5.51 (bs, 1H), 4.86-4.82 (m, 1H), 4.72-4.67 (m, 1H), 3.77-3.75 (m, 1H), 3.60-3.50 (m, 3H), 3.34-3.29 (m, 2H), 3.27-3.22 (m, 2H), 3.12-3.11 (m, 2H), 2.99-2.98 (m, 2H), 1.23-1.14 (m, 6H), 1.10-1.05 (t, 1.5H), 0.99-0.94 (t, 1.5H)

$^{13}$C NMR (CD$_3$OD) d 173.6, 173.4, 163.7, 159.9, 159.3, 157.3, 156.8, 155.2, 155.1, 152.1, 150.8, 150.2, 141.4, 141.2, 135.9, 134.0, 132.7, 130.0, 129.7, 125.8, 125.7, 121.3, 121.2, 107.9, 107.4, 54.8, 54.7, 42.0, 36.4, 35.8, 35.3, 35.1, 12.8, 12.5, 11.9, 11.8

MS m/z 653.2 (MH+)

Example 56

Preparation of 2-{2-diethylamino-5-[(4-fluorobenzenesulfonyl)-n-propylamino]pyrimidin-4-ylamino}-3-(4-dimethylcarbamoyloxyphenyl) propionic acid Steps 1, 2, 3, 4, 5 and 7 were performed as for Example 36. Step 6 was performed using 1-propyl iodide in place of dimethyl sulfate.

$^1$H NMR (CDCl$_3$) δ 0.75 (m, 3H), 1.00-1.50 (m, 8H), 3.00 (s, 3H), 3.08 (s, 3H), 3.20-3.70 (m, 8H), 4.79 (q, J=6.3, 0.6H), 4.91 (q, J=6.6, 0.4H), 5.73 (bs, 0.6H), 5.92 (bs, 0.4H), 6.90-7.45 (m, 7H), 7.76 (m, 2H)

MS m/z 617.2 (MH$^+$)

Example 57

Preparation of 2-{2-diethylamino-5-[(4-fluorobenzenesulfonyl)allylamino]pyrimidin-4-ylamino}-3-(4-dimethylcarbamoyloxyphenyl)propionic acid Steps 1, 2, 3, 4, 5 and 7 were performed as for Example 36. Step 6 was performed using allyl bromide in place of dimethyl sulfate.

$^1$H NMR (CDCl$_3$) δ 1.20 (m, 6H), 2.98 (s, 3H), 3.06 (s, 3H), 3.10-4.30 (m, 8H), 4.75-4.95 (m, 1H), 5.07 (m, 2H), 5.48 (m, 0.6H), 5.67 (m, 0.4H), 6.90-7.45 (m, 8H), 7.76 (m, 2H), 11.07 (bs, 1H)

MS m/z 615.2 (MH$^+$)

Example 58

Preparation of 2-{2-diethylamino-5-[(4-fluorobenzenesulfonyl)isobotylamino]pyrimidin-4-ylamino}-3-(4-dimethylcarbamoyloxyphenyl)propionic acid Steps 1, 2, 3, 4, 5 and 7 were performed as for Example 36. Step 6 was performed using isobutyl iodide in place of dimethyl sulfate.

MS m/z 631.2 (MH$^+$)

Example 59

Preparation of 2-{2-diethylamino-5-[(4-fluorobenzenesulfonyl)-n-butylamino]pyrimidin-4-ylamino}-3-(4-dimethylcarbamoyloxyphenyl)propionic acid Steps 1, 2, 3, 4, 5 and 7 were performed as for Example 36. Step 6 was performed using 1-butyl iodide in place of dimethyl sulfate.

$^1$H NMR (CDCl$_3$) δ 0.82 (q, J=7.1, 3H), 1.05-1.40 (m, 10H), 3.01 (s, 3H), 3.10 (s, 3H), 3.15-3.80 (m, 8H), 4.75 (q, J=6.3, 0.6H), 4.91 (q, J=5.9, 0.4H), 5.79 (d, J=5.4, 0.6H), 5.91 (d, J=6.6, 0.4H), 7.00-7.40 (m, 7H), 7.77 (m, 2H)

Example 60

Preparation of 2-{2-diethylamino-5-[(2,5-difluorobenzenesulfonyl)methylamino]pyrimidin-4-ylamino}-3-(4-dimethylcarbamoyloxyphenyl) propionic acid Steps 1, 2, 3, 4, 6 and 7 were performed as for Example 36. Step 5 was performed using 2,6-difluorobenzenesulfonyl chloride in place of 4-fluorobenzenesulfonyl chloride.

$^1$H NMR (CD$_3$OD) d 8.38-8.37 (m, 1H), 7.99-7.95 (m, 1H), 7.55-7.54 (m, 2H), 7.50-7.42 (m, 2H), 7.27-7.22 (m, 2H), 5.08-5.06 (m, 1H), 3.76-3.74 (m, 4H), 3.59-3.54 (m, 3H), 3.49-3.42 (m, 4H), 3.36-3.34 (m, 2H), 3.23-3.21 (m, 2H), 1.40 (bs, 6H)

$^{13}$C NMR (CD$_3$OD) d 161.4, 159.2, 155.8, 153.1, 148.1, 147.1, 133.6, 132.0, 127.8, 119.0, 111.1, 110.8, 110.7, 108.5, 105.8, 94.8, 86.4, 66.7, 54.0, 52.8, 39.7, 35.8, 34.2, 33.7, 32.9, 32.8, 9.4

Example 61

Preparation of 2-{2-diethylamino-5-[(2,3-difluorobenzenesulfonyl)ethylamino]pyrimidin-4-ylamino}-3-(4-dimethylcarbamoyloxyphenyl) propionic acid Steps 1, 2, 3, 4, 6 and 7 were performed as for Example 36. Step 5 was performed using 2,3-difluorobenzenesulfonyl chloride in place of 4-fluorobenzenesulfonyl chloride. 2,3-Difluorobenzenesulfonyl chloride was prepared by the following procedure.

$^1$H NMR (CD$_3$OD) d 8.32 (bs, 1H), 7.90-7.80 (m, 2H), 7.59-7.48 (m, 3H), 7.27-7.23 (m, 2H), 5.09-5.08 (m, 1H), 3.77-3.70 (m, 4H), 3.60-3.51 (m, 3H), 3.50-3.42 (m, 2H), 3.39-3.31n (m, 3H), 3.32-3.18 (m, 2H), 1.43-1.41 (m, 6H)

$^{13}$C NMR (CD$_3$OD) d 170.4, 160.8, 158.1, 156.1, 153.0, 151.6, 150.5, 148.9, 148.2, 147.3, 147.2, 143.9, 143.5, 142.6, 141.1, 140.9, 131.8, 127.7, 125.1, 123.8, 120.8, 120.6, 119.2, 40.5, 35.7, 33.4, 32.9, 32.7, 9.0

Preparation of 2,3-Difluorobenzenesulfonyl Chloride. The following procedure was executed using two flasks. In the first flask, 2,3-difluoroaniline (2.0 g, 0.015 mol) was dissolved in concentrated HCl (15.9 mL), and the resulting solution was cooled to −5° C., using an ice/NaCl bath. A solution of sodium nitrite (1.18 g, 0.017 mol) in distilled water (13.6 mL) was added in portions with stirring, while maintaining the temperature below 0° C., and the mixture was stirred for 10 min. In the second flask, thionyl chloride (5.08 mL, 0.069 mol) was added dropwise to distilled water (30.6 mL), which had been pre-cooled to −5° C., using an ice/NaCl bath. The resulting solution was allowed to warm to room temperature, and then Cu(I)Cl (0.08 g, 0.77 mmol) was added, and then the reaction mixture was re-cooled to −5° C. With continued cooling and stirring, the contents of the first flask were added in 2 mL portions to the contents of the second flask, and the mixture was stirred for 30 min, during which time a precipitate formed. The precipitate was isolated by filtration, rinsed with cold water, and stored under vacuum to give 3.25 g (98%) 10 as a white solid.

Example 62

Preparation of 2-{2-Diethylamino-5-[(4-fluorobenzenesulfonyl) propargylamino]pyrimidin-4-ylamino}-3-(4-dimethylcarbamoyloxyphenyl) propionic acid Steps 1, 2, 3, 4, 5 and 7 were performed as for Example 36. Step 6 was performed using propargyl bromide in place of dimethyl sulfate.

$^1$H NMR (CDCl$_3$) δ 1.15 (m, 6H), 2.27 (d, J=2.1, 1H), 2.97 (s, 3H), 3.06 (s, 3H), 3.10-3.70 (m, 6H), 3.75 (dd, J=17.7, 2.0, 0.6H), 3.95 (dd, J=18.1, 2.0, 0.4H), 4.51 (dd, J=19.5, 2.2, 0.6H), 4.54 (dd, J=18.1, 2.2, 0.4H), 4.79 (q, J=5.9, 0.6H), 4.88 (q, J=6.6, 0.4H), 6.42 (bd, 0.4H), 6.65 (bs, 0.6H), 6.85-7.30 (m, 6H), 7.52 (s, 0.6H), 7.56 (s, 0.4H), 7.85 (m, 2H), 8.20 (bs, 1H)

MS m/z 613.2 (MH$^+$)

Example 63

Preparation of 2-{2-Diethylamino-5-[(2,4-difluorobenzenesulfonyl)propargylamino]pyrimidin-4-ylamino}-3-(4-dimethylcarbamoyloxyphenyl)propionic acid Steps 1, 2, 3, 4, 5 and 7 were performed as for Example 52. Step 6 was performed using propargyl bromide in place of dimethyl sulfate.

$^1$H NMR (CDCl$_3$) δ 1.16 (q, J=7.5, 6H), 2.27 (m, 1H), 2.99 (s, 3H), 3.09 (s, 3H), 3.10-3.70 (m, 6H), 4.04 (dd, J=17.7, 2.4, 0.6H), 4.24 (dd, J=17.9, 2.2, 0.4H), 4.47 (m, 1H), 4.81 (q, J=5.9, 0.6H), 4.89 (q, J=6.3, 0.4H), 6.27 (d, J=7.5, 0.4H), 6.41 (d, J=5.7, 0.6H), 6.90-7.10 (m, 4H), 7.16 (d, J=8.3, 1H), 7.28 (d, J=8.3, 1H), 7.55 (bs, 1H), 7.66 (s, 0.6H), 7.67 (s, 0.4H), 7.81 (m, 1H)

Example 64

Preparation of 2-{2-diethylamino-5-[(4-fluorobenzenesulfonyl)-(2,2,2-trifluoroethyl)amino]pyrimidin-4-ylamino}-3-(4-dimethylcarbamoyl-oxyphenyl)propionic acid Steps 1, 2, 3, 4, 5 and 7 were performed as for Example 36. Step 6 was performed using 2,2,2-trifluoroethyl triflate and cesium carbonate in place of dimethyl sulfate and potassium carbonate.

$^1$H NMR (CDCl$_3$) δ 1.14 (m, 6H), 2.98 (s, 3H), 3.06 (s, 3H), 3.10-4.20 (m, 8H), 4.80 (q, J=5.9, 0.6H), 4.87 (q, J=6.2, 0.4H), 6.09 (d, J=5.9, 0.4H), 6.18 (bd, 0.6H), 6.80-7.50 (m, 7H), 7.55 (bs, 1H), 7.77 (m, 2H);

MS m/z 657.2 (MH+)

General Methods of Examples 65-104: Proton ($^1$H) and carbon ($^{13}$C) nuclear magnetic resonance spectra (NMR) were obtained using a Gemini 2000 or Bruker Avance 300 spectrometer. The presence of the polyethylene glycol (PEG) protons can be detected by a large, broad singlet at 3.6 ppm. The integration of this signal can vary depending on the size of the PEG moiety. Presence of the conjugated VLA-4 antagonist can also be detected in the $^1$H NMR spectra of conjugates. Thin layer chromatography was performed on pre-coated sheets of silica 60 F$_{254}$ (EMD 15341-1) or pre-coated MKC18F silica 60 Å (Whatman 4803-110). Mass spectrometry was performed on an Agilent mass spectrometer (LC/MSD VL) in positive ion single quad mode.

HPLC Methods for PEG Products and PEG Conjugates:

Preparative reverse phase HPLC was performed using a Varian Prep Star (Model SD-1) module with a Varian UV detector set at 210 nm. Method A: Samples of PEG products and PEG conjugates were purified using reverse phase HPLC on a Vydac C18, 300 Å pore size column (250 mm×21.2 mm), typically using a gradient of 35-50% ACN+0.1% TFA in 100 min at 20 mL/min. Method B: Samples of PEG products and conjugates were purified using reverse phase HPLC on a Vydac C18, 300 Å pore size column (250 mm×50 mm), typically using a gradient of 35-50% ACN+0.1% TFA in 100 min at 60 mL/min.

Method C: The purity of PEG products and conjugates was confirmed via reverse phase analytical HPLC using an Agilent Series 1100 Quaternary system equipped with a Waters Symmetry 300 Å pore size, 3.5μ C18 column (150 mm×4.6 mm), using a gradient of 40-50% ACN w/0.1% TFA at a flow rate of 1.5 mL/min. and coupled to an Agilent 1100 variable wavelength detector set at 210 nm and a Sedex 75 evaporative light scattering detector (40° C., gain=5).

PEG Reagents: PEG starting materials were acquired through NOF Corporation (Yebisu Garden Place Tower, 20-3 Ebisu 4-chome, Shibuya-ku, Tokyo 150-6019) or Nektar Therapeutics (150 Industrial Road, San Carlos, Calif. 94070) as follows: 30 kDa PEG diamine (NOF Cat. Sunbright DE-300PA); 5 kDa Boc-NH-PEG-NHS ester (Nektar Cat. 4M530H02); 20 kDa tetra-amine (NOF Cat. Sunbright PTE-200PA);

40 kDa 4-arm PEG alcohol (NOF Cat. Sunbright PTE-40000); 40 kDa 3-arm PEG alcohol (NOF Cat. Sunbright GL-400).

Example 65

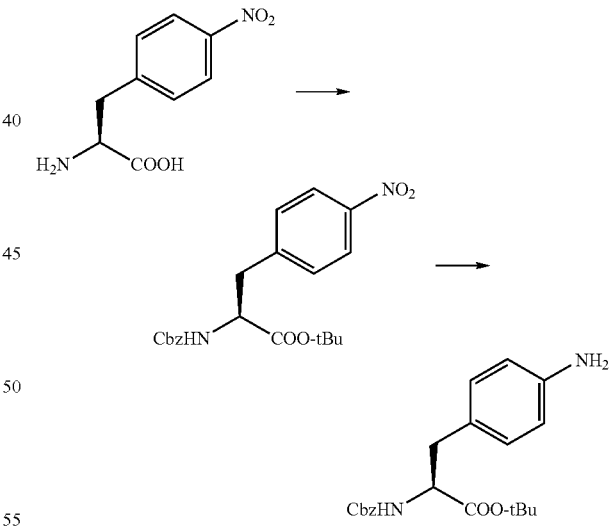

Sodium hydroxide (10 g, 0.25 m) is dissolved in water (300 ml). To this solution 4-nitrophenylalanine (50.3 g, 0.22 m) is added and stirred until complete dissolution. To the resulting solution the sodium carbonate (28.8 g, 0.26 m) is added and stirred suspension is cooled in an ice bath to +8° C. Benzyl chloroformate (44.7 g, 0.26 m) is added dropwise with vigorous stirring, maintaining internal temperature in +6° to +9° C. range. The mixture is stirred at +6° C. for additional 1 hr, transferred to the separatory funnel and washed with ether (2×150 ml). Aqueous phase is placed in a large Erlenmeyer flask (2L) and is cautiously acidified with dil. aq. HCl to pH=2 and extracted with ethyl acetate (4×500 ml). The combined extracts are washed with water and dried with MgSO$_4$. The solution is filtered and filtrate evaporated, residue is dissolved in ethyl acetate (150 ml) and diluted with hexane (500 ml). Crystalline material is filtered off and rinsed with cold solvent, air dried to give Cbz-4-nitrophenylalanine, 75 g (99.5% yield).

$^1$H-NMR, DMSO-d6, (δ): 12.85 (bs, 1H), 8.12 (d, 2H, J=9 Hz), 7.52 (d, 2H, J=9 Hz), 7.30 (m, 5H), 4.95 (s, 2H), 4.28 (m, 1H), 3.32 (bs, 1H), 3.10 (m, 2H). $^{13}$C-NMR (δ): 173.1, 156.3, 146.6, 137.3, 130.8, 128.5, 128.0, 127.8, 123.5, 65.6, 55.1, 36.6.

MS (m/z): 367.1 [M+23].

The Cbz-4-nitrophenylalanine (75 g, 0.22 m) is dissolved in dioxane (300 ml). The resulted stirred solution is cooled in Dry Ice bath to −20° C. (internal). The liquefied isobutylene (approx. 290 ml) is added followed by conc. sulfuric acid (35 ml) added in three equal portions, 30 min apart. The addition of acid is a very exothermic process, accompanied by substantial degree of polymerization. Efficient mechanical stirring is essential at this stage. Resulted mixture is stirred for 20 hr, allowing to warm up to ambient temperature then is cautiously poured into sat. aq. sodium carbonate solution (2L) and diluted with ethyl acetate (600 ml). Organic layer is separated and aqueous layer is extracted with ethyl acetate (2×200 ml). Combined extracts are washed with water and dried with sodium sulfate. The solution is filtered and evaporated to dryness. The residue is taken up in ethyl acetate/hexane mixture (500 ml; 1:1) and filtered through plug of silica gel (ca. 2×2 in). The silica is rinsed with an additional amount of the same solvent (2 L total) and the filtrates are evaporated to give fully protected 4-nitrophenylalanine as a viscous oil, 73 g (83% after two steps).

$^1$H-NMR, CDCl$_3$, (δ): 8.12 (d, 2H, J=8.4 Hz), 7.36 (m, 7H), 5.35 (m, 1H), 5.10 (m, 2H), 4.57 (m, 1H), 3.31 (m, 2H), 1.43 (s, 9H).

$^{13}$C-NMR, CDCl$_3$, (δ): 169.7, 155.3, 146.9, 143.9, 136.0, 130.2, 128.4, 128.2, 128.0, 123.3, 82.9, 66.9, 54.7, 38.2, 31.4, 27.8, 13.9.

MS (m/z): 423.1 [M+23].

Protected 4-nitrophenylalanine (73 g, 0.18 m) is dissolved in ethanol (500 ml) and platinum oxide catalyst (1.5 g) is added. The resulting solution is vigorously stirred in hydrogen atmosphere (50-60 psi) at ambient temperature until further hydrogen adsorption ceased (3 hr). The catalyst is filtered off and the filtrate is evaporated to dryness, the residue is taken up in ethyl acetate (200 ml) and filtered through plug of silica gel (2×2 in) using ethyl acetate-hexane mixture (3:2, 2L) to rinse silica. The filtrate is concentrated to approx. 200 ml and hexane (500 ml) is added. The crystalline product is filtered off, rinsed with cold solvent and air-dried. Yield—56 g, 84%.

$^1$H-NMR, CDCl$_3$, (δ): 7.30 (bs, 5H), 6.92 (d, 2H, J=8.1 Hz), 6.58 (d, 2H, J=8.1 Hz), 5.21 (m, 1H), 5.10 (d, 2H, J=2.1 Hz), 4.46 (m, 1H), 3.59 (bs, 2H), 2.97 (s, 2H, J=5.4 Hz), 1.42 (s, 9H).

$^{13}$C-NMR, CDCl$_3$, (δ): 170.6, 145.1, 136.3, 130.2, 128.3, 127.9, 125.6, 115.0, 81.9, 66.6, 55.2, 37.4, 27.8

MS (m/z): 393.1 [M+23].

Example 66

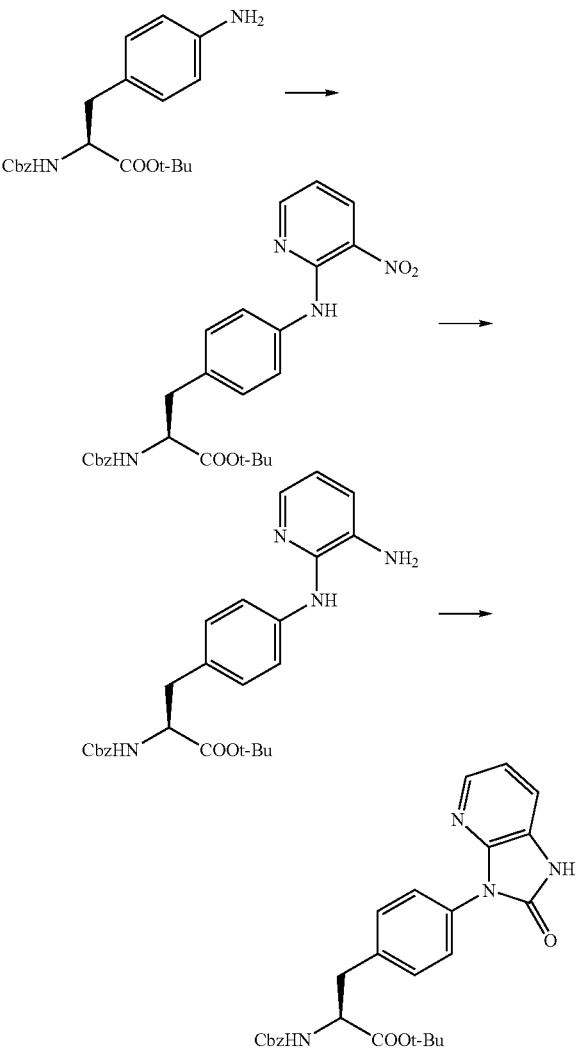

The product of Example 65, 4-aminophenylalanine, (20 g, 0.054 m) was dissolved in ethanol (200 ml) and treated with Hunig's base (21 g, 0.162 m, 3 eq) and 2-chloro-3-nitropyridine (10.3 g, 0.65 m, 1.2 eq). Resulted solution was stirred under nitrogen atmosphere and heated to reflux for 24 hr. LC analysis indicated presence of small amount of unreacted amine. The small additional amount of chloronitropyridine (1.1 g, 0.13 eq) was added and reflux continued for another 24 hr. Reaction mixture was cooled and evaporated to dryness. Residue was dissolved in ethyl acetate (600 ml) and obtained solution was washed with water (1×200 ml), dil. aq. citric acid (0.2 N, 2×200 ml), brine (1×200 ml) and dried with sodium sulfate. Solids were filtered off and filtrate evaporated to give 37 g of deep-red oil, containing expected product contaminated with excess of chloronitropyridine. Impure product was purified by flash chromatography (Biotage 75L system) eluting with ethyl acetate:hexane (3:17) mixture. Fractions containing pure product were combined and evaporated to give deep-red, viscous oil, 26 g (99%).

¹H-NMR, CDCl₃, (δ): 10.10 (s, 1H), 8.49 (m, 2H), 7.57 (d, 2H, J=9 Hz), 7.35 (bs, 5H), 7.19 (d, 2H, J=9 Hz), 6.84 (m, 1H), 5.30 (m, 1H), 5.13 (d, 2H, J=3 Hz), 4.57 (m, 1H), 3.11 (m, 2H), 1.45 (s, 9H).
¹³C-NMR, CDCl₃, (δ): 170.4, 155.5, 155.1, 150.0, 136.7, 136.3, 135.4, 132.4, 129.9, 128.5, 128.3, 128.0, 127.9, 122.2, 113.7, 82.2, 66.7, 55.1, 37.7, 27.8, 20.9.
MS (m/z): 493.1 [M+1], 515.1 [M+23].

The red nitro compound (26 g, 0.054 m) was dissolved in THF (350 ml) and platinum oxide catalyst (1.35 g) was added. Resulted mixture was vigorously stirred under hydrogen atmosphere (50-60 psi) until hydrogen adsorption ceased (2 hr). Catalyst was filtered off and filtrate evaporated to dryness. Residue was dissolved in ethyl acetate (100 ml) and diluted with hexane (50 ml) till beginning of crystallization. Mixture was further diluted with ethyl acetate/hexane (1:1) mixture (300 ml) and was left standing in refrigerator for 3 hr. Crystalline solids were filtered off, rinsed with cold solvent and air-dried to give product, 23 g, 94%.
¹H-NMR, CDCl₃, (δ): 7.81 (dd, 1H, J1=1.5 Hz, J2=4.8 Hz), 7.33 (bs, 5H), 7.17 (d, 2H, J=8.4 Hz), 7.03 (d, 2H, J=8.4 Hz), 6.96 (dd, 1H, J1=1.5 Hz, J2=7.5 Hz), 6.75 (dd, 1H, J1=5.0 Hz, J2=7.7 Hz), 6.22 (s, 1H), 5.31 (m, 1H), 5.09 (bs, 2H), 4.50 (m, 1H), 3.41 (bs, 2H), 3.02 (m, 2H), 1.43 (s, 9H).
¹³C-NMR, CDCl₃, (δ): 170.6, 155.6, 145.5, 140.21, 138.8, 136.3, 130.8, 129.9, 128.5, 128.3, 127.9, 123.4, 118.2, 117.0, 82.0, 66.6, 55.2, 37.4, 27.9.
MS (m/z): 407.1 [M−56], 463.1 [M+1], 485.1 [M+23].

The aminopyridine (19 g, 0.041 m) was suspended in dichloromethane (200 ml) and CDI (12 g, 0.074 m, 1.8 eq) was added. Resulted mixture was stirred at ambient temperature for 20 hr. Reaction mixture was washed with sat. aq. bicarbonate (2×100 ml), brine (1×100 ml) and dried with sodium sulfate. Solids were filtered off and filtrate evaporated to dryness. Residue was dissolved in ethyl acetate (hot, 300 ml) and set to crystallize. Crystalline product was filtered off, rinsed with cold ethyl acetate and air-dried to give 19.9 g, 81% of the imidazolone.
¹H-NMR, CDCl₃, (δ): 10.63 (s, 1H), 8.06 (d, 1H, J=3 Hz), 7.66 (d, 2H, J=9 Hz), 7.32 (m, 8H), 7.05 (m, 1H), 5.36 (m, 1H), 5.13 (s, 2H), 4.59 (m, 1H), 3.17 (m, 2H), 1.45 (s, 9H).
¹³C-NMR, CDCl₃, (δ): 170.4, 155.6, 154.3, 143.8, 141.0, 136.2, 135.8, 131.8, 130.2, 128.3, 128.0, 125.9, 122.2, 118.3, 116.0, 82.4, 66.8, 55.0, 37.7, 27.8.
MS (m/z): 433.1 [M−56], 489.2 [M+1], 511.2 [M+23].

Example 67

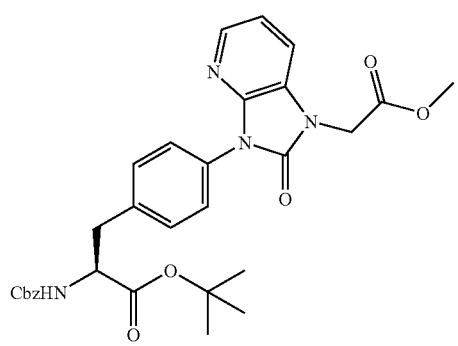

To a solution of the product of Example 66 (4.0 g, 8.19 mmol) in DMF (40 ml) crushed potassium carbonate (1.58 g, 11.47 mmol) was added followed by the addition of methyl bromoacetate (1.0 ml, 11.47 mmol). The reaction mixture was stirred under nitrogen at room temperature over night. The reaction mixture was concentrated in vacuo and the residue was taken up in ethyl acetate (100 ml). The organic phase was washed with H₂O, brine, dried over Na₂SO₄, filtered, and concentrated in vacuo. The crude material was purified by column chromatography (100% ethyl acetate) to yield 4.5 g (100%) of the title compound as a white foam. R_f=0.42 (5% MeOH/CH₂Cl₂).

MS m/z=561, (M+H)⁺.

¹H NMR (CDCl₃) δ 8.10-8.08 (d, 1H), δ 7.67-7.65 (d, 2H), δ 7.37-7.30 (m, 7H), δ 7.20-7.17 (m, 1H), δ 7.10-7.05 (m, 1H), δ 5.30-5.27 (d, 1H), δ 5.11 (s, 2H), δ 4.58-4.55 (q, 1H), δ 3.81 (s, 3H), δ 3.16-3.14 (d, 2H), δ 1.42 (s, 9H).

Example 68

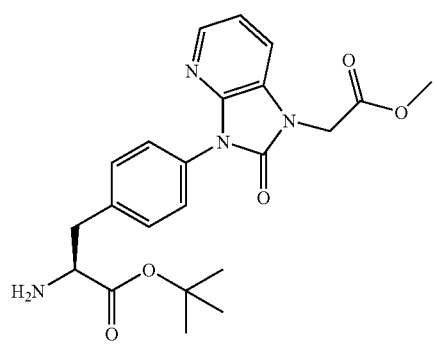

A solution of the product of Example 67 (2.25 g, 4.01 mmol) in MeOH (20 ml) with Degussa Pd/C catalyst (113 mgs) was placed under H2 (55 psi) over night. The reaction mixture was filtered through Celite and concentrated in vacuo to yield 1.65 g (97%) of the title compound as a brown oil. R_f=0.32 (5% MeOH/CH₂Cl₂).

MS m/z=449, (M+Na)⁺.

¹H NMR (CDCl₃) δ 8.11-8.09 (d, 1H), δ 7.68-7.65 (d, 2H), δ 7.41-7.38 (d, 2H), δ 7.20-7.17 (m, 1H), δ 7.10-7.06 (m, 1H), δ 4.73 (s, 2H), δ 3.81 (s, 3H), δ 3.67-3.62 (m, 1H), δ 3.16-3.09 (m, 1H), δ 2.91-2.84 (m, 1H), δ 1.46 (s, 9H).

Example 69

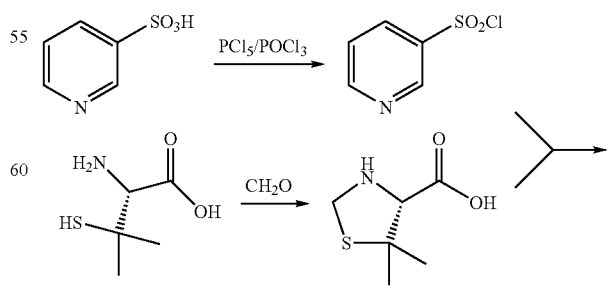

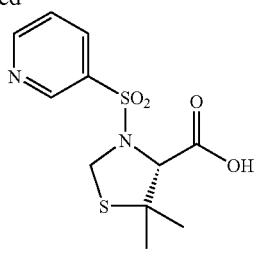

Pyridine-3-sulfonic acid (125 g, 0.78 m) was placed in a 1L, 3-necked flask equipped with mechanical stirrer, reflux condenser, thermometer and nitrogen inlet. Next, the phosphorus pentachloride (250 g, 1.19 m, 1.5 eq) was added, followed immediately by the phosphorus oxychloride (330 ml, 3.8 m, 4.5 eq). The contents of flask were initially stirred at ambient temperature for 30 min, then brought slowly to gentle reflux (internal temp. approx. 110° C.) over the next hour, kept at this temperature for approx. 3.5 hr then allowed over the next 12 hr to cool back to ambient temperature. Gas evolution was observed during this time. The volatiles were stripped under reduced pressure (at 12 mmHg/40° C.) and yellow semi-solid residue was diluted with DCM (1 L). The slurry was poured slowly into the stirred, ice-cold sat. aq. bicarbonate, maintaining pH=7. Gas evolution was observed. The organic layer was separated and aqueous layer was back-extracted with DCM. The combined extracts were washed with cold sat. aq. bicarbonate, brine and dried with magnesium sulfate. The solids were filtered off and filtrate evaporated, leaving pyridine-3-sulfonyl chloride as a pale yellow, oily liquid, 123 g (93% pure; 88% theory).

$^1$H-NMR, CDCl$_3$, ($\delta$): 9.26 (d, 1H), 8.98 (dd, 1H), 8.34 (m, 1H), 7.62 (m, 1H).

$^{13}$C-NMR, CDCl$_3$, ($\delta$): 155.3, 147.4, 140.9, 134.6, 124.2.

MS (m/z): 178.0 [M+1].

L-penicillamine (150 g, 1.0 m) was dissolved with stirring in DI water (1500 ml), cooled in ice-bath to +8° C. and treated with formalin (150 ml, 37% aq.). The reaction mixture was stirred at +8° C. for 2 hr, then cooling bath was removed and stirring continued for 12 hr. The clear solution was concentrated under reduced pressure (14 mmHg/50°) leaving white residue. The solids were re-suspended, then dissolved in hot MeOH (2500 ml) and left standing at ambient temperature for 12 hr. The white, fluffy precipitate was filtered off and rinsed with cold methanol. The filtrate was concentrated and set to crystallize again. The collected precipitate was combined with the first crop and dried in vacuum oven for 24 hr at 55° C. at 45 mmHg. The yield of (R)-5,5-dimethylthiazolidine-4-carboxylic acid was 138 g (>99% pure; 86% theory).

$^1$H-NMR, DMSO-d6, ($\delta$): 4.25 (d, 1H), 4.05 (d, 1H), 3.33 (s, 1H), 1.57 (s, 3H), 1.19 (s, 3H).

$^{13}$C-NMR, DMSO-d6, ($\delta$): 170.8, 74.4, 57.6, 51.8, 28.9, 27.9.

MS (m/z): 162.3 [M+1].

In a 4 L reactor equipped with mechanical stirrer and thermometer, a buffer solution was prepared from potassium monobasic phosphate (43 g, 0.31 m) and potassium dibasic phosphate (188.7 g, 1.08 m) in DI water (2 L). The (R)-5,5-dimethylthiazolidine-4-carboxylic acid (107 g, 0.675 m) was added and stirred until complete dissolution. The solution was cooled in an ice-bath to +8° C. A separately prepared solution of pyridine-3-sulfonyl chloride (124 g, 0.695 m) in DCM (125 ml) was added dropwise to the reactor with vigorous stirring over the 1 hr. The pH of reaction mixture was monitored and after 4 hr, found to be pH=5 and adjusted to pH=6 by addition of solid bicarbonate. The mixture was allowed to warm up to ambient temperature over 18 hr. The pH was adjusted to 2 with dil. aq. sulfuric acid, stirred for 1 hr and precipitated yellow solids were filtered off, rinsed with water to neutral. The solid cake was transferred into 2 L Erlenmayer flask, suspended in DCM (500 ml) with occasional swirling for 5 min and filtered off again. The filter cake was washed with DCM and air-dried. The yield of the title compound, (R)-5,5-dimethyl-3-(pyridin-3-ylsulfonyl)thiazolidine-4-carboxylic acid was 148.9 g (98% pure; 73% theory).

$^1$H-NMR, DMSO-d6, ($\delta$): 9.05 (d, 1H), 8.89 (m, 1H), 8.32 (m, 1H), 7.69 (m, 1H), 4.68 (q, 2H), 4.14 (s, 1H), 1.35 (s, 3H), 1.29 (s, 3H).

$^{13}$C-NMR, DMSO-d6, ($\delta$): 170.0, 154.3, 147.9, 135.8, 134.1, 124.8, 72.6, 54.3, 50.2, 29.4, 25.0.

MS (m/z): 303.2 [M+1].

Example 70

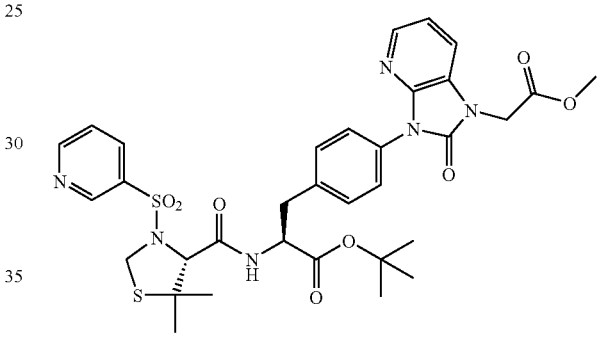

To a solution of the product of Example 68 (1.65 g, 3.88 mmol) in acetonitrile (35 ml) was added the product of Example 69 (1.06 g, 3.53 mmol), HATU (1.75 g, 3.88 mmol), and triethylamine (5.3 ml). The homogeneous brown solution was stirred under nitrogen for 72 hours. The organic reaction mixture was concentrated in vacuo, taken up in ethyl acetate (40 ml), washed with 1N HCl, sat. NaHCO$_3$, and brine. The organic layer was dried over Na$_2$SO$_4$, filtered, and concentrated in vacuo to yield 2.67 g (97%) 3 as an orange foam. R$_f$=0.36 (5% MeOH/CH$_2$Cl$_2$).

MS m/z=711, (M+H)$^+$.

$^1$H NMR (CDCl$_3$) $\delta$ 9.09-9.08 (d, 1H), $\delta$ 8.86-8.84 (m, 1H), $\delta$ 8.18-8.15 (m, 1H), $\delta$ 8.07-8.05 (m, 1H), $\delta$ 7.66-7.63 (d, 2H), $\delta$ 7.52-7.48 (m, 1H), $\delta$ 7.41-7.38 (d, 2H), $\delta$ 7.19-7.16 (m, 1H), $\delta$ 7.08-7.04 (m, 1H), $\delta$ 6.93-6.90 (d, 1H), $\delta$ 4.83-4.76 (q, 1H), δ 4.71 (s, 2H), δ 4.62-4.59 (d, 1H), δ 4.49-4.46 (d, 1H), δ 3.91 (s, 1H), δ 3.80 (s, 3H), δ 3.22-3.08 (m, 2H), δ 1.46 (s, 9H), δ 1.20-1.17 (d, 6H).

Example 71

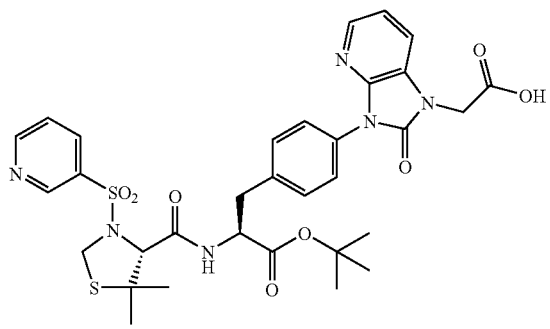

To a solution of the product of Example 70 (2.67 g, 3.75 mmol) in THF (12 ml) was added a solution of LiOH.H$_2$O (245 mgs, 5.97 mmol) in H$_2$O (3 ml). The reaction mixture was stirred at room temperature over night under nitrogen. Upon completion the reaction mixture was concentrated in vacuo, dissolved in H$_2$O (100 ml), and acidified to pH 4 with a 1M HCl solution. The desired product precipitated out as a white solid and was filtered and rinsed with H$_2$O to yield 1.87 g (72%) of the title compound.

MS m/z=697, (M+H)$^+$.

$^1$H NMR (CD$_3$OD) δ 9.02 (s, 1H), δ 9.80 (s, 1H), δ 8.47-8.44 (d, 1H), δ 8.21-8.19 (d, 1H), δ 7.98-7.96 (d, 1H), δ 7.63-7.59 (m, 3H), δ 7.52-7.48 (m, 3H), δ 7.17-7.13 (m, 1H), δ 4.75 (s, 2H), δ 4.72-4.61 (m, 3H), δ 4.14 (s, 1H), δ 3.22-3.16 (m, 2H), δ 1.45 (s, 9H), δ 1.25-1.19 (d, 6H).

$^{13}$C NMR (CD$_3$OD) δ 169.9, 169.5, 168.9, 153.1, 152.8, 147.5, 142.8, 140.2, 136.6, 135.8, 134.0, 131.7, 129.9, 126.0, 124.2, 123.9, 117.8, 114.9, 81.8, 72.6, 54.1, 49.9, 41.3, 36.4, 28.5, 26.6, 23.4.

Example 72

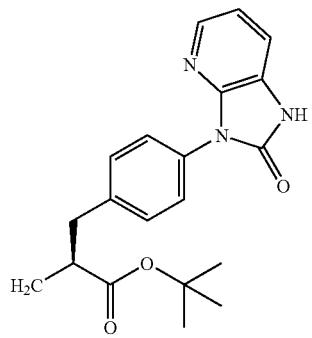

The product of Example 66 (52 g, 0.106 m) was slurried in MeOH (450 ml), hydrogenation catalyst (8.7 g, 5% Pd/C, Degussa) was added and the mixture was stirred under the hydrogen atmosphere (60 psi) until further absorption ceased (ca. 2 hrs). THF (150 ml) was added to dissolve precipitated solids and the solution was filtered through plug of Celite, using DCM to rinse the filter. The filtrate was evaporated to dryness, re-dissolved in DCM (300 ml) and stripped again. This operation was repeated twice. The foamy solids were kept under high vacuum for 3 hrs. The yield of title compound was 38.3 g (101% of theory).

$^1$H-NMR, CDCl$_3$, (δ): 8.08 (m, 1H), 7.56 (AB q, 4H), 7.37 (m, 1H), 7.06 (m, 1H), 3.68 (m, 1H), 2.03 (m, 2H), 1.49 (s, 9H).

$^{13}$C-NMR, CDCl$_3$, (δ): 173.8, 154.6, 143.9, 141.0, 137.4, 131.5, 130.2, 126.1, 122.3, 118.0, 116.1, 81.4, 56.0, 40.6, 27.9.

MS (m/z): 299.3 [M−56], 355.4 [M+1], 377.4 [M+23].

Example 73

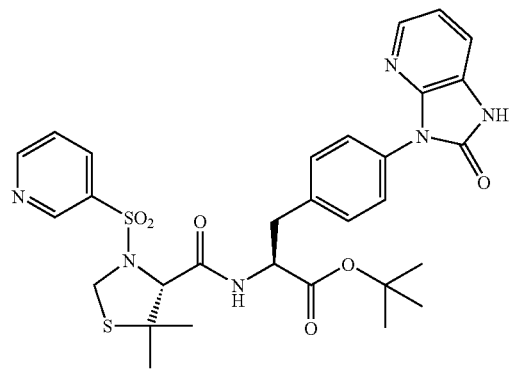

The product of Example 72 (38.3 g, assume 0.106 m) was dissolved in DCM (500 ml) and treated successively with: N-methylmorpholine (27 g, 30 ml, 0.266 m; 2.5 eq), HOBt (17.3 g, 0.128 m; 1.2 eq), and the product of Example 69 (33.8 g, 0.112 m; 1.06 eq). The resulting non-homogenous solution was cooled in an ice-bath to +4° C. and treated with EDC (22.5 g, 0.117 m; 1.1 eq) in one portion. The reaction mixture was stirred, allowing it to warm up to ambient temperature over the next 4 hr and then for 18 hr more. The solvent was stripped and residue dissolved in ethyl acetate (1.2 L), washed with sat. aq. bicarbonate (2×250 ml), water (250 ml), brine (300 ml) and dried with magnesium sulfate. The solution was filtered and evaporated to dryness, leaving a light orange, viscous oil, 76 g (>>100%). The crude product was purified by flash chromatography on silica gel (Biotage 75L, in ethylacetate/methanol (3%) mixture. Fractions, containing pure product, were combined and evaporated to give 54 g of the title compound (yield 83%).

$^1$H-NMR, CDCl$_3$, (δ): 10.37 (s, 1H), 9.11 (s, 1H), 8.87 (m, 1H), 8.19 (m, 1H), 8.05 (m, 1H), 7.56 (AB q, 4H), 7.52 (m, 1H), 7.36 (m, 1H), 7.06 (m, 2H), 4.83 (m, 1H), 4.58 (AB a, 2H), 3.96 (s, 1H), 3.19 (m, 2H), 1.49 (s, 9H), 1.22 (s, 3H), 1.18 (s, 3H).

$^{13}$C-NMR, CDCl$_3$, (δ): 169.7, 167.6, 153.9, 148.4, 143.8, 140.9, 135.8, 135.6, 132.9, 131.9, 130.2, 125.9, 123.8, 122.1, 118.0, 115.9, 82.8, 73.6, 60.3, 54.8, 53.7, 50.6, 37.8, 29.1, 27.8, 23.9, 14.1.

MS (m/z): 583.3[M−56], 639.4 [M+1], 661.3 [M+23].

Example 74

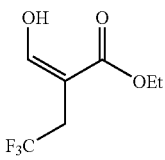

To an ice chilled solution of ethyl trifluorobutyrate (15 g, 89 mmol) and ethyl formate (36 mL, 444 mmol) in THF (200 mL) under $N_2$ was added a solution of 1 M KOtBu in THF (107 mmol, 107 mL) over a 25-minute period. After 15 minutes the ice bath was removed and the reaction mixture was stirred one hour at room temperature. Additional ethyl formate (18 mL, 222 mmol) was then added and the reaction mixture was stirred overnight. The reaction mixture was concentrated and the residue partitioned between cold ether (100 mL) and cold water (300 mL). The pH of the aqueous phase was adjusted to 2 with concentrated HCl. The product was extracted with dichloromethane (1×100 mL, 45×75 mL) and the combined organic extracts were washed with brine (1×100 mL), dried ($MgSO_4$), filtered, and concentrated to yield the title compound as thick oil which solidified upon standing, 10.2 g (58.5%).

MS (m/z)=198 $(M+H)^+$.

Example 75

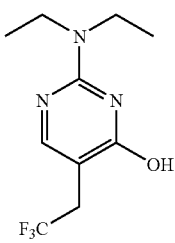

To a solution of the product of Example 74 (10 g, 51 mmol) and diethylguanidine sulfate (8.3 g, 25.2 mmol) in EtOH (60 mL) under $N_2$, was added NaOEt, 21% solution in EtOH (20.7 mL, 55.5 mmol) over a 10-minute period. The reaction mixture was then heated at reflux for 5 hours. The heterogeneous solution was cooled and poured into cold water (100 mL) to give a homogenous solution. The pH of the solution was adjusted to approximately 3.5 with conc. HCl and 1 N HCl. A solid precipitated from solution, which was collected by filtration. The light tan solid was washed with water and air-dried, yielding 2.9 g, (23%) of the title compound.

MS (m/z)=250 $(M+H)^+$.

$^1$H NMR (300 MHz, $CD_3OD$) δ 7.65 (br s, 1H), 3.55 (q, 4H), 3.30 (q, 2H), 1.25 (t, 6H).

Example 76

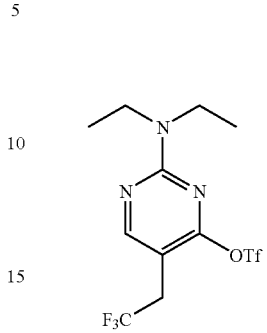

A flask was charged with the product of Example 75 (2.0 g, 8.02 mmol), DIEA (1.5 mL, 8.83 mmol), DMAP (0.98 g, 0.8 mmol), and dichloromethane (30 mL). The mixture was cooled to 0° C. and trifluoroacetic anhydride (1.5 mL, 8.83 mmol) was added. The reaction became homogeneous and was stirred at 0° C. for 3 hours. The mixture was quenched with sat. $NaHCO_3$ and extracted with dichloromethane. The organic phase was washed with 0.2 N citric acid, dried over $Na_2SO_4$, filtered, and concentrated in vacuo to yield 2.87 g (94%) of the title compound as a brown solid.

$^1$H NMR (300 MHz, $CDCl_3$) δ 8.28 (s, 1H), 3.65-3.52 (m, 4H), 3.29-3.19 (q, 2H), 1.22-1.17 (t, 6H).

Example 77

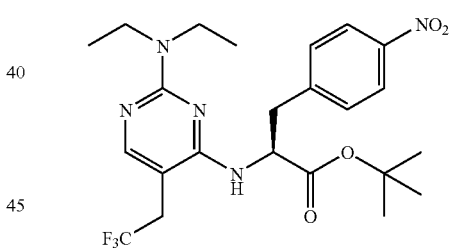

A solution of the product of Example 76 (1.3 g, 3.5 mmol), H-Phe(p-$NO_2$)OtBu (1.1 g, 4.2 mmol), and DIEA (0.9 mL, 5.3 mmol) in $CH_3CN$ (14 mL) under $N_2$ was heated to reflux overnight. The next day additional H-Phe(p-$NO_2$)OtBu (0.8 g, 3 mmol) was added and reflux was continued for 3 days. The reaction mixture was then cooled and concentrated The residue taken-up in EtOAc (50 mL) and the organic portion washed with 0.5 N $KHSO_4$ (3×50 mL), water (1×50 mL), brine (1×10 mL), dried ($MgSO_4$), filtered and concentrated to a brownish gum. The crude material was purified by flash chromatography (5:1 hexanes/EtOAc) to yield 640 mg (38%) of the title compound as a golden gum. TLC: 3:1 hexanes/EtOAc, $R_f$=0.30

MS (m/z)=498 $(M+H)^+$

¹H NMR, (300 MHz, CDCl₃) δ 8.19 (d, 2H), 7.80 (s, 1H), 7.25 (d, 2H), 5.19 (br d, 1H), 4.95 (q, 1H), 3.70-3.50 (m, 4H), 3.45-3.25 (m, 2H), 3.10 (q, 2H), 1.40 (s, 9H), 1.05 (t, 6H).

Example 78

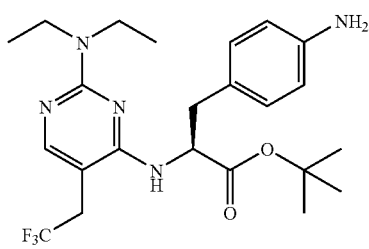

The product of Example 77 (635 mg, 1.27 mmol) was dissolved in absolute EtOH (5 mL) to which was added 35 mg of Pd/C, 10 wt %. The reaction was subjected to hydrogenation (45 psi H₂) for 2.5 hours at which time 50 mgs of Pd/C, 10 wt % was added and the reaction mixture again subjected to hydrogenation (45 psi H₂) overnight. The reaction mixture was filtered through a pad of Celite and the filtrate was concentrated to give 452 mg (76%) of the title compound.

MS (m/z)=468 (M+H)⁺
¹H NMR (300 MHz, CDCl₃) δ 7.75 (s, 1H), 6.90 (d, 2H), 6.60 (d, 2H), 5.05 (br d, 1H), 4.80 (q, 1H), 3.70-3.45 (m, 6H), 3.10-2.90 (m, 4H), 1.40 (s, 9H), 1.15 (t, 6H).

Example 79

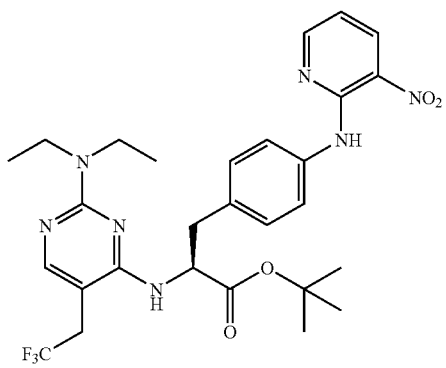

A solution of the product of Example 78 (598 mg, 1.28 mmol), 2-chloro-3-nitropyridine (243 mg, 1.53 mmol), and DIEA (0.67 mL, 3.83 mmol) in EtOH (5 mL) under N₂ was heated at reflux. The next day the reaction was cooled and additional 2-chloro-3-nitropyridine (40 mg, 0.25 mmol) and DIEA (0.11 mL, 0.60 mmol) was added and the reaction was heated at reflux for one day. The reaction mixture was then concentrated and the residue taken-up in EtOAc (20 mL). The organic phase was washed with water (2×20 mL). The combined aqueous washes was back extracted with EtOAc (2×10 mL). The combined organic extracts were washed with 0.2 N citric acid (3×20 mL), water (1×10 mL), sat. NaHCO₃ (3×20 mL), brine (1×10 mL), dried (MgSO₄), filtered and stripped to an orange gum. The crude product was purified by flash chromatography eluting with 4:1 hexanes/EtOAc (R_f=0.14) to yield 610 mg (81%) of the title compound as a red oil.

MS (m/z)=590 (M+H)⁺
¹H NMR (300 MHz, CDCl₃) δ 10.10 (s, 1H), 8.55 (d, 1H), 8.50 (m, 1H), 7.79 (s, 1H), 7.75 (d, 2H), 7.15 (d, 2H), 6.80 (q, 1H), 5.10 (br d, 1H), 4.90 (m, 1H), 3.70-3.45 (m, 4H), 3.25 (m, 2H), 3.10 (q, 2H), 1.40 (s, 9H), 1.10 (t, 6H).

Example 80

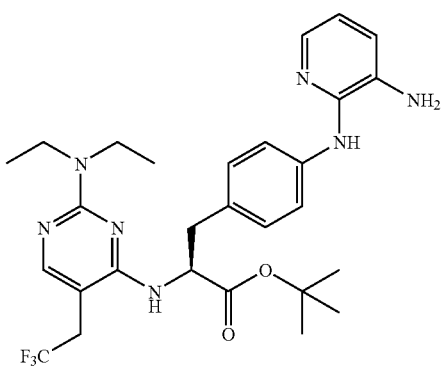

To a solution of the product of Example 79 (610 mg, 1.03 mmol) in absolute EtOH (5 mL) was added 60 mg of Pd/C, 10 wt %. The mixture was subjected to hydrogenation (45 psi H₂) overnight. The next day the reaction mix was filtered through Celite and the filtrate concentrated to give 500 mg (87%) of the title compound.

MS (m/z)=560 (M+H)⁺
¹H NMR (300 MHz, CDCl₃) δ 7.85 (d, 2H), 7.80 (s, 1H), 7.20 (d, 2H), 7.05 (d, 2H), 7.00 (d, 1H), 7.75 (m, 1H), 6.20 (br s 1H), 5.15 (br s, 1H), 4.85 (m, 1H), 3.75-3.45 (m, 4H), 3.40 (br s, 2H), 3.15 (m, 2H), 3.05 (q, 2H), 1.40 (s, 9H), 1.15 (t, 6H).

Example 81

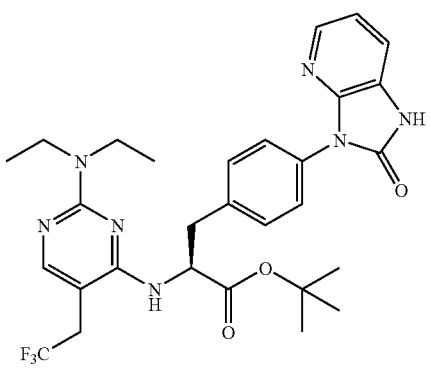

A solution of the product of Example 80 (141 mg, 0.250 mmol) and CDI (62 mg, 0.378 mmol) in CH₂Cl₂ (3 mL) was stirred overnight. The next day additional CDI (30 mg, 0.185 mmol) was added and the reaction was stirred another day. The reaction mixture was then concentrated and taken-up in EtOAc (10 mL) and the organic portion washed with 0.2 N citric acid (3×5 mL), water (1×5 mL), sat. NaHCO₃ (3×5 mL), brine (1×5 mL), dried (MgSO₄), filtered and concentrated to yield 69 mg (47%) the title compound as a foam which was used without further purification.

MS (m/z)=586 (M+H)+
$^1$H NMR (300 MHz, CDCl$_3$) δ 8.20 (br s, 1H), 8.05 (d, 1H), 7.80 (s, 1H), 7.65 (d, 2H), 7.90 (m, 3H), 7.05 (m, 1H), 5.15 (br d, 1H), 4.95 (m, 1H), 3.70-3.45 (m, 4H), 3.25 (app d, 2H), 3.10 (q, 2H), 1.40 (s, 9H), 1.15 (t, 6H).

Example 82

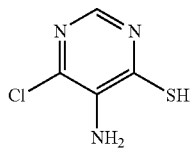

To a solution of 4,6-dichloro-5-aminopyrimidine (5.0 g, 30.7 mmol) in DMSO (30 mL) was added Na$_2$S.9H$_2$O (7.4 g, 30.8 mmol). The mixture was stirred at room temperature overnight. Water (40 mL) was then added to the mixture and the solution evaporated under reduced pressure to approximately 6 mL. To this solution was added conc. HCl (0.5 mL) and water to precipitate the product. The solution was filtered and the orange solid was washed with water and dried to afford 4.3 g (86%) of the title compound.
$^1$H NMR (300 MHz, DMSO-d$_6$) δ 5.84 (2H, s), 7.79 (1H, s), 14.37 (1H, br s)
MS (m/z): MH$^+$=162.

Example 83

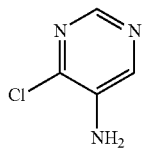

To the product of Example 82 (4.3 g, 26 mmol) dissolved in conc. NH$_4$OH (4 mL) was added EtOH (40 mL). To this solution, Raney Nickel (excess) was added in portions. The reaction was stirred at room temperature overnight and then heated at 80° C. for 2 hrs. The mixture was filtered through Celite and the filtrate concentrated. The crude product was purified by flash chromatography on silica using EtOAc/hexanes to afford 1.6 g (47%) of the title compound as a yellow solid.
$^1$H NMR (300 MHz, DMSO-d$_6$) δ 5.90 (2H, s), 8.20 (2H, s)
MS (m/z) MH$^+$=130.

Example 84

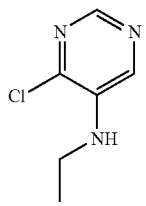

To the product of Example 83 (0.51 g, 3.9 mmol) in MeOH (20 mL) and HOAc (0.5 mL) was added CH$_3$CHO (0.52 mL, 9.2 mmol). Then NaBH$_3$CN (590 mg, 9.2 mmol) was added in one portion. The reaction was stirred at room temperature overnight and additional HOAc, CH$_3$CHO, and NaBH$_3$CN were added. The reaction was stirred overnight, concentrated, and the residue was taken up in EtOAc and sat. NaHCO$_3$. The separated aqueous layer was back extracted with EtOAc. The combined organic layer was dried and concentrated to a residue. The residue was dissolved in MeOH and treated with HOAc, CH$_3$CHO and NaBH$_3$CN as described above. Following the work up procedure described above the crude product was purified by flash chromatography on silica using EtOAc/hexanes, to afford 0.35 g (57%) of the title compound as a yellow oil.
$^1$H NMR (300 MHz, CDCl$_3$) δ 1.35 (3H, q, J=12 Hz), 3.29 (2H, m), 4.21 (1H, bs), 8.04 (1H, s), 8.36 (1H, s)
MS (m/z): MH$^+$=158.

Example 85

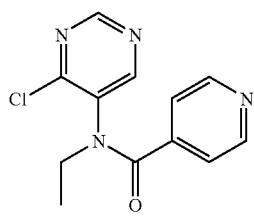

To the product of Example 84 (70 mg, 0.45 mmol) dissolved in DMF (1 mL) was added TEA (93 uL) and isonicotinoyl chloride (0.12 g, 0.67 mmol). The reaction mixture was stirred at room temperature for 2 days and then partitioned between EtOAc and sat. NaHCO$_3$. The separated aqueous layer was back extracted with EtOAc. The combined organic layer was dried and concentrated to give 67 mg (57%) of the title compound which was used without further purification.
$^1$H NMR (300 MHz, CDCl$_3$) δ 1.26 (3H), 3.65-3.69 (1H), 4.21 (1H), 7.17 (2H), 8.43 (1H), 8.54 (2H), 8.86 (1H) Note: $^1$H NMR shows evidence of rotamers as demonstrated of broadness of all peaks
MS (m/z): MH$^+$=263.

Example 86

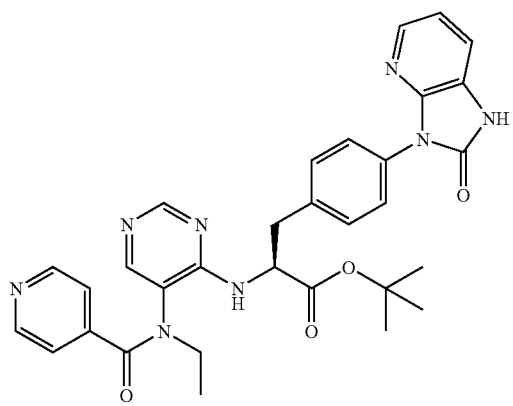

To a solution of the product of Example 85 (0.11 g, 0.42 mmol) and the product of Example 72 (0.135 g, 0.38 mmol) in IPA (2.5 ml) was added DIEA (0.35 ml, 1.9 mmol). The reaction mixture was stirred in a sealed tube at 130° C. for 2 days. The crude mixture was concentrated and the oil was purified by flash column chromatography with a solvent gradient of 0-10% MeOH in $CH_2Cl_2$ to yield the title compound as an oil.

$^1$H NMR (300 MHz, $CDCl_3$) δ 1.16 (1.2H, m), 1.26-1.31 (1.8H, m), 1.50-1.53 (9H, d, J=9 Hz), 3.0 (1H, m), 3.2 (0.8H, m), 3.36 (1.2H, m), 4.12-4.18 (1.2H, m), 4.96-5.10 (0.8H, m), 5.80-5.95 (1H, m), 6.93-6.96 (1H, m), 7.07 (1H, m), 7.31-7.45 (5H, m), 7.66-7.75 (3H, m), 8.06 (1H, m), 8.44-8.51 (2H, m); HPLC/MS: single peak at 1.29 min, $MH^+$=581.

Example 87

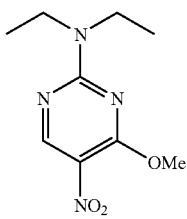

To 2,4-dichloro-5-nitropyrimidine (2.0 g, 10.3 mmol) in MeOH (7 mL) at 0° C. under $N_2$ was added NaOMe (0.5 M in MeOH, 25 mL) dropwise. After the addition was completed, the reaction mixture was stirred at 0 C for 15 min. Then diethylamine (5 mL) was added and the mixture was stirred at rt overnight. The reaction mixture was concentrated and the residue was partitioned between EtOAc and $H_2O$. The organic layer was dried and concentrated to a residue which was purified by flash chromatography on silica using EtOAc/Hexanes, to afford the title compounds as an off white solid (1.1 g, 4.9 mmol, 47% yield).

$^1$H NMR (300 MHz, $CDCl_3$) δ 1.26 (6H, t, J=6.6 Hz), 3.70 (4H, m), 4.08 (3H, s), 9.01 (1H, s)

HPLC/MS: $MH^+$=227.

Example 88

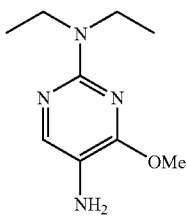

To the product of Example 87 (1.1 g, 4.9 mmol) in MeOH/EtOAc (1:1, 20 mL) was reduced with Pd/C (5% degussa, 0.5 g) and $H_2$ (50 psi) in a Parr shaker overnight. The reaction mixture was filtered and the filtrated was concentrated under reduced pressure to afford the title compound as a solid (0.85 g, 4.3 mmol, 88.5% yield).

$^1$H NMR (300 MHz, $CDCl_3$) δ 1.18 (6H, t, J=6.9 Hz), 3.03 (2H, br), 3.57 (6H, t, J=6.9 Hz), 3.96 (3H, s), 7.71 (1H, s)

HPLC/MS: $MH^+$=197.

Example 89

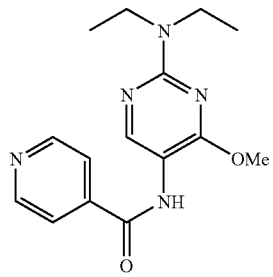

To the product of Example 88 (0.85 g, 4.3 mmol) in $CH_2Cl_2$ (15 mL) and TEA (1.4 mL, 10 mmol) was added isonicotinyl chloride HCl salt (1.13 g, 6.3 mmol). After 15 min, TLC showed no starting material. The mixture was extracted between EtOAc and sat. $NaHCO_3$. The aqueous layer was washed with EtOAc twice. The combined organic layers were washed with sat. $NaHCO_3$ and brine. It was dried over $MgSO_4$ and filtered. The filtrate was concentrated to give the title compound as a brown solid (1.3 g, 4.3 mmol, 100% yield).

$^1$H NMR (300 MHz, $CDCl_3$) δ 1.20 (6H, t, J=6.9 Hz), 3.60 (4H, q, J=6.9 Hz), 3.96 (3H, s), 7.72 (2H, d, J=6.0 Hz), 7.75 (1H, bs), 8.80 (2H, d, J=6.0 Hz), 8.89 (1H, s)

HPLC/MS: $MH^+$=302.

Example 90

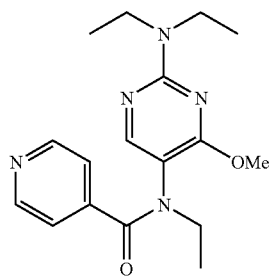

To the product of Example 89 (100 mg, 0.33 mmol) in THF (1 mL) was added KOtBu (1M in THF, 0.5 mL) slowly followed by EtI (40 μL, 0.5 mmol). The reaction mixture was stirred at rt overnight. TLC showed the disappearance of the starting material. The mixture was partitioned between EtOAc and $H_2O$. The aqueous layer was washed with EtOAc. The combined organic layers were washed with sat. $NaHCO_3$ and brine. It was dried and concentrated to give the title compound (90 mg, 0.27 mmol, 83%) that was used without further purification.

$^1$H NMR (300 MHz, $CDCl_3$) δ 1.10 (9H, m), 3.47 (5H, m), 3.92 (1H, m), 7.14 (2H, d, J=6.0 Hz), 7.78 (1H, bs), 8.44 (2H, d, J=6.0 Hz)

HPLC/MS: MH+=330.

Example 91

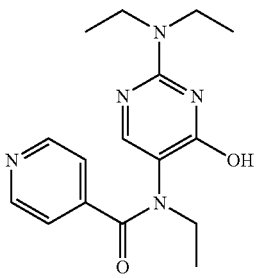

To the product of Example 90 (200 mg, 0.61 mmol) in DMF (4 mL) was added EtSNa (66 mg, 0.79 mmol) and the reaction mixture was heated at 100 C for 1 hr. LC/MS showed starting material still present. Another portion of NaSEt (66 mg, 0.79 mmol) was added and the reaction heated for another 2 hr. LC/MS showed product only. DMF was removed under reduced pressure and $H_2O$ (10 mL) was added followed by conc. HCl (0.132 mL). Evaporating of the solvent left a residue. It was dissolved in EtOH and filtered. The filtrate was concentrated to yield the title compound (190 mg, 100%) that was used without further purification.

$^1$H NMR (300 MHz, $CD_3OD$) δ 1.24 (9H, m), 3.60 (4H, m), 3.60-4.00 (2H, br), 8.12 (3H, d, J=5.7 Hz), 8.92 (2H, d, J=5.7 Hz)

HPLC/MS: MH+=316.

Example 92

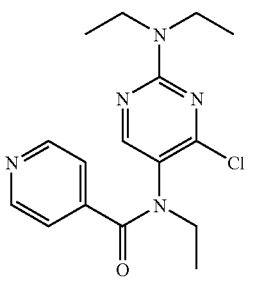

To the product of Example 91 (70 mg, 0.22 mmol) in $POCl_3$ (3 mL) at rt was added diethylaniline (30 μL). The reaction mixture was heated to 100 C for 30 min. Then it was concentrated. The residue was partitioned between EtOAc and $H_2O$. The organic layer was washed with $H_2O$ twice. Then it was dried and concentrated to give the title compound (50 mg, 0.15 mmol, 68%) and used for the next reaction without further purification.

HPLC/MS: MH+=334

Example 93

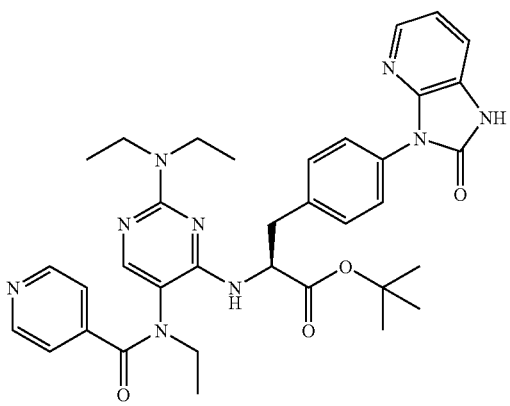

To a solution of the product of Example 92 (50 mg, 0.15 mmol) and the product of Example 72 (60 mg, 0.17 mmol) in IPA (0.75 mL) was added DIEA (0.15 mL, 0.8 mmol). The reaction mixture was stirred in a sealed tube at 130 degrees for 7 days. The crude mixture was concentrated and the residue was purified by preparative HPLC and silica gel flash chromatography to yield an off white solid (10 mg).

$^1$H NMR (300 MHz, $CDCl_3$) δ 1.10-1.30 (9H, m), 1.48 (4.5H, s), 1.51 (4.5H, s), 2.80-3.38 (3H, m), 3.53 (4H, m), 4.05-4.30 (1H, m), 4.83 (0.5H, m), 4.96 (0.5H, m), 5.15-5.50 (1H, m), 6.95-7.10 (2H, m), 7.25-7.50 (5H, m), 7.69 (0.5H, d, J=8.4 Hz), 7.76 (0.5H, d, J=8.4 Hz), 8.08 (1H, d, J=5.1 Hz), 8.51 (2H, m), 8.83 (0.5H, br), 8.95 (0.5H, br);

HPLC/MS: MH+=652.

Example 94

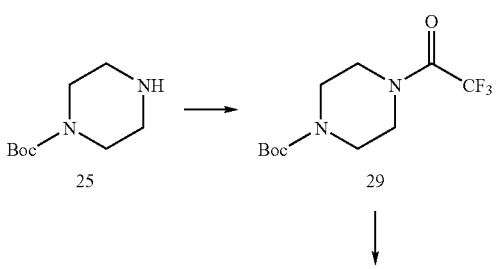

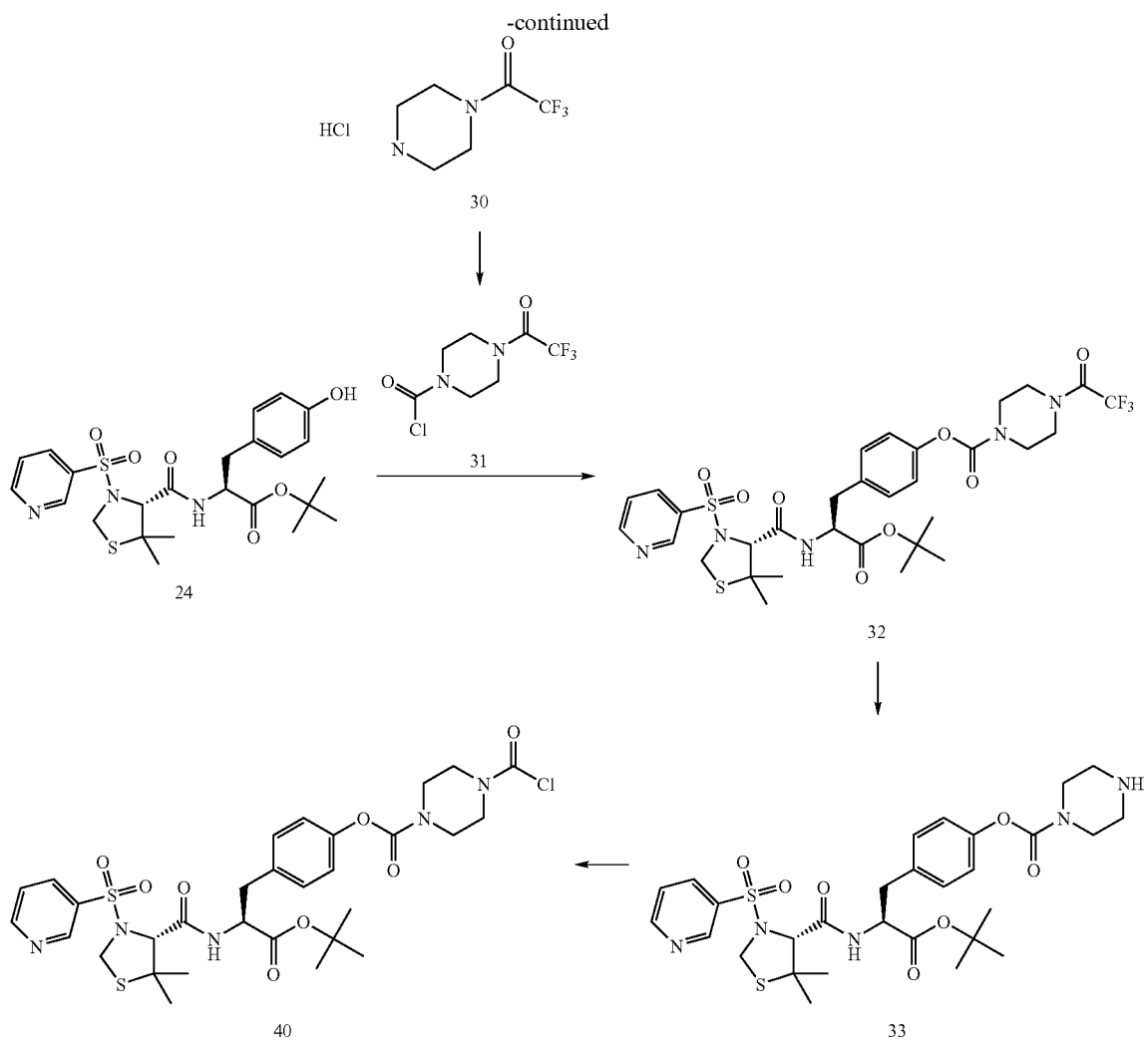

Compound 25 (20 g, 0.11 mol) was dissolved in CH$_2$Cl$_2$ (500 mL) under N$_2$. The reaction mixture was cooled to 0° C. Triethylamine (18.12 mL, 0.13 mol) was added, followed by trifluoroacetic anhydride (18.14 mL, 0.13 mol) in portions. The reaction was allowed to warm to room temperature overnight. The reaction mixture was concentrated in vacuo and the residue was taken up in ethyl acetate (200 mL). The organic phase was washed with H$_2$O, sat. NaHCO$_3$, brine, dried over Na$_2$SO$_4$, filtered, and concentrated in vacuo to yield 29.7 g (96%) 29 as a yellow solid.

$^1$H NMR (CDCl$_3$) δ 3.64-3.60 (m, 2H), 3.55-3.53 (m, 2H), 3.49-3.45 (m, 4H), 1.44 (s, 9H).

$^{13}$C NMR (CDCl$_3$) δ 155.7 (J$_{C-F}$=36 Hz), 154.3, 116.4 (J$_{C-F}$=288 Hz), 80.8, 45.7, 43.3, 28.3.

Compound 29 (29.26 g, 0.10 mol) was added in portions to a 500 mL flask containing a solution of 4N HCL in dioxane (200 mL) at 0° C. The reaction was stirred in ice bath for 4 hours when TLC (3:1 hexanes:ethyl acetate) showed 100% conversion to product. The reaction mixture was concentrated in vacuo and treated with ethyl ether (500 mL). The product was filtered and dried to yield 22.5 g (99%) 30 as a white mono-hydrochloride salt.

$^1$H NMR (DMSO-d$_6$) δ 3.82-3.79 (m, 4H), 3.53 (s, 1H), 3.18-3.16 (m, 4H).

$^{13}$C NMR (DMSO-d$_6$) δ 154.3 (J$_{C-F}$=35 Hz), 115.9 (J$_{C-F}$=289 Hz), 66.1, 42.0, 41.9, 41.5.

A 250 mL flask was charged with 30 (1.0 g, 4.6 mmol), CH$_2$Cl$_2$ (40 mL), and sat. NaHCO$_3$ (40 mL). The reaction mixture was stirred vigorously at 0° C. for 15 minutes. Stirring was ceased and the layers were allowed to separate. A 2.0 M solution of phosgene in toluene (9 mL, 18 mmol) was added to the reaction mixture which was stirred vigorously for 30 minutes, maintaining temperature at 0° C. The layers were separated and the aqueous phase was washed with CH$_2$Cl$_2$ (15 mL). The combined organic layers were washed with brine, dried over Na$_2$SO$_4$, filtered, and concentrated in vacuo. The residue was taken up in CH$_2$Cl$_2$ and concentrated in vacuo again to yield 1.0 g (92%) 31 as a white solid.

MS (m/z) 245, (M+H)$^+$.

$^1$H NMR (CDCl$_3$) δ 3.80-3.68 (m, 8H).

$^{13}$C NMR (CDCl$_3$) δ 155.9 (J$_{C-F}$=37 Hz), 148.7 (J$_{C-F}$=12 Hz), 116.3 (J$_{C-F}$=289 Hz), 48.3, 47.8, 45.7, 45.3, 45.1, 42.9, 42.7.

A 25 mL flask was charged with 24 (5.97 g, 0.011 mol), DMAP (1.34 g, 0.011 mol), and CH$_2$Cl$_2$ (22 mL). Triethylamine (2.4 mL, 0.017 mol) was added followed by 31 (4.2 g, 0.017 mol). The reaction mixture was heated at reflux for 20 hours. The reaction mixture was concentrated in vacuo and the residue was taken up in ethyl acetate. The organic phase was washed with sat. NaHCO$_3$, H$_2$O, brine, dried over Na$_2$SO$_4$, filtered, and concentrated in vacuo to yield 9.3 g pink foam. The crude material was purified by flash chromatography (gradient of 50% ethyl acetate/hexanes to 75% ethyl acetate/hexanes) to yield 6.1 g (76%) 32 as a pale pink foam. $R_f$=0.14 (1:1 hexanes:ethyl acetate).

MS (m/z) 730, (M+H)$^+$.

$^1$H NMR (CDCl$_3$) δ 9.08-9.07 (m, 1H), 8.87-8.85 (m, 1H), 8.16-8.14 (m, 1H), 7.52-7.48 (m, 1H), 7.25-7.22 (d, 2H), 7.03-7.00 (d, 2H), 6.91-6.88 (d, 1H), 4.78-4.70 (q, 1H), 4.60-4.44 (dd, 2H), 3.88 (s, 1H), 3.75-3.60 (m, 8H), 3.09-3.06 (m, 2H), 1.42 (s, 9H), 1.18 (s, 3H), 1.16 (s, 3H).

To a solution of 32 (6.11 g, 8.4 mmol) dissolved in MeOH (90 mL) was added a solution of potassium carbonate (5.79 g, 42 mmol) in H$_2$O (10 mL). The reaction was stirred at room temperature for 15 minutes and then concentrated in vacuo. The residue was filtered and washed with copious amounts of H$_2$O to yield 4.65 g (88%) 33 as a white solid. $R_f$=0.08 (5% MeOH/CH$_2$Cl$_2$).

MS (m/z) 634, (M+H)$^+$.

$^1$H NMR (CDCl$_3$) δ 9.09-9.08 (m, 1H), 8.87-8.85 (m, 1H), 8.16-8.14 (m, 1H), 7.52-7.48 (m, 1H), 7.23-7.20 (d, 2H), 7.03-7.00 (d, 2H), 6.91-6.88 (d, 1H), 4.78-4.70 (q, 1H), 4.59-4.46 (dd, 2H), 3.89 (s, 1H), 3.65-3.50 (m, 4H), 3.09-3.06 (m, 2H), 2.92-2.88 (m, 4H), 1.43 (s, 9H), 1.19 (s, 3H), 1.17 (s, 3H).

$^{13}$C NMR (CDCl$_3$) δ 170.1, 167.9, 154.5, 153.9, 150.7, 148.8, 136.0, 133.4, 133.2, 130.6, 124.1, 121.9, 83.0, 73.9, 55.0, 53.7, 50.7, 46.0, 45.7, 45.0, 37.9, 29.3, 28.0, 24.0.

A 250 mL flask was charged with 33 (2.5 g, 3.9 mmol), CH$_2$Cl$_2$ (40 mL), and sat. NaHCO$_3$ (40 mL). The reaction mixture was stirred vigorously at 0° C. for 15 minutes. Stirring was ceased and the layers were allowed to separate. A 2.0 M solution of phosgene in toluene (7.9 mL, 16 mmol) was quickly added to the reaction mixture, which was stirred vigorously for 60 minutes maintaining the temperature at 0° C. The layers were separated and the aqueous phase was washed with CH$_2$Cl$_2$ (30 mL). The combined organic layers were washed with 0.2 N citric acid, brine, dried over Na$_2$SO$_4$, filtered, and concentrated in vacuo to yield 2.8 g (100%) white foam. The crude material was purified through a silica plug, eluting with 100% ethyl acetate, to yield 2.2 g (78%) 40 as a white foam. $R_f$=0.43 (3:1 ethyl acetate:hexanes).

$^1$H NMR (CDCl$_3$) δ 9.09-9.08 (m, 1H), 8.87-8.85 (m, 1H), 8.16-8.14 (d, 1H), 7.52-7.48 (m, 1H), 7.25-7.22 (d, 2H), 7.03-7.01 (d, 2H), 6.90-6.88 (d, 1H), 4.78-4.70 (q, 1H), 4.60-4.45 (dd, 2H), 3.88 (s, 1H), 3.79-3.65 (m, 8H), 3.10-3.07 (m, 2H), 1.43 (s, 9H), 1.18 (s, 3H), 1.17 (s, 3H).

$^{13}$C NMR (CDCl$_3$) δ 169.9, 167.9, 154.1, 153.6, 150.2, 148.5, 136.1, 133.8, 130.6, 124.2, 121.7, 82.9, 73.7, 54.8, 53.8, 50.6, 48.3, 45.8, 37.7, 29.2, 27.9, 23.9.

Example 95

A. Synthesis of Carbamate-Linked bis-PEG Conjugate t-butyl Ester

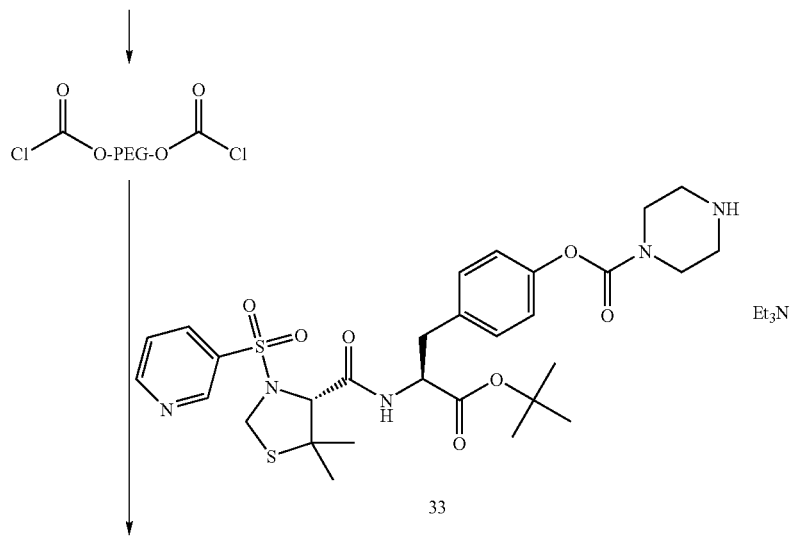

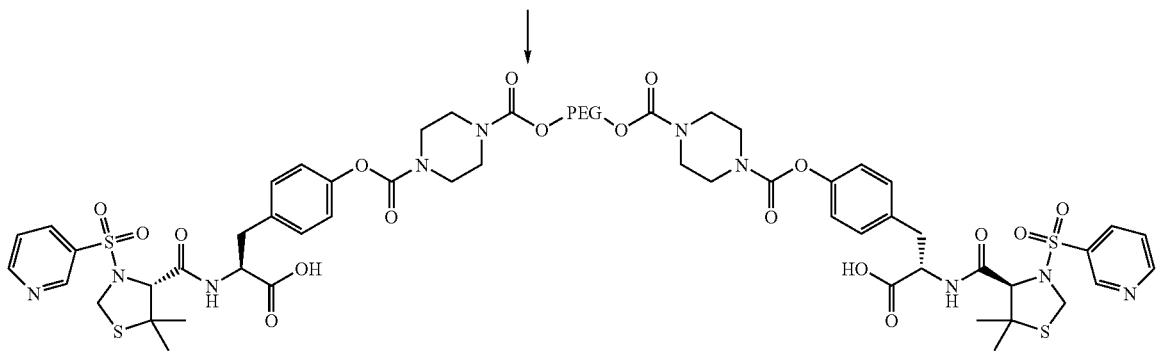

The carbamate linked conjugates were prepared based on a method modified from WO 92/16555, which is hereby incorporated by reference. Thus, the 6 kDa PEG-diol (500 mg, 0.083 mmol) was dissolved in a minimal amount of $CH_2Cl_2$ (0.1 mL). To this was added a 2.0 M solution of phosgene in toluene (0.6 mL, 1.2 mmol). The reaction mixture was stirred at room temperature for 18 hours and then concentrated in vacuo to yield 500 mg (100%) of the 6 kDa PEG bis-chloroformate as a white solid.

A solution of 33 (211 mg, 0.33 mmol) in $CH_2Cl_2$ (3 mL) (see Example 94) was added to the 6 kDa PEG bis-chloroformate (500 mg, 0.08 mmol) dissolved in $CH_2Cl_2$ (2 mL). Triethylamine (11 μL, 0.08 mmol) was added, and the reaction mixture was stirred at room temperature for 18 hours. The reaction mixture was concentrated in vacuo, and the residue was dissolved in MeOH (10 mL). 2% cross-linked polystyrene sulfonic acid resin (410 mg) was added, and the reaction vessel was swirled for 2 hours. The mixture was filtered, and the filtrate was concentrated in vacuo to yield 500 mg (87%) of a white solid. A portion of the material (246 mg) was purified by HPLC, yielding 156 mg of the 6 kDa PEG bis-conjugate t-butyl ester as a white solid. HPLC determined the conjugate to be >99% pure (retention time=9.655 min).

$^1$H NMR (CDCl$_3$) δ 9.07 (bs, 2H), 8.86-8.84 (m, 2H), 8.18-8.15 (d, 2H), 7.53-7.48 (m, 2H), 7.22-7.19 (d, 4H), 7.03-6.99 (d, 4H), 6.86-6.83 (d, 2H), 4.73-4.70 (m, 2H) 4.58-4.44 (dd, 4H), 4.27-4.24 (m, 4H), 3.62 (bs, 621H), 3.40-3.37 (m, 6H), 3.07-3.05 (m, 4H), 1.41 (s, 18H), 1.20-1.16 (d, 12H).

B. Synthesis of Carbamate-Linked bis-PEG Conjugate

The purified 6 kDa carbamate-linked bis-PEG conjugate t-butyl ester (100 mg, 0.01 mmol) was dissolved in formic acid (5 mL) and heated at 40° C. for 24 hours. The reaction was concentrated in vacuo. The residue was dissolved in water, concentrated in vacuo, dissolved again in water, and lyophilized to yield 100 mg (100%) of the 6 kDa carbamate-linked bis-PEG conjugate carboxylic acid as a white powder. HPLC determined conjugate to be >99% pure (retention time=7.63 min).

$^1$H NMR (CDCl$_3$) δ 9.06 (bs, 2H), 8.84-8.83 (m, 2H), 8.17-8.14 (d, 2H), 7.53-7.49 (m, 2H), 7.24-7.21 (d, 4H), 7.02-6.99 (d, 4H), 6.94-6.92 (d, 2H), 4.81-4.79 (m, 2H), 4.57-4.48 (dd, 4H), 4.28-4.25 (m, 4H) 3.64 (bs, 621H), 3.41-3.38 (m, 6H), 3.23-3.08 (m, 4H), 1.23-1.18 (d, 12H).

Example 96

A. Synthesis of Carbamate-Linked Octa-PEG Conjugate t-butyl Ester

Nektar cat. no. 0J00T08 8-arm PEG: MW 40 kDa

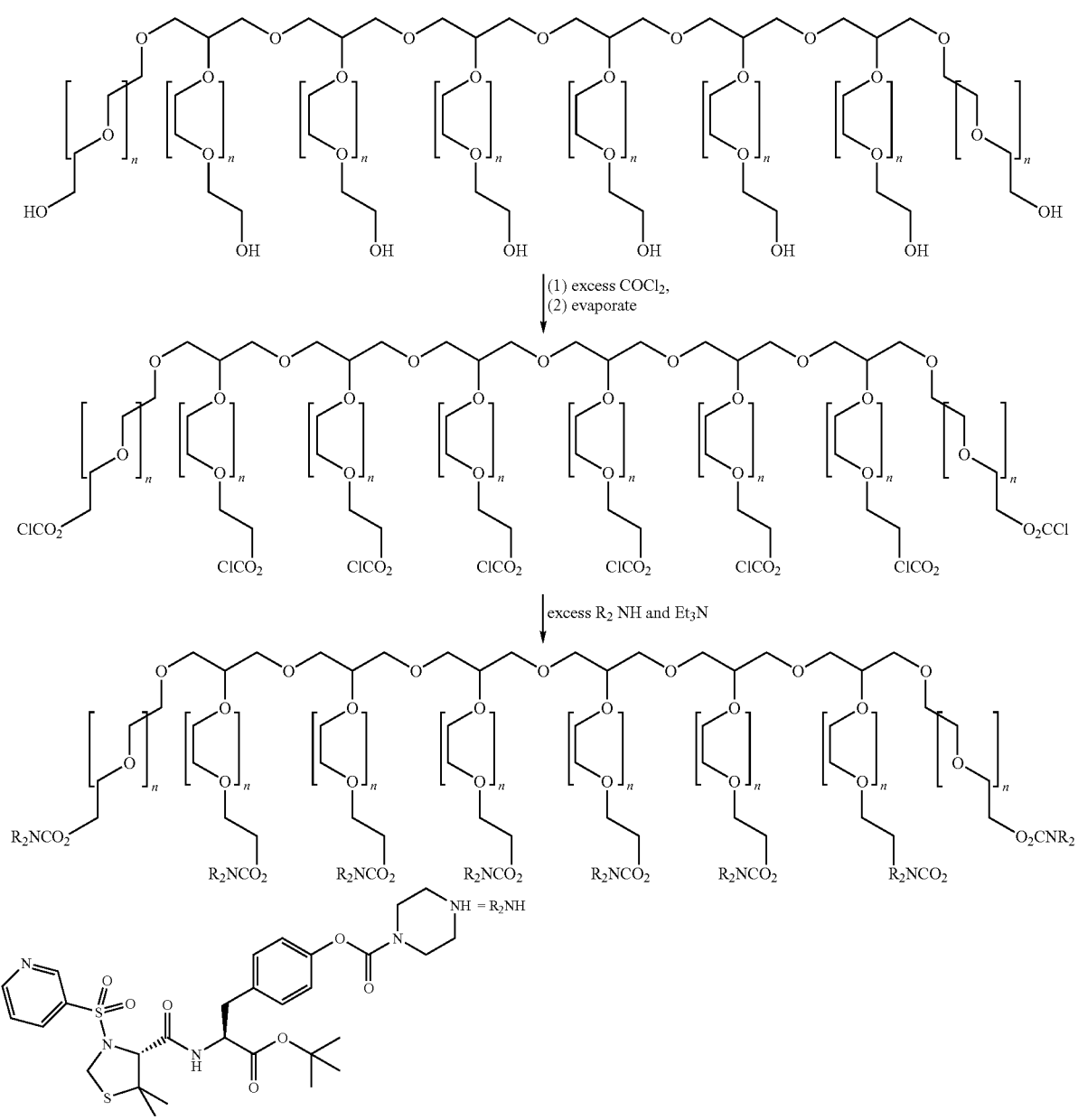
Scheme E
By following the procedures used in Example 95 above and employing an octa-pegylated hub molecule, the title compound was prepared.
Example 97

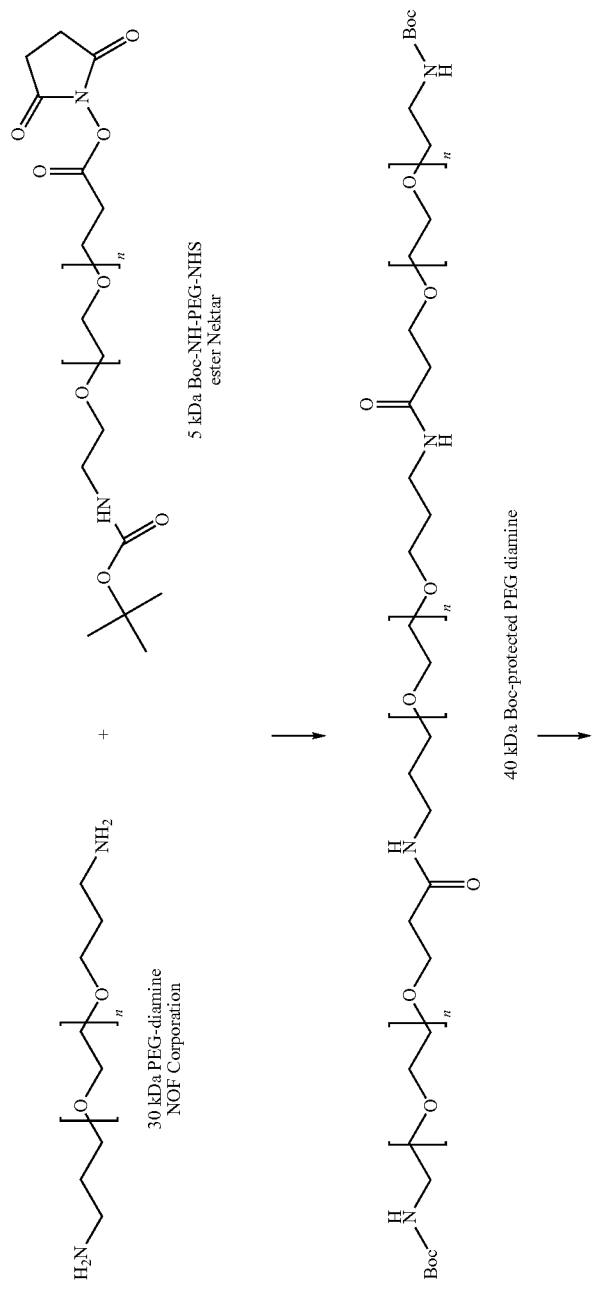

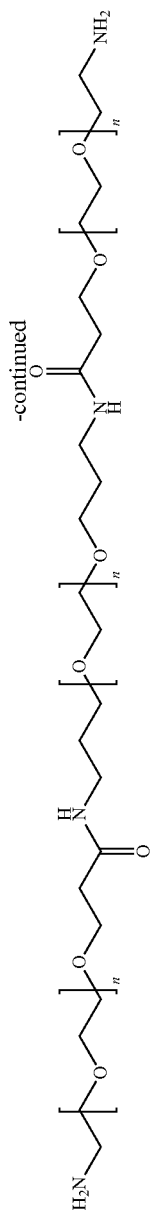
40 kDa PEG diamine
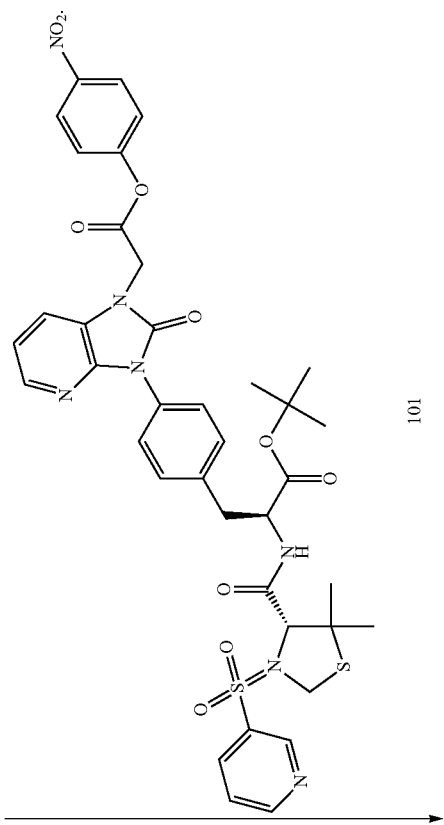
101

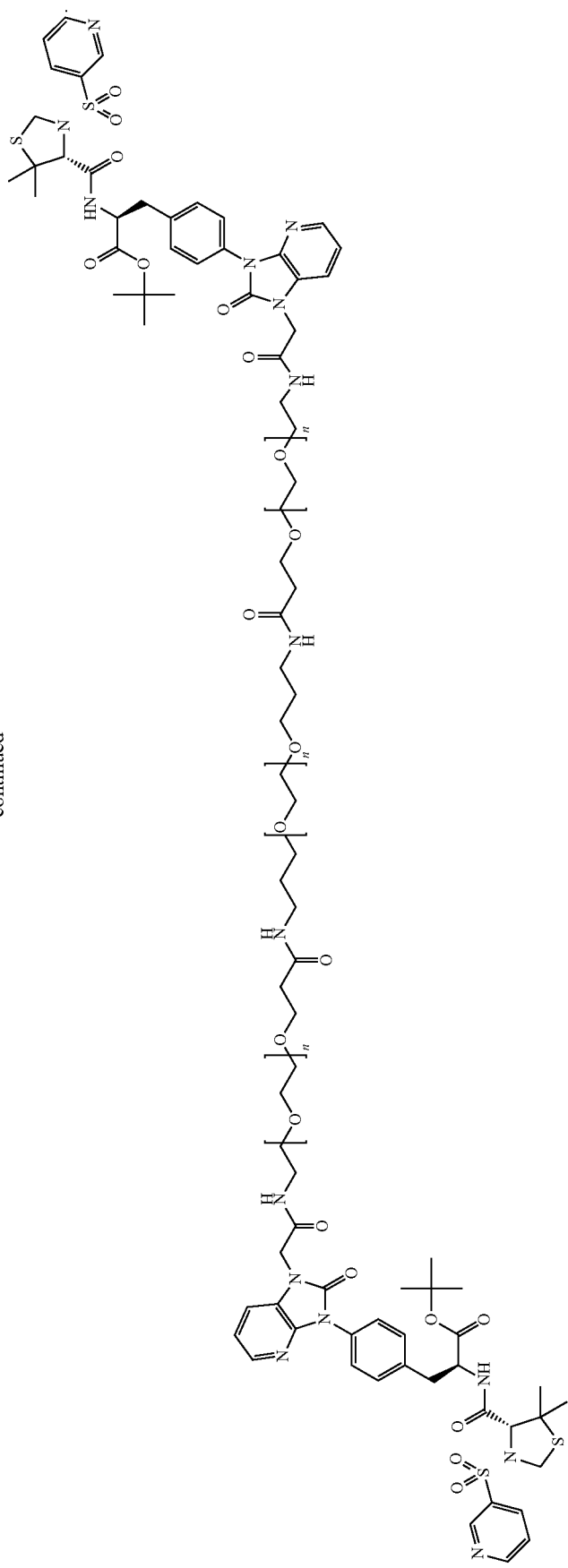

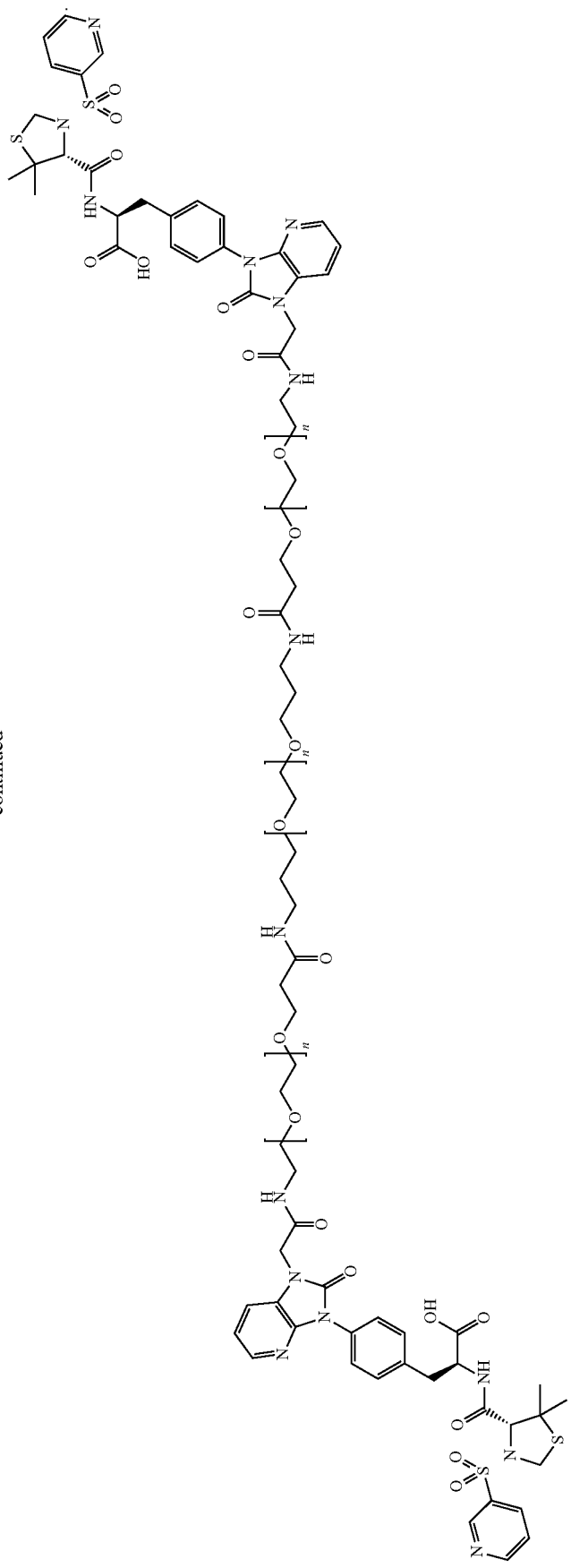

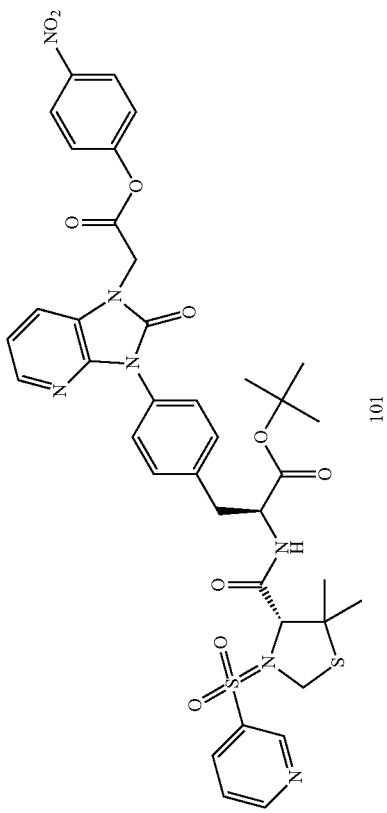
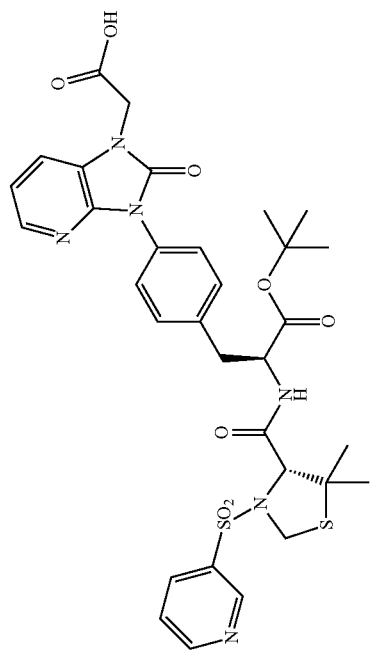
Nitro-phenyl ester (101)

A solution of 100 (100 mg, 0.14 mmol) and 4-nitrophenol (24 mg, 0.17 mmol) in THF (0.7 mL) was cooled in an ice bath. A suspension of EDC (33 mg, 0.17 mmol) in $CH_2Cl_2$ (0.7 mL) was added and the reaction was stirred at 0° C. for 4 hours. The reaction was diluted with ethyl acetate (100 mL) and washed with 0.2 N citric acid. The organic layer was washed with 10% $K_2CO_3$, brine, dried over $Na_2SO_4$, filtered, and concentrated in vacuo to yield 90 mg (96%) of 101, which was used immediately.

$^1$H NMR (CDCl$_3$) δ 9.07 (bs, 1H), 8.84-8.83 (d, 1H), 8.28-8.25 (d, 2H), 8.16-8.14 (d, 1H), 8.09-8.07 (d, 1H), 7.65-7.63 (d, 2H), 7.51-7.47 (dd, 1H), 7.41-7.39 (d, 2H), 7.36-7.35 (d, 2H), 7.12-7.07 (m, 1H), 6.95-6.92 (d, 1H), 5.00 (s, 2H), 4.82-4.76 (m, 1H), 4.62-4.45 (dd, 2H), 3.91 (s, 1H), 3.18-3.12 (m, 2H), 1.44 (s, 9H), 1.18-1.16 (d, 6H).

concentrated in vacuo and purified according to HPLC Method A to yield 0.14 g (68%) of 103 as a white solid. HPLC Method C determined the conjugate to be >99% pure (retention time=7.3 minutes).

$^1$H NMR (CDCl$_3$) δ 9.05 (bs, 2H), 8.82-8.81 (m, 2H), 8.17-8.14 (d, 2H), 8.05-8.04 (d, 2H), 7.65-7.58 (m, 4H), 7.54-7.48 (m, 2H), 7.41-7.34 (d, 4H), 7.10-7.05 (m, 2H) 6.95-6.93 (d, 2H), 4.90 (m, 2H), 4.63-4.49 (m, 6H), 3.64 (bs, 3042H, PEG), 3.35-3.29 (m, 6H), 3.22 (m, 5H), 2.45-2.41 (t, 4H), 1.79-1.74 (m, 4H), 1.29-1.27 (d, 12H).

Example 98

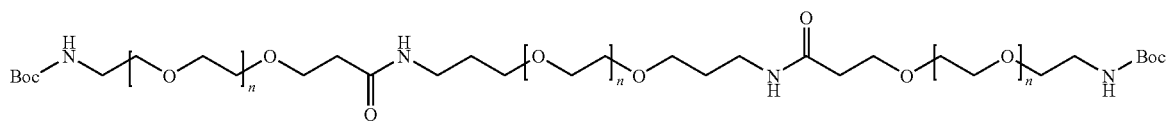

40 kDa Boc-Protected PEG Diamine

The 30 kDa PEG diamine (1 g, 0.033 mmol) and the 5 kDa Boc-NH-PEG-NHS ester (0.67 g, 0.13 mmol) were dissolved in $CH_2Cl_2$ (10 mL). Diisopropylethylamine (0.116 mL, 0.67 mmol) was added and the reaction stirred at room temperature for 18 hours. The reaction was concentrated in vacuo to yield crude product. The residue was purified according to HPLC Method B to yield 0.46 g of the 40 kDa Boc-protected PEG diamine as a white solid. HPLC Method C determined the product to be >96% pure (retention time=7.6 minutes).

$^1$H NMR (CDCl$_3$) δ 6.75 (bs, 2H), 5.15 (bs, 2H) 3.64 (s, 2940H, PEG), 3.33-3.31 (m, 10H), 2.47-2.43 (m, 4H), 1.44 (s, 18H).

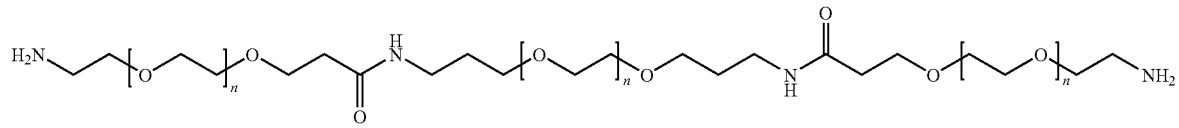

40 kDa PEG Diamine

The 40 kDa Boc-protected PEG diamine (0.2 g, 0.005 mmol) was dissolved in TFA (4 mL) and stirred at room temperature for 2 hours. The reaction was concentrated in vacuo to yield 200 mg (100%) crude 40 kDa PEG diamine as a beige residue. HPLC Method C determined the product to be >96% pure (retention time=6.5 minutes).

$^1$H NMR (CDCl$_3$) δ 7.85 (bs, 1H), 6.75 (bs, 1H), 3.64 (s, 2432H, PEG), 3.34-3.32 (m, 10H), 2.47-2.45 (m, 4H).

t-butyl Ester (102)

The 40 kDa PEG diamine (0.2 g, 0.005 mmol) was dissolved in $CH_2Cl_2$ (4 mL). Diisopropylethylamine (17 μL, 0.1 mmol) was added, followed by compound 101 (0.082 g, 0.1 mmol). Another portion of diisopropylethylamine (17 μL) was added and the reaction was stirred at room temperature for 18 hours. The reaction was concentrated in vacuo to yield 300 mg (150%) crude 102 as a white solid. HPLC Method C determined the product to be >70% pure (retention time=8.9 minutes). Crude product was used as is.

Conjugate 103

102 (0.3 g, 0.007 mmol) was dissolved in formic acid (5 mL) and heated at 40° C. for 24 hours. The reaction was

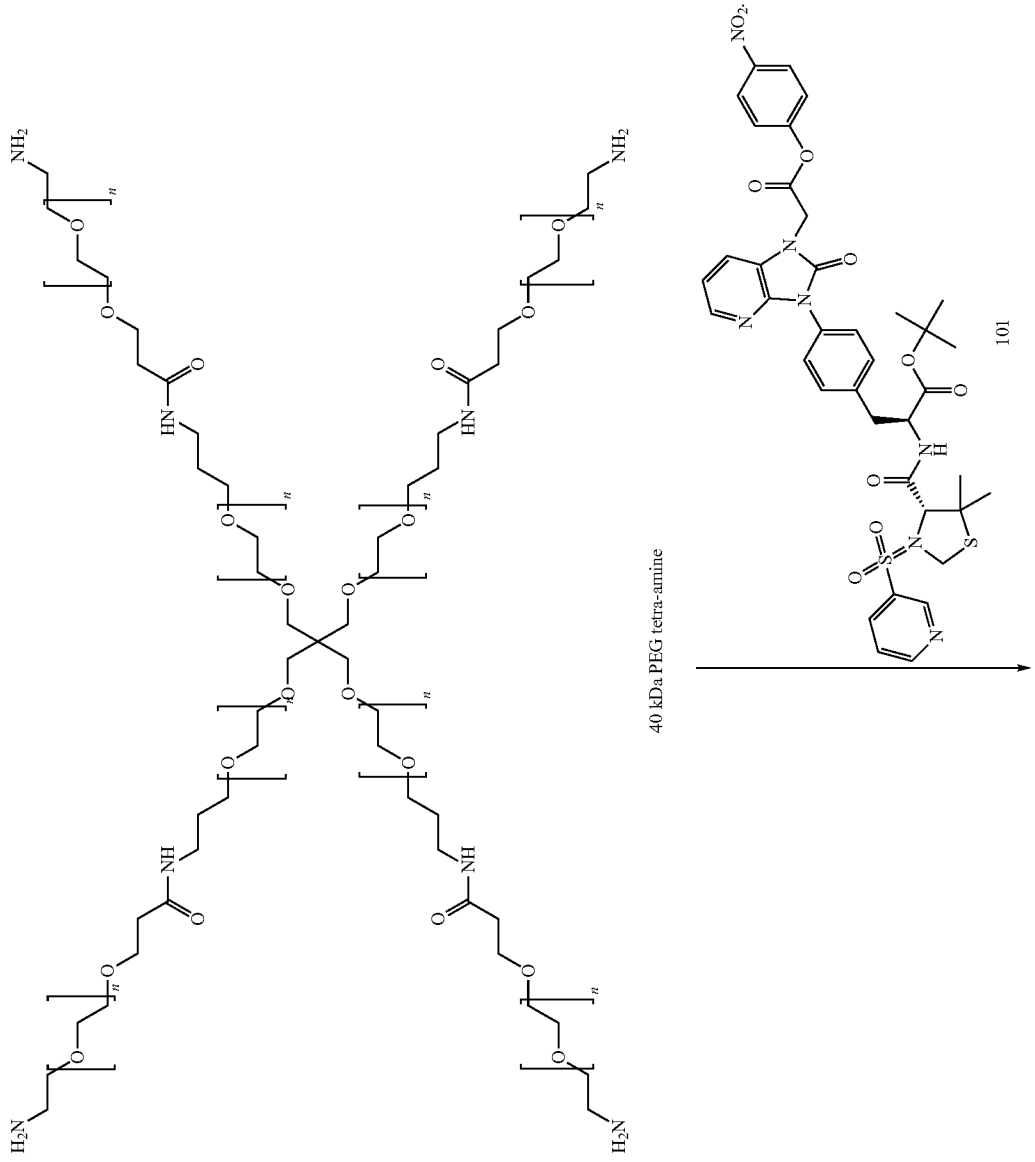

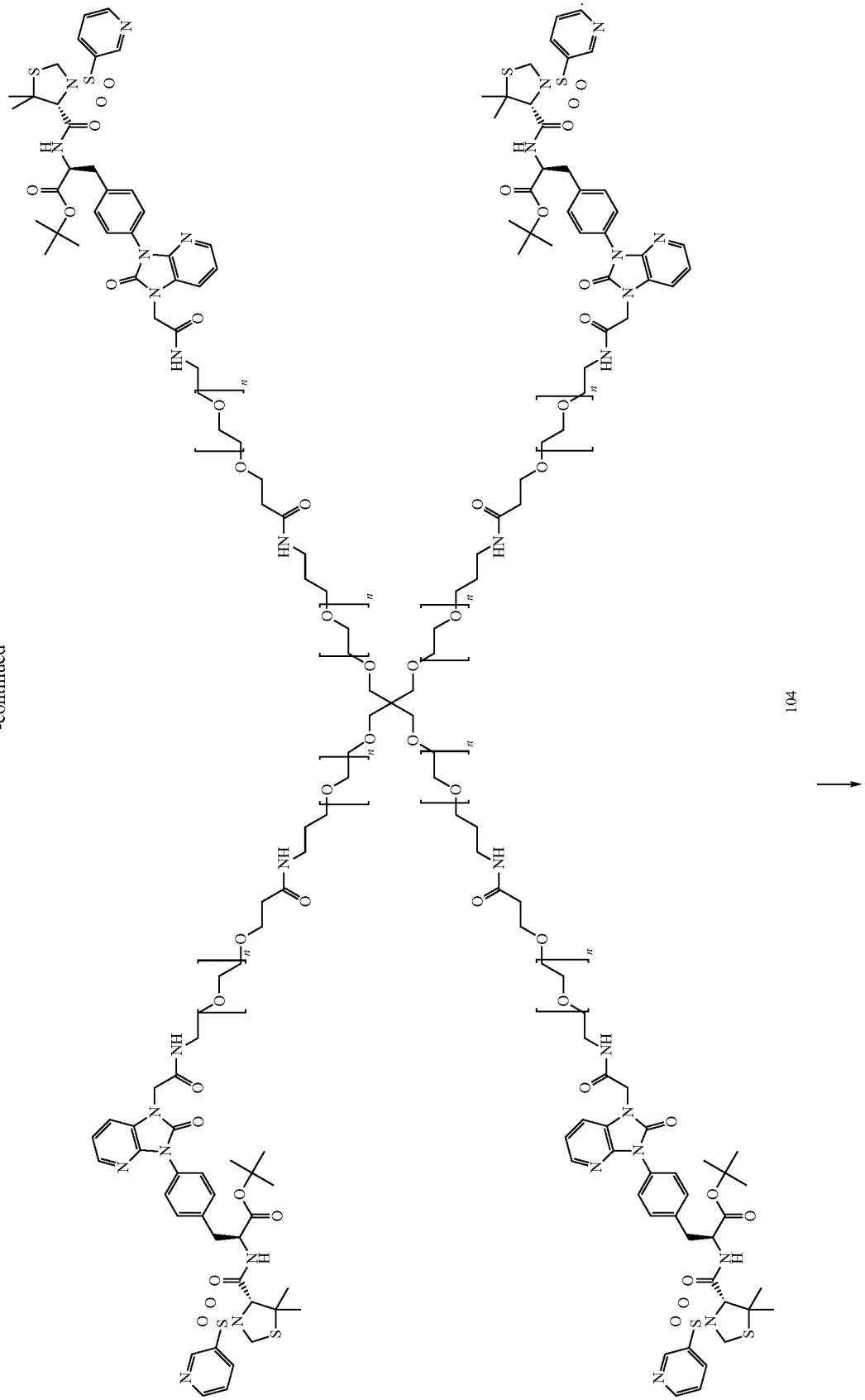

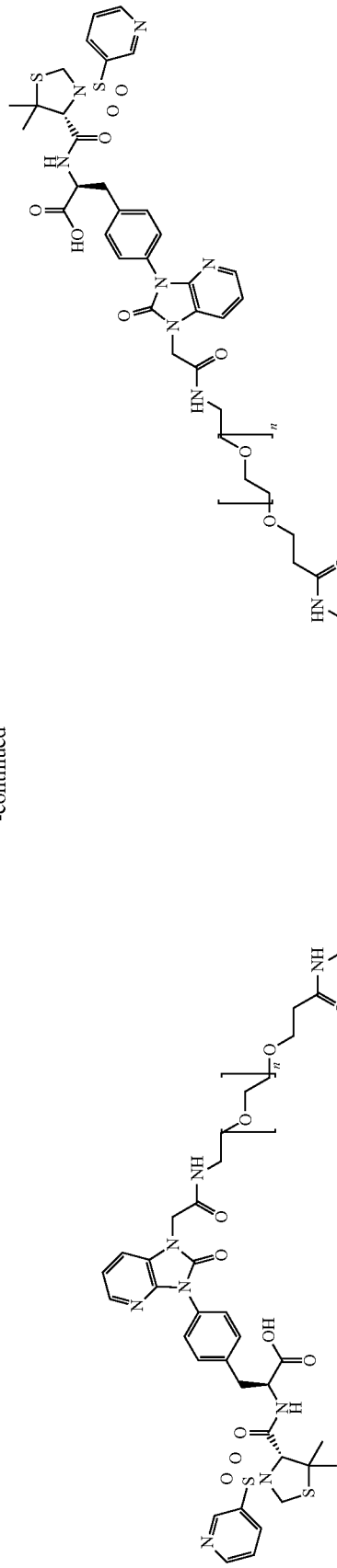
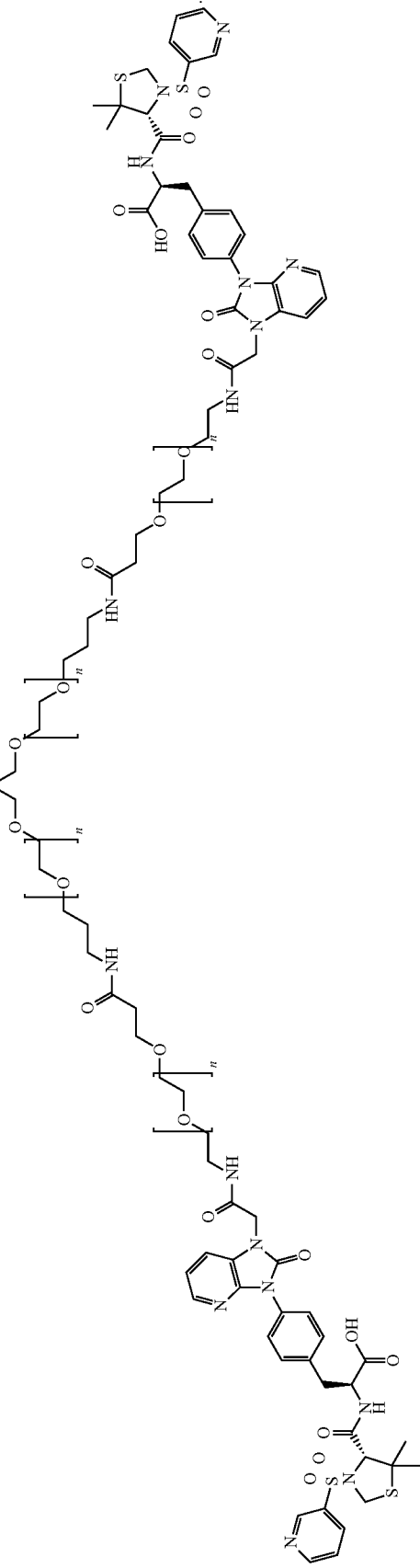

Synthesis of Polymer
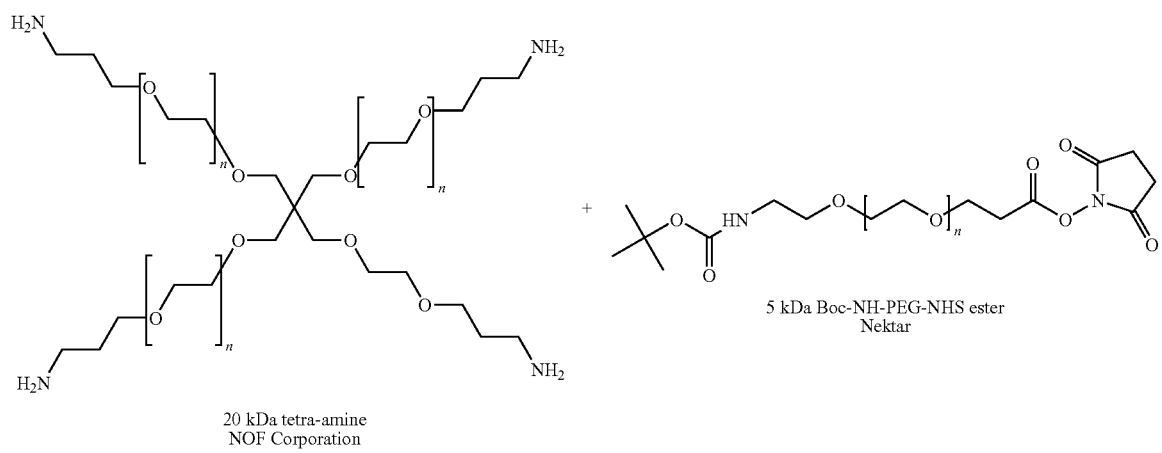
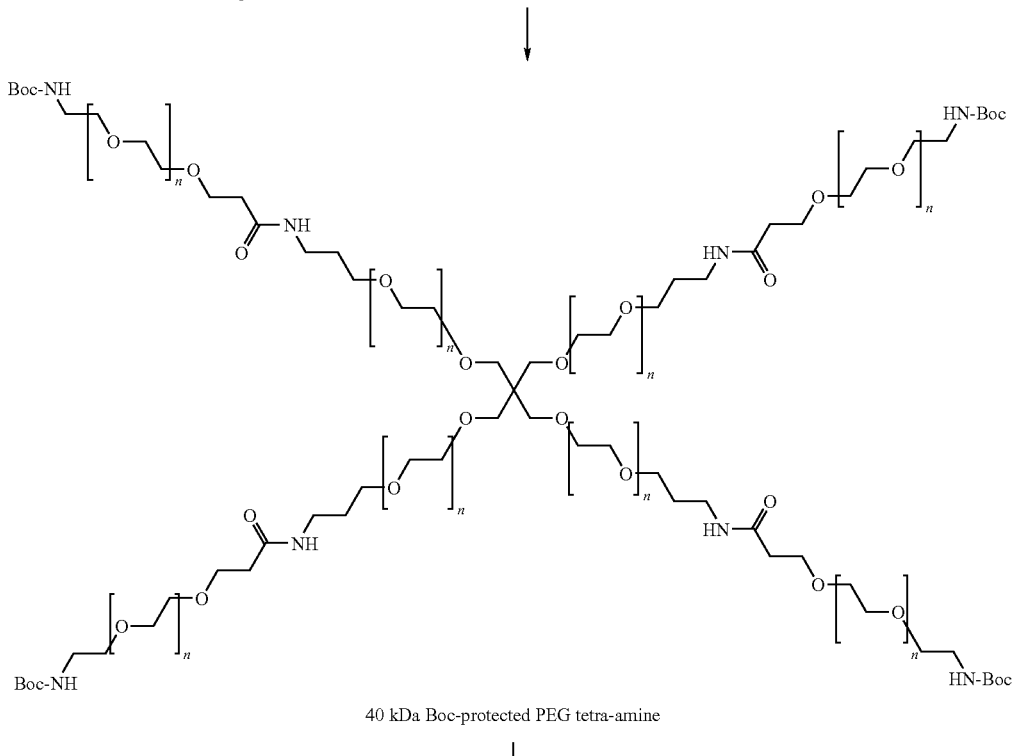

-continued

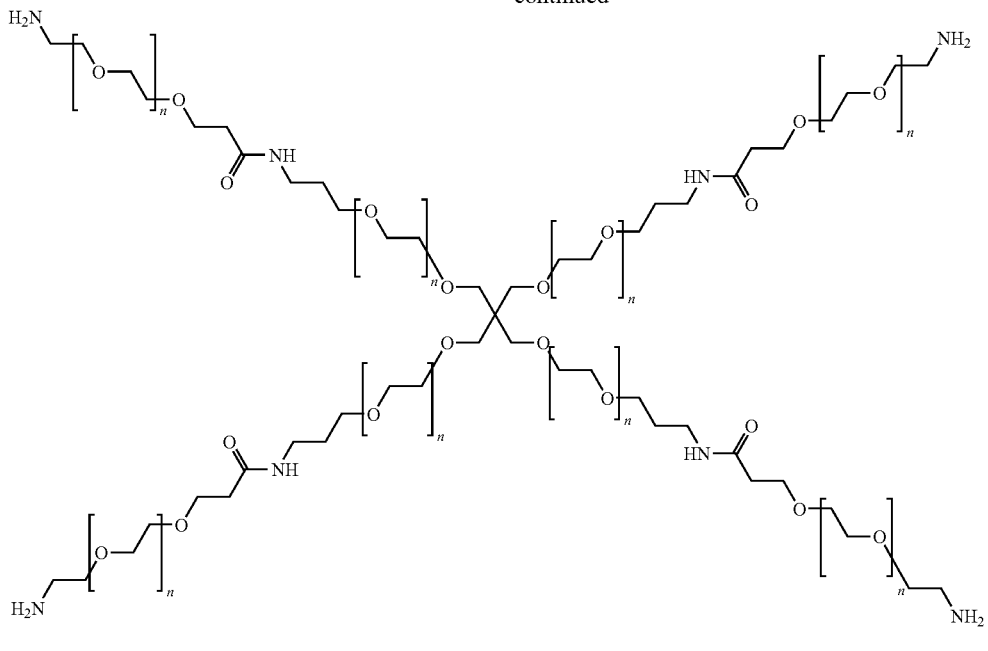

40 kDa PEG tetra-amine 40 kDa Boc-Protected PEG Tetra-Amine

The 20 kDa PEG tetra-amine (0.5 g, 0.025 mmol) and the 5 kDa Boc-NH-PEG-NHS ester (1 g, 0.2 mmol) were dissolved in $CH_2Cl_2$ (5 mL). Diisopropylethylamine (0.087 mL, 0.5 mmol) was added and the reaction stirred at room temperature for 18 hours. The reaction was concentrated in vacuo and taken up in MeOH (10 mL). 2% cross-linked polystyrene sulfonic acid resin (1.17 g) was added and the reaction vessel was swirled for 2 hours. The mixture was filtered and concentrated in vacuo to yield 1.4 g crude product as a beige solid. The residue was purified according to HPLC Method B to yield 0.44 g (44%) of the 40 kDa Boc-protected PEG tetra-amine as a white solid. HPLC Method C determined the product to be >96% pure (retention time=8.4 minutes).

$^1$H NMR ($CDCl_3$) δ 6.75 (bs, 1H), 5.15 (bs, 1H), 3.64 (s, 2970H, PEG), 3.33-3.29 (m, 15H), 2.46-2.42 (t, 8H), 1.79-1.75 (m, 8H), 1.44 (s, 36H).

40 kDa PEG Tetra-Amine

The 40 kDa Boc-protected PEG tetra-amine (0.1 g, 0.0025 mmol) was dissolved in TFA (4 mL) and stirred at room temperature for 1.5 hours. The reaction was concentrated in vacuo to yield 120 mg 40 kDa PEG tetra-amine as a transparent residue. HPLC Method C determined the product to be >96% pure (retention time=6.2 minutes).

$^1$H NMR ($CDCl_3$) δ 7.39 (bs, 1H), 6.75 (bs, 1H), 4.49-4.48 (m, 4H), 3.64 (s, 3253H, PEG), 3.35-3.33 (m, 15H), 2.49-2.46 (m, 8H), 1.80-1.75 (m, 8H).

t-butyl Ester (104)

The 40 kDa PEG tetra-amine (0.1 g, 0.0025 mmol) was dissolved in $CH_2Cl_2$ (2 mL). Diisopropylethylamine (9 µL, 0.05 mmol) was added, followed by compound 101 (82 mg, 0.1 mmol). Another portion of diisopropylethylamine (9 µL) was added and the reaction was stirred at room temperature for 48 hours. The reaction was concentrated in vacuo to yield 110 mg crude 104 as a white solid. HPLC Method C determined the product to be >80% pure (retention time=10.9 minutes).

Conjugate 105

104 (0.1 g, 0.0024 mmol) was dissolved in formic acid (5 mL) and heated at 40° C. for 24 hours. The reaction was concentrated in vacuo and was purified according to HPLC Method A to yield 0.05 g (48%) of 105 as a white solid. HPLC Method C determined the conjugate to be >99% pure (retention time=7.6 minutes).

$^1$H NMR ($CDCl_3$) δ 9.06 (bs, 4H), 8.83-8.82 (m, 4H), 8.20-8.17 (d, 4H), 8.05-8.03 (d, 4H), 7.63-7.61 (m, 8H), 7.53-7.49 (m, 4H), 7.42-7.33 (m, 8H), 7.09-7.05 (m, 4H) 6.70 (m, 4H), 4.84 (m, 4H), 4.62-4.50 (m, 12H), 3.64 (bs, 2357H, PEG), 3.36-3.29 (m, 12H), 2.46-2.42 (t, 8H), 1.79-1.74 (m, 8H), 1.30-1.25 (m, 24H).

Example 99

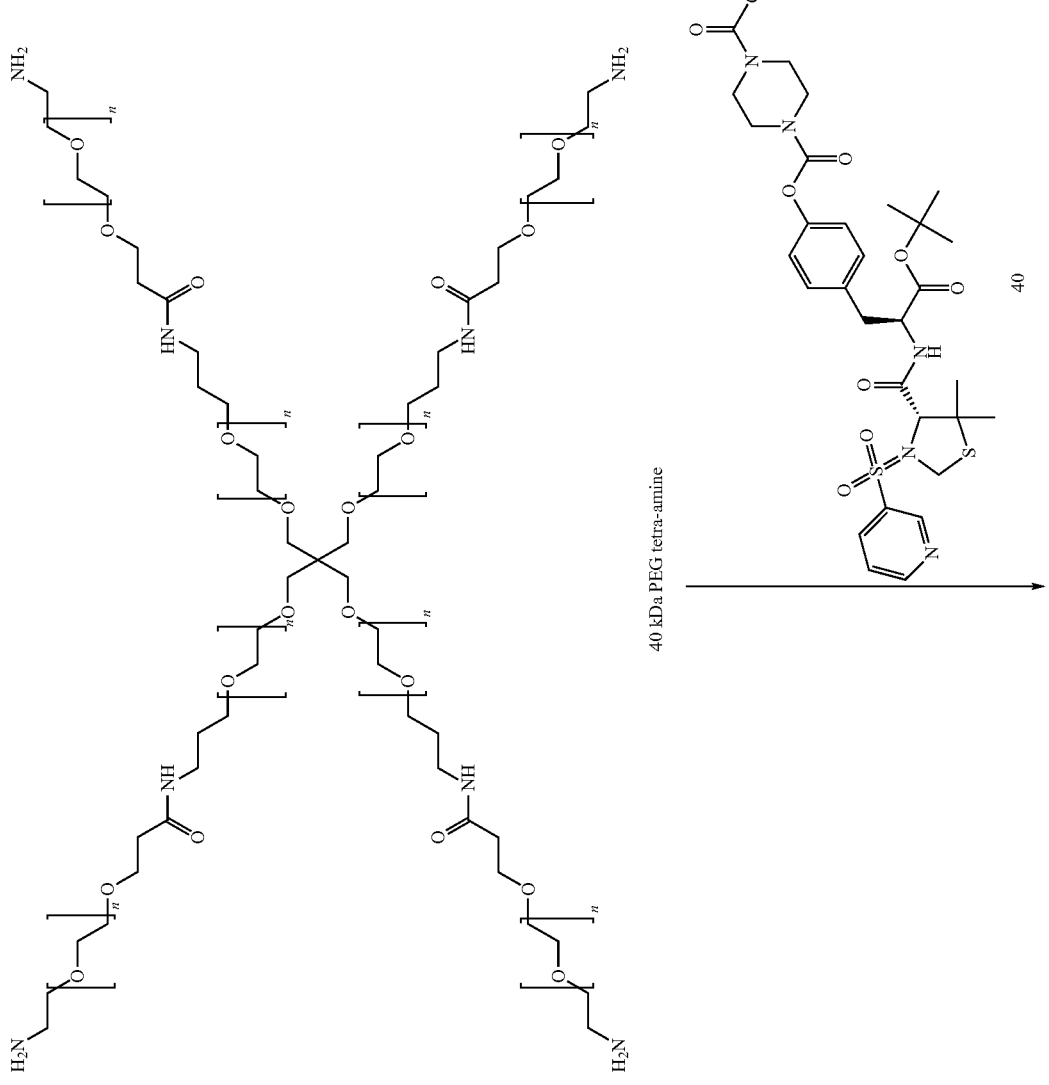

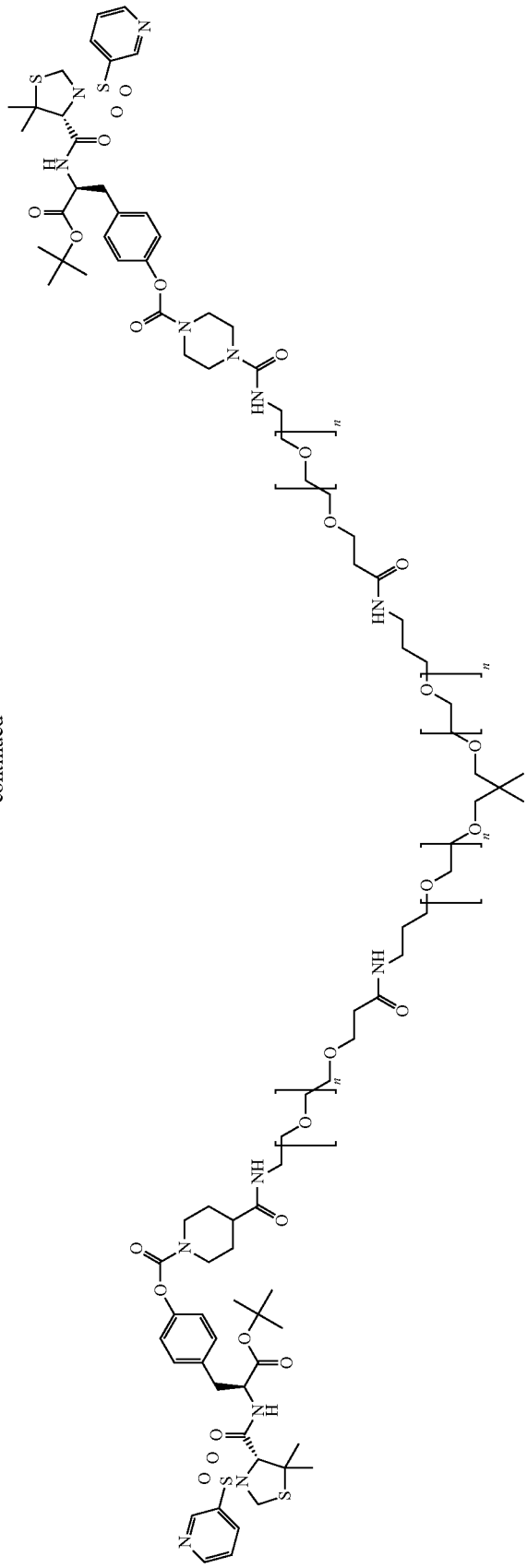

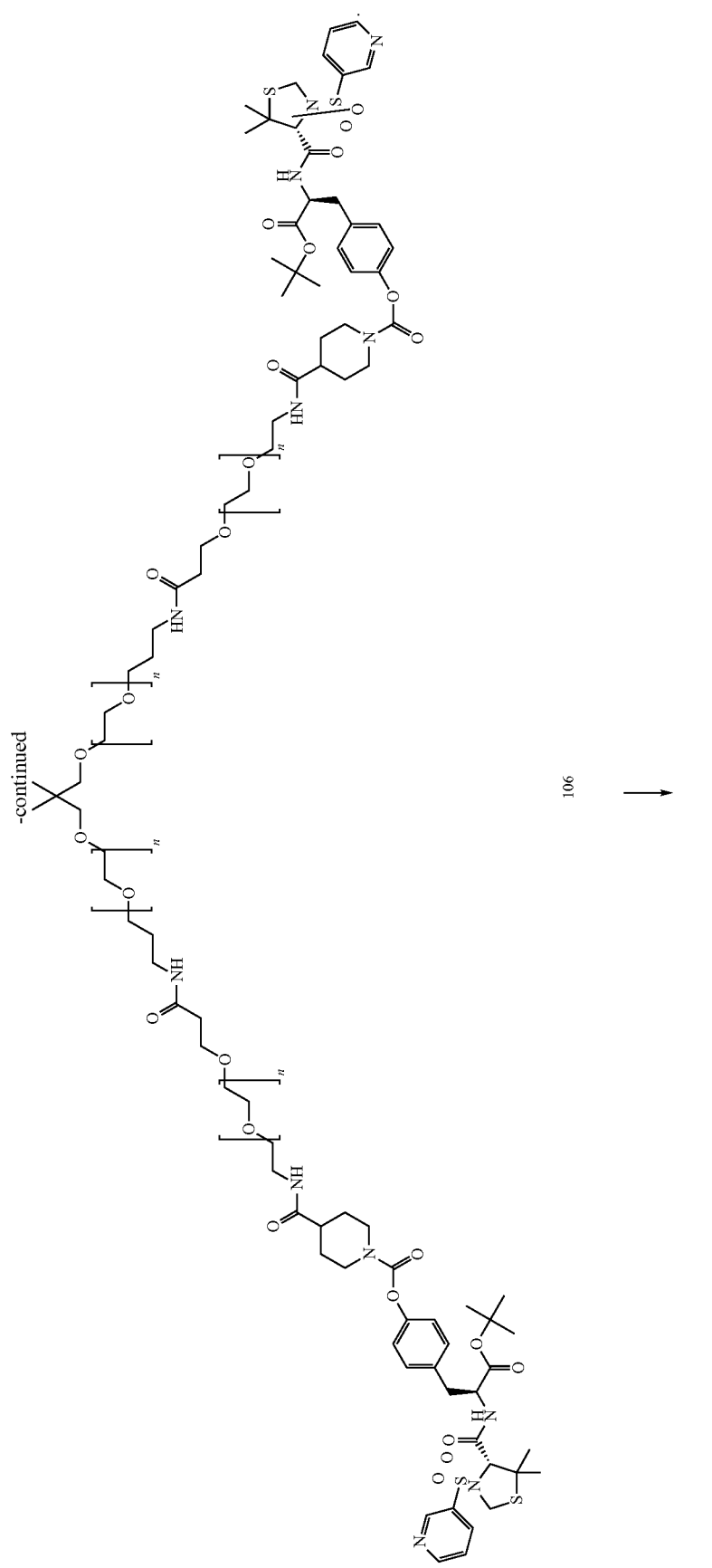

t-butyl Ester (106)

The 40 kDa PEG tetra-amine (37 mg, 0.000925 mmol) and DMAP (0.5 mg, 0.0037 mmol) were dissolved in $CH_2Cl_2$ (0.5 mL). Triethylamine (3 μL, 0.019 mmol) was added, followed by 40 (26 mg, 0.037 mmol). Another portion of triethylamine (3 μL) was added and the reaction was stirred at room temperature for 18 hours. The reaction was concentrated in vacuo to yield 34 mg crude 106 as a white solid. HPLC Method C determined the product to be >80% pure (retention time=10.9 minutes).

Conjugate 107

106 (34 mg, 0.0008 mmol) was dissolved in formic acid (4 mL) and heated at 40° C. for 24 hours. The reaction was concentrated in vacuo and purified according to HPLC Method A to yield 17 mg (50%) of 107 as a white solid. HPLC Method C determined the conjugate to be >99% pure (retention time=7.6 minutes).

$^1$H NMR ($CDCl_3$) δ 9.06 (bs, 4H), 8.86 (bs, 4H), 8.17-8.15 (d, 4H), 7.52 (d, 4H), 7.26-7.23 (d, 8H), 7.02-6.99 (d, 8H), 6.72 (m, 4H), 5.69 (m, 4H), 4.80 (m, 4H), 4.60-4.47 (dd, 8H), 3.64 (bs, 1602H, PEG), 3.36-3.30 (dd, 8H), 3.16 (m, 8H), 2.46-2.42 (t, 8H), 1.24 (bs 24H).

Example 100

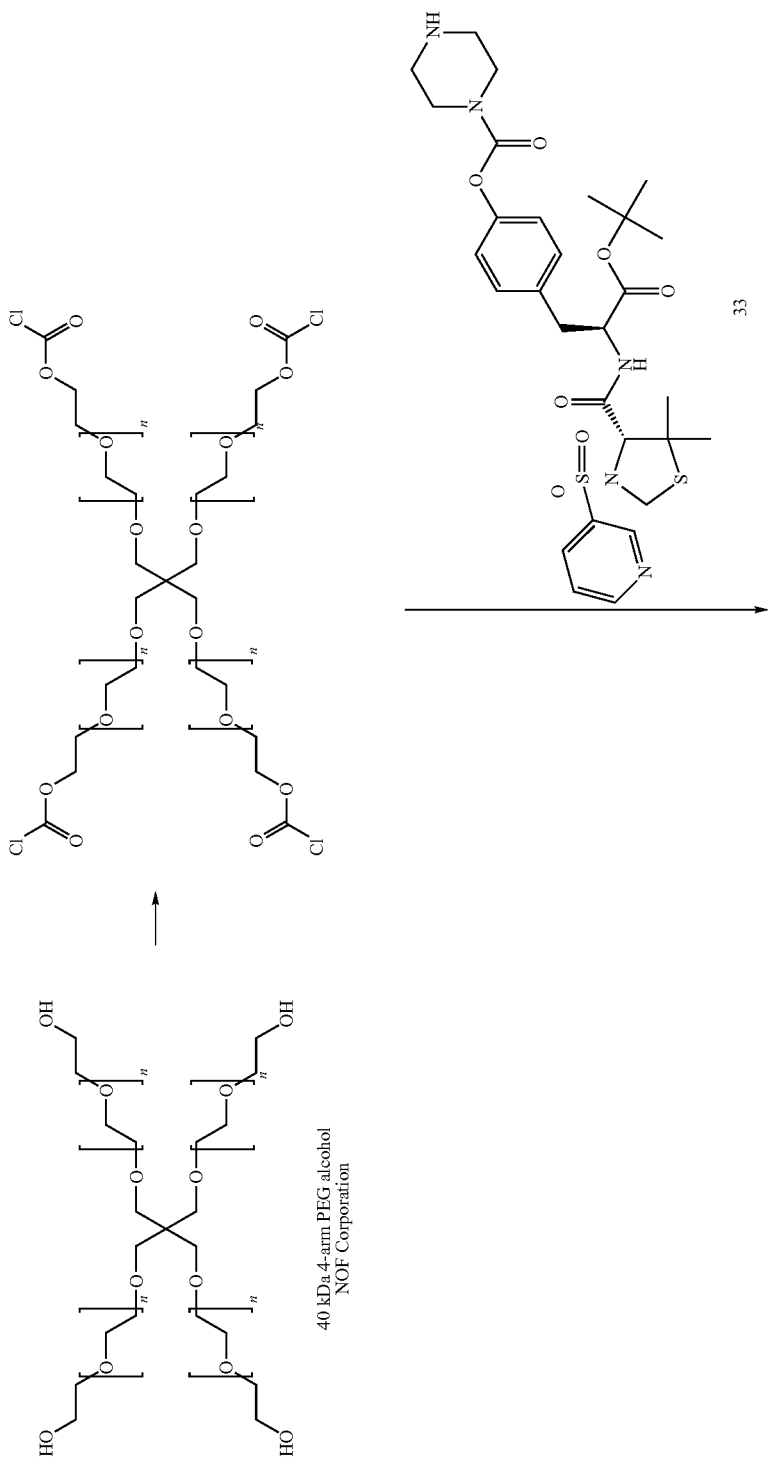

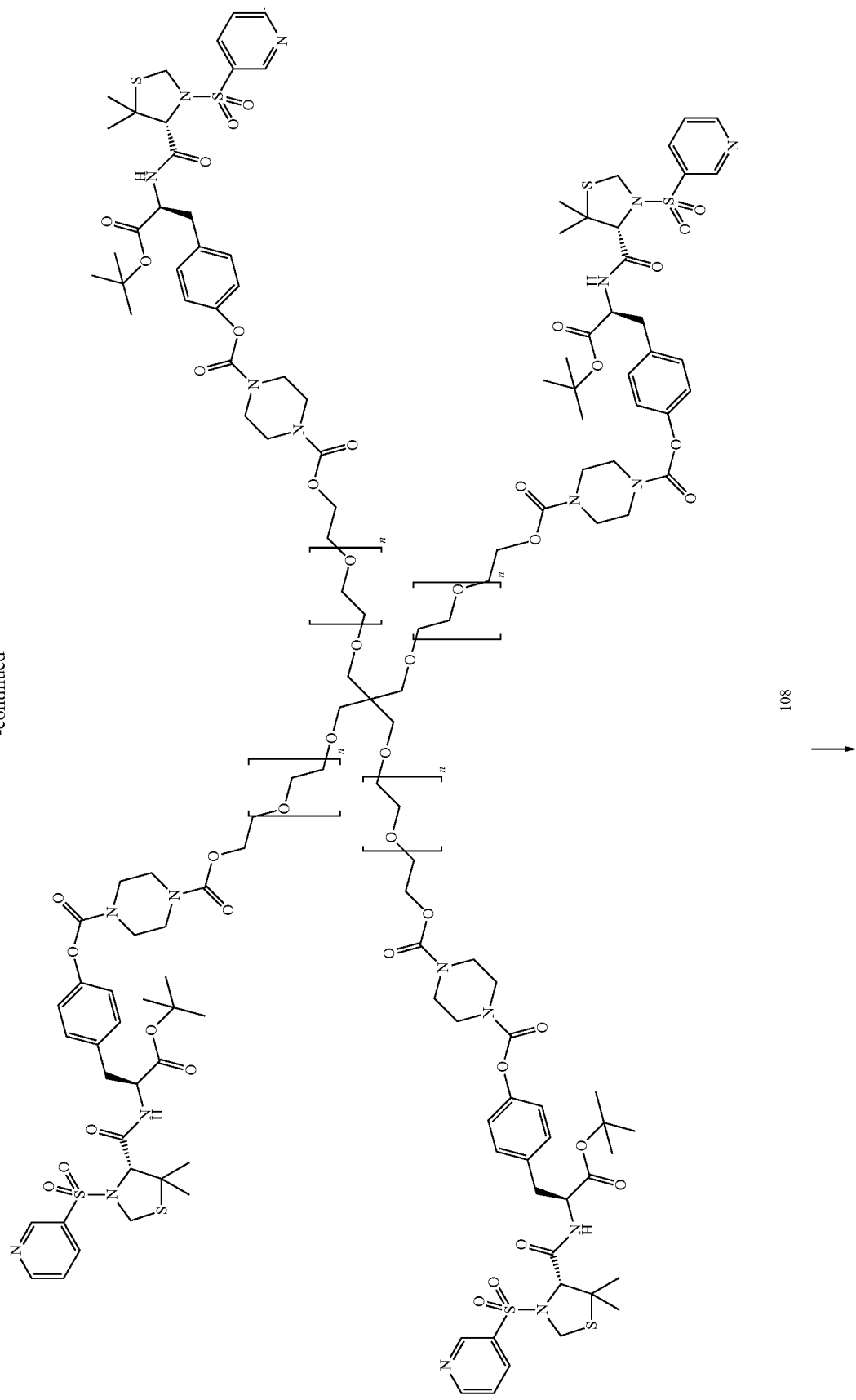

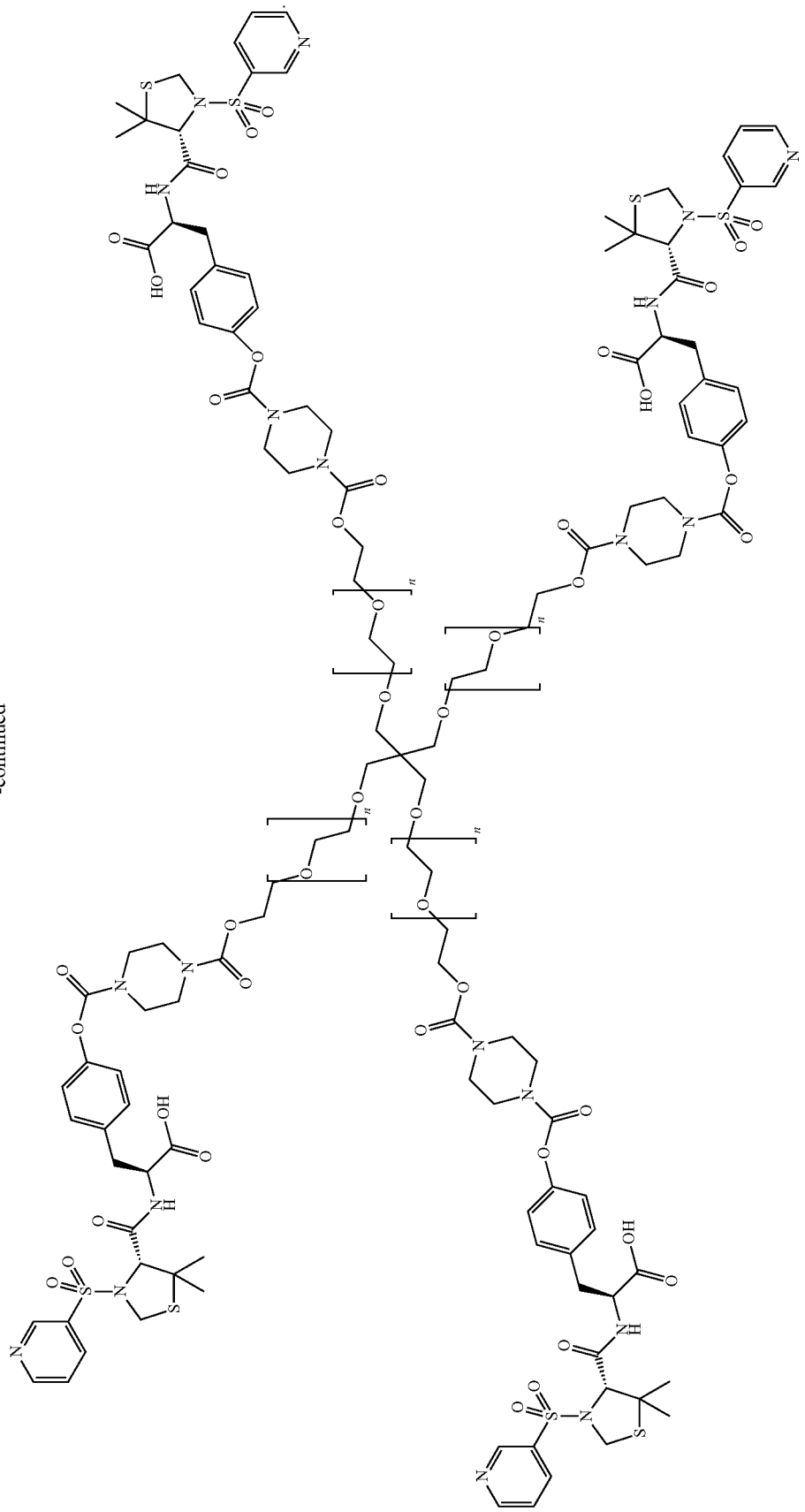

-continued
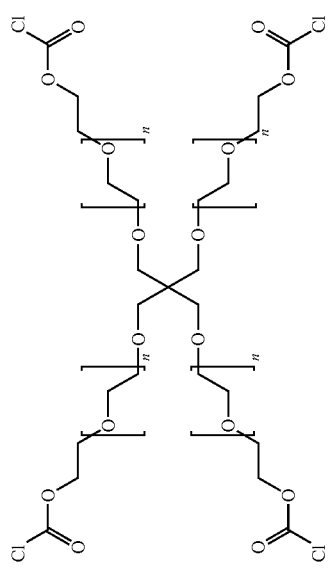

40 kDa PEG tetra-Chloroformate

The 40 kDa 4-arm PEG alcohol (0.2 g, 0.005 mmol) was dissolved in CH$_2$Cl$_2$ (1 mL). To this was added a 2.0 M solution of phosgene in toluene (0.15 mL, 0.3 mmol). The reaction was stirred at room temperature for 18 hours. The reaction was concentrated in vacuo to yield 200 mg of the 40 kDa PEG tetra-chloroformate as a white solid.

t-butyl Ester (108)

The 40 kDa PEG tetra-chloroformate (0.2 g, 0.005 mmol) was dissolved in CH$_2$Cl$_2$ (2 mL). To this was added 33 (63 mg, 0.1 mmol), followed by triethylamine (3.5 µL, 0.025 mmol). The reaction was stirred at room temperature for 72 hours. The reaction was concentrated in vacuo to yield 270 mg of 108 as a white solid.

Conjugate 109

108 (0.26 g, 0.006 mmol) was dissolved in formic acid (5 mL) and heated at 40° C. for 24 hours. The reaction was concentrated in vacuo and was purified according to HPLC Method A to yield 0.105 g (42%) of 109 as a white solid. HPLC Method C determined the conjugate to be >99% pure (retention time=8.3 minutes).

$^1$H NMR (CDCl$_3$) δ 9.06 (bs, 4H), 8.85-8.84 (m, 4H), 8.17-8.14 (d, 4H), 7.53-7.49 (m, 4H), 7.26-7.22 (d, 8H), 7.01-6.98 (d, 8H), 4.81-4.78 (m, 4H), 4.59-4.46 (dd, 8H), 4.28-4.35 (m, 8H), 3.64 (bs, 3872H, PEG), 3.15-3.13 (m, 8H), 1.24-1.19 (m, 24H).

Example 101

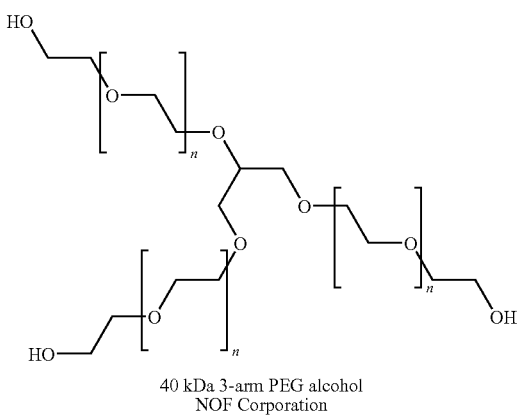

40 kDa 3-arm PEG alcohol
NOF Corporation

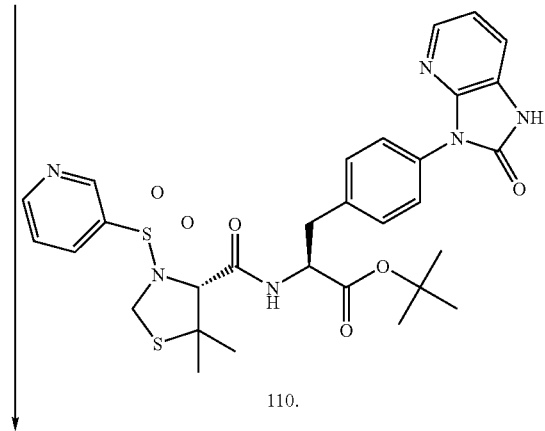

110.

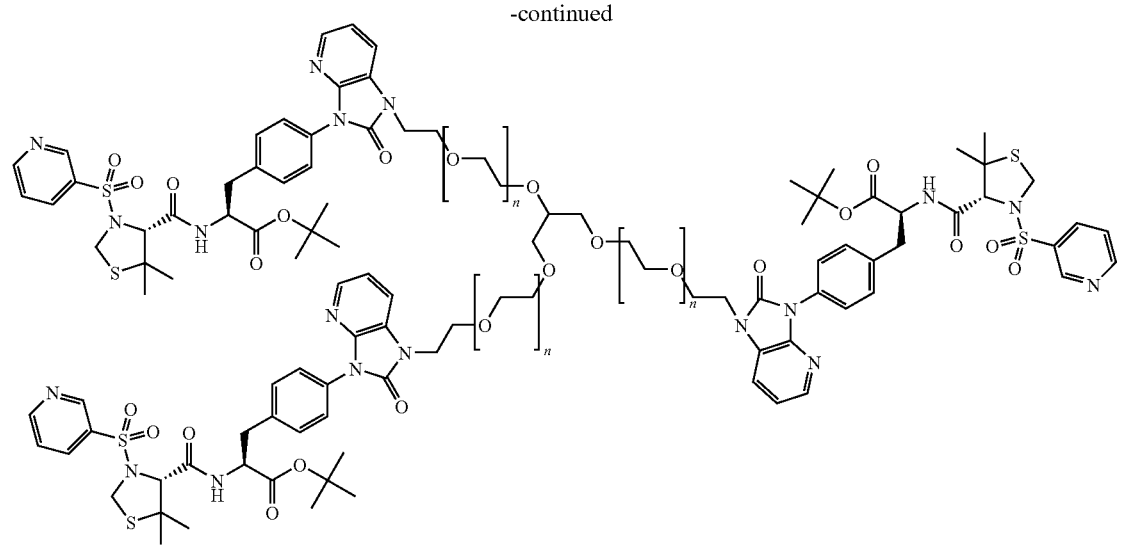

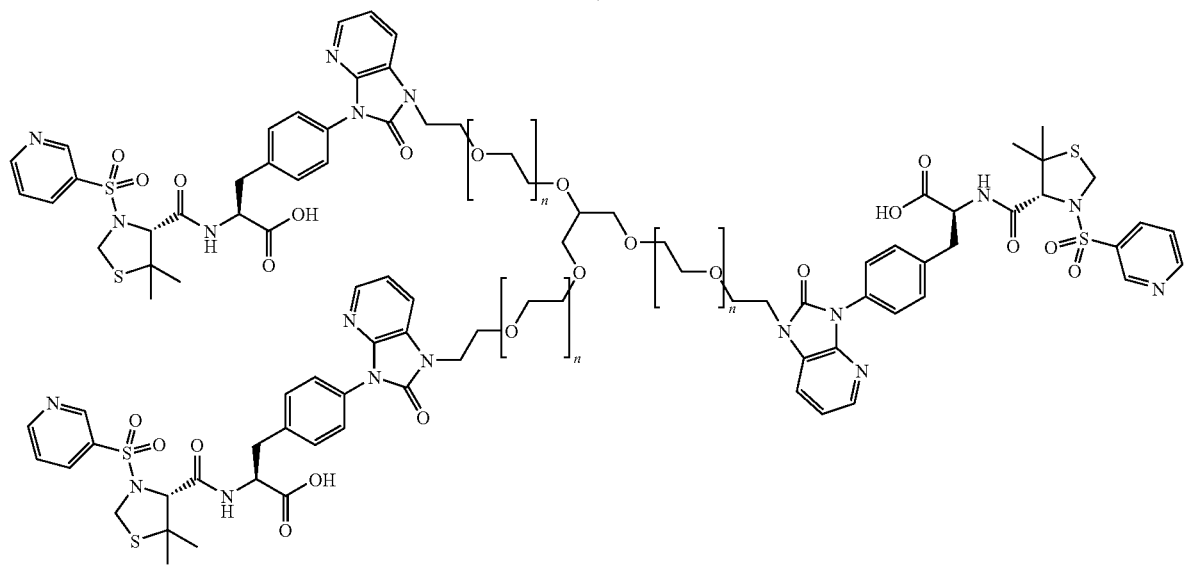

t-butyl Ester (111)

The 40 kDa 3-arm PEG alcohol (0.25 g, 0.00625 mmol), 110 (0.04 g, 0.056 mmol), and triphenylphosphine (0.025 g, 0.094 mmol) were dried by azeotropic distillation from toluene (5 mL). Half of the volume was distilled over (2.5 mL), and the mixture was cooled to room temperature. $CH_2Cl_2$ (0.5 mL) was added to make the reaction homogeneous. Diethylazodicarboxylate (0.015 mL, 0.094 mmol) was added dropwise and the reaction stirred for 48 hours. HPLC Method C showed the complete disappearance of the starting PEG alcohol. The reaction was concentrated in vacuo to yield the t-butyl ester 111 as a white solid.

Conjugate 112

111 (0.2 g, 0.005 mmol) was dissolved in formic acid (3 mL) and heated at 40° C. for 24 hours. The reaction was concentrated in vacuo and was purified according to HPLC Method A to yield 0.1 g (48%) of 112 as a white solid. HPLC Method C determined the conjugate to be >99% pure (retention time=8.1 minutes).

$^1$H NMR (CDCl$_3$) δ 9.08 (bs, 3H), 8.84 (bs, 3H), 8.18-8.16 (d, 3H), 8.02-8.00 (d, 3H), 7.67-7.61 (m, 6H), 7.47-7.38 (m, 9H), 7.08-7.04 (m, 3H), 6.91 (m, 3H), 4.88 (m, 3H), 4.62-4.49 (dd, 6H), 4.13 (m, 6H), 3.64 (bs, 5919H PEG), 3.23 (m, 6H), 1.25-1.24 (d, 18H).

Similar methods were used to synthesize the following conjugates:

Example 102

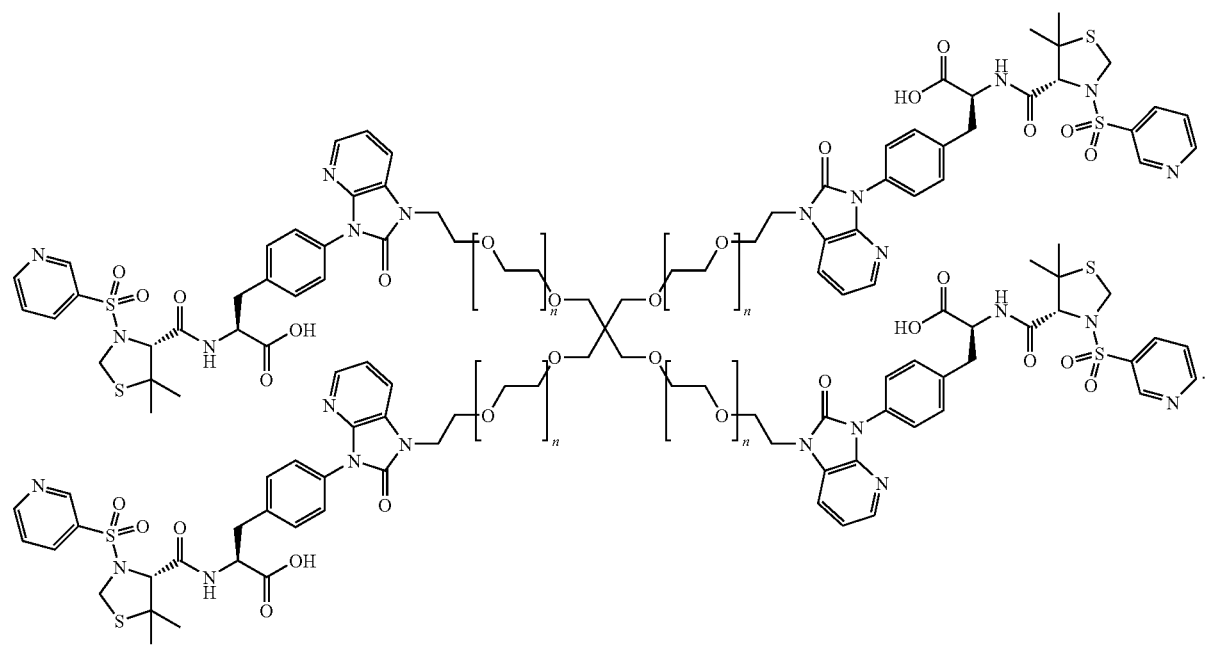
113
40 kDa 4-arm PEG alcohol was coupled to 110 and deprotected to final product using similar methods as with 112. The product was purified according to HPLC Method A. HPLC Method C determined the conjugate to be >95% pure (retention time=7.5-8.1 minutes).
$^1$H NMR (CDCl$_3$) δ 9.08 (bs, 4H), 8.84 (bs, 4H), 8.18-8.16 (d, 4H), 8.02-8.00 (d, 4H), 7.67-7.61 (m, 8H), 7.47-7.38 (m, 12H), 7.08-7.04 (m, 4H), 6.91 (m, 4H), 4.88 (m, 4H), 4.62-4.49 (dd, 8H), 4.13 (m, 8H), 3.64 (bs, 10101H PEG), 3.23 (m, 8H), 1.25-1.24 (d, 24H).
Example 103
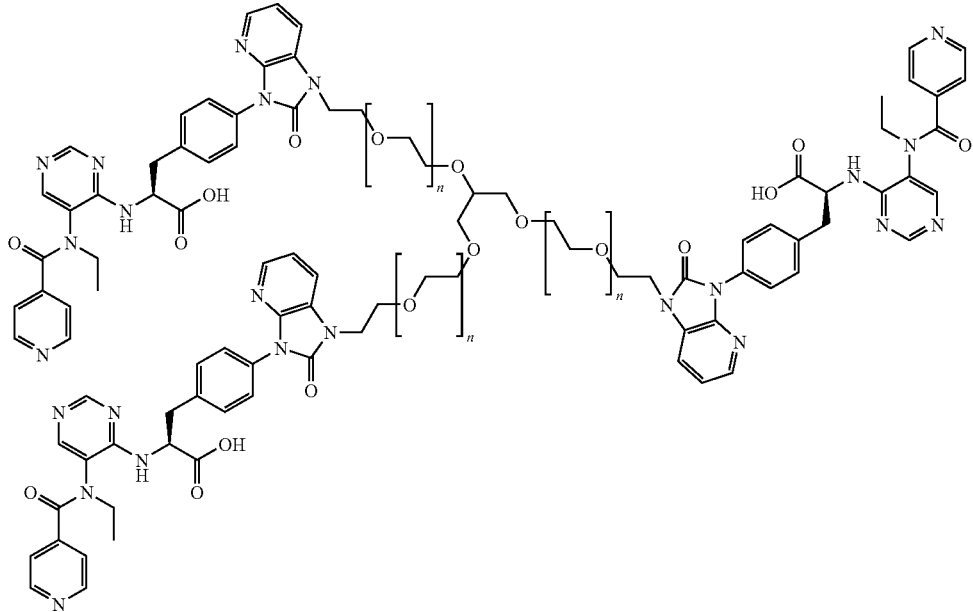
115 wherein each n is independently an integer such that the aggregate of the n's is about 100 to 1360. In an embodiment, each n is independently an integer such that there are a sufficient number of [—O—CH$_2$—CH$_2$—] repeating units that the conjugate of 115 has a molecular weight of about 40-45 kDa.

40 kDa 3-arm PEG alcohol was coupled to the t-butyl ester 114 (shown below) and deprotected to final product using similar methods as 112. The product was purified according to HPLC Method A. HPLC Method C determined the conjugate to be >95% pure (retention time=7.3 minutes).

$^1$H NMR (CDCl$_3$) δ 8.66 (bs, 3H), 8.44 (bs, 3H), 8.04-8.02 (d, 3H), 7.75-7.30 (m, 24H), 7.10-7.06 (m, 3H), 6.93 (s, 3H), 5.60-5.50 (m, 3H), 4.15 (m, 6H), 3.66 (bs, 4270H PEG), 3.00 (m, 3H), 3.40-3.20 (m, 6H), 1.27 (d, 9H).

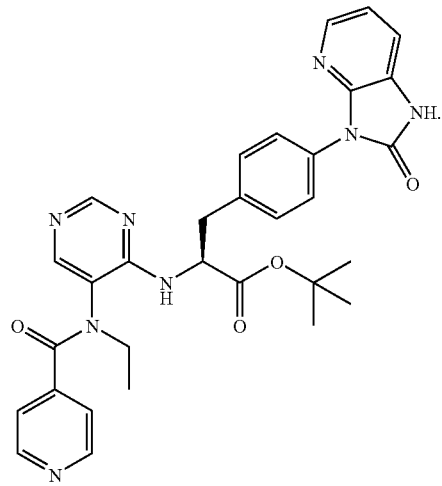

Example 104

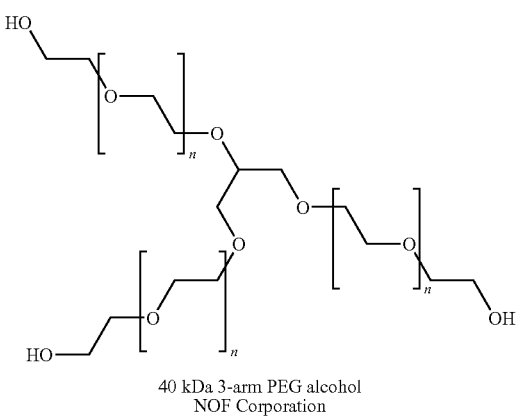

40 kDa 3-arm PEG alcohol
NOF Corporation

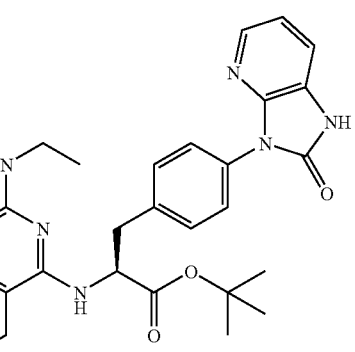

116.

-continued

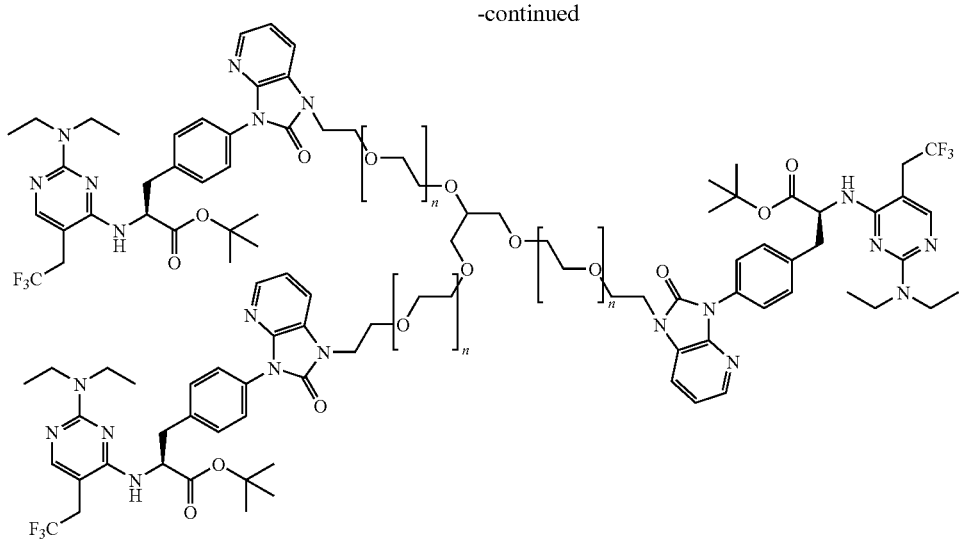

117.

↓

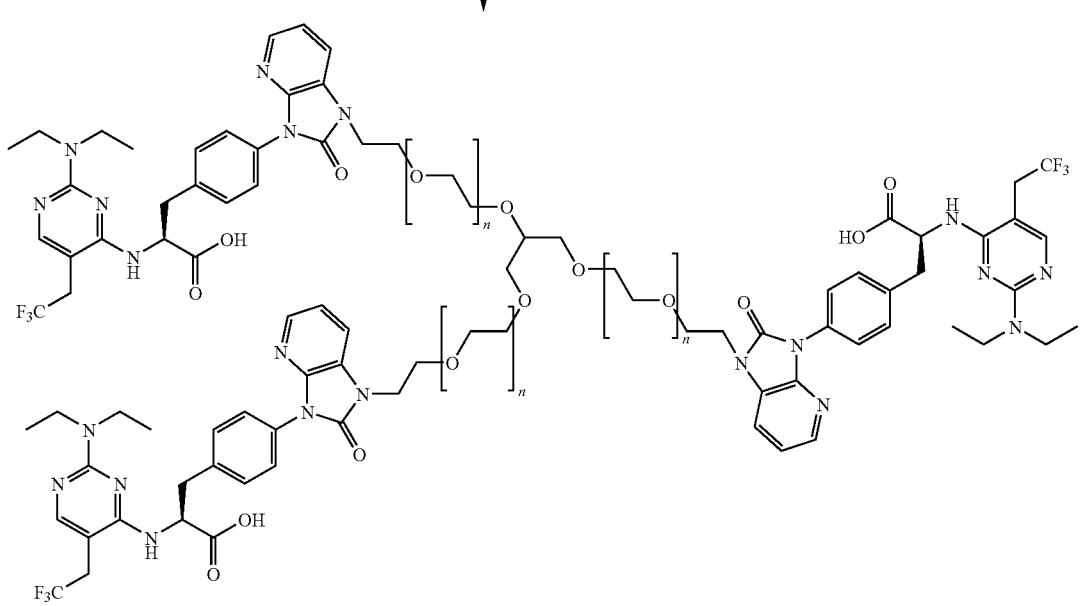

118.

t-butyl Ester (117)

The 40 kDa 3-arm PEG alcohol (0.00625 mmol), 116 (0.056 mmol), and triphenylphosphine (0.094 mmol) are dried by azeotropic distillation from toluene (5 mL). Half of the volume is distilled over (2.5 mL), and the mixture is cooled to room temperature. $CH_2Cl_2$ (0.5 mL) is added to make the reaction homogeneous. Diethylazodicarboxylate (0.094 mmol) is added drop-wise and the reaction stirred for 48 hours. The reaction is concentrated in vacuo to yield the t-butyl ester 111.

Conjugate 118

118 (0.005 mmol) is dissolved in formic acid (3 mL) and heated at 40° C. for 24 hours. The reaction is concentrated in vacuo and is purified according to HPLC Method A to yield 112.

The following conjugates in Tables 9 and 10 are prepared according to the Examples 65-104 and Schemes 5-19 and D and E described herein.

TABLE 9
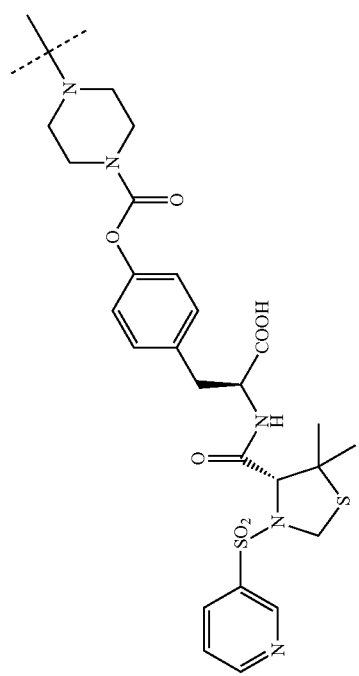

TABLE 9-continued

| B Moieties | A Moieties |
|---|---|
| t | |
| 4 homo tetramer | |
| 8 homo octomer | |
| 2 homo dimer | |

TABLE 9-continued
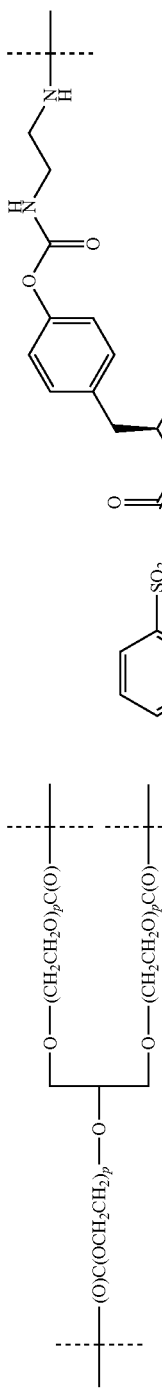

TABLE 9-continued
| t | B Moieties | A Moieties |
|---|---|---|
| homo dimer | —C(O)O(CH$_2$CH$_2$O)$_p$—C(O)— | 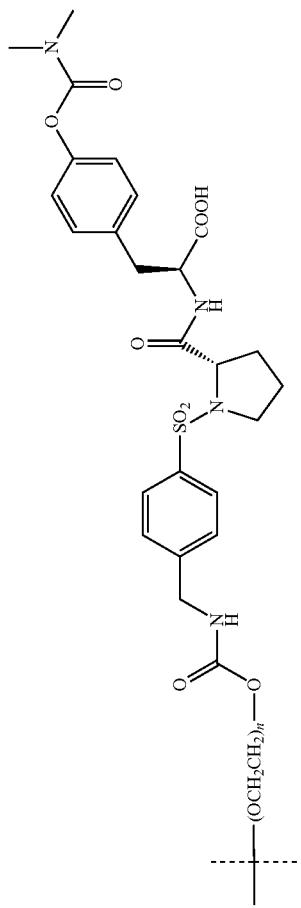 |
| hetero dimer | —C(O)O(CH$_2$CH$_2$O)$_p$—C(O)— | First A Moiety 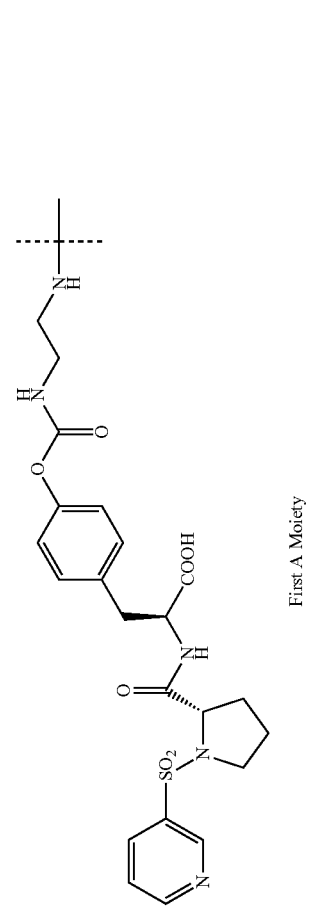  Second A Moiety 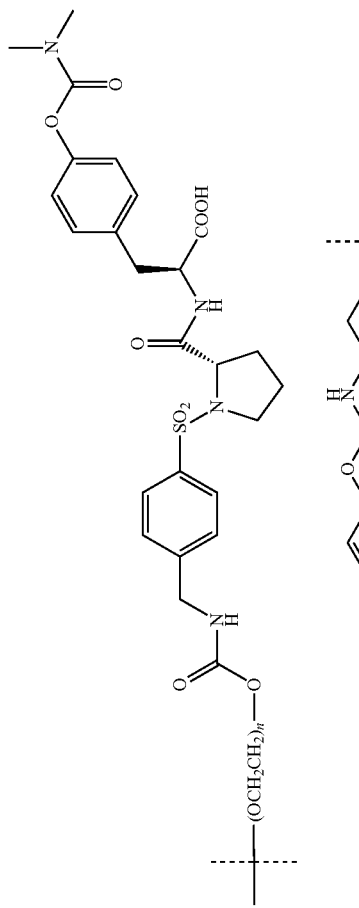 |

TABLE 9-continued
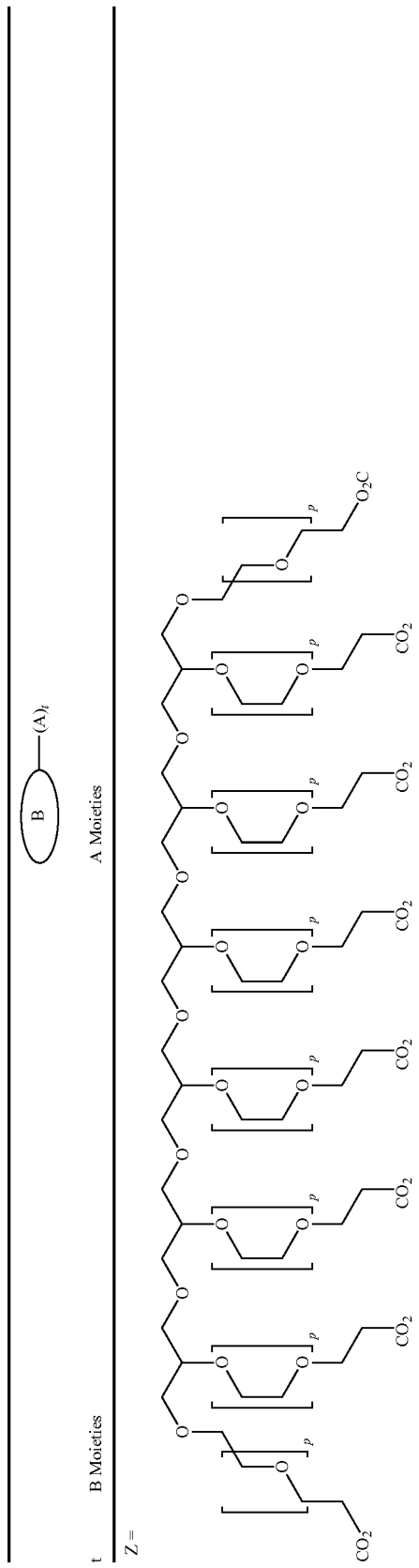

where in each of the structures the sum of all p's is from 100 to 1360.
TABLE 10
| B Moieties | A Moieties |
|---|---|
| ZZ (total Mw of conjugate is about 42,000) | 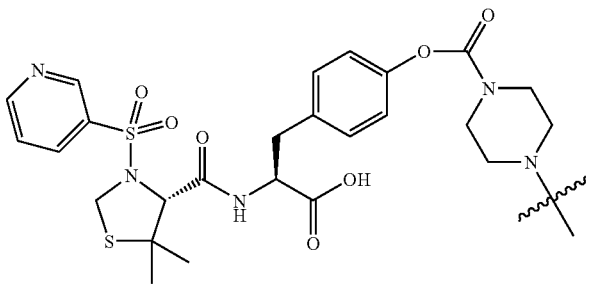 |
| ZZ (total Mw of conjugate is about 42,000) | 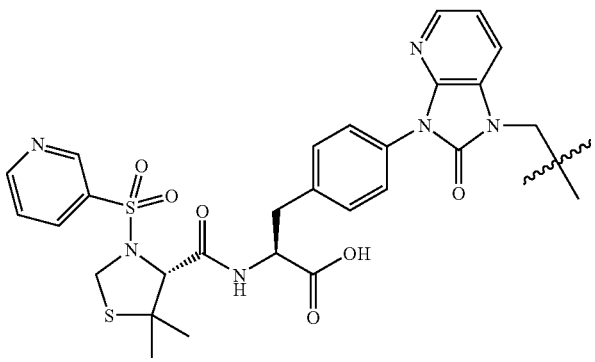 |
| ZZZ (total Mw of conjugate is about 41,000) | 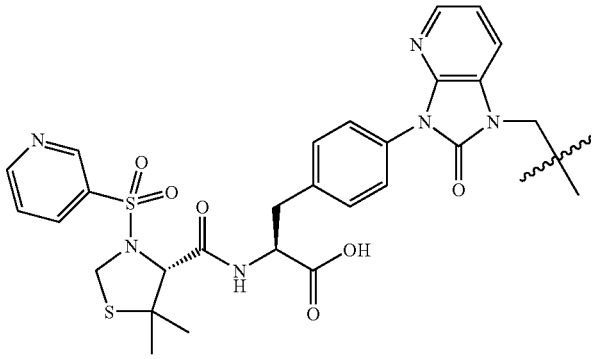 |
| 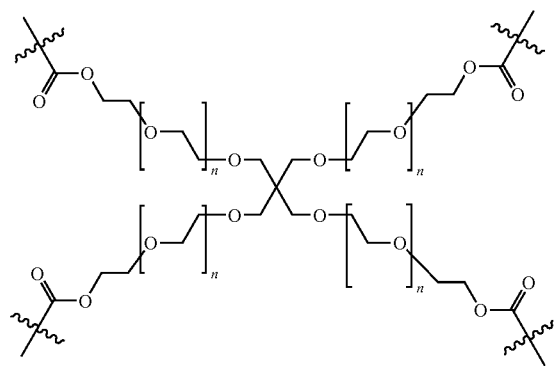 (total Mw of conjugate is about 42,000) | |

TABLE 10-continued
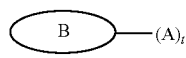
| B Moieties | A Moieties |
|---|---|
| 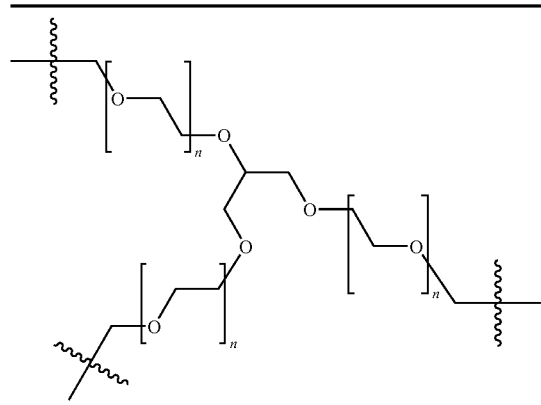<br>(total Mw of conjugate is about 41,500) | 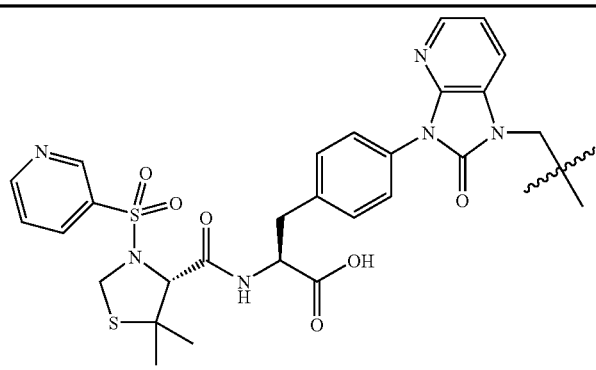 |
| 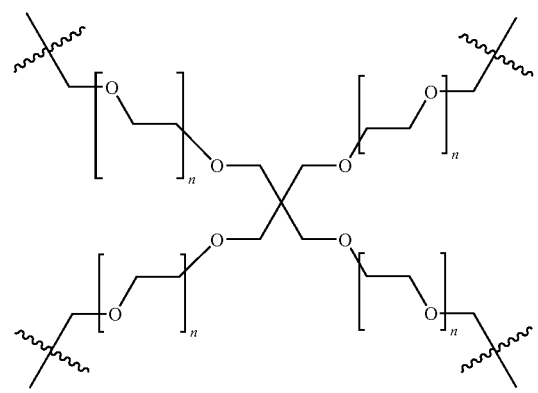<br>(total Mw of conjugate is about 42,000) | 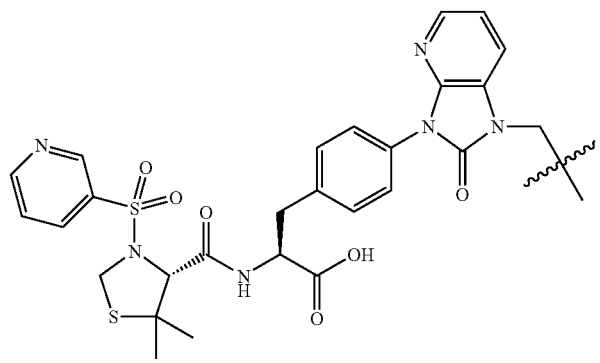 |
| 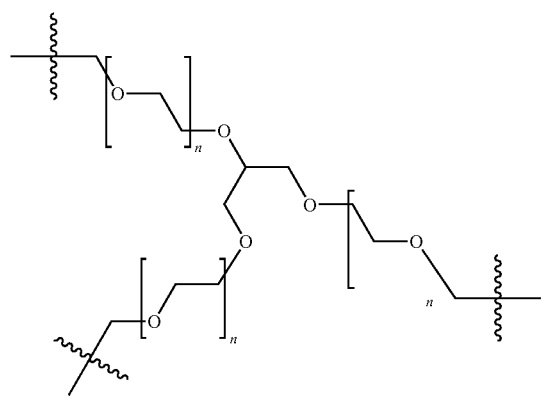<br>(total Mw of conjugate is about 41,500) | 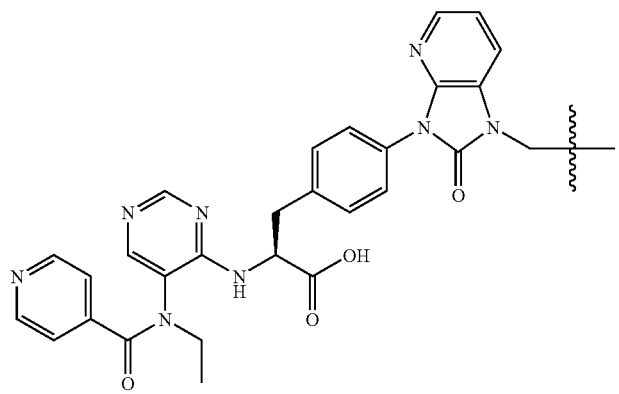 |
ZZ = 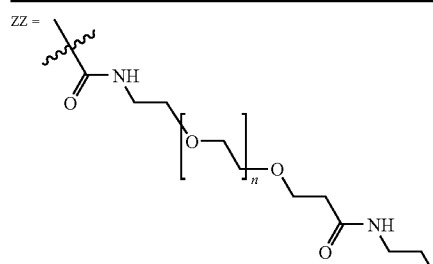 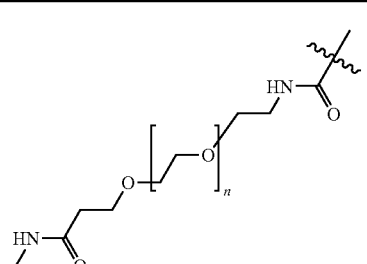

Example 105

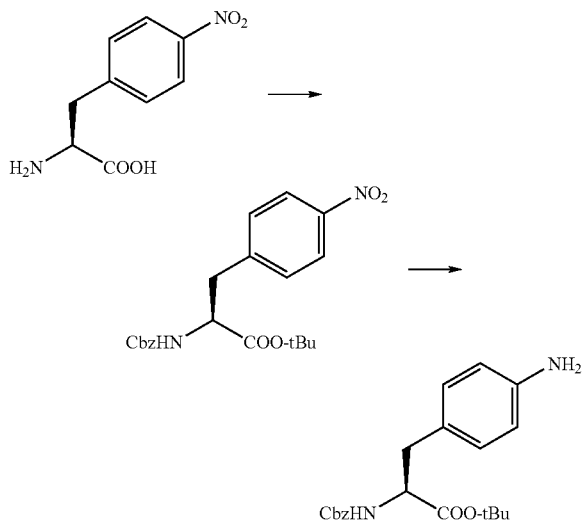

Sodium hydroxide (10 g, 0.25 m) is dissolved in water (300 ml). To this solution 4-nitrophenylalanine (50.3 g, 0.22 m) is added and stirred until complete dissolution. To the resulting solution the sodium carbonate (28.8 g, 0.26 m) is added and stirred suspension is cooled in an ice bath to +8° C. Benzyl chloroformate (44.7 g, 0.26 m) is added dropwise with vigorous stirring, maintaining internal temperature in +6° to +9° C. range. The mixture is stirred at +6° C. for additional 1 hr, transferred to the separatory funnel and washed with ether (2×150 ml). Aqueous phase is placed in a large Erlenmeyer flask (2 L) and is cautiously acidified with dil. aq. HCl to pH=2 and extracted with ethyl acetate (4×500 ml). The combined extracts are washed with water and dried with MgSO$_4$. The solution is filtered and filtrate evaporated, residue is dissolved in ethyl acetate (150 ml) and diluted with hexane (500 ml). Crystalline material is filtered off and rinsed with cold solvent, air dried to give Cbz-4-nitrophenylalanine, 75 g (99.5% yield).

$^1$H-NMR, DMSO-d6, (δ): 12.85 (bs, 1H), 8.12 (d, 2H, J=9 Hz), 7.52 (d, 2H, J=9 Hz), 7.30 (m, 5H), 4.95 (s, 2H), 4.28 (m, 1H), 3.32 (bs, 1H), 3.10 (m, 2H).

$^{13}$C-NMR (δ): 173.1, 156.3, 146.6, 137.3, 130.8, 128.5, 128.0, 127.8, 123.5, 65.6, 55.1, 36.6.

MS (m/z): 367.1 [M+23].

The Cbz-4-nitrophenylalanine (75 g, 0.22 m) is dissolved in dioxane (300 ml). The resulted stirred solution is cooled in Dry Ice bath to −20° C. (internal). The liquefied isobutylene (approx. 290 ml) is added followed by conc. sulfuric acid (35 ml) added in three equal portions, 30 min apart. The addition of acid is a very exothermic process, accompanied by substantial degree of polymerization. Efficient mechanical stirring is essential at this stage. Resulted mixture is stirred for 20 hr, allowing to warm up to ambient temperature then is cautiously poured into sat. aq. sodium carbonate solution (2 L) and diluted with ethyl acetate (600 ml). Organic layer is separated and aqueous layer is extracted with ethyl acetate (2×200 ml). Combined extracts are washed with water and dried with sodium sulfate. The solution is filtered and evaporated to dryness. The residue is taken up in ethyl acetate/hexane mixture (500 ml; 1:1) and filtered through plug of silica gel (ca. 2×2 in). The silica is rinsed with an additional amount of the same solvent (2 L total) and the filtrates are evaporated to give fully protected 4-nitrophenylalanine as a viscous oil, 73 g (83% after two steps).

$^1$H-NMR, CDCl$_3$, (δ): 8.12 (d, 2H, J=8.4 Hz), 7.36 (m, 7H), 5.35 (m, 1H), 5.10 (m, 2H), 4.57 (m, 1H), 3.31 (m, 2H), 1.43 (s, 9H).

$^{13}$C-NMR, CDCl$_3$, (δ): 169.7, 155.3, 146.9, 143.9, 136.0, 130.2, 128.4, 128.2, 128.0, 123.3, 82.9, 66.9, 54.7, 38.2, 31.4, 27.8, 13.9.

MS (m/z): 423.1 [M+23].

Protected 4-nitrophenylalanine (73 g, 0.18 m) is dissolved in ethanol (500 ml) and platinum oxide catalyst (1.5 g) is added. The resulting solution is vigorously stirred in hydrogen atmosphere (50-60 psi) at ambient temperature until further hydrogen adsorption ceased (3 hr). The catalyst is filtered off and the filtrate is evaporated to dryness, the residue is taken up in ethyl acetate (200 ml) and filtered through plug of silica gel (2×2 in) using ethyl acetate-hexane mixture (3:2, 2 L) to rinse silica. The filtrate is concentrated to approx. 200 ml and hexane (500 ml) is added. The crystalline product is filtered off, rinsed with cold solvent and air-dried. Yield—56 g, 84%.

$^1$H-NMR, CDCl$_3$, (δ): 7.30 (bs, 5H), 6.92 (d, 2H, J=8.1 Hz), 6.58 (d, 2H, J=8.1 Hz), 5.21 (m, 1H), 5.10 (d, 2H, J=2.1 Hz), 4.46 (m, 1H), 3.59 (bs, 2H), 2.97 (s, 2H, J=5.4 Hz), 1.42 (s, 9H).

$^{13}$C-NMR, CDCl$_3$, (δ): 170.6, 145.1, 136.3, 130.2, 128.3, 127.9, 125.6, 115.0, 81.9, 66.6, 55.2, 37.4, 27.8

MS (m/z): 393.1 [M+23].

Example 106

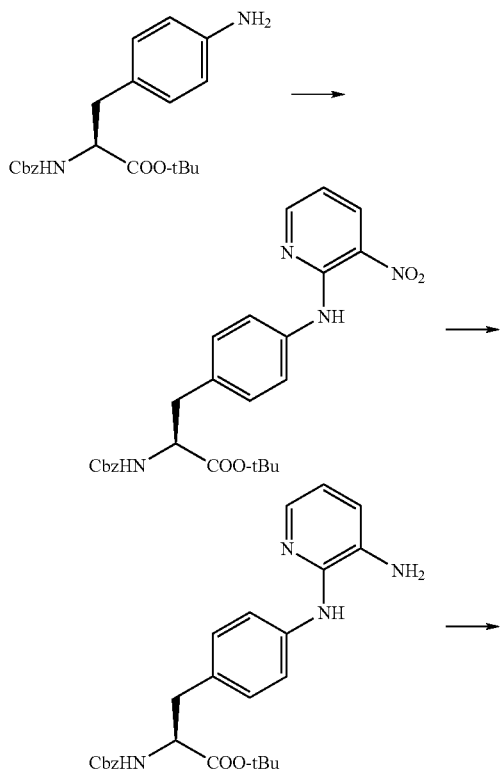

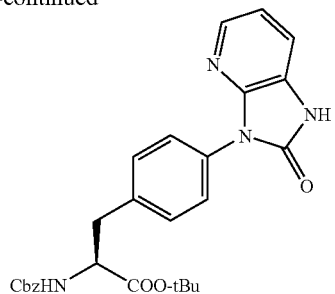

The product of Example 105, 4-aminophenylalanine, (20 g, 0.054 m) was dissolved in ethanol (200 ml) and treated with Hunig's base (21 g, 0.162 m, 3 eq) and 2-chloro-3-nitropyridine (10.3 g, 0.65 m, 1.2 eq). Resulted solution was stirred under nitrogen atmosphere and heated to reflux for 24 hr. LC analysis indicated presence of small amount of unreacted amine. The small additional amount of chloronitropyridine (1.1 g, 0.13 eq) was added and reflux continued for another 24 hr. Reaction mixture was cooled and evaporated to dryness. Residue was dissolved in ethyl acetate (600 ml) and obtained solution was washed with water (1×200 ml), dil. aq. citric acid (0.2 N, 2×200 ml), brine (1×200 ml) and dried with sodium sulfate. Solids were filtered off and filtrate evaporated to give 37 g of deep-red oil, containing expected product contaminated with excess of chloronitropyridine. Impure product was purified by flash chromatography (Biotage 75L system) eluting with ethyl acetate:hexane (3:17) mixture. Fractions containing pure product were combined and evaporated to give deep-red, viscous oil, 26 g (99%).

$^1$H-NMR, CDCl$_3$, ($\delta$): 10.10 (s, 1H), 8.49 (m, 2H), 7.57 (d, 2H, J=9 Hz), 7.35 (bs, 5H), 7.19 (d, 2H, J=9 Hz), 6.84 (m, 1H), 5.30 (m, 1H), 5.13 (d, 2H, J=3 Hz), 4.57 (m, 1H), 3.11 (m, 2H), 1.45 (s, 9H).

$^{13}$C-NMR, CDCl$_3$, ($\delta$): 170.4, 155.5, 155.1, 150.0, 136.7, 136.3, 135.4, 132.4, 129.9, 128.5, 128.3, 128.0, 127.9, 122.2, 113.7, 82.0, 66.7, 55.1, 37.7, 27.8, 20.9.

MS (m/z): 493.1 [M+1], 515.1 [M+23].

The red nitro compound (26 g, 0.054 m) was dissolved in THF (350 ml) and platinum oxide catalyst (1.35 g) was added. Resulted mixture was vigorously stirred under hydrogen atmosphere (50-60 psi) until hydrogen adsorption ceased (2 hr). Catalyst was filtered off and filtrate evaporated to dryness. Residue was dissolved in ethyl acetate (100 ml) and diluted with hexane (50 ml) till beginning of crystallization. Mixture was further diluted with ethyl acetate/hexane (1:1) mixture (300 ml) and was left standing in refrigerator for 3 hr. Crystalline solids were filtered off, rinsed with cold solvent and air-dried to give product, 23 g, 94%.

$^1$H-NMR, CDCl$_3$, ($\delta$): 7.81 (dd, 1H, J1=1.5 Hz, J2=4.8 Hz), 7.33 (bs, 5H), 7.17 (d, 2H, J=8.4 Hz), 7.03 (d, 2H, J=8.4 Hz), 6.96 (dd, 1H, J1=1.5 Hz, J2=7.5 Hz), 6.75 (dd, 1H, J1=5.0 Hz, J2=7.7 Hz), 6.22 (s, 1H), 5.31 (m, 1H), 5.09 (bs, 2H), 4.50 (m, 1H), 3.41 (bs, 2H), 3.02 (m, 2H), 1.43 (s, 9H).

$^{13}$C-NMR, CDCl$_3$, ($\delta$): 170.6, 155.6, 145.5, 140.21, 138.8, 136.3, 130.8, 129.9, 128.5, 128.3, 127.9, 123.4, 118.2, 117.0, 82.0, 66.6, 55.2, 37.4, 27.9.

MS (m/z): 407.1 [M−56], 463.1 [M+1], 485.1 [M+23].

The aminopyridine (19 g, 0.041 m) was suspended in dichloromethane (200 ml) and CDI (12 g, 0.074 m, 1.8 eq) was added. Resulted mixture was stirred at ambient temperature for 20 hr. Reaction mixture was washed with sat. aq. bicarbonate (2×100 ml), brine (1×100 ml) and dried with sodium sulfate. Solids were filtered off and filtrate evaporated to dryness. Residue was dissolved in ethyl acetate (hot, 300 ml) and set to crystallize. Crystalline product was filtered off, rinsed with cold ethyl acetate and air-dried to give 19.9 g, 81% of the imidazolone.

$^1$H-NMR, CDCl$_3$, ($\delta$): 10.63 (s, 1H), 8.06 (d, 1H, J=3 Hz), 7.66 (d, 2H, J=9 Hz), 7.32 (m, 8H), 7.05 (m, 1H), 5.36 (m, 1H), 5.13 (s, 2H), 4.59 (m, 1H), 3.17 (m, 2H), 1.45 (s, 9H).

$^{13}$C-NMR, CDCl$_3$, ($\delta$): 170.4, 155.6, 154.3, 143.8, 141.0, 136.2, 135.8, 131.8, 130.2, 128.3, 128.0, 125.9, 122.2, 118.3, 116.0, 82.4, 66.8, 55.0, 37.7, 27.8.

MS (m/z): 433.1 [M−56], 489.2 [M+1], 511.2 [M+23].

Example 107

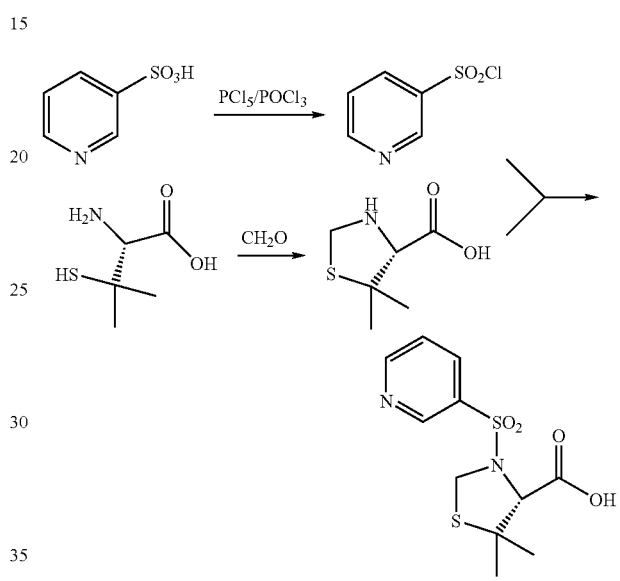

Pyridine-3-sulfonic acid (125 g, 0.78 m) was placed in a 1L, 3-necked flask equipped with mechanical stirrer, reflux condenser, thermometer and nitrogen inlet. Next, the phosphorus pentachloride (250 g, 1.19 m, 1.5 eq) was added, followed immediately by the phosphorus oxychloride (330 ml, 3.8 m, 4.5 eq). The contents of flask were initially stirred at ambient temperature for 30 min, then brought slowly to gentle reflux (internal temp. approx. 110° C.) over the next hour, kept at this temperature for approx. 3.5 hr then allowed over the next 12 hr to cool back to ambient temperature. Gas evolution was observed during this time. The volatiles were stripped under reduced pressure (at 12 mmHg/40° C.) and yellow semi-solid residue was diluted with DCM (1 L). The slurry was poured slowly into the stirred, ice-cold sat. aq. bicarbonate, maintaining pH=7. Gas evolution was observed. The organic layer was separated and aqueous layer was back-extracted with DCM. The combined extracts were washed with cold sat. aq. bicarbonate, brine and dried with magnesium sulfate. The solids were filtered off and filtrate evaporated, leaving pyridine-3-sulfonyl chloride as a pale yellow, oily liquid, 123 g (93% pure; 88% theory).

$^1$H-NMR, CDCl$_3$, ($\delta$): 9.26 (d, 1H), 8.98 (dd, 1H), 8.34 (m, 1H), 7.62 (m, 1H).

$^{13}$C-NMR, CDCl$_3$, ($\delta$): 155.3, 147.4, 140.9, 134.6, 124.2.

MS (m/z): 178.0 [M+1].

L-penicillamine (150 g, 1.0 m) was dissolved with stirring in DI water (1500 ml), cooled in ice-bath to +8° C. and treated with formalin (150 ml, 37% aq.). The reaction mixture was stirred at +8° C. for 2 hr, then cooling bath was removed and stirring continued for 12 hr. The clear solution was concentrated under reduced pressure (14 mmHg/50°) leaving white residue. The solids were re-suspended, then dissolved in hot MeOH (2500 ml) and left standing at ambient temperature for 12 hr. The white, fluffy precipitate was filtered off and rinsed with cold methanol. The filtrate was concentrated and set to crystallize again. The collected precipitate was combined with the first crop and dried in vacuum oven for 24 hr at 55° C. at 45 mmHg. The yield of (R)-5,5-dimethylthiazolidine-4-carboxylic acid was 138 g (>99% pure; 86% theory).

¹H-NMR, DMSO-d6, (δ): 4.25 (d, 1H), 4.05 (d, 1H), 3.33 (s, 1H), 1.57 (s, 3H), 1.19 (s, 3H).

¹³C-NMR, DMSO-d6, (δ): 170.8, 74.4, 57.6, 51.8, 28.9, 27.9.

MS (m/z): 162.3 [M+1].

In a 4 L reactor equipped with mechanical stirrer and thermometer, a buffer solution was prepared from potassium monobasic phosphate (43 g, 0.31 m) and potassium dibasic phosphate (188.7 g, 1.08 m) in DI water (2 L). The (R)-5,5-dimethylthiazolidine-4-carboxylic acid (107 g, 0.675 m) was added and stirred until complete dissolution. The solution was cooled in an ice-bath to +8° C. A separately prepared solution of pyridine-3-sulfonyl chloride (124 g, 0.695 m) in DCM (125 ml) was added dropwise to the reactor with vigorous stirring over the 1 hr. The pH of reaction mixture was monitored and after 4 hr, found to be pH=5 and adjusted to pH=6 by addition of solid bicarbonate. The mixture was allowed to warm up to ambient temperature over 18 hr. The pH was adjusted to 2 with dil. aq. sulfuric acid, stirred for 1 hr and precipitated yellow solids were filtered off, rinsed with water to neutral. The solid cake was transferred into 2 L Erlenmayer flask, suspended in DCM (500 ml) with occasional swirling for 5 min and filtered off again. The filter cake was washed with DCM and air-dried. The yield of the title compound, (R)-5,5-dimethyl-3-(pyridin-3-ylsulfonyl)thiazolidine-4-carboxylic acid was 148.9 g (98% pure; 73% theory).

¹H-NMR, DMSO-d6, (δ): 9.05 (d, 1H), 8.89 (m, 1H), 8.32 (m, 1H), 7.69 (m, 1H), 4.68 (q, 2H), 4.14 (s, 1H), 1.35 (s, 3H), 1.29 (s, 3H).

¹³C-NMR, DMSO-d6, (δ): 170.0, 154.3, 147.9, 135.8, 134.1, 124.8, 72.6, 54.3, 50.2, 29.4, 25.0.

MS (m/z): 303.2 [M+1].

Example 108

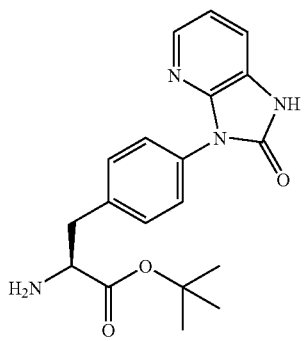

The product of Example 106 (52 g, 0.106 m) was slurried in MeOH (450 ml), hydrogenation catalyst (8.7 g, 5% Pd/C, Degussa) was added and the mixture was stirred under the hydrogen atmosphere (60 psi) until further absorption ceased (ca. 2 hrs). THF (150 ml) was added to dissolve precipitated solids and the solution was filtered through plug of Celite, using DCM to rinse the filter. The filtrate was evaporated to dryness, re-dissolved in DCM (300 ml) and stripped again. This operation was repeated twice. The foamy solids were kept under high vacuum for 3 hrs. The yield of title compound was 38.3 g (101% of theory).

¹H-NMR, CDCl₃, (δ): 8.08 (m, 1H), 7.56 (AB q, 4H), 7.37 (m, 1H), 7.06 (m, 1H), 3.68 (m, 1H), 2.03 (m, 2H), 1.49 (s, 9H).

¹³C-NMR, CDCl₃, (δ): 173.8, 154.6, 143.9, 141.0, 137.4, 131.5, 130.2, 126.1, 122.3, 118.0, 116.1, 81.4, 56.0, 40.6, 27.9.

MS (m/z): 299.3 [M−56], 355.4 [M+1], 377.4 [M+23].

Example 109

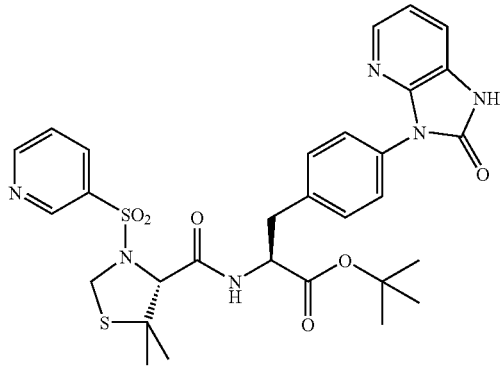

The product of Example 108 (38.3 g, assume 0.106 m) was dissolved in DCM (500 ml) and treated successively with: N-methylmorpholine (27 g, 30 ml, 0.266 m; 2.5 eq), HOBt (17.3 g, 0.128 m, 1.2 eq), and the product of Example 107 (33.8 g, 0.112 m; 1.06 eq). The resulting non-homogenous solution was cooled in an ice-bath to +4° C. and treated with EDC (22.5 g, 0.117 m; 1.1 eq) in one portion. The reaction mixture was stirred, allowing it to warm up to ambient temperature over the next 4 hr and then for 18 hr more. The solvent was stripped and residue dissolved in ethyl acetate (1.2 L), washed with sat. aq. bicarbonate (2×250 ml), water (250 ml), brine (300 ml) and dried with magnesium sulfate. The solution was filtered and evaporated to dryness, leaving a light orange, viscous oil, 76 g (>>100%). The crude product was purified by flash chromatography on silica gel (Biotage 75L, in ethyl-acetate/methanol (3%) mixture. Fractions, containing pure product, were combined and evaporated to give 54 g of the title compound (yield 83%).

¹H-NMR, CDCl₃, (δ): 10.37 (s, 1H), 9.11 (s, 1H), 8.87 (m, 1H), 8.19 (m, 1H), 8.05 (m, 1H), 7.56 (AB q, 4H), 7.52 (m, 1H), 7.36 (m, 1H), 7.06 (m, 2H), 4.83 (m, 1H), 4.58 (AB a, 2H), 3.96 (s, 1H), 3.19 (m, 2H), 1.49 (s, 9H), 1.22 (s, 3H), 1.18 (s, 3H).

¹³C-NMR, CDCl₃, (δ): 169.7, 167.6, 153.9, 148.4, 143.8, 140.9, 135.8, 135.6, 132.9, 131.9, 130.2, 125.9, 123.8, 122.1, 118.0, 115.9, 82.8, 73.6, 60.3, 54.8, 53.7, 50.6, 37.8, 29.1, 27.8, 23.9, 14.1.

MS (m/z): 583.3[M−56], 639.4 [M+1], 661.3 [M+23].

Example 110

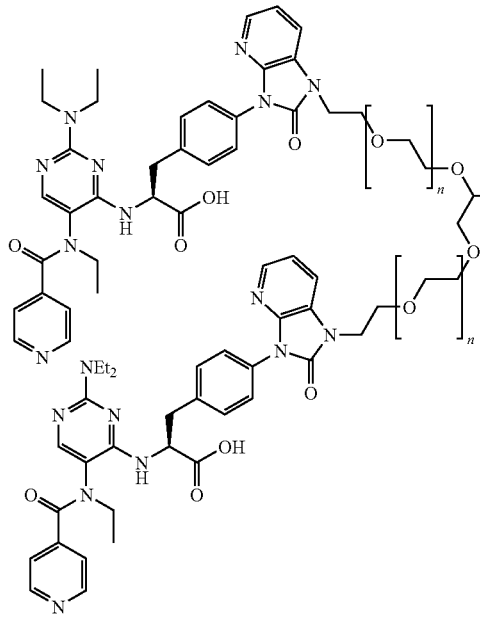

120

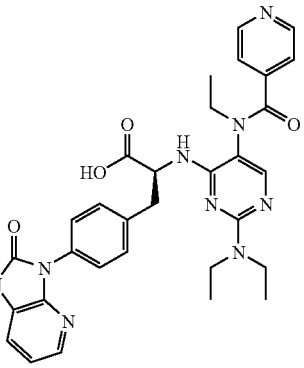

wherein each n is independently an integer such that the aggregate of the n's is about 100 to 1360. In an embodiment, each n is independently an integer such that there are a sufficient number of [—O—CH$_2$—CH$_2$—] repeating units that the conjugate of 120 has a molecular weight of about 40-45 kDa.

40 kDa 3-arm PEG alcohol was coupled to the t-butyl ester 119 (shown below) and deprotected to final product using similar methods as 112. The product was purified according to HPLC Method A. HPLC Method C determined the conjugate to be >95% pure (retention time=7.3 minutes). $^1$H NMR (CDCl$_3$) δ 8.66 (bs, 3H), 8.44 (bs, 3H), 8.04-8.02 (d, 3H), 7.75-7.30 (m, 24H), 7.10-7.06 (m, 3H), 6.93 (s, 3H), 5.60-5.50 (m, 3H), 4.15 (m, 6H), 3.66 (bs, 4270H PEG), 3.00 (m, 3H), 3.40-3.20 (m, 6H), 1.27 (d, 9H).

119

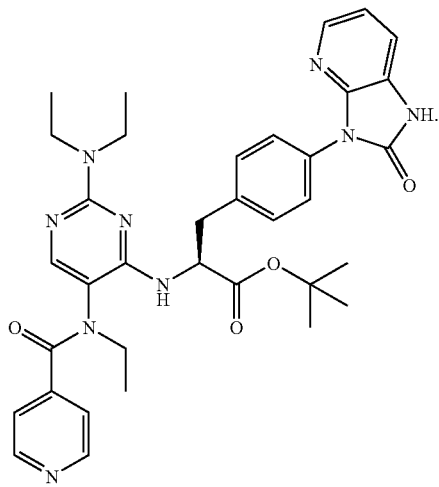

Example A

The efficacy of the compounds of the present invention in inhibiting liquid tumor growth, malignancies thereof and/or development of metastases thereof may be assayed. The compounds are assayed for their ability to inhibit liquid tumor growth, reduce liquid tumor mass, effect the loss of metastatic lesions, inhibit development of new metastatic lesions after treatment has started, or reduce tumors such that there is no detectable disease. The presence of liquid tumors and malignant diseases such as leukemias or myelomas may be assessed by radiologic imaging, biological fluid analysis, cytogenetics, fluorescence in situ hybridization, immunocytochemistry, colony assays, multiparameter flow cytometry, or polymerase chain reaction, as well as other assays methods known in the art.

For example, human tumor cell lines may be screened for expression of alpha-4 and alpha-9 by immunohistochemistry (IHC) and flow cytometry. Functionality of the alpha-4 and alpha-9 may be confirmed by an in vitro binding assay. Any cytotoxicity or induction of cell proliferation in human tumor cells may be evaluated by thymidine incorporation. Evaluation of positive or negative effects on proliferation of the tumors may be performed, for example, using $^3$H-thymidine incorporation assays.

Example B

The conjugate of formula A as illustrated below is a permanent conjugate of a selective and potent, small molecule inhibitor of α4 integrins, with selectivity for α4β1 over α4β7, and a 3-arm, of about 45 kD, polyethylene glycol (PEG). The small molecule inhibitor portion of the conjugate of formula A contains a tertiary arylsulfonamide group.

Formula A

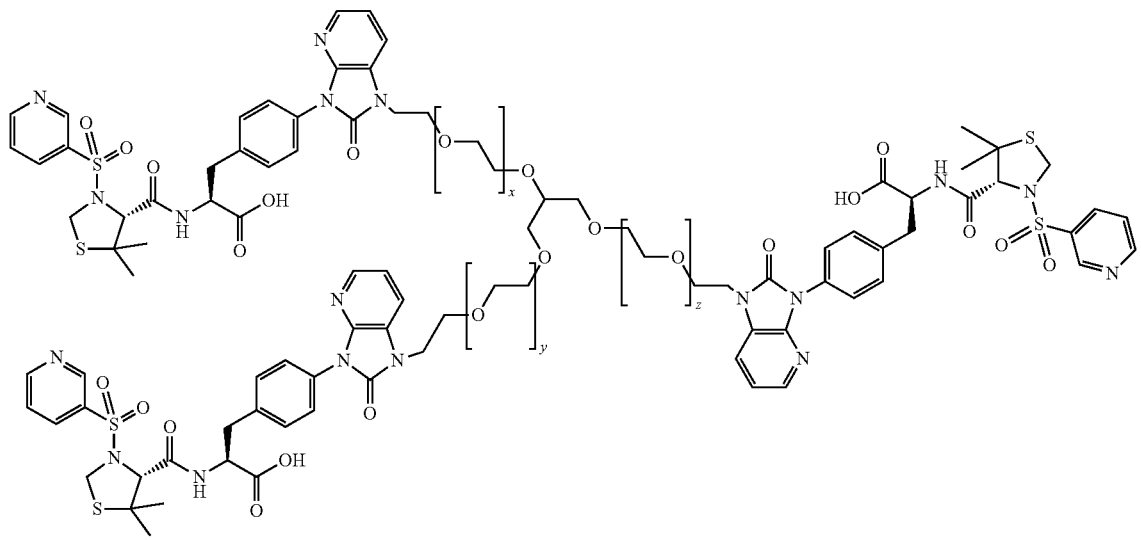

wherein x, y, and z are independently an integer such that the aggregate of x, y, and z is about 100 to 1360. Preferably, x, y, and z are independently an integer such that there are a sufficient number of [—O—CH$_2$—CH$_2$—] repeating units that the conjugate of formula A has a molecular weight of about 40-45 kDa.

The conjugate of formula A is specific for binding to α4β1 integrin. Testing in four different α4β1 integrin assays evaluating inhibition of FN capture, FN-mediated adhesion, VCAM-1-mediated adhesion, and multi-valent competition against a small molecule inhibitor of α4β1 integrin gave ED/EC$_{50}$ values of 0.05, 0.2, 0.5 and 16.5 nM, respectively. The conjugate of formula A activity was examined in four non-α4β1-dependent integrin assays selected to assess specificity across a diverse range of integrin subsets: α4β7 (measured as inhibition of MadCAM-1 adhesion), αLβ2 (measured as inhibition of ICAM adhesion), α5β1 (measured as inhibition of FN adhesion) and α9β1 (the integrin most closely related to α4, measured in multi-valent competition). ED/EC$_{50}$ values of 38 nM, >1 µM, >1 µM, and 51 nM were obtained in these assays, respectively. While difficult to directly compare ED/EC$_{50}$ values due to assay format differences, these values indicate selectivity of the conjugate of formula A for α4β1 integrin over the closely related α4β7 and α9β1 integrins and no indication of cross-reactivity to other non-α4 integrins.

The potency of the conjugate of formula A as measured in the multivalent competition assay was not significantly altered in the presence of 100% rat, dog or human serum. Thus, this conjugate does not bind to serum proteins to a significant degree. Binding of the conjugate of formula A across species was tested in a fluorescence-activated cell sorting assay (FACS assay) using rat, guinea pig, dog, cynomolgus monkey, rhesus monkey, and human lymphocytes. The conjugate of formula A had similar potency for α4β1 integrin in all species, with an EC$_{50}$ range of 0.0004-0.003 µg/mL (human ED$_{50}$=0.008 µg/mL). The secondary pharmacological activity of the conjugate of formula A was tested at 1 µM in an in vitro screen of enzyme, radioligand binding, and cellular assays to characterize its selectivity and identify possible toxicity targets. The conjugate of formula A did not demonstrate activity in these assays.

In oncology, the use of the conjugate of formula A to block α4 integrin may result in direct anti-tumor activity by inhibiting tumor associated angiogenesis/lymphangiogenesis, metastasis, and or cell adhesion mediated drug resistance. Critical events in support of tumor metastasis are angiogenesis and lymphangiogenesis (Hwang R, Varner et al., *Hematol Oncol Clin North Am* 2004; 18(5): 991-1006, vii). Antagonists of α4β1, but not of other integrins, blocked the adhesion of monocytes to endothelium in vitro and in vivo, as well as their extravasation into tumor tissue (Jin H et al., *Cancer Res.* 2006 Feb. 15; 66(4): 2146-52). These antagonists prevented monocyte stimulation of angiogenesis in vivo, macrophage colonization of tumors, and tumor angiogenesis. These studies indicate the usefulness of antagonists of integrin α4β1 in suppressing macrophage colonization of tumors and subsequent tumor angiogenesis. The conjugate of formula A was evaluated in the mouse corneal micropocket angiogenesis assay for its' ability to inhibit angiogenesis in vivo. In the mouse cornea micropocket angiogenesis assay, a dose dependent inhibition in neovascularization of the cornea in the presence of the conjugate of formula A was observed. These results are discussed in further detail in Example E, supra.

Additional activities of the conjugate of formula A beneficial in oncology include inhibition of metastasis, as well as positive effects on bone complications in myeloma, independent of tumor response. Metastasis in multiple myeloma cells is thought to occur, at least in part, via binding of α4β1 integrin on myeloma cells to VCAM-1 on bone-marrow stromal cells; an interaction that leads to bone destruction by osteoclasts (Michigami T et al., *Blood* 2000; 96(5): 1953-60). In preclinical studies in mice, an α4 antibody suppressed the development of multiple myeloma, metastasis of myeloma cells to bone marrow, and resulting osteoclastic osteolysis.

In a separate study, Mori showed that prophylactic administration of the anti-alpha-4 Ab decreased 5TGM1/luc tumor burden in the bone and spleen (Mori Y et al., *Blood* 2004; 104(7): 2149-54). Reduction of osteoclastic lesions in trabecular bone of antibody treated mice were also noted, indicating VLA-4 adhesion interactions also contributed to the osteoclastogenic activities of myeloma cells. This effect has also been observed in vitro, where the co-culture of myeloma cells with primary bone marrow stromal cells resulted in osteoclast stimulation. Neutralizing antibodies to either VLA-4 or VCAM-1 inhibited stimulation.

Integrins play a role in protecting cells of hematologic malignancies from cytotoxic chemotherapies (de la Fuente M T et al., *J Leukocyte Biol* 2002; 71(3): 495-502 Paavonen T et al., *Int J Cancer* 1994; 58(20:298-302). Thus, the conjugate of formula A may be useful in overcoming cell adhesion-mediated drug resistance (CAM-DR) resulting from over-expression of α4β1 integrin (Matsunaga T et al., *Nat Med* 2003; 9(9): 1158-65). In a recent report, the expression of leukemic cell α4 integrin was associated with chemoresistance, persistence of residual disease, and poor prognosis in patients with acute myelogenous leukemia, presumably due to binding of α4 integrin to the matrix molecule, fibronectin, on stromal cells (Matsunaga T et al., *Nat Med* 2003; 9(9): 1158-65). This report also showed that an α4 antibody prevented resistance to AraC in a murine model of leukemia. Disruption of interactions between α4 integrin and fibronectin results in reversal of drug sensitive phenotype (de la Fuente M T et al., *J Leukocyte Biol* 2002; 71(3): 495-502 Paavonen T et al., *Int Cancer* 1994; 58(20:298-302).

In a therapeutic paradigm, Mori showed that addition of the anti-VLA-4 Ab to melphalan after the metastatic myeloma was established did result in significant reduction of IgG2a levels and tumor burden compared to melphalan therapy alone (Mori Y et al., *Blood* 2004; 104(7): 2149-54). However, therapeutic administration of the antibody alone did not substantially reduce tumor burden in the bone.

Often, patients initially respond to front-line chemotherapeutic agent only to eventually develop drug resistance and become unresponsive. A major factor for treatment failure for multiple myeloma is the development of drug resistance to standard of care chemotherapeutic agent, such as melphalan or doxorubicin (Damiano J S et al., *Blood* 1999; 93(5): 1658-67). Damiano (1999) has demonstrated a correlation between levels of α4 expression and drug resistance in 8226 myeloma cell line. (Damiano J S et al., *Blood* 1999; 93(5): 1658-67; Damiano J S et al., *Curr Cancer Drug Targets* 2002; 2(1): 37-43) In vitro studies utilizing 8226 human melanoma cell lines confirmed that acquired resistance to doxorubicin or melphalan was associated with an increase in α4 expression as determined by fluorescence-activated cell sorting (FACS) analysis. The conjugate of formula A may be useful in overcoming cell adhesion-mediated drug resistance (CAM-DR) resulting from over-expression of α4β1 integrin.

TABLE 11

FACS Analysis of Integrin Subunits on Drug Sensitive And Drug Resistant Cell Lines

| Cell Line | α4 | β1 |
|---|---|---|
| 8226/S | 10.41 | 8.43 |
| 8226/LR5 | 46.53* | 44.63* |
| 8226/DOX6 | 69.00* | 26.21 |

Values reported are the mean fluorescence intensity of representative histograms from three different experiments.
*Integrin subunit expression is significantly higher than 8226/S at the P < 0.05 level (n = 3).
8226/S = drug sensitive human myeloma cell line
8226/LR5 = drug resistant human myeloma cell line selected from 8226/S using step-wise increases in melphalan TABLE 11-continued FACS Analysis of Integrin Subunits on Drug Sensitive And Drug Resistant Cell Lines

| Cell Line | α4 | β1 |
|---|---|---|

8226/DOX6 = drug resistant human myeloma cell line selected from 8226/S using step-wise increases in doxorubicin In summary, evidence from the literature regarding the role of α4 integrin in angiogenesis/lymphangiogenesis, tumor metastasis and CAM-DR along with direct preclinical studies of the conjugate of formula A in models of angiogenesis and tumor burden is supportive of the conjugate of formula A's role in oncology.

Example C

The single-dose plasma PK profile of the conjugate of formula A was characterized in C57/B16 mice, Sprague-Dawley rats, Hartley guinea pigs, Beagle dogs and Yorkshire swine. A summary of the PK data in these species at 1 and 10 mg/kg is shown in Table 12.

Following either intravenous (IV) or subcutaneous (SC) administration, the conjugate of formula A demonstrates increased exposure with increasing dose across each of the species evaluated. In general, AUC increased in a greater than expected manner, resulting from a dose related prolongation in the elimination half-life of the conjugate of formula A. The SC PK behavior of the conjugate of formula A was defined by increasing half-life and bioavailability as the amount of the conjugate of formula A administered was increased. Similar to SC administration, the conjugate of formula A demonstrated a nonlinear behavior apparently resulting from the saturation of its elimination following IV administration in rats and dogs. The IV PK behavior of the conjugate of formula A was defined by decreased systemic clearance, increased apparent volume of distribution and half-life as the amount of the conjugate of formula A administered was increased. The half-life observed with the conjugate of formula A does not appear to be dependent upon the absorption of the conjugate from the site of injection, as this phenomenon was observed following both SC and IV administration.

TABLE 12

Mean Pharmacokinetic Parameters for the conjugate of formula A Following Single-Dose Administration at 1 and 10 mg/kg Administered Dose (mg/kg)

|  | Mouse | | Guinea Pig | | Rat | | Dog | | Swine |
|---|---|---|---|---|---|---|---|---|---|
| Parameter | 1 | 10 | 1 | 10 | 1 | 10 | 1 | 10 | 10 |
| Intravenous+− | | | | | | | | | |
| $C_0$ (μg/mL) | ND | ND | ND | ND | 19.6 | 124 | 18.4 | 199 | ND |
| $AUC_{0-\infty}$ (μg · h/mL) | ND | ND | ND | ND | 760 | 10470 | 1345 | 31444 | ND |
| Half-life (hours) | ND | ND | ND | ND | 20.2 | 60.8 | 48.6 | 97.9 | ND |
| Cl (mL/hr/kg) | ND | ND | ND | ND | 1.34 | 0.96 | 0.75 | 0.32 | ND |
| $V_{ss}$ (mL/kg) | ND | ND | ND | ND | 40.1 | 77.0 | 50.2 | 54.0 | ND |
| Subcutaneous | | | | | | | | | |
| $C_{max}$ (μg/mL) | 5.51 | 59.6 | 5.42 | 55.8 | 2.51 | 40.2 | 3.01 | 60.0 | 84.4 |
| $AUC_{0-\infty}$ (μg · h/mL) | 247 | 5300 | 271 | 7570 | 160 | 5390 | 444 | 20936 | 20444 |
| $T_{max}$ (hours) | 24 | 8 | 24 | 24 | 28 | 42 | 56 | 60 | 32 |
| Half-life (hours) | 15.2 | 59 | 18.1 | 42.5 | 36.0 | 67 | 56.1 | 109 | 103 |
| Bioavailability | ND | ND | ND | ND | 20% | 52% | 33% | 67% | ND |

Abbreviations:
$AUC_{0-last}$ = Area under the plasma concentration curve from time = 0 to the last measurable time point;
$C_{max}$ = Maximal plasma concentration;
$T_{max}$ = Time of maximal plasma concentration;
$C_0$ = Maximal plasma concentration at time = 0;
Cl = Plasma clearance;
$V_{ss}$ = Volume of distribution at steady-state,
ND = Not determined Following repeated administration to rats and dogs, exposure and maximal plasma concentrations of the conjugate of formula A increased with increasing dose but in a greater than expected manner (see Table 13 and Table 14). This observed accumulation was consistent with the half-life of the conjugate of formula A 137235 (see Table 13 and Table 14). Based on trough level concentrations, steady state appeared to be reached between Week 6 and Week 12 for rats and between Week 4 and Week in dogs 6 for the conjugate of formula A. Although no gender differences in exposure of the conjugate of formula A were observed in the dog, AUC and $C_{max}$ values were higher in female rats as compared to male rats.

TABLE 13

Pharmacokinetic Parameters for the conjugate of formula A Following SC Administration to Sprague-Dawley Rats for up to 3 Months (Study 132-001-06)

| | Administered Dose (mg/kg) | | | | | | | | | |
|---|---|---|---|---|---|---|---|---|---|---|
| | 3 | | 10 | | 30 | | 100 | | 1000 | |
| Parameter | Males | Females | Males | Females | Males | Females | Males | Females | Males | Females |
| Week 1 (first dose) | | | | | | | | | | |
| $C_{max}$ (μg/mL) | 2.29 | 6.86 | 16.9 | 40.6 | 83.2 | 164 | 355 | 681 | 4280 | 5100 |
| $T_{max}$ (hours) | 24.0 | 24.0 | 24.0 | 24.0 | 72.0 | 24.0 | 96.0 | 72.0 | 96.0 | 72.0 |
| $AUC_{0-120}$ (μg · h/mL) | 164 | 455 | 1540 | 3220 | 7570 | 15,300 | 31,000 | 63,200 | 366,000 | 493,000 |
| $AUC_{0-168}$ (μg · h/mL) | 164 | 472 | 1770 | 3680 | 9560 | 18,700 | 40,500 | 77,600 | 461,000 | 665,000 |
| $AUC_{0-\infty}$ (μg · h/mL) | 192 | 472 | 1990 | 4070 | 13,400 | 23,000 | 59,400 | 99,300 | 637,000 | 1,070,000 |
| Half-life (hours) | 41.6 | 17.1 | 42.0 | 41.8 | 75.9 | 59.6 | 75.6 | 60.3 | 66.3 | 94.3 |
| Week 13 (last dose) | | | | | | | | | | |
| $C_{max}$ (μg/mL) | 6.02 | 13.2 | 36.4 | 68.9 | 71.6 | 287 | 341 | 1250 | 7220 | 10,800 |
| $T_{max}$ (hours) | 72.0 | 72.0 | 24.0 | 72.0 | 72.0 | 72.0 | 96.0 | 96.0 | 72.0 | 120 |
| $AUC_{0-120}$ (μg · h/mL) | 554 | 1340 | 3340 | 7010 | 7760 | 32,200 | 35,900 | 108,000 | 744,000 | 1,200,000 |
| Half-life (hours) | 106 | 90.3 | 132 | 83.7 | NC | NC | NC | NC | NC | NC |

Abbreviations:
AUC = Area under the plasma concentration curve;
$C_{max}$ = Maximal plasma concentration;
$T_{max}$ = Time of maximal plasma concentration;
NC = Not Reported, erratic terminal phase or unable to regress due to rising or erratic terminal phase.

TABLE 14

Summary of Pharmacokinetic Parameters for the conjugate of formula A Following
SC Administration to Dogs for up to 3 Months (Study 132-002-06)

| | Administered Dose (mg/kg) | | | | | | | |
|---|---|---|---|---|---|---|---|---|
| | 3 | | 30 | | 100 | | 1000 | |
| Parameter | Males | Females | Males | Females | Males | Females | Males | Females |
| Week 1 (first dose) | | | | | | | | |
| $C_{max}$ (μg/mL) | 19.3 | 125 | 306 | 286 | 973 | 980 | 6790 | 9010 |
| $T_{max}$ (hours) | 80.0 | 88.0 | 80.0 | 72.0 | 72.0 | 72.0 | 88.0 | 128 |
| $AUC_{0-\square}$ (μg · h/mL) | 2470 | 4940 | 37,200 | 36,400 | 124,000 | 116,000 | 818,000 | 965,000 |
| $AUC_{0-\infty}$ (μg · h/mL) | 4890 | 6650 | 88,800 | 108,000 | 419,000 | 298,000 | 2,220,000 | NC |
| Half-life (hours) | 134 | 141 | NC | 240 | 260 | 155 | 182 | NC |
| Week 13 (last dose) | | | | | | | | |
| $C_{max}$ (μg/mL) | 45.3 | 42.4 | 597 | 577 | 2230 | 1970 | 9950 | 11,500 |
| $T_{max}$ (hours) | 72.0 | 56.0 | 80.0 | 72.0 | 40.0 | 24.0 | 24.0 | 17.3 |
| $AUC_{0-\square}$ (μg · h/mL) | 6600 | 5920 | 82,100 | 86,000 | 324,000 | 266,000 | 1,390,000 | 1,600,000 |
| Half-life (hours) | 141 | 163 | NC | 344 | 156 | 171 | NC | 263 |

Abbreviations:
AUC = Area under the plasma concentration curve;
$C_{max}$ = Maximal plasma concentration;
$T_{max}$ = Time of maximal plasma concentration;
NC = Not Calculated, erratic terminal phase or unable to regress due to rising or erratic terminal phase.

The metabolic stability of the conjugate of formula A has been evaluated in several in vitro metabolizing systems, including hepatic microsomal preparations and hepatocytes. However, the conjugate of formula A has been found to be stable with no identifiable routes of biotransformations by typical drug metabolizing systems.

The excretion of $^{14}C$-equivalents was determined in male Sprague-Dawley Rats following both SC and IV administration of $^{14}C$- the conjugate of formula A. The primary route of excretion of the conjugate of formula A derived $^{14}C$-equivalents was via the urine. The $^{14}C$-equivalents detected in the feces appeared to be due to biliary elimination. Furthermore, the majority of the dose was excreted within the first 24 hours after administration of $^{14}C$- the conjugate of formula A regardless of the route of administration (Table 15). However, by 672 hours approximately 22% of the administered dose was associated with the carcass following SC administration of $^{14}C$- the conjugate of formula A.

TABLE 15

Excretion of 14C-Equivalents Following Administration of 3 mg/kg
of 14C-the conjugate of formula A to the Male Sprague-Dawley Rat

| Route of Administration | Percent of Administered Dose (mean ± standard deviation) | | | |
|---|---|---|---|---|
| | Urine | Feces | Carcass | Total |
| Subcutaneous | 56.2 ± 2.7 | 13.3 ± 4.3 | 22.5 ± 3.9 | 91.9 ± 2.5 |
| Intravenous | 67.7 ± 5.3 | 8.1 ± 0.8 | 14.0 ± 1.3 | 89.8 ± 13.5 |

Urine and feces were collected over a 672-hour period and carcass was collected at 672 hours after 14C-the conjugate of formula A administration.

Human Equivalent Dose

The human equivalent dose (HED) was determined from the NOAEL determinations for rat and dog 3-month repeat-dose toxicity studies. In accordance with the FDA CDER Guidance document (Food and Drug Administration, Center for Drug Evaluation and Research. Guidance of Industry: Estimating the Maximum Safe Starting Dose in Initial Clinical Trials for Therapeutics in Adult Healthy Volunteers. July 2005). The NOAELs used in determining the HED are based on one early sacrifice of a 100 mg/kg rat and clinical signs (thin body condition and swelling, thickening of skin, and scabbing at dosing sites) observed in the 100 mg/kg dogs. The equation for determining HED was:

$$HED = NOAEL\ Dose * (BWtest\ species/BWhuman)^{(0.33)}$$

Where $(BWtest\ species/BWhuman)^{(0.33)}$ is the standard conversion factor

TABLE 16

Human Equivalent Dose Calculations

| | NOAEL Dose (mg/kg) | (BWtest species/ BWhuman)$^{(0.33)}$ | HED (mg/kg) | Margin over Proposed Starting Dose of 0.2 mg/kg | Margin over Proposed Highest Dose of 2.0 mg/kg |
|---|---|---|---|---|---|
| Rat | 30 | 0.162 | 4.86 | 24.3X | 2.43X |
| Dog | 30 | 0.541 | 16.23 | 81.15X | 8X |

[1]Assumes average human weight of 60 kg

Example D

The objective of the following in vitro studies was to evaluate the potency and binding characteristics of the conjugate of formula A, its ligand specificity, species specificity, and its ability to regulate α4 integrin receptor expression.

The potency of the conjugate of formula A was determined using four assays to measure α4β1-dependent ligand interaction (Table 17). The most stringent potency assay examined the ability of the conjugate of formula A to compete with binding of a multivalent, high-affinity α4β1 reagent (27/1-69302). This reagent carries multiple copies of a small molecule (ELN69302) that binds to α4β1 integrin with high affinity and selectivity. The carrier portion of the reagent is an irrelevant mouse antibody, 27/1. Specificity of the reagent 27/1-ELN69302 was previously demonstrated by the inhibition of binding with antibodies to α4 (21/6 and GG5/3). Compounds that can prevent binding of the 27/1-ELN69302 reagent are assumed to be directly interacting with α4β1. The $EC_{50}$ values for three lots of the conjugate of formula A were comparable (13.8 to 21.6 nM) in this assay.

The potency of the conjugate of formula A was also evaluated in α4β1-dependent cell adhesion assays using two physiologically relevant substrates, vascular cell adhesion molecule-1 (VCAM-1) and fibronectin (FN). In these assays, the conjugate of formula A blocks adhesion of Jurkat TM cells (human lymphocytic cell line) to VCAM-1 and FN-coated plates with an $ED_{50}$ of 0.5 nM and 0.2 nM, respectively.

The fourth potency assay measured the ability of the conjugate of formula A to inhibit capture of human serum FN by lymphocytes ($ED_{50}$=0.05 nM).

TABLE 17

Summary of Potency Assays with the conjugate of formula A ($ED_{50}$ values)

| Lot No. | Multivalent Competition | VCAM-1 Adhesion | FN Adhesion | FN Capture |
|---|---|---|---|---|
| the conjugate of formula A-1 | 13.8 nM (n = 6) CV = 32% | ND | ND | ND |
| the conjugate of formula A-2 | 14.1 nM (n = 3) CV = 22% | 0.5 nM (n = 1) | ND | 0.05 nM (n = 1) |
| the conjugate of formula A-5 | 21.6 nM (n = 1) | ND | 0.2 nM (n = 1) | ND |

ND: not determined
Multivalent competition assay (mean value): 27/1-ELN69302, an α4β1-specific competitive binding assay
a4β1-VCAM-1 adhesion: Jurkat cell adhesion to VCAM-1 coated plates
a4β1-FN adhesion: Jurkat cell adhesion to FN-coated plates
a4β1-FN capture: Binding of human FN to Jurkat cells The potency of the conjugate of formula A as measured in the multivalent competition assay was not significantly altered in the presence of serum; thus it is presumed that the conjugate does not bind to serum proteins to a significant degree (Table 18).

TABLE 18

Summary of Potency Assessment by Multivalent Competition Assay Under Different Serum Conditions ($ED_{50}$, n = 1)

| Assay Conditions | the conjugate of formula A |
|---|---|
| H/S++0.3% BSA | 9.24 nM |
| 100% Human Serum | 4.72 nM |
| 100% Rat Serum | 11.39 nM |
| 100% Dog Serum | 6.91 nM |

Multivalent competition assay: 27/1-ELN69302 α4β1 specific competitive binding assay
H/S++: Hepes/Saline plus calcium and magnesium, assay buffer
BSA: bovine serum albumin The conjugate of formula A activity was examined in four non-α4β1-dependent integrin assays to assess specificity across a diverse range of integrin subsets (Table 19). These assays included: 1) α4β7-dependent adhesion to mucosal addressin cellular adhesion molecule (MadCAM), to assess P1 specificity; 2) αLβ2 (LFA-1)-dependent adhesion to intercellular adhesion molecule (ICAM), to assess a non-α4, non-β1 class of integrin; 3) α5β1-dependent adhesion to FN, to assess an integrin with similar but broader functionality; and 4) α9β1 integrin, the integrin most closely related to α4 potency as measured by the multivalent competition assay on α9β1-expressing cells.

The conjugate of formula A had no measurable activity against αLβ2 (LFA-1) and α5β1 integrin. It showed approximately 100-fold selectivity for α4β1 over α4β7 integrin. The $EC_{50}$ of α4β1 mediated adhesion was 0.2-0.5 nM (Table 17) versus an $EC_{50}$ for α4β7-mediated adhesion of 38 nM (Table 19). The conjugate of formula A potency for the related integrin, α9β1, was within 3-fold of the potency of α4β1 (average MV competition $EC_{50}$=16.5 nM vs $EC_{50}$ α9β1=51 nM), which is not unexpected based on the homology between α4 and α9 and the overlapping ligands.

TABLE 19

Summary of the conjugate of formula A Binding in Four Specificity Assays for Non-α4β1-Dependent Integrin In Vitro

| | Integrin-Specific Assay-$EC_{50}$ | | | |
|---|---|---|---|---|
| Matrix | α4β7-MadCAM Adhesion | αLβ2-ICAM-1 Adhesion | α5β1-FN Adhesion | α9β1 MV Competition |
| H/S++/0.3% BSA | 38 nM (n = 1) | >1 μM (n = 2) | >1 μM (n = 1) | 51 nM (n = 2) |

H/S++: Hepes/Saline plus calcium and magnesium, assay buffer
BSA: bovine serum albumin
α4β7 MadCAM: 8866 cell adhesion to MadCAM (mucosal addressin cellular adhesion molecule)- Fc coated plate
αLβ2 ICAM: 8866 cell adhesion to ICAM (intracellular adhesion molecule-1) Fc coated plate
α5β1 FN: THP-1 cells adhesion to FN coated plates
α9β1 MV competition: 27/1-69302 multivalent competition assay on SW480/a9b1 transfected cells (FACS analysis)

Figure 7:
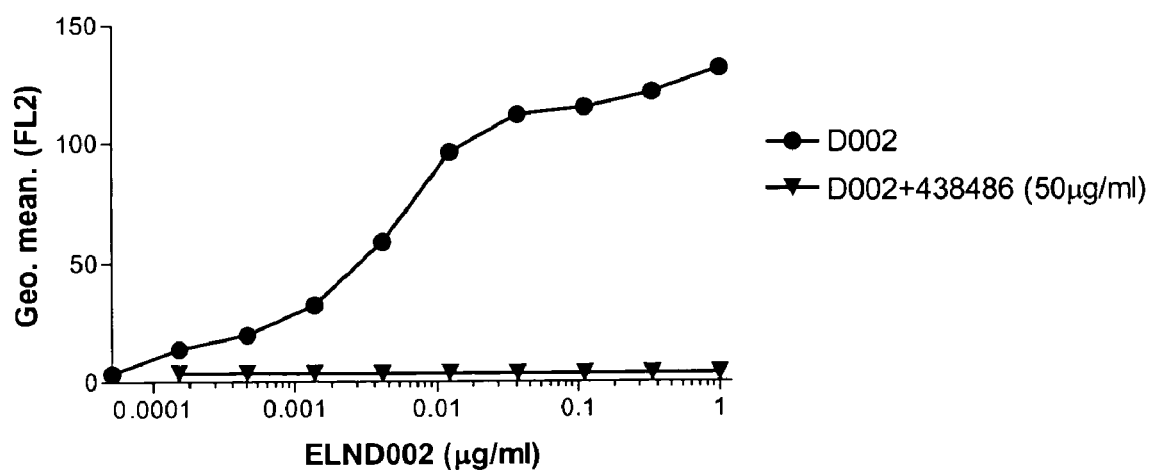
FIG. 7 shows a graph illustrating the binding of the conjugate of formula XXII with guinea pig lymphocytes.
Figure 8:
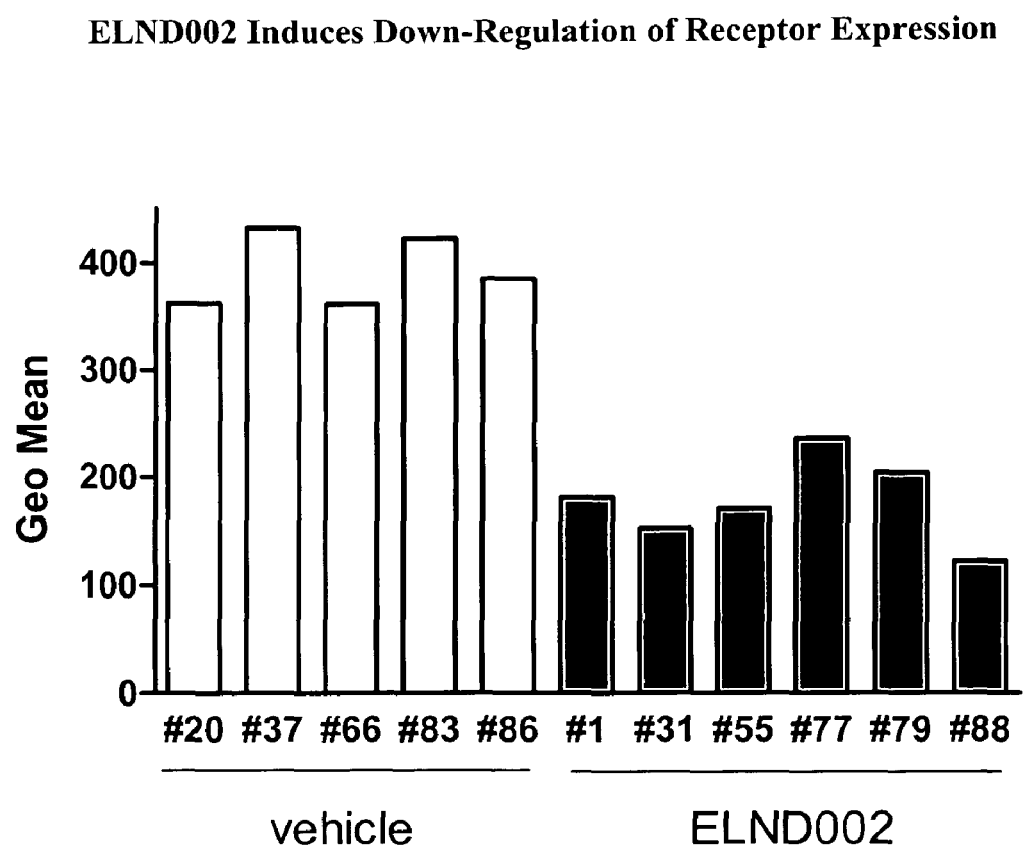
FIG. 8 shows a graph illustrating the down-regulation of receptor expression of the conjugate of formula XXII.

To demonstrate that the conjugate of formula A binds to rat, guinea pig, dog, monkey, and human lymphocytes, an assay was developed to directly detect the binding of the conjugate of formula A using a biotinylated antibody against polyethylene glycol (PEG) (AGP-3-Biotin). Background binding was determined by competition with ELN438-486, a small molecule that binds to α4β1 with high affinity. Primary lymphocytes from whole blood samples of rat, guinea pig, dog, monkey (rhesus and cynomolgus) and human were incubated with increasing concentrations of the conjugate of formula A with or without excess ELN438486. The binding was similar for all species (Table 20). An example of the conjugate of formula A binding to guinea pig lymphocytes is illustrated in FIG. 7.

TABLE 20

Summary of the conjugate of formula A In Vitro Binding Activity to Rat, Guinea Pig, Dog, and Human Lymphocytes

| | $EC_{50}$ (μg/mL) | | | | |
|---|---|---|---|---|---|
| Conjugate | Rat | Guinea Pig | Dog | Monkey | Human |
| the conjugate of formula A | 0.003 | 0.005 | 0.0005 | 0.004 (Rhesus) 0.0004 (Cyno.) | 0.008 |

The conjugate of formula A Binding Induces Down-Regulation of α4β1

To assess α4β1 expression upon treatment with the conjugate of formula A, an assay was developed with the anti-PEG antibody AGP-3 that detects the conjugate of formula A bound to cells. A 10 mg/kg dose of the conjugate of formula A administered to guinea pigs during an efficacy study induced reduction of receptor expression on lymphocytes as compared to expression levels on lymphocytes from vehicle-treated EAE animals.

In summary, this set of in vitro studies demonstrated that the conjugate of formula A binds to α4β1 integrin with low nM affinity. Binding was not significantly altered in the presence of serum from humans, dogs, or rats. The conjugate of formula A is selective for α4β1 integrin over other integrins, although it shows cross-reactivity with α9β1, which is expected based on homology between α4 and α9. The conjugate of formula A binds to rat, guinea pig, dog, cynomolgus and rhesus monkey, and human lymphocytes. Treatment with the conjugate of formula A down-regulate α4β1 integrin receptor levels on guinea pig lymphocytes.

Example E

Mouse Corneal Micropocket Assay

The activity of the small molecule of the conjugate of formula A is believed to inhibit trafficking of proinflammatory lymphocytes into the central nervous system. In addition, the integrin alpha4beta1 has been implicated in the angiogenesis process. It has been shown that alpha4beta1 binding to VCAM-1 promotes close intercellular adhesion between endothelial cells and pericytes (a type of mural cell along with vascular smooth muscle cells) and that this interaction is required for blood vessel formation (B Garmy-Susini, et al. *J. of Clin. Invest.*, Vol 115, No. 6, 1542-1551). Integrin alpha4beta1 is expressed by proliferating but not quiescent endothelial cells, while its ligand VCAM-1 is expressed by proliferating, but not quiescent mural cells. Antagonists of this integrin-ligand pair block adhesion of mural cells to proliferating endothelia in vitro and in vivo, thereby inhibiting neovascularization (Garmy-Susini). As a potent inhibitor of alpha4beta1 and VCAM-1 interactions, the conjugate of formula A inhibit neovascularization and angiogenesis.

Fifty-five Charles River (Wilmington, N.C.) female C57BL/6 mice were available for the study. A total of 40 mice that received the VEGF (vascular endothelial growth factor) Hydron pellets were placed on study, 8 per group; with three animals were in a control group that did not receive VEGF in the Hydron implantation. On Day 1 (Oct. 9, 2007) the Hydron pellets were implanted into corneal pocket cut in one eye of mice; pellets containing 200 ng/animal VEGF were implanted in Groups 2-6. Mice were anesthetized with 90 mg/kg pentobarbital, IP, immediately prior to implantation surgery; pellet implantation was performed according to Piedmont SOP which the test facility described as an adaptation of the method described by Kenyon et al (B M Kenyon, E E Voest, C C Chen, E Flynn, J Folkman, R J D'Amato, 1996, A model of angiogenesis in the mouse cornea, Investigative Opthalmology & Visual Science, Vol 37 No 8, 1625-1632).

Pellets were implanted on Day 1 approximately 1 mm from the limbus. Pellets without VEGF were implanted in the Group 1 mice (n=3) and served as negative control (no vascularization); these animals were dosed with vehicle (PBS) on Days 2 and 5 by subcutaneous (SC) administration. Group 2 served as the VEGF-treated negative control; implanted with VEGF and receiving vehicle (PBS) by SC administration on Days 2 and 5 (n=8), this group was considered to have 100% neovascularization. Group 3 served as the positive treatment control, implanted with VEGF and receiving bevacizumab (Avastin, Genentech), an anti-VEGF monoclonal antibody dosed by interperitoneal (IP) administration every day for 6 days starting on Day 2 (Avastin is dosed intravenously in the clinic and IP is the acceptable route of administration for mice). Groups 4, 5, and 6 (n=8 per group) were implanted with VEGF and received SC administration of 3, 10, and 30 mg/kg the conjugate of formula A, respectively, on Days 2 and 5.

Body weights were taken every day throughout the study. Vascularization measurement was performed on Day 8. On Day 8, the cornea of the implanted eye of all mice was examined by a trained technician. The cornea of the eye was viewed using a slit lamp and measurements were made using the eyepiece reticule. The vessel length of the longest blood vessel to have grown upward from the limbus was measured (VL) as was the circumference of vessel growth or clock hour (CH). The area of neovascularization was calculated using the formula: Area $(mm^2)=\pi VL \times CH \times 0.2$. In addition to reporting the vessel length, clock hour, and calculated area of neovascularization, the percent neovascularization compared to the VEGF-treated negative control (Group 2) was reported. statistical significance by Kruskal-Wallis-Dunn with comparison to Group 2 and mean body weight nadir (the lowest group mean body weight, as a percent change from Day 1.

TABLE 21

Group Assignments

| | | 1 Drug/Testing Agent | | | | 2 Drug/Testing Agent | | | |
|---|---|---|---|---|---|---|---|---|---|
| Gr. | N | Agent | mg/kg | Route | Schedule | Agent | mg/kg | Route | Schedule |
| 1 | 3 | VEGF- | 0* | cp | day 1 | vehicle | — | SC | day 2, day 5 |
| 2 | 8 | VEGF | 200* | cp | day 1 | vehicle | — | SC | day 2, day 5 |
| 3 | 8 | VEGF | 200* | cp | day 1 | bevacizumab | 10 | IP | qd x 6 (Start Day 2) |
| 4 | 8 | VEGF | 200* | cp | day 1 | the conjugate of formula A[a] | 3 | SC | day 2, day 5 |
| 5 | 8 | VEGF | 200* | cp | day 1 | the conjugate of formula A | 10 | SC | day 2, day 5 |
| 6 | 8 | VEGF | 200* | cp | day 1 | the conjugate of formula A | 30 | SC | day 2, day 5 |

[a] referred to as RZ1 by Piedmont

Female C57BL/6 mice, aged 6 weeks, weights ranging from 14.0 to 17.8 grams at Day 1 of study, were shipped from Charles River Laboratories and randomly housed four per cage in Piedmont Research Center Animal Facility. Mice were acclimated for 7 days prior to the start of the experiment, and were provided food and water ad libitum throughout the study.

Mice have been successfully used as a model of angiogenesis in the cornea with VEGF as the angiogenic cytokine (B M Kenyon, E E Voest, C C Chen, E Flynn, J Folkman, R J D'Amato, 1996, A model of angiogenesis in the mouse cornea, *Investigative Opthalmology & Visual Science*, Vol 37 No 8, 1625-1632). The corneal micropocket assay is reported as a quantitative and reproducible assessment of angiogenesis in vivo (M S Rogers, A E Birsner, R J D'Amato, 2007, The mouse cornea micropocket angiogenesis assay, *Nature Pro-* tocols, Vol 2 No 10, 2545-2550). It has the advantage that the measurement of background vessels is unnecessary because in the assay the vessels grow on normally avascular tissue; eliminating a source of variation, and eliminating the possibility of vessel dilation being mistaken for angiogenesis (M S Rogers, A E Birsner, R J D'Amato, 2007, The mouse cornea micropocket angiogenesis assay, *Nature Protocols*, Vol 2 No 10, 2545-2550). Mice were assigned to groups in the order they were caged; no formal randomization or assignment procedure was used. Study number, group number, and animal numbers were used to identify each cage. Animals were identified with individual marks tattooed on the base of the tail using indelible ink.

The 1×PBS vehicle and the conjugate of formula A dose solutions (0.6, 2 and 6 mg/mL) were prepared. Dose solutions were prepared from a 50 mg/mL stock solution. The 0.6 to 6 mg/mL dose solutions are stable at refrigerated temperature for two weeks; the 50 mg/mL solution is stable at refrigerated temperatures for one year.

Mice were dosed with the conjugate of formula A and vehicle (PBS) on Days 2 and 5 via SC injection of the nuchal area with a Terumo 27-gauge needle (0.5 inch); SC injection is the expected route of administration in the clinic. The dose level of 30 mg/kg of the conjugate of formula A was based on the NOAEL from previous rat and dog studies (132-001-06, 132-002-06). The low dose of 3 mg/kg is the lowest dose to show efficacy in the guinea pig EAE model. Animals were dosed 5 mL/kg of the 50 mg/mL and PBS solutions based on most current body weight.

Mice dosed with bevacizumab were dosed every day for 6 days starting on Day 2 via IP injection with a Terumo 27-gauge needle (0.5 inch); SC injection is the expected route of administration in the clinic. Bevacizumab was diluted into saline. The dose level of 10 mg/kg bevacizumab was determined as demonstrating optimal antiangiogenic activity during assay development.

There were no significant changes in body weight between the untreated group and the conjugate of formula A and bevacizumab groups, supporting that the results reported here were not affected by toxicity caused by administration of the conjugates. Animals were implanted with VEGF pellets (200 ng/pellet) on Day 1 and neovascular changes measured on Day 8; it has been reported that new vessels are seen within one day of implantation with continued growth peaking around one week post-implantation (M S Rogers, A E Birsner, R J D'Amato, 2007, The mouse cornea micropocket angiogenesis assay, Nature Protocols, Vol 2 No 10, 2545-2550). Animals were dosed with the conjugate of formula A on Days 2 and 5, thus, within the time frame in which vessels are expected to began to grow.

Reported parameters of angiogenesis in the cornea were: the measurement of the circumference of the vessels growth (clock hour, CH), vessel length (VL), and area of neovascularization (mm$^2$). The Kruskal-Wallis Dunn test was performed on the last parameter to determine statistical significant difference. Significant decrease in the area of neovascularization was seen between the VEGF-treated negative control group, Group 2, and the highest dose of the conjugate of formula A, Group 6 (30 mg/kg of the conjugate of formula A) at $p<0.05$. Statistical significance was also observed between the bevacizumab group and Group 2 with p value of 0.001. The percent area of neovascularization of the conjugate of formula A treated groups compared to the VEGF-treated negative control group (Group 2) were 81%, 57%, and 46% for the 3, 10 and 30 mg/kg groups. The mean for area of neovascularization of the VEGF-treated negative control group (Group 2) was 1.3 mm$^2$, and at 3, 10, and 30 mg/kg of the conjugate of formula A the mean for area of neovascularization was 1.1, 0.7, and 0.6 mm$^2$, respectively. The standard error of means were consistent between these groups, ranging from 0.06 to 0.13 mm$^2$. Bevacizumab, having direct effect on the VEGF treatment, had 0% neovascularization. These results show the conjugate of formula A demonstrated dose-dependent inhibition of neovascularization of the VEGF-treated cornea.

It was noted that one animal in the 30 mg/kg the conjugate of formula A group was excluded from the data analysis because the pellet location was "too close to vessel" which hindered accurate measurements. Therefore, the results of the 30 mg/kg the conjugate of formula A group were based on seven animals.

Rogers et al. reported that VEGF doses up to 160-180 ng generate an approximately linear dose-response curve up to approximately 1.2 mm$^2$, with higher doses of VEGF producing only modest increases in vessel area (2007, The mouse cornea micropocket angiogenesis assay, Nature Protocols, Vol 2 No 10, 2545-2550). This is consistent with the results seen in this study as the VEGF-treated negative control group (Group 2) had an area of neovascularization of 1.3 mm$^2$. They also report that angiogenesis inhibitors that inhibit greater than 50% of vessel area are likely to be effective in implanted tumor models, whereas those showing less than 25% inhibition are rarely effective. It is uncommon for an angiogenesis inhibitor to have greater than 80% inhibition unless the inhibitor directly targets the pathway of the growth factor in the pellet, such as bevacizumab in this study. The conjugate of formula A at 30 mg/kg had a neovascularization area that was 46% of the VEGF-treated negative control which is equivalent to 54% inhibition, suggesting that the conjugate of formula A will be effective in implanted tumor models.

In summary, subcutaneous administration of 3, 10 and 30 mg/kg of the conjugate of formula A resulted in dose-dependent decreases in the area of neovascularization of the cornea following implantation of VEGF in the cornea. The percent of neovascularization compared to control animals implanted with VEGF and receiving the PBS vehicle (with 100% neovascularization) was 81%, 57%, and 46%, respectively. The inhibition of neovascularization at 30 mg/kg was significant at $p<0.05$.

It was shown that binding of the conjugate of formula A to alpha4 integrins blocks lymphocyte adherence to the endothelium substrates, vascular cell adhesion molecule-1 (VCAM-1) and fibronectin (FN). The blockade of α4 integrins prevents trafficking of lymphocytes across the endothelium and into the parenchymal tissue. It is through this mechanism that the conjugate of formula A demonstrates efficacy in mouse, rat, and guinea pig experimental autoimmune encephalomyelitis (EAE) and animal models of MS. The results from the corneal micropocket assay support that the conjugate of formula A will be efficacious in blocking other alpha4 integrin-mediated processes including angiogenesis.

Example F

Determination of Tumor Growth Delay of the MOLT-4 Human Leukemia Model by the Conjugate of Formula A and Topotecan in Combination The activity of the conjugate of formula A is believed to inhibit trafficking of proinflammatory lymphocytes into the central nervous system. The use of the conjugate of formula A to block α4 integrin results in direct antitumor activity when tumor cells express α4 integrins and/or in inhibition of metastasis, angiogenesis and lymphangiogenesis, and reversal of cell adhesion-mediated drug resistance (CAM-DR). Alpha4β1 or α4β7 integrins are expressed on myeloma, chronic lymphocytic leukemia, B-cell non-Hodgkin's lymphoma (NHL), and melanoma cells at various stages of tumor development, invasiveness and dissemination. (See Albelda et al., *Cancer Res* 1990 1990; 50(20)6757-64; Csanaky G, et al., *Leukemia* 1997; 22(3): 408-15; Drillenburg P Et al., *Am J Pathol* 1997; 150(3) 919-27; Paavonen T et al., *Int J Cancer* 1994; 58(2): 298-302; and Moller P et al., *Leukemia* 1992; 6(4): 256-64).

The objective of this study was to assess the ability of the conjugate of formula A to affect tumor growth when dosed alone or in combination with a common chemotherapeutic agent. Of the one hundred eighty (180) female HRLN CB.17 SCID mice available for the study, 90 were enrolled. Xenografts were initiated from MOLT-4 human leukemia cells lines that were maintained and serially subcutaneously implanted in SCID mice at Piedmont. On day of tumor implant, each SCID mouse received a 1 mm$^3$ MOLT-4 tumor fragment implanted subcutaneously in the right flank, and the growth of tumors was monitored as the average size approached the targeted range of 80-120 mg. The animals were sorted by pair-match when the target tumor sizes were reached the target range and enrolled into 9 groups (n=10) for analysis of efficacy. On Day 1, the group mean tumor volumes was 117 mm$^3$ with individual tumor sizes ranging from 108 to 126 mm$^3$ and the conjugate of formula A and topotecan treatments were initiated. Tumor volume was calculated using the formula:

$$\text{Tumor Volume(mm}^3\text{)}=(w^2 \times l) \div 2$$

Where w=width and l=length in mm of a MOLT-4 tumor. The calipers were placed on the edge of the tumor where it grows on the flank of the mouse. Tumor weight may be estimated with the assumption that 1 mg is equivalent to 1 mm$^3$ of tumor volume.

Mouse body weights and tumors sizes using calipers were measured twice each week for the duration of the study. Group 1 mice served as the control group and received PBS. Groups 2 and 3 served as the topotecan treatment monotherapy groups and received 12 and 6 mg/kg topotecan, respectively. Groups 4 and 5 served as the conjugate of formula A monotherapy treatment groups and received 10 and 100 mg/kg the conjugate of formula A, respectively. Groups 6 to 7 received both topotecan at 12 mg/kg and the conjugate of formula A at 10 and 100 mg/kg respectively as a combination therapy. Groups 8 to 9 received both topotecan at 6 mg/kg and the conjugate of formula A at 10 and 100 mg/kg respectively as a combination therapy. When doses were administered on the same day, topotecan was administered first, followed by the conjugate of formula A within 10-15 minutes. Starting on Day 1, the conjugate of formula A was administered once weekly SC until study termination; topotecan was administered IP every four days for a total of three doses.

The maximum tolerated dose for the conjugate of formula A in rats is 300 mg/kg/week. 100 mg/kg/week was identified as the appropriate high dose in the mouse. The low dose of 10 mg/kg/week has been shown to be efficacious in the mouse, rat and guinea pig EAE models.

The dose level of 12 mg/kg topotecan was determined as maximum tolerated dose in the MOLT-4 cell line by Piedmont Research Center. Since maximal biologic effect can occur at a dose much lower than the MTD, we had included ½ the maximum tolerated (½MTD=6 mg/kg) (see Marx, G M et al., *Journal of Clin One* 2002; 20(6): 1446-1448). Moreover, including the ½ MTD topotecan dose in combination with the conjugate of formula A may potentially show incremental effects of the drug.

Tumors were measured using calipers twice each week. Each animal was euthanized when its tumor reached the endpoint size of 2 gms or at the conclusion of the study on Day 60, whichever came first. The time to endpoint (TTE) for each mouse was calculated from the equation:

$$\text{TTE(days)}=[\log_{10}(\text{endpoint volume,mm}^3)-b]/m$$

where b is the intercept and m is the slope of the line obtained by linear regression of a log transformed tumor growth data set. The data set is comprised of the first observation that exceeded the study enpoint volume and the three consecutive observations that immediately preceded the attainment of the endpoint volume. Animals that do not reach the endpoint are assigned a TTE value equal to the last day of the study. Animals classified as NTR (non-treatment related) deaths due to accident (NTRa) or due to unknown causes (NTRu) are excluded from TTE calculations (and all further analysis). Animals classified as TR (treatment-related) deaths or NTRm (non-treatment-related death due to metastasis) are assigned a TTE value equal to the day of death.

Treatment outcome was evaluated by tumor growth delay (TGD), which is defined as the increase in the median time to endpoint (TTE) in a treatment group compared to the control group:

$$\text{TGD}=T-C$$

Expressed in days, or as percentage of the median TTE of the control group:

$$\%\text{ TGD}=[(T-C)/C]\times 100$$

where:
T median TTE for the treatment group
C=median TTE for the control group (Group 1).

Treatment may cause partial regression (PR) or complete regression (CR) of the tumor in an animal. In a PR response, the tumor volume is 50% or less of its Day 1 volume for three consecutive measurements during the course of the study and equal to or greater than 13.5 mm$^3$ for one or more of these three measurements. In a CR response, the tumor volume is less the 13.5 mm$^3$ for three consecutive measurements during the course of the study. An animal with a CR at the termination of a study is additionally classified as a tumor-free survivor (TFS). Regression responses were monitored and recorded.

Animals were weighed daily for the first five days of the study and then twice weekly. The mice were observed frequently for overt signs of any adverse, treatment related side effects, and clinical signs of toxicity were recorded when observed. Acceptable toxicity is defined as a group mean body-weight loss of less than 20% during the study and not more than one treatment-related (TR) death among ten treated animals. Any dosing regimen that results in greater toxicity is considered above the maximum tolerated dose (MTD). A death is classified as TR if attributable to treatment side effects as evidenced by clinical signs and/or necropsy, or may also be assessed as TR if due to unknown causes during the dosing period or within 10 days of the last dose. A death is classified as an NTR if there is no evidence that death was related to treatment side effects.

Prism (GraphPad) for Windows 3.03 was used for all graphic presentations and statistical analyses. The logrank test was used to analyze the significance of the differences between the TTE values of treated or control groups. Two-tailed statistical analyses were conducted at significance P=0.05. Median tumor growth curves show group median tumor volumes as a function of time. When an animal exited the study due to tumor size, the final tumor volume recorded for the animal was included with the data used to calculate the group median tumor volume at subsequent time points. Curves are truncated after 50% of the animals in a groups had exited the study. Mean tumor growth curves, with one standard error of the mean (SEM) indicated by error bars, were similarly plotted. Kaplan-Meier plots were constructed to show percentage of animals remaining in the study as a function of time. These plots used the same data set as the logrank test.

TABLE 22

Study Design

| | | Treatment 1 | | | Treatment 2 | | | | |
|---|---|---|---|---|---|---|---|---|---|
| Gr | Treatment | Route | Dose (mg/kg) | Dose Frequency | Treatment | Route | Dose (mg/kg) | Dose Frequency | N |
| 1[#] | Vehicle | SC | — | Qwk to end | — | — | — | — | 10 |
| 2 | Topotecan[a] | IP | 12 | Q4d x 3 | — | — | — | — | 10 |
| 3 | Topotecan | IP | 6 | Q4d x 3 | — | — | — | — | 10 |
| 4 | The conjugate of formula A[b] | SC | 10 | Qwk to end | — | — | — | — | 10 |
| 5 | The conjugate of formula A | SC | 100 | Qwk to end | — | — | — | — | 10 |
| 6 | Topotecan | IP | 12 | Q4d x 3 | the conjugate of formula A | SC | 10 | Qwk to end | 10 |
| 7 | Topotecan | IP | 12 | Q4d x 3 | the conjugate of formula A | SC | 100 | Qwk to end | 10 |
| 8 | Topotecan | IP | 6 | Q4d x 3 | the conjugate of formula A | SC | 10 | Qwk to end | 10 |
| 9 | Topotecan | IP | 6 | Q4d x 3 | the conjugate of formula A | SC | 100 | Qwk to end | 10 |

Gr—Group
[#]Control Group
[a]Topotecan was formulated with Hycamtin in D5W
[b]the conjugate of formula A was formulated in PBS buffer
SC = Subcutaneous
IP = Intraperitoneal
Qwk to end - Every week until study completion
Q4d x 3 - Every four days for 3 cycles The SCID mouse human leukemia model has been a useful tool for evaluating new chemotherapy drugs, new drug combinations and novel treatment strategies (Teicher B A. Tumor models in cancer research, 2002). MOLT-4 human leukemia cell line was identified for this xenograft efficacy study based FACS analysis data demonstrating its α4 expression and functionality. One hundred eighty (180) female HRLN CB.17 SCID mice were approximately 4 weeks old on day of tumor implantation. Mice were acclimated for at least 7 days prior to the start of the experiment, and were provided food and water ad libitum throughout the study. Day 1 of the study, the animals were sorted by tumor size into 9 groups (n=10) for analysis of efficacy. The group mean tumor volumes was 107 mm³ with individual tumor sizes ranging from 108 to 126 mm³.

The dosing concentrations for the 10 and 100 mg/kg doses were 2 and 20 mg/mL, respectively. The doses were formulated according to Elan's "Instructions for Solution Preparation and Proper Handling of the conjugate of formula A.

Mice were dosed with the conjugate of formula A and vehicle (PBS) once a week starting on Day 1 (day of enrollment) via SC injection of the nuchal area with a 23-gauge needle (1-1.5 inch). Animals were dosed 5 mL/kg of the 2 and 20 mg/mL and PBS solutions based on most current body weight.

Mice dosed with topotecan were dosed every 4 days starting on Day 1 for 3 cycles via IP injection with a 23-gauge needle (1-1.5 inch); SC injection is the expected route of administration in the clinic. Topotecan was diluted into D5W.

A further study was performed to assess the ability of the conjugate of formula A to disrupt α4β1 mediated binding interaction of the human acute lymphoblastic leukemia cell line, MOLT-4 in vitro. Expression of functional α4β1 on MOLT-4 was confirmed by FACS analysis. VCAM-1/Fc bound to MOLT-4 in an α4-dependent fashion and the conjugate of formula A completely blocked the binding with an $EC_{50}$ of 0.12 nM. Previous studies demonstrated that multiple myeloma cell lines express α4 integrin (Uchiyama H et al., Blood 1992; 80 (9): 2306-14).

MOLT-4 (human acute lymphoblastic leukemia cell line) was obtained from Piedmont Research Center. The cell line was prepared from the primary tumors that were implanted in mice on study 132-030-mONC. MOLT-4 Growth medium was prepared as RPMI1640 media that contains 10% heat inactivated FBS, 2 mM L-glutamine, 10 mM HEPES, 0.075% sodium bicarbonate, 1 mM sodium pyruvate, 25 µg/ml Gentamicin, 0.25 µg/ml Amphotericin B (Fungizone) and penstrep at 37° C., 5% $CO_2$.

MOLT-4 cells were collected and washed with assay buffer once. The cells were then incubated with 10 µg/ml of either 21/6, an α4 specific mouse antibody, or AIIB2, a β1 specific mouse antibody, or buffer alone at room temperature for 30 minutes. After the cells were washed with assay buffer twice, they were incubated with goat anti-mouse IgG (Fc)-PE at 1:150 on ice in the dark for 30 minutes. After being washed with assay buffer once, the cells were fixed in PBS++/2% FBS/1% paraformaldehyde and stored on ice for FACS analysis (Becton-Dickinson).

Figure 9:
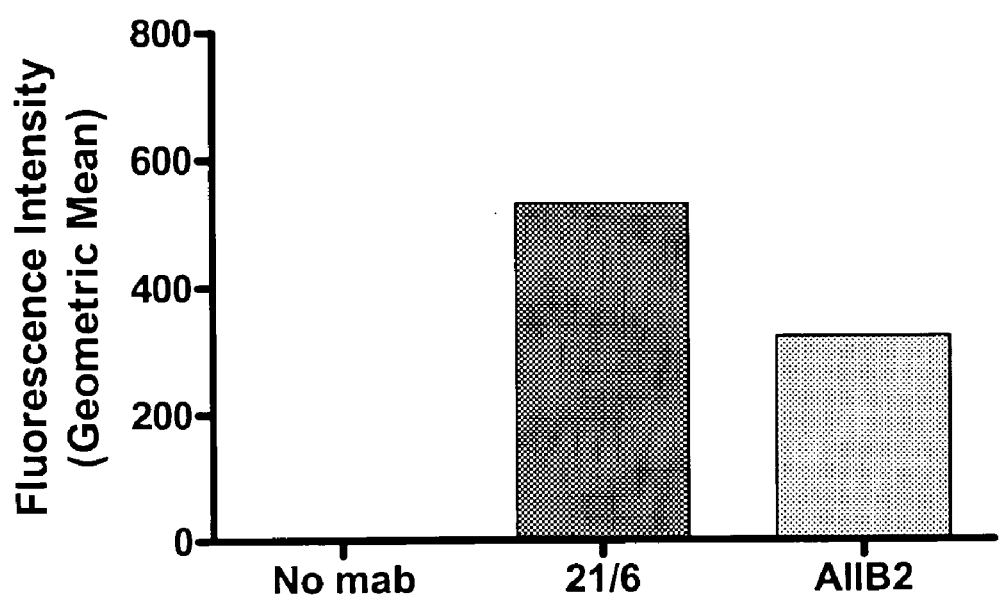
FIG. 9 shows a graph illustrating alpha-4 and beta-1 expression on MOLT-4 cells.

MOLT-4 cells were collected and washed with assay buffer once. The cells were then pre-incubated at room temperature for 15 minutes with either 2×21/6 at 20 μg/ml, or 2× of various concentrations of the conjugate of formula A-5 starting at 6 μg/ml, or assay buffer. Recombinant soluble human VCAM-1/Fc at 20 μg/ml was added and incubated at room temperature for 30 minutes. Next, the cells were washed with assay buffer twice, and then incubated with mouse anti-human IgG (Fc)-PE at 1:100 on ice in the dark for 30 minutes. After being washed with assay buffer once, the cells were fixed in PBS++/2% FBS/1% paraformaldehyde and stored on ice for FACS analysis (Becton-Dickinson).

α4 and β1 Expression on MOLT-4 Cells

α4 and β1 expression on MOLT-4 cells was evaluated with two in-house mouse antibodies, 21/6 and AIIB2, targeting α4 and β1 integrin subunits respectively. As shown in FIG. 9, MOLT-4 cells express both α4 and β1 integrin subunits.

VCAM-1/Fc Binding to MOLT-4 Cells

Figure 10:
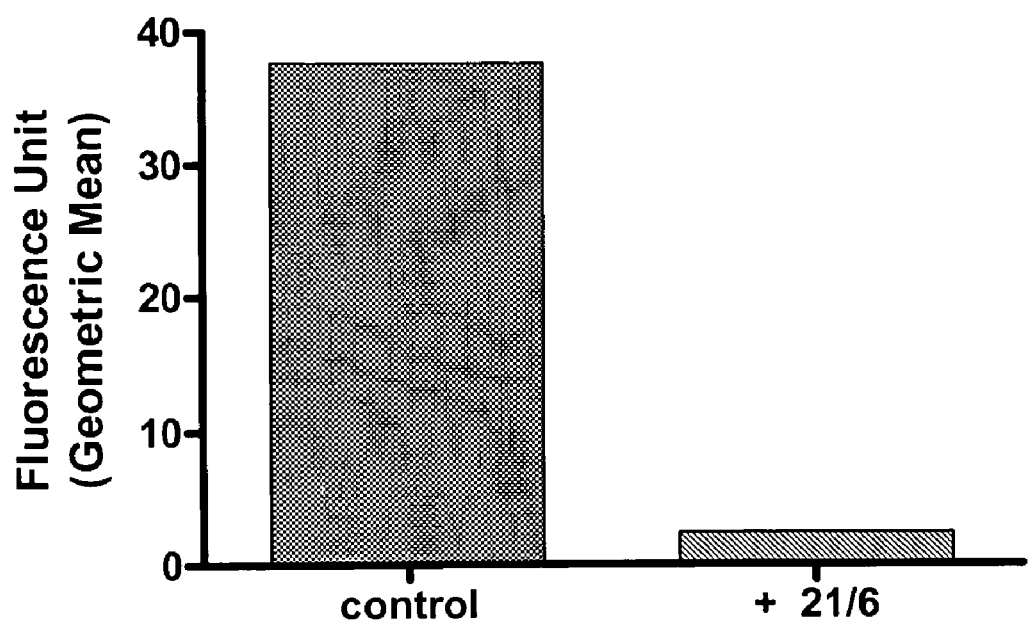
FIG. 10 shows a graph illustrating VCAM-1/Fe binding with MOLT-4 cells.
Figure 11:
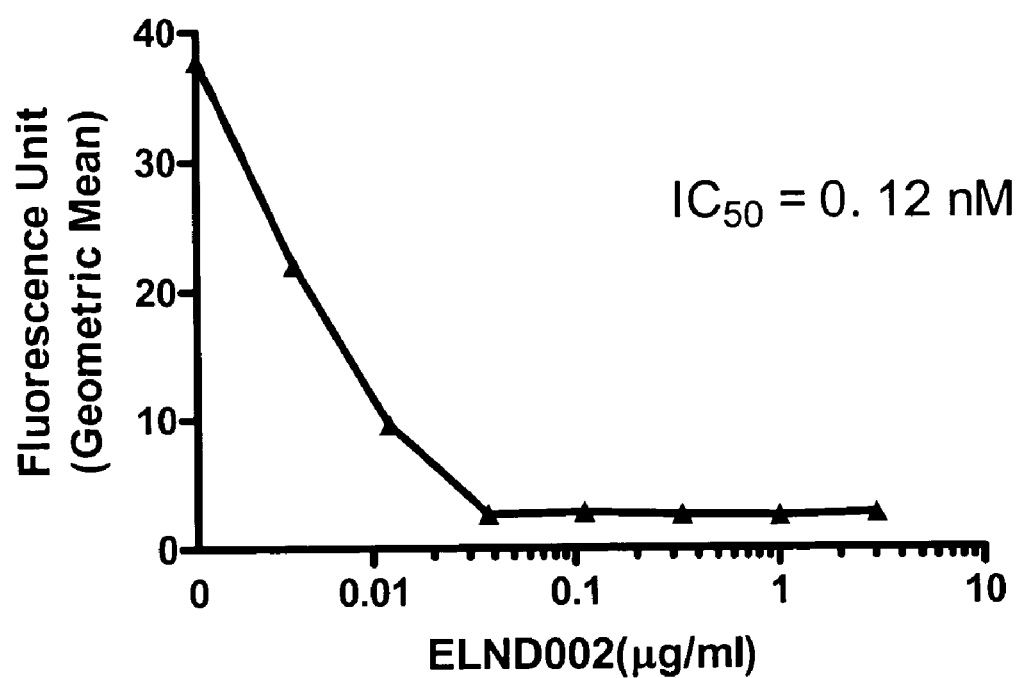
FIG. 11 shows a graph illustrating the inhibition of VCAM-1/Fe binding to MOLT-4 cells by the conjugate of formula XXII.

The ability of MOLT-4 to bind human VCAM-1/FC was evaluated in a binding assay measured by flow cytometry analysis. VCAM-1/Fc binding was detected with an antibody to the human Fc portion. The recombinant soluble VCAM-1/Fc binds to MOLT-4 cells in a α4-dependent fashion as demonstrated by complete inhibition with saturating concentration of 21/6, as shown in FIG. 10. the conjugate of formula A-5 inhibited VCAM-1/Fc binding to MOLT-4 cells in a dose response fashion with an $IC_{50}$ of 0.12 nM, as shown in FIG. 11.

The data demonstrate that the human acute lymphoblastic leukemia MOLT-4 cells express functional α4β1 and the conjugate of formula A inhibits human VCAM-1/Fc binding to these cells in vitro.

Although the present invention has been described in detail with reference to examples below, it is understood that various modifications can be made without departing from the spirit of the invention, and would be readily known to the skilled artisan.

That which is claimed is:

1. A method for inhibiting liquid tumor growth, malignancies thereof and/or development of metastases thereof comprising administering a therapeutically effective amount of a conjugate of formula XXII below:

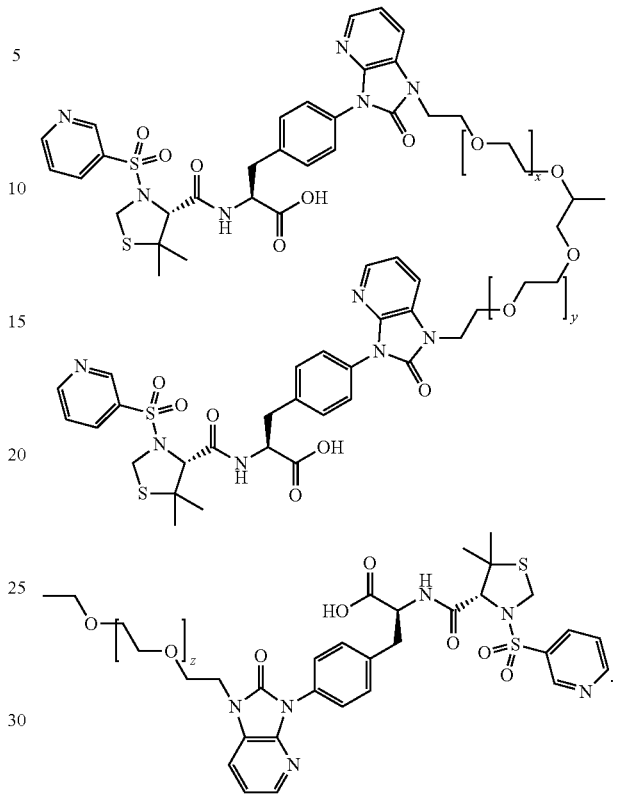

XXII wherein x, y, and z are independently an integer such that the aggregate of x, y, and z is about 100 to 1360.

2. The method of claim 1, wherein x, y, and z are independently an integer such that the conjugate of formula XXII has a molecular weight of about 40-45 kDa.

3. The method of claim 1, wherein the malignancy is a hematological malignancy.

4. The method of claim 3, wherein the hematological malignancy is a leukemia or multiple myeloma.

5. The method of claim 4, wherein the leukemia is selected from the group consisting of acute lymphoblastic leukemia (ALL), acute myelogenous leukemia (AML), chronic myelogenous leukemia (CML), and chronic lymphocytic leukemia (CLL).

6. A pharmaceutical composition for inhibiting liquid tumor growth, malignancies thereof and/or development of metastases thereof in a patient in need thereof, comprising a therapeutically effective amount of a conjugate of formula XXII of claim 1, or a pharmaceutically acceptable salt thereof, and a pharmaceutically acceptable carrier, vehicle, or diluent.

7. A combination therapy for inhibiting tumor growth, malignancies and/or metastatic progression and/or development of metastases comprising administering a conjugate of formula XXII of claim 1 and a chemotherapeutic, and immunotherapeutic, and/or radiation therapy.

* * * * *